(12) United States Patent
Amegadzie et al.

(10) Patent No.: US 7,320,994 B2
(45) Date of Patent: Jan. 22, 2008

(54) TRIAZOLE DERIVATIVES AS TACHYKININ RECEPTOR ANTAGONISTS

(75) Inventors: Albert Kudzovi Amegadzie, Indianapolis, IN (US); Kevin Matthew Gardinier, Indianapolis, IN (US); Erik James Hembre, Indianapolis, IN (US); Jian Eric Hong, Carmel, IN (US); Louis Nickolaus Jungheim, Indianapolis, IN (US); Brian Stephen Muehl, Greenwood, IN (US); David Michael Remick, Fishers, IN (US); Michael Alan Robertson, Indianapolis, IN (US); Kenneth Allen Savin, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 411 days.

(21) Appl. No.: 10/512,249

(22) PCT Filed: Apr. 22, 2003

(86) PCT No.: PCT/US03/10681

§ 371 (c)(1),
(2), (4) Date: Oct. 20, 2004

(87) PCT Pub. No.: WO03/091226

PCT Pub. Date: Nov. 6, 2003

(65) Prior Publication Data

US 2005/0239786 A1    Oct. 27, 2005

Related U.S. Application Data

(60) Provisional application No. 60/376,121, filed on Apr. 26, 2002.

(51) Int. Cl.
*A61K 31/41* (2006.01)
*C07D 249/04* (2006.01)
(52) U.S. Cl. ...................................... 514/359; 548/255
(58) Field of Classification Search ................ 514/359; 548/255
See application file for complete search history.

(56) References Cited

U.S. PATENT DOCUMENTS

| 5,998,444 | A | 12/1999 | Russell |
| 6,060,478 | A | 5/2000 | Gilligan et al. |
| 6,407,106 | B1 * | 6/2002 | Jasserand et al. ........ 514/235.2 |
| 7,179,804 | B2 * | 2/2007 | Amegadzie et al. ..... 514/227.8 |

FOREIGN PATENT DOCUMENTS

| EP | 0 699 665 A1 | 3/1996 |
| EP | 0 699 665 | 5/2003 |
| FR | 2 329 275 | 10/1976 |
| JP | P2002-123925 A | 4/2002 |
| WO | WO 95/11880 | 5/1995 |
| WO | WO 97/40025 | 10/1997 |
| WO | WO 98/03510 | 1/1998 |
| WO | WO 99/07677 | 2/1999 |
| WO | WO 01/44200 | 6/2001 |
| WO | WO 02/08232 A1 | 1/2003 |

OTHER PUBLICATIONS

Duffy et al., Correlation of NK-1 receptor occupancy in gerbil striatum with behavorial effects of NK1 antagonists, J. Pharm. And Ex. Th., vol. 301, No. 2, 2002, especially pp. 536-542.*
L'Abbé, et al., "Synthesis and Thermolysis of 4-Substituted 5-Azido-1-Phenyl-1,2,3- Triazoles", *Tetrahedron*, 44:12, pp. 3617-3626 (1988).
Hajjaji, et al., "Synthesis and Evaluation of the Inhibitor Effect of a New Class of Triazole Compounds," *Progress in Organic Coatings*, 38, pp. 207-212 (2000).
Abu-Orabi, et al., "Dipolar Cycloaddition Reactions of Organic Azides," *J. Heterocyclic Chem.*, 26, pp. 1461-1468 (1989).
Theocharis, et al., "Synthesis and Spectral Data of 4,5-Bix[5-aryl-1,3,4- oxadiazol-2-yl]-1-benzyl-1,2,3-triazoles," *J. Heterocyclic Chem*, 27, pp. 1685-1688 (1990).
Al-Talib, et al., "Synthesis of 4,5-*Bis*-[5-aryl-1,3,4-oxadiazol-2-YL]-1-Substgituted Benzyl-1,2,3-Triazoles," *Indian J. of Heterocyclic Chem.*, 8, pp. 183-188 (1999).
Cottrell, "An Improved Procedure for the Preparation of 1-Benzyl-1 *H*-1,2,3- triazoles from Benzyl Azides," *J. Heterocyclic Chem.*, 28, pp. 301-304 (1990).
ACS Chemcats 2001:1613994, Publication Date Jan. 7, 2001, Order No. AN-666/14744011, CAS Registry No. 354780-46-4.
Biagi, et al., "N<6>-Cycloalkyl-2-Phenyl-3-Deaza-8-Azaad Nines: A New Class of A1 Adenosine Receptor Ligands. A Comparison With the Corresponding Adenines and 8-Azaadenines", *European J. of Medicinal Chemistry*, 38, pp. 983-990 (2003).
Ivanov, et al., "Synthesis of 1,2,3-Triazolo '5,4-e!-1,4-diazepine", *J. of Organic Chemistry of the USSR*, XP009037402, 25:9, pp. 1785-1789 (1989).
Katritzky, et al., "Synthesis of C-Carbamoyl-1,2,3-triazoles by Microwave-Induced 1,3-Dipolar Cycloaddition of Organic Azides to Acetylenic Amides", *J. Organ. Chem.*, XP002299474, 67, pp. 9077-9079 (2002).
Katritzky, et al., "1,3-Dipolar Cycloadditions of Organic Azides to Ester or Benzotriazolylcarbonyl Activated Acetylenic Amides", *ARKIVOC*, 15, XP002299475, 15, pp. 47-64 (2003).

* cited by examiner

*Primary Examiner*—Rebecca Anderson
*Assistant Examiner*—Susannah Chung
(74) *Attorney, Agent, or Firm*—Manisha A. Desai

(57) ABSTRACT

This application relates to a compound of Formula (I) or a pharmaceutically acceptable salt thereof, pharmaceutical compositions thereof, and its use as an inhibitor of the NK-1 subtype of tachykinin receptors, as well as a process for its preparation and intermediates therefor. (I) wherein: D is a $C_1$-$C_3$ alkane-diyl; $R^1$ is phenyl, which is optionally substituted with one to three substitutents independently selected from the group consisting of: halo, $C_1$-$C_4$ alkyl, $C_1$-$C_4$ alkoxy, cyano, difluoromethyl, trifluoromethyl, and trifluoromethoxy; $R^4$ is a radical selected from the group consisting of: (IA), (IB), (IC), (ID), (IE), (IF), (IG), (IH)

(I)
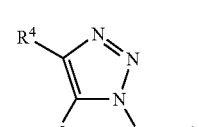
(IA)
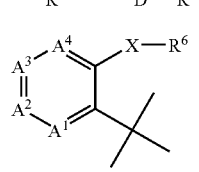
(IB)
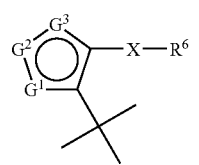
(IC)
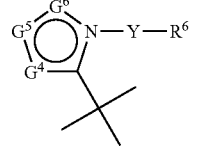
(ID)
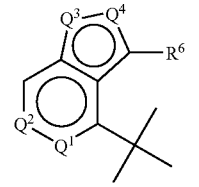
-continued
(IE)
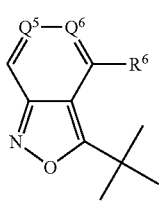
(IF)
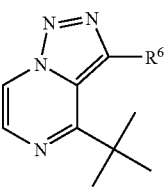
(IG)
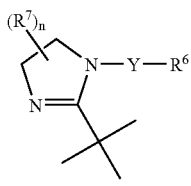
(IH)
34 Claims, No Drawings

TRIAZOLE DERIVATIVES AS TACHYKININ RECEPTOR ANTAGONISTS

This application is a United States national phase entry, pursuant to 35 U.S.C. 371, of PCT/US03/10681, filed Apr. 22, 2003, which claims the benefit of U.S. provisional patent application Ser. No. 60/376,121, filed Apr. 26, 2002.

The present invention provides compounds of Formula (I), compositions thereof, and a method of antagonizing the NK-1 subtype of tachykinin receptor that comprises administering to a patient in need thereof an effective amount of a compound of Formula (I). In addition, the present invention relates to processes for preparing the compounds of Formula I and intermediates thereof.

BACKGROUND OF THE INVENTION

Tachykinins are a family of peptides that are widely distributed in both the central and peripheral nervous systems. These peptides exert a number of biological effects through actions at tachykinin receptors. To date, three such receptors have been characterized, including the NK-1, NK-2, and NK-3 subtypes of tachykinin receptor.

The role of the NK-1 receptor subtype in numerous disorders of the central nervous system and the periphery has been thoroughly demonstrated in the art. For instance, NK-1 receptors are believed to play a role in depression, anxiety, and central regulation of various autonomic, as well as cardiovascular and respiratory functions. NK-1 receptors in the spinal cord are believed to play a role in pain transmission, especially the pain associated with migraine and arthritis. In the periphery, NK-1 receptor activation has been implicated in numerous disorders, including various inflammatory disorders, asthma, and disorders of the gastrointestinal and genitourinary tract.

There is an increasingly wide recognition that selective NK-1 receptor antagonists would prove useful in the treatment of many diseases of the central nervous system and the periphery. While many of these disorders are being treated by new medicines, there are still many shortcomings associated with existing treatments. For example, the newest class of anti-depressants, selective serotonin reuptake inhibitors (SSRIs), are increasingly prescribed for the treatment of depression; however, SSRIs have numerous side effects, including nausea, insomnia, anxiety, and sexual dysfunction. This could significantly affect patient compliance rate. As another example, current treatments for chemotherapy-induced nausea and emesis, such as the 5-HT$_3$ receptor antagonists, are ineffective in managing delayed emesis. The development of NK-1 receptor antagonists will therefore greatly enhance the ability to treat such disorders more effectively. Thus, the present invention provides a class of potent, non-peptide NK-1 receptor antagonists, compositions comprising these compounds, and methods of using the compounds.

BRIEF SUMMARY OF THE INVENTION

This invention provides compounds of Formula I:

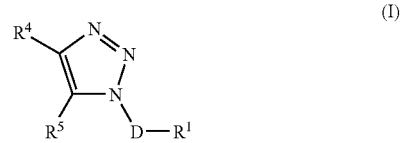

wherein:
D is a $C_1$-$C_3$ alkane-diyl;
$R^1$ is phenyl,
which is optionally substituted with one to three substitutents independently selected from the group consisting of halo, $C_1$-$C_4$ alkyl, $C_1$-$C_4$ alkoxy, cyano, difluoromethyl, trifluoromethyl, and trifluoromethoxy;
$R^4$ is a radical selected from the group consisting of:

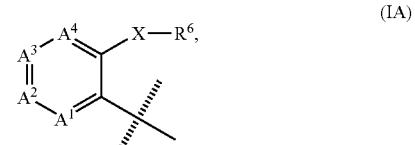

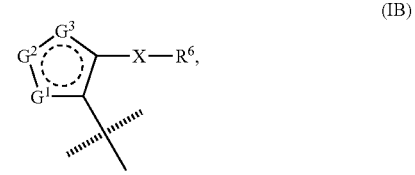

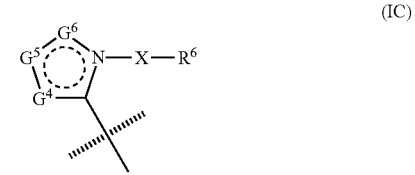

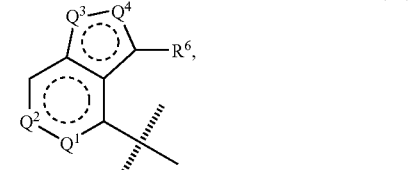

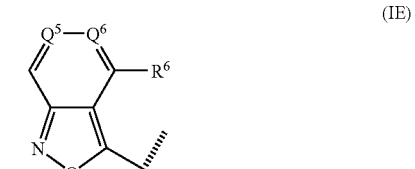

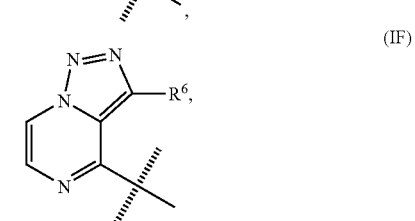

-continued

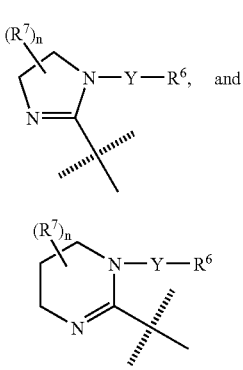

(IG)

(IH)

wherein
-A$^1$-A$^2$-A$^3$-A$^4$-, together with the atoms to which they are attached, form an aromatic carbocyclic or heterocyclic ring in which each of A$_1$, A$^2$, A$^3$, and A$^4$ is independently —CR$^8$— or nitrogen, wherein at least one of A$^1$, A$^2$, A$^3$, and A$^4$ must be —CR$^8$—;
-G$^1$-G$^2$-G$^3$-, together with the atoms to which they are attached, form an aromatic heterocyclic ring in which each of G$^1$, G$^2$, and G$^3$ is independently —CR$^8$—, nitrogen, oxygen, or sulfur, wherein only one of G$^1$, G$^2$, and G$^3$ can be oxygen or sulfur;
-G$^4$-G$^5$-G$^6$-, together with the atoms to which they are attached, form an aromatic heterocyclic ring in which each of G$^4$, G$^5$, and G$^6$ is independently —CR$^8$—, or nitrogen;
  each R$^8$ is independently selected from the group consisting of hydrogen, halo, C$_1$-C$_4$ alkyl, substituted C$_1$-C$_4$ alkyl, C$_3$-C$_6$ cycloalkyl, —NR$^{12}$R$^{13}$, trifluoromethyl, and trifluoromethoxy;
    R$^{12}$ and R$^{13}$ are each independently hydrogen, C$_1$-C$_4$ alkyl, or —C(O)—CH$_3$, or R$^{12}$ and R$^{13}$, together with the nitrogen to which they are attached, form a 4-7 membered ring;
Q$^1$, Q$^2$, Q$^5$, and Q$^6$ are each independently —H—, or nitrogen;
Q$^3$ and Q$^4$ are each independently oxygen or nitrogen, wherein at least one of Q$^3$ and Q$^4$ must be nitrogen;
R$^6$ is C$_1$-C$_4$ alkyl, C$_3$-C$_6$ cycloalkyl, phenyl, or pyridyl,
  which phenyl or pyridyl is optionally substituted with one to three substituents independently selected from the group consisting of halo, cyano, C$_1$-C$_4$ alkyl, C$_1$-C$_4$ alkoxy, trifluoromethyl, trifluoromethoxy, morpholino, and —NR$^{14}$R$^{15}$;
    R$^{14}$ and R$^{15}$ are each independently hydrogen or C$_1$-C$_4$ alkyl, or R$^{14}$ and R$^{15}$, together with the nitrogen to which they are attached, form a 4-7 membered ring;
X is a bond, C$_1$-C$_3$ alkane-diyl, —CH(OH)—, —C(O)—, —O—, —S(O)$_p$—, or C=N—OR$^9$—;
  p is 0, 1, or 2;
  R$^9$ is hydrogen, C$_1$-C$_4$ alkyl, or benzyl;
Y is a bond, C$_1$-C$_3$ alkane-diyl, or —C(O)—;
n is 0, 1, or 2;
each R$^7$ is independently C$_1$-C$_4$ alkyl;
R$^5$ is hydrogen, halo, trifluoromethyl, C$_1$-C$_4$ alkyl, C$_3$-C$_6$ cycloalkyl, furyl, thienyl, pyrrolyl, imidazolyl, —NR$^{16}$R$^{17}$, pyridyloxy, phenyl, phenoxy, phenylthio, anilino,
  which phenyl, phenoxy, phenylthio, or anilino group may be optionally substituted on the phenyl ring with one or two substituents independently selected from the group consisting of halo, C$_1$-C$_4$ alkyl, C$_1$-C$_4$ alkoxy, and —S(O)$_q$(C$_1$-C$_4$ alkyl),
or a radical selected from the group consisting of:

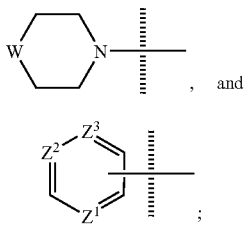

(IJ)

(IK)

wherein
W is a bond, —CH$_2$—, —O—, —NR$^{11}$, or —S(O)$_q$—;
  q is 0, 1, or 2;
  R$^{11}$ is selected from the group consisting of hydrogen, C$_1$-C$_4$ alkyl, acetyl, phenyl, benzyl, and —S(O)$_2$CH$_3$;
Z$^1$, Z$^2$, and Z$^3$ are each independently —CH— or nitrogen;
R$^{16}$ and R$^{17}$ are each independently hydrogen or C$_1$-C$_4$ alkyl;
or a pharmaceutically acceptable salt thereof.

The compounds of Formula I are antagonists of tachykinin receptors. Specifically, the compounds of Formula I are antagonists of the NK-1 subtype of tachykinin receptor. Because these compounds inhibit the physiological effects associated with an excess of tachykinins, the compounds are useful in the treatment of numerous disorders related to tachykinin receptor activation. These disorders include: anxiety, depression, psychosis, and schizophrenia and other psychotic disorders; neurodegenerative disorders such as dementia, including senile dementia of the Alzheimer's type, Alzheimer's disease, AIDS-associated dementia, and Down syndrome; demyelinating diseases such as multiple sclerosis and amyotrophic lateral sclerosis and other neuropathological disorders, such as peripheral neuropathy, diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculoskeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthyrnic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyper-reflexia and incontinence; atherosclerosis; fibrosin and collagen diseases such as scleroderma and eosinophilic fascioliasis; irritative symptoms of benign prostatic hypertrophy; disorders associated with blood pressure, such as hypertension; or disorders of blood flow caused by vasodilation and vasospastic diseases, such as angina, migraine, and Reynaud's disease; emesis, including chemotherapy-induced nausea and emesis; and pain or nociception, for example, that attributable to or associated with any of the foregoing conditions.

In one embodiment, this invention provides a pharmaceutical composition comprising, as an active ingredient, a compound of Formula I, or a pharmaceutically acceptable salt thereof, in combination with one or more pharmaceutically acceptable carriers, diluents, or excipients.

In a further embodiment, the present invention relates to a method of making a compound represented by Formula I, and intermediates thereof.

In another embodiment, the present invention provides a method of selectively antagonizing an NK-1 receptor by contacting the receptor with a compound of Formula I, or a pharmaceutically acceptable salt thereof.

In another embodiment, this invention provides methods of treating a condition associated with an excess of tachykinins, comprising: administering to a patient in need thereof an effective amount of a compound of Formula I, or a pharmaceutically acceptable salt thereof. That is, the present invention provides for the use of a compound of Formula I, or a pharmaceutical composition thereof, for the treatment of a disorder associated with an excess of tachykinins.

In another aspect, the present invention provides for the use of a compound of Formula I, or a pharmaceutically acceptable salt thereof, in the manufacture of a medicament for antagonizing the NK-1 receptor. Thus, the present invention provides for the use of a compound of Formula I, or a pharmaceutically acceptable salt thereof, in the manufacture of a medicament for the treatment of a disorder associated with an excess of tachykinins by means of the method described above.

Of the disorders listed above, depression, anxiety, schizophrenia and other psychotic disorders, emesis, pain, asthma, inflammatory bowel disease, irritable bowel syndrome, and dermatitis are of importance. Of these disorders, depression and anxiety are of particular importance.

Thus, in a preferred embodiment, the present invention provides a method for treating major depressive disorder, comprising: administering to a patient in need thereof an effective amount of a compound of Formula I, or a pharmaceutically acceptable salt thereof.

In another preferred embodiment, the present invention provides a method for treating generalized anxiety disorder, comprising: administering to a patient in need thereof an effective amount of a compound of Formula I, or a pharmaceutically acceptable salt thereof.

In another preferred embodiment, the present invention provides a method for treating panic disorder, comprising: administering to a patient in need thereof an effective amount of a compound of Formula I, or a pharmaceutically acceptable salt thereof.

In another preferred embodiment, the present invention provides a method for treating obsessive compulsive disorder, comprising: administering to a patient in need thereof an effective amount of a compound of Formula I, or a pharmaceutically acceptable salt thereof.

In another preferred embodiment, the present invention provides a method for treating social phobia, comprising: administering to a patient in need thereof an effective amount of a compound of Formula I, or a pharmaceutically acceptable salt thereof.

DETAILED DESCRIPTION OF THE INVENTION

The terms and abbreviations used in the preparations and examples have their normal meanings unless otherwise designated. For example "°C." refers to degrees Celsius; "N" refers to normal or normality; "mol" refers to mole or moles; "eq" refers to equivalent; "g" refers to gram or grams; "L" refers to liter or liters; "M" refers to molar or molarity; "brine" refers to a saturated aqueous sodium chloride solution; "MS" refers to mass spectrometry; "NMR" refers to nuclear magnetic resonance spectroscopy; "TLC" refers to thin layer chromatography; "ACN" refers to acetonitrile; "DMF" refers to N,N-dimethylformamide; "DMSO" refers to dimethylsulfoxide; "Et$_2$O" refers to diethyl ether; "EtOAc" refers to ethyl acetate; "MeOH" refers to methanol; "EtOH" refers to ethanol; "iPrOH" refers to isopropanol; "TEA" refers to triethylamine; "TFA" refers to trifluoroacetic acid; "THF" refers to tetrahydrofuran.

As used herein, the term "$C_1$-$C_4$ alkyl" refers to straight or branched, monovalent, saturated aliphatic chains of 1 to 4 carbon atoms and includes, but is not limited to, methyl, ethyl, propyl, isopropyl, butyl, isobutyl, and tert-butyl. The term "$C_1$-$C_4$ alkyl" includes within its definition the term "$C_1$-$C_3$ alkyl."

The term "substituted $C_1$-$C_4$ alkyl" refers to a straight or branched, monovalent, saturated aliphatic chain of 1 to 4 carbon atoms, as encompassed in the definition of $C_1$-$C_4$ alkyl above, that is further substituted on any of the carbon atoms with one to three substituents independently selected from the group consisting of hydroxy, oxo, halo, $C_1$-$C_4$ alkoxy, $C_1$-$C_4$ alkoxycarbonyl, =N(OH), morpholino, and —NR$^a$R$^b$, wherein R$^a$ is H or $C_1$-$C_4$ alkyl, R$^b$ is H, $C_1$-$C_4$ alkyl, or —C(O)—CH$_3$, or R$^a$ and R$^b$, together with the N to which they are attached, form a 4-7 membered ring. Such 4-7 membered rings include, but are not limited to, pyrrolidinyl, and piperidino.

"$C_1$-$C_3$ alkane-diyl" refers to a straight or branched, divalent, saturated aliphatic chain of 1 to 3 carbon atoms and includes, but is not limited to, methylene, ethylene, ethane-1,1-diyl, propane-1,1-diyl, propane-1,2-diyl, propane-1,3-diyl, and propane-2,2-diyl.

"$C_1$-$C_4$ alkoxy" represents a straight or branched alkyl chain having from one to four carbon atoms attached to an oxygen atom. Typical $C_1$-$C_4$ alkoxy groups include methoxy, ethoxy, propoxy, isopropoxy, butoxy, tert-butoxy, and the like. The term "$C_1$-$C_4$ alkoxy" includes within its definition the term "$C_1$-$C_3$ alkoxy".

"$C_3$-$C_6$ cycloalkyl" represents a saturated hydrocarbon ring structure containing from three to six carbon atoms. Typical $C_3$-$C_6$ cycloalkyl groups include cyclopropyl, cyclopentyl, cyclohexyl, and the like.

"Halo," "halogen," and "halide" represent a chloro, fluoro, bromo or iodo atom. Preferred halogens include chloro and fluoro.

"$C_1$-$C_4$ alkoxycarbonyl" represents a straight or branched $C_1$-$C_4$ alkoxy chain, as defined above, that is attached via the oxygen atom of the alkoxy to a carbonyl moiety. Typical $C_1$-$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "Pg" refers to an alcohol, carboxyl, or amino protecting group. Typical protecting groups include tetrahydropyranyl (THP), silanes such as trimethylsilane (TMS), tert-butyldimethylsilane (TBDMS), and tert-butyldiphenylsilane (TBDPS), methoxymethyl (MOM), benzyl (Bn), p-methoxybenzyl, formyl, acetyl (Ac), and tert-butoxycarbonyl (t-BOC). Typical carboxylprotecting groups may include methyl, ethyl, and tert-butyl. The selection and use of protecting groups is well known and appreciated in the art. See for example, *Protecting Groups in Organic Synthesis*, Theodora Greene (Wiley-Interscience); *Protecting Groups*, Philip J. Kocienski, Thieme Medical Publishers, inc: New York 1994, chapters 2,4,6.

It is understood that when $R^6$ is pyridyl, the radical may be a pyridin-2-yl, pyridin-3-yl, or pyridin-4-yl. When $R^5$ is furyl or thienyl, the radical may be attached at the 2-, or 3-position of the radical. When $R^5$ is pyrrolyl, or imidazolyl, the radical may be attached at the 1-, 2-, or 3-position of the radical.

The compounds of the present invention may exist as stereoisomers. The Cahn-Prelog-Ingold designations of (R)- and (S)- and the designations of L- and D- for stereochemistry relative to the isomers of glyceraldehyde are used herein to refer to specific isomers. The specific stereoisomers can be prepared by stereospecific synthesis or can be resolved and recovered by techniques known in the art, such as chromatography on chiral stationary phases, and fractional recrystallization of addition salts formed by reagents used for that purpose. Useful methods of resolving and recovering specific stereoisomers are known in the art and described in E. L. Eliel and S. H. Wilen, *Stereochemistry of Organic Compounds*, (Wiley-Interscience 1994), and J. Jacques, A. Collet, and S. H. Wilen, *Enantiomers, Racemates, and Resolutions*, Wiley-Interscience 1981). It is understood that the present invention contemplates all enantiomers and mixtures of enantiomers, including racemates.

The skilled artisan will recognize that compounds of the present invention may exist as tautomers. It is understood that tautomeric forms of the compounds of Formula (I) are also encompassed in the present invention.

This invention includes the pharmaceutically acceptable salts of the compounds of Formula I. A compound of this invention can possess a sufficiently basic functional group, which can react with any of a number of inorganic and organic acids, to form a pharmaceutically acceptable salt.

The term "pharmaceutically-acceptable salt" as used herein, refers to a salt of a compound of the above Formula I. It should be recognized that the particular counterion forming a part of any salt of this invention is usually not of a critical nature, so long as the salt as a whole is pharmacologically acceptable and as long as the counterion does not contribute undesired qualities to the salt as a whole.

The compound of Formula I and the intermediates described herein form pharmaceutically-acceptable acid addition salts with a wide variety of organic and inorganic acids and include the physiologically-acceptable salts which are often used in pharmaceutical chemistry. Such salts are also part of this invention. A pharmaceutically-acceptable acid addition salt is formed from a pharmaceutically-acceptable acid, as is well known in the art. Such salts include the pharmaceutically acceptable salts listed in *Journal of Pharmaceutical Science*, 66, 2-19 (1977), which are known to the skilled artisan. Typical inorganic acids used to form such salts include hydrochloric, hydrobromic, hydriodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, α-hydroxybutyrate, butyne-1,4 dicarboxylate, hexyne-1,4-dicarboxylate, caprate, caprylate, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartarate, and the like.

As used herein, the term "patient" refers to a mammal that is afflicted with one or more disorders associated with excess tachykinins. Guinea pigs, dogs, cats, rats, mice, horses, cattle, sheep, and humans are examples of mammals within the scope of the meaning of the term. It will be understood that the most preferred patient is a human. It is also understood that this invention relates specifically to the inhibition of mammalian NK-1 receptors.

It is also recognized that one skilled in the art may affect the disorders by treating a patient presently afflicted with the disorders or by prophylactically treating a patient afflicted with the disorders with an effective amount of the compound of Formula I. Thus, the terms "treatment" and "treating" are intended to refer to all processes wherein there may be a slowing, interrupting, arresting, controlling, or stopping of the progression of the disorders described herein, and is intended to include prophylactic treatment of such disorders, but does not necessarily indicate a total elimination of all disorder symptoms.

As used herein, the term "effective amount" of a compound of Formula I refers to an amount that is effective in treating the disorders described herein.

As with any group of pharmaceutically active compounds, some groups are preferred in their end use application. Preferred embodiments of the present invention are discussed below.

Preferred compounds are those in which $R^4$ is a radical of Formula (IA), (13), or (IC). The most preferred $R^4$ group is a radical of Formula (IA).

Preferred embodiments of the present invention when $R^4$ is a radical of Formula (IA) are given below.:

(a) -$A^1$-$A^2$-$A^3$-$A^4$- is —N—$CR^8$—$CR^8$—$CR^8$—.
(b) -$A^1$-$A^2$-$A^3$-$A^4$- is —N—N—$CR^8$—$CR^8$—.
(c) -$A^1$-$A^2$-$A^3$-$A^4$- is —N—$CR^8$—N—$CR^8$—.
(d) -$A^1$-$A^2$-$A^3$-$A^4$- is —N—CH—CH—$CR^8$—.
(e) -$A^1$-$A^2$-$A^3$-$A^4$- is N—N—CH—$CR^8$—.
(f) -$A^1$-$A^2$-$A^3$-$A^4$- is —N—CH—N—$CR^8$—.
(g) $R^8$ is hydrogen.
(h) $R^8$ is —$NR^{12}R^{13}$.
(i) $R^{12}$ and $R^{13}$ are each hydrogen.
(j) $R^1$ is phenyl substituted with two substituents selected from the group consisting of halo and trifluoromethyl.
(k) $R^1$ is 3,5-bis-trifluoromethyl-phenyl
(l) $R^5$ is a radical of Formula (IK) in which $Z^2$ is nitrogen.
(m) $R^5$ is phenyl.
(n) $R^5$ is pyridin-4-yl.
(o) $R^5$ is pyridin-3-yl.
(p) X is —C(O)—.
(q) X is $C_1$-$C_3$ alkane-diyl.

(r) $R^6$ is phenyl, which is optionally substituted with one to three substituents independently selected from the group consisting of halo, cyano, $C_1$-$C_4$ alkyl, $C_1$-$C_4$ alkoxy, trifluoromethyl, trifluoromethoxy, morpholino, and —$NR^{14}R^{15}$.

(s) $R^6$ is 2-chloro-phenyl.

(t) Preferred compounds in which $R^4$ is a radical of Formula (IA) include: {2-[1-(3,5-bis-trifluoromethyl-benzyl)-5-pyridin-4-yl-1H-[1,2,3]triazol-4-yl]-pyridin-3-yl}-(2-chloro-phenyl)-methanone, {4-Amino-2-[1-(3,5-bistrifluoromethylbenzyl)-5-phenyl-1H-[1,2,3]triazol-4-yl]-pyridin-3-yl}-(2-chloro-phenyl)-methanone, {5-Amino-3-[1-(3,5-bis-trifluoromethyl-benzyl)-5-phenyl-1H-[1,2,3]triazol-4-yl]-pyridazin-4-yl}-(2-chloro-phenyl)-methanone, {4-Amino-2-[1-(3,5-bis-trifluoromethyl-benzyl)-5-pyridin-4-yl-1H-[1,2,3]triazol-4-yl]-pyridin-3-yl}-(2-chloro-phenyl)-methanone, {5-Amino-3-[1-(3,5-bis-trifluoromethyl-benzyl)-5-pyridin-4-yl-1H-[1,2,3]triazol-4-yl]-pyridazin-4-yl}-(2-chloro-phenyl)-methanone, {2-[1-(3,5-bis-trifluoromethyl-benzyl)-5-pyridin-3-yl-1H-[1,2,3]triazol-4-yl]-pyridin-3-yl}-(2-chloro-phenyl)-methanone, {2-[1-(3,5-bis-trifluoromethyl-benzyl)-5-pyridin-4-yl-1H-[1,2,3]triazol-4-yl]-pyridin-3-yl}-phenyl-methanone, {5-Amino-3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone, {4-Amino-2-[1-(3,5-bis-trifluoromethyl-benzyl)-5-morpholin-4-yl-1H-[1,2,3]triazol-4-yl]-pyridin-3-yl}-(2-chloro-phenyl)-methanone, {2-[1-(3,5-bis-trifluoromethyl-benzyl)-5-pyrazin-2-yl-1H-[1,2,3]triazol-4-yl]-pyridin-3-yl}-(2-chloro-phenyl)-methanone, {3-[1-(3,5-bis-trifluoromethyl-benzyl)-5-pyridin-3-yl-1H-[1,2,3]triazol-4-yl]-pyridazin-4-yl}-(2-chloro-phenyl)-methanone, {3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone, {2-[1-(3,5-bis-trifluoromethyl-benzyl)-5-pyridin-4-yl-1H-[1,2,3]triazol-4-yl]-pyridin-3-yl}-(2-trifluoromethyl-phenyl)-methanone, {2-[1-(3,5-bis-trifluoromethyl-benzyl)-5-pyridin-4-yl-1H-[1,2,3]triazol-4-yl]-pyridin-3-yl}-(2-fluoro-phenyl)-methanone, {3-[1-(3,5-bis-trifluoromethyl-benzyl)-5-pyridin-4-yl-1H-[1,2,3]triazol-4-yl]-pyridin-2-yl}-(2-chloro-phenyl)-methanone, and {2-[1-(3,5-bis-trifluoromethyl-benzyl)-5-pyridin-4-yl-1H-[1,2,3]triazol-4-yl]-pyridin-3-yl}-(2-chloro-phenyl)-methanol.

Preferred embodiments of the present invention in which $R^4$ is a radical of Formula (IB) are given below.

(a) -$G^1$-$G^2$-$G^3$- is —N—O—$CR^8$—.

(b) -$G^1$-$G^2$-$G^3$- is —O—N—$CR^8$—.

(c) $R^8$ is a $C_1$-$C_4$ substituted alkyl.

(d) $R^1$ is phenyl substituted with two substituents selected from the group consisting of halo and trifluoromethyl.

(e) $R^1$ is 3,5-bis-trifluoromethyl-phenyl (f) $R^5$ is a radical of Formula (IK) in which $Z^2$ is nitrogen.

(g) $R^5$ is phenyl.

(h) $R^5$ is pyridin-4-yl.

(i) $R^5$ is pyridin-3-yl.

(j) X is —C(O)—.

(k) X is $C_1$-$C_3$ alkane-diyl.

(l) $R^6$ is phenyl, which is optionally substituted with one to three substituents independently selected from the group consisting of halo, cyano, $C_1$-$C_4$ alkyl, $C_1$-$C_4$ alkoxy, trifluoromethyl, trifluoromethoxy, morpholino, and —$NR^{14}R^{15}$.

(m) $R^6$ is 2-chloro-phenyl.

(n) Preferred compounds in which $R^4$ is a radical of Formula (IB) include: [3-[1-(3,5-bis-trifluoromethyl-benzyl)-5-pyridin-4-yl-1H-[1,2,3]triazol-4-yl]-5-(1-hydroxy-1-methyl-ethyl)-isoxazol-4-yl]-(2-chloro-phenyl)-methanone, and [3-[1-(3,5-bis-trifluoromethyl-benzyl)-5-pyridin-3-yl-1H-[1,2,3]triazol-4-yl]-5-(1-hydroxy-1-methyl-ethyl)-isoxazol-4-yl]-(2-chloro-phenyl)-methanone.

Preferred embodiments of the present invention in which $R^4$ is a radical of Formula (IC) are given below.

(a) -$G^4$-$G^5$-$G^6$- is —N—N—$CR^8$— or —N—N—N—.

(b) $R^8$ is a $C_1$-$C_4$ substituted alkyl.

(c) $R^1$ is phenyl substituted with two substituents selected from the group consisting of halo and trifluoromethyl.

(d) $R^1$ is 3,5-bis-trifluoromethyl-phenyl.

(e) $R^5$ is a radical of Formula (IK).

(f) $R^5$ is phenyl.

(g) $Z^2$ is nitrogen.

(h) $R^5$ is a radical of Formula (IJ), wherein W is —O— or —$NR^{11}$—.

(i) $R^{11}$ is $C_1$-$C_4$ alkyl.

(j) Y is a bond.

(k) Y is $C_1$-$C_3$ alkane-diyl.

(l) $R^6$ is phenyl, which is optionally substituted with one to three substituents independently selected from the group consisting of halo, cyano, $C_1$-$C_4$ alkyl, $C_1$-$C_4$ alkoxy, trifluoromethyl, trifluoromethoxy, morpholino, and —$NR^{14}R^{15}$.

(m) $R^6$ is 2-chloro-phenyl.

The skilled artisan will appreciate that additional preferred embodiments may be selected by combining the preferred embodiments above, or by reference to the examples given herein.

Schemes

The compounds disclosed herein can be made according to the following schemes and examples. The examples should in no way be understood to be limiting in any way as to how the compounds may be made.

The skilled artisan will appreciate that the introduction of certain substituents will create asymmetry in the compounds of Formula (I). The present invention contemplates all enantiomers and mixtures of enantiomers, including racemates. It is preferred that the compounds of the invention containing chiral centers are single enantiomers.

The compounds of the present invention can be prepared by a variety of procedures, some of which are illustrated in the Schemes below. It will be recognized by one of skill in the art that the individual steps in the following schemes may be varied to provide the compounds of Formula (I). The particular order of steps required to produce the compounds of Formula (I) is dependent upon the particular compound being synthesized, the starting compound, and the relative lability of the substituted moieties.

Scheme 1:

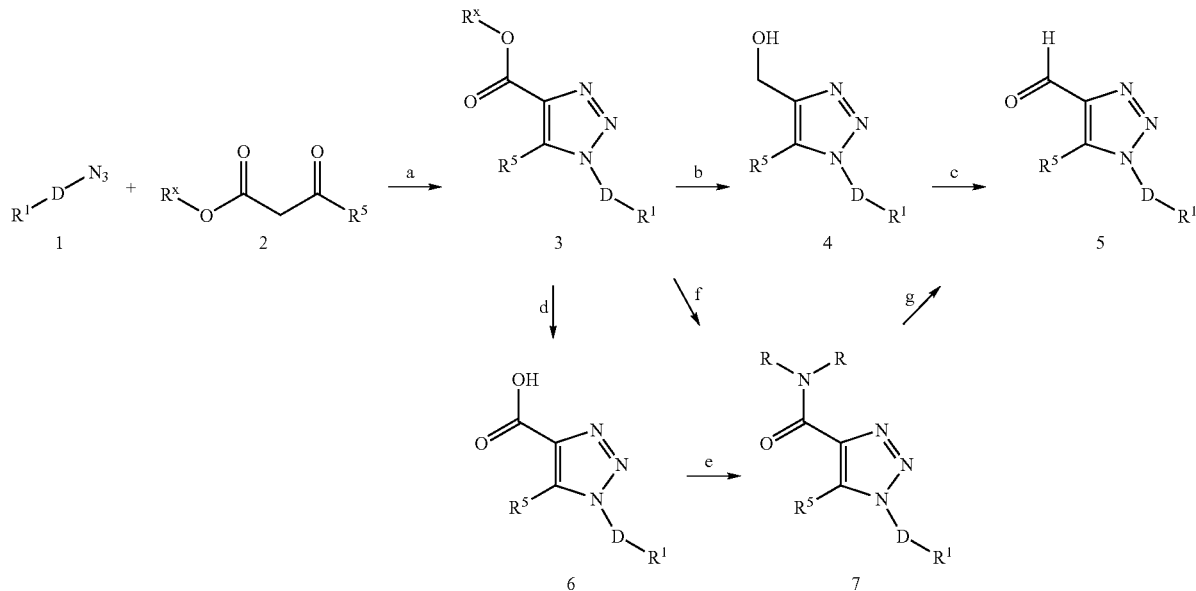

In Scheme 1, the triazole compounds of Formula (3), are formed by reacting a beta keto ester of Formula (2), such as a beta keto $C_1$-$C_6$ alkyl or benzyl ester, with an azide of Formula (1). Such ring formations are well known and appreciated in the art. See Savini et al., *Farmaco* (1994) 49(5): 363-370; Martini et al., *J. Pharm. Sci.* (1988) 77(11): 977-980; Sun et al., *Magn. Reson. Chem.* (1998) 36(6): 459-460; Settimo et al., *Farmaco Ed. Sci.* (1983) 38(10): 725-737; Olesen et al., *J. Heterocycl. Chem.* (1984) 21: 1603-1608; L'abbe et al., *Bull. Soc. Chim. Belg.* (1987) 96(10): 823-824; Julino et al., *J. Chem. Soc. Perkin Trans.* 1 (1998) 10: 1677-1684; Mamedov et al., *Chem. Heterocycl. Compd.(Engl.Transl.)* (1993) 29(5): 607-611; Wender et al., *Tetrahedron Lett.* (1987) 28(49): 6125-6128; Freitas et al., *J. Heterocycl. Chem.* (1995) 32(2): 457-462; Cottrell et al., *J. Heterocycl. Chem.* (1991) 28(2): 301-304. The product of Formula (3) can be isolated and purified by techniques well known in the art, such as precipitation, filtration, extraction, evaporation, trituration, chromatography, and recrystallization.

Azides of Formula (1) are commercially available or can be synthesized from the corresponding halide or sulfonate ester derivatives by reaction with an azide source, such as $NaN_3$, $LiN_3$, or tetrabutyl ammonium azide ($Bu_4NN_3$), with $NaN_3$ being preferred in a suitable solvent mixture as DMSO and water.

Alternatively, the skilled artisan would also appreciate that a malonate derivative may be used in the reaction of step a, instead of a beta keto ester. Both the malonates and the beta keto esters are well known and appreciated in the art. See Benetti, S.; Romagnoli, R.; De Risi, C.; Zanirato, Z "Mastering β-Keto Esters," Chem. Rev. 1995, 95, 1065-1114.

When dialkylmalonates are chosen as the starting reagent, $R^5$ in the resulting product of Formula (3) is a hydroxyl group. The hydroxyl group may be readily converted to the corresponding halide intermediate. This type of transformation is well known and appreciated in the art. See Buckle, D. R.; Rockell, C. J. M. *J. Chem. Soc., Perkin* 1,1982,627-630.

Step b depicts the reduction of 1H-[1,2,3]triazole-4-carboxylic acid ester of Formula (3) to give a 1H-[1,2,3]triazol-4-yl-methanol of Formula (4). Such reduction steps are well known and appreciated in the art. See Larock, R. C., *Comprehensive Organic Transformations*, 2$^{nd}$ Ed., copyright 1999, John Wiley & Sons, pp 1117-1120.

In one variation of step b, the 1H-[1,2,3]triazole-4-carboxylic acid ester of Formula (3) may be reduced by a suitable reducing agent, such as sodium borohydride, lithium aluminumhydride, lithium borohydride, or diisobutyl aluminumhydride, with sodium borohydride being the preferred reducing agent. Such reductions are generally carried out in a solvent, such as MeOH, EtOH, iPrOH, THF, toluene, methylene chloride, or mixtures thereof. The preferred solvent is absolute ethanol. The product can be isolated and purified by techniques described above.

Oxidation of an alkyl-hydroxy group of Formula (4) is well known in the art. A representative example is shown in step c, in which the 1H-[1,2,3]triazol-4-yl-methanol of Formula (4) can be oxidized by reacting it with an appropriate oxidizing agent, such as manganese oxide. Other oxidizing agents include pyridine sulfurtrioxide complex, 1,1,1-triacetoxy-1,1-dihydro-1,2-benziodoxol-3(1H)-one (Dess-Martin reagent), pyridinium chlorochromate, pyridinium dichromate, and catalytic tetrapropylammonium perruthenate (TPAP) with N-methylmorpholine N-oxide (NMO) as a co-oxidant. The aldehydes of Formula (5) can be isolated by techniques described above.

Hydrolysis of the carboxyl esters of Formula (3) to give the corresponding carboxylic acids of Formula (6) is well known reaction. See Larock, R. C., *Comprehensive Organic Transformations*, 2$^{nd}$ Ed., copyright 1999, John Wiley & Sons, pp 1959-1968. For example, an appropriate ester of Formula (3) is dissolved in a suitable solvent, such as methanol or dioxane and water, and treated with a suitable base, such as NaOH or LiOH, to give a compound of Formula (6).

The reaction of step e, in which a carboxylic acid, such as that of Formula (6), is coupled with an appropriate amine, under standard peptide coupling conditions, is well known to the skilled artisan. Specifically, the amine and the carboxylic acid are coupled in the presence of a peptide coupling reagent, optionally in the presence of a catalyst.

Suitable peptide coupling reagents include N,N'-carbonyldiimidazole (CDI), N,N'-dicyclohexylcarbodiimide (DCC), 1-(3-dimethylaminopropyl)-3-ethylcarbodiimide hydrochloride (EDC), and 1-(3-(1-pyrrolidinyl)propyl)-3-ethylcarbodiimide (PEPC). Suitable catalysts for the coupling reaction include N,N-[dimethyl]-4-aminopyridine (DMAP). Such coupling reactions are well known and appreciated in the art. See Larock, R. C., *Comprehensive Organic Transformations*, $2^{nd}$ Ed., copyright 1999, John Wiley & Sons, pp 1941-1949.

Alternatively, a compound of Formula (6) may be converted to an acid chloride derivative, preferably by reaction with oxalyl chloride and DMF, and used to acylate the appropriate amine to give a compound of Formula (7). Such acylation reactions are well known and appreciated in the art. See Larock, R. C., *Comprehensive Organic Transformations*, $2^{nd}$ Ed., copyright 1999, John Wiley & Sons, pp 1929-1930. The product can be isolated and purified by techniques described above.

One skilled in the art could also appreciate the formation of the amides of Formula (7) by a direct conversion of the carboxyl ester of Formula (3) by the use of a trialkylaluminum reagent with an appropriate amine or by use of a magnesium amide to afford compounds of Formula (7). Formula (7) can further undergo a reduction, step g, by treatment of a suitable reducing agent, such as diisobutylaluminum hydride, lithium aluminum hydride or a borane-methyl sulfide complex to afford aldehydes of Formula (5). See Larock, R., *Comprehensive Organic Transformations*, $2^{nd}$ ed. Wiley-VCH: New York, 1999, pp1269-1271.

Scheme 2

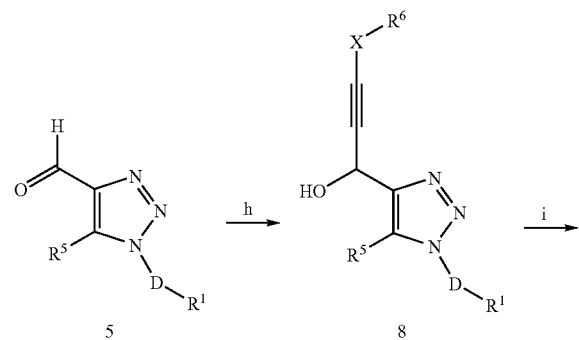

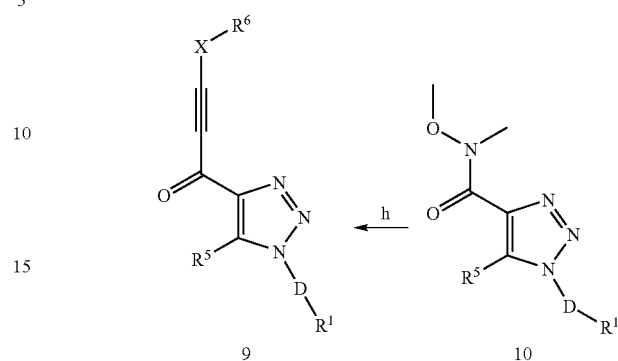

The alkynyl-ketones of Formula (9) can be synthesized from the aldehydes of Formula (5) (see Scheme 1) or the N-methyl-N-methoxyamide derivatives of Formula (10).

Step h depicts the addition of an alkynyl anion to an aldehyde of Formula (5) or a N-methyl-N-methoxyamide of Formula (9). The alkynyl anion is generated by treating the appropriate alkyne with a suitable base, such as methyl lithium, n-butyl lithium, tert-butyl lithium, lithium diisopropylamine, preferably methyl or ethyl magnesium bromide. When the aldehydes of Formula (5) are used, the hydroxy intermediate, Formula (8), can be oxidized to afford the ketone of Formula (9). Such reactions are well known in the art. See Larock, R. C., *Comprehensive Organic Transformations*, $2^{nd}$ ed., Wiley-VCH: New York, 1999, pp 1234-1246. Alternatively, when the N-methyl-N-methoxyamide derivatives of Formula (10) are used compounds of Formula (9) are obtained directly.

Scheme 3

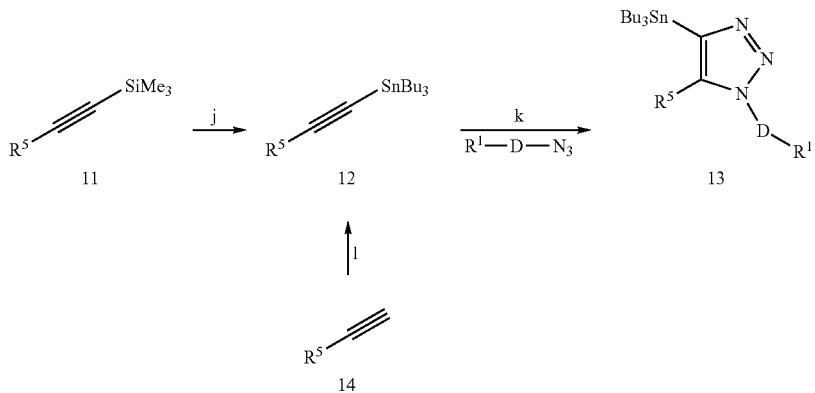

Stannanes of Formula (13) can be made from the reaction of an appropriate azide, Formula (1), with an appropriate stannyl-acetylene of Formula (12). The reactants are combined in a suitable solvent, such as benzene, chloroform, THF, preferably toluene, and heated until the reaction is complete. The compound of Formula (13) is isolated and purified by techniques known in the art and described above.

The stannyl-acetylenes of Formula (12) are readily available from commercial sources or can be prepared from compounds of Formula (11) or (14). A compound of Formula (11) may be dissolved in an appropriate solvent, such as THF, followed by addition of bis(tributyl)tin oxide and an appropriate desilylating agent, such as TBAF (tetrabutyl ammonium fluoride), or potassium trimethylsilanolate. Alternatively, the compound of Formula (12) is made by dissolving an alkyne in an appropriate solvent, such as ether or THF, at −15 to −10° C. To this mixture is added nBuLi, followed by tributyltin chloride. The compound of Formula (12) may be used directly or isolated and purified by techniques described above.

The formation of various stannyl acetylenes of Formula (12) has been described elsewhere. For example, see WO 00/51614; WO 00/01702; WO 98/46228; Lambert et al., *Journal of the Chemical Society, Perkin Transactions* 2 (2001) 6: 964-974; Yamamoto et al., *J. Chem. Soc., Perkin Trans.* 1 (1991) 12: 3253-7; Zhou et al., *J. Chem. Soc., Perkin Trans.* 1 (1991) 11: 2827-30; Warner et al., *J. Org. Chem.* (1994), 59(19): 5822-23; and Jacobi et al., *Journal of the American Chemical Society* (2000), 122(18): 4295-4303.

The silyl-acetylenes of Formula (11) are readily available from commercial sources. Alternatively, the skilled artisan will recognize that compounds of Formula (11) may be prepared by reacting an appropriate aryl halide compound with trimethylsilyl acetylene to give the silyl-alkyne. The reaction proceeds in the presence of copper iodide and a palladium catalyst, such as dichlorobis(triphenyl-phosphine) palladium (II). Other suitable catalysts include $Pd(Ph_3)_4$, $Pd_2dba_3 \cdot CHCl_3$, or $Pd(OAc)_2$.

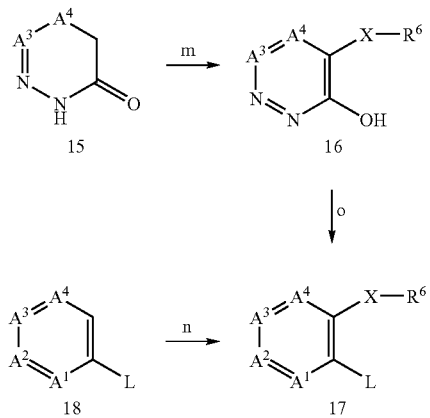

Scheme 4

To make the compound of Formula (17), where L can be a halide, trimethylsilyl (TMS) or trifluoromethanesulfonate (triflate), preferably a bromide, a heteroaryl of Formula (18) is treated with a suitable base, such as LDA (lithium diisopropyl amide) or LiTMP (lithium tetramethylpiperidine), in a suitable solvent, such as ether, or preferably THF, and then reacted with a commercially available aldehyde, step n, to give the substituted heteroaryl of Formula (17), in which X is —CH(OH)—. Compounds of Formula (17) can be isolated and purified by techniques described above.

Alternatively, for compounds of Formula (17) in which $A^2$ and $A^4$ are both nitrogen, the 5-bromopyrimidine of Formula (18) and a commercially available aldehyde are dissolved in a suitable solvent, such as ether, and heated to reflux. A suitable base such as LDA is added to afford the compound of Formula (17), which may be isolated and purified by techniques described above. See reference: Kress, T. J., *J. Org. Chem.*, 1979, 44(13), 2081-2082. One skilled in the art would appreciate the use of an appropriate substituted disulfide compound, of the form $R^6$—X—X—$R^6$, instead of an aldehyde, to also afford compounds of Formula (17), where X is a sulfur.

Compounds of Formula (17) in which X is —CH(OH)— can be oxidized by techniques well known in the art to give a ketone of Formula (17), in which X is —C(O)—. For instance, the alcohol may be dissolved in a suitable solvent, such as toluene or $CH_2Cl_2$, followed by addition of $MnO_2$. The ketone can be isolated and purified by techniques that are well known in the art. It will be generally recognized that other oxidizing conditions can be used to give the compound of Formula (17), in which X is —C(O)—. For example, oxidation can be achieved by use of Dess-Martin periodinane. Other oxidizing conditions are well known in the art. See Larock, R. C., *Comprehensive Organic Transformations*, 2$^{nd}$ ed., Wiley-VCH: New York, 1999, pp 1234-1246.

As shown in step m, ketones of Formula (17) in which $A^1$ and $A^2$ are both nitrogen can alternatively be made by reacting the dihydropyridazinone of Formula (15) with the appropriate aldehyde of Formula (19) in the presence of a suitable base, such as NaOH, or KOH, in a suitable solvent, such as MeOH or EtOH. The preferred combination is KOH in EtOH. The compound of Formula (16), in which X is methylene, is isolated and purified by techniques well known in the art and described above. The methylene can be further oxidized to give a compound of Formula (16) in which X is —C(O)— by treating with a solution of acetic acid and sodium dichromate and heating. The hydroxy pyridazine of Formula (16) is then combined with a brominating agent, such as phosphorous oxybromide to give a compound of Formula (17), which is isolated and purified as described above. See references Kandile, N., *Acta Chimica Hungarica.*, 1990, pg. 829; Ismail, M., *Indian J. Chem.* 1998, pg. 1007; Ismail, M. *Synthetic Communications*, 1998, pg. 3609.

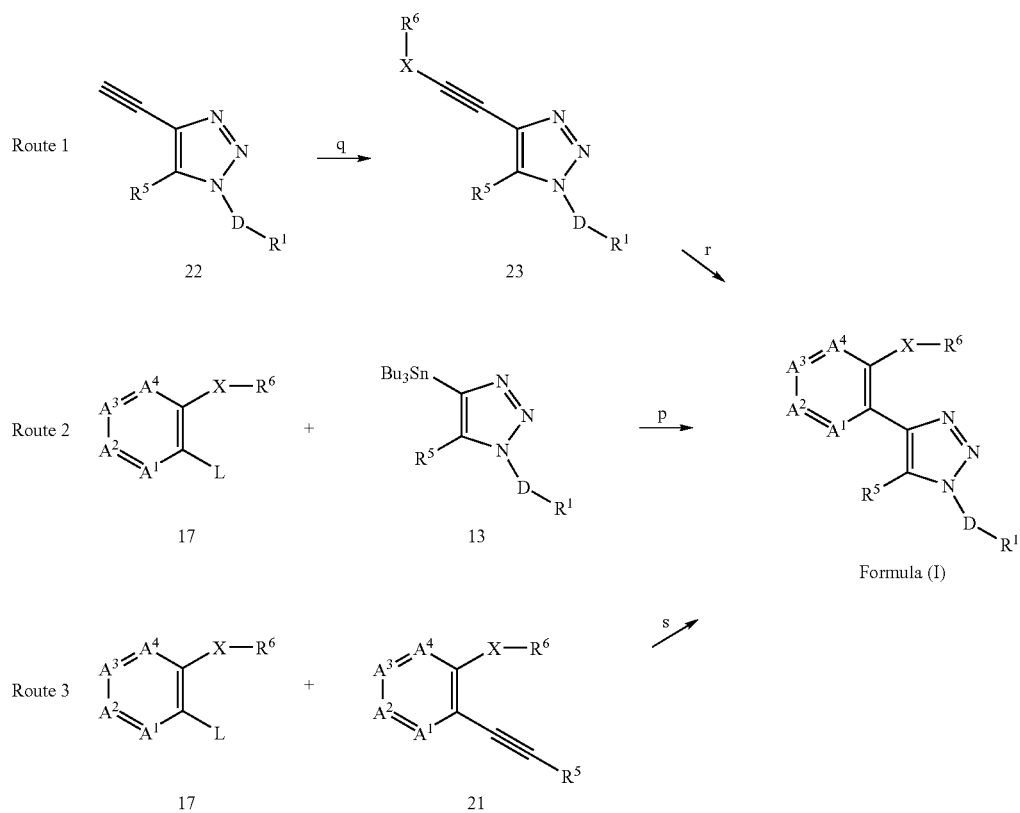

Scheme 5

In Scheme 5, Route 1, compounds of Formula (I) in which each of $A^1$, $A^2$, $A^3$, and $A^4$ is $CR^8$ may be prepared from compounds of Formula (23), wherein X is —C(O)—. The skilled artisan will recognize that conditions for preparation of such aryl groups are well known in the art. For example, a compound of Formula (23) in which X is —C(O)— may be reacted in chlorobenzene with pyrone to give compounds of Formula (24), in which $A^1$, $A^2$, $A^3$, and $A^4$ are each —CH—. The product of Formula (I) is conveniently purified by techniques well known to the skilled artisan, such as silica gel chromatography. Compounds of Formula (22) may be prepared from an aldehyde of Formula (5), which is described in Scheme 1. The aldehyde is reacted with an ester, such as (1-diazo-2-oxo-propyl)-phosphonic acid dimethyl ester, to give an alkyne of Formula (23). The reaction is carried out in an appropriate solvent, such as MeOH or EtOH. The skilled artisan will recognize that a compound of Formula (23) in which X is —CH(OH)— can be made from alkynes of Formula (22) using a reaction similar to that described in Scheme 2 above. Furthermore, a compound of Formula (23), in which X is —CH(OH)—, may be oxidized to give a compound of Formula (23) in which X is —C(O)—, by techniques well known in the art and as described above in Scheme 4.

In Scheme 5, Route 2, step p, a palladium catalyst, such as Pd(PPh$_3$)$_4$, Pd$_2$dba$_3$.CHCl$_3$, Pd(OAc)$_2$, or dichlorobis(triphenylphosphine) palladium is added to a degassed solution of the halide or triflate of Formula (17) and the stannane of Formula (13). The preferred palladium catalyst for the reaction of step p is Pd$_2$dba$_3$.CHCl$_3$. The reaction is carried out in a suitable solvent, such as benzene, toluene, or, preferably, DMF, in a sealed vessel under N$_2$. The product of Formula (24) can be isolated and purified as described above.

Ketone compounds of Formula (I) can be reduced to give compounds wherein X is —CH(OH)— by treatment with lithium aluminum hydride. The product can be isolated and purified by techniques described above. Similar transformations have been described and are known in the art.

Alternatively, the compound of Formula (I) may be made through the intermediate of Formula (21), as shown in Route 3. The bromide of Formula (17) is dissolved in an appropriate solvent, such as benzene or toluene, and an alkyne or alkynyl-stannane is added. The reaction proceeds in the presence of a palladium catalyst, such as Pd(PPh$_3$)$_2$Cl$_2$, Pd$_2$dba$_3$.CHCl$_3$, or tetrakis(triphenyl-phosphine)palladium, alone or in combination with CuI. The product, an alkyne of Formula (21), is further combined with an appropriate azide of Formula (I), the formation of which is described in Scheme 1, in a suitable solvent such as toluene, and heated to afford a compound of Formula (I). Compounds of Formula (I) can be isolated and purified by techniques known in the art and described above.

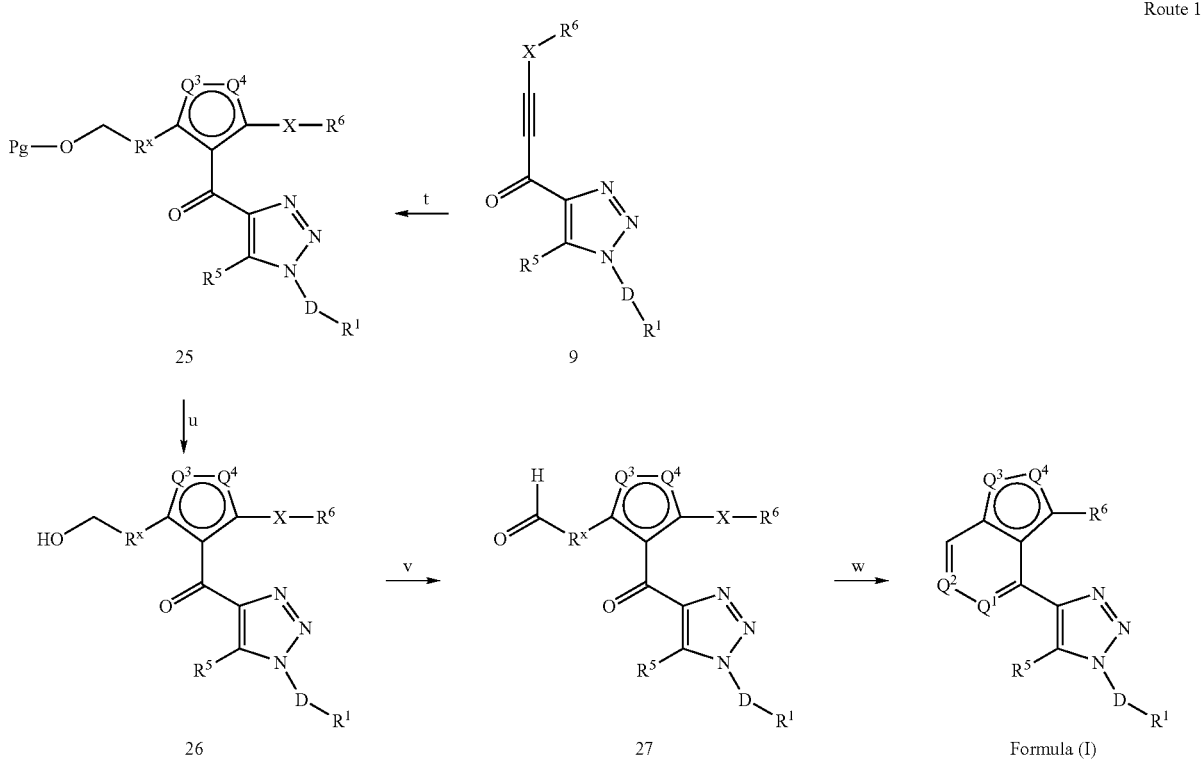

Scheme 6

Compounds of Formula (I) in which R⁴ is a radical of Formula (ID) are prepared as shown in Scheme 6, Route 1. In each of compounds of Formula (9), (25), (26), and (27), X is a bond. Compounds of Formula (25) can be prepared from alkynes of Formula (9) (described in Scheme 2). A skilled artisan would appreciate the cyclization of an alkyne of Formula (9) with a nitrile oxide, generated by combining an appropriately substituted nitroalkane in the presence of an isocyanate and a base, such as triethylamine, or by combining an optionally substituted chloro-oxime in the presence of triethylamine, to afford compounds of Formula (25) in which Q³ and Q⁴ are N and O respectively. For examples of such cyclizations, see Joule, J. A.; Mills, K., *Heterocyclic Chemistry*, 4ᵗʰ ed. Blackwell Science, Inc.:Malden, Mass., 2000, pp 442-448; Hussein, Ahmed Q.; El-Abadelah, Mustafa M.; Sabri, Wail S. Heterocycles from nitrile oxides I; *J. Heterocycl. Chem.* (1983), 20(2), 301-4. The skilled artisan will recognize that compounds of Formula (25), in which Pg is a protecting group such as THP or trimethylsilane, may be deprotected as shown in step u. The protected alcohol is dissolved in a suitable solvent, such as MeOH or EtOH, and treated with an acid, such as p-TsOH.H₂O (para-toluene sulfonic acid) or CSA (camphor sulfonic acid). Alternatively, the alcohol may be liberated by treating with a mixture of THF, water, and acetic acid. The product is isolated and purified as described previously, or can be used without purification. For compounds of Formula (25) or (26) when R⁵ is a halide, such as a chloride, a substitution can be performed with an appropriate nucleophile such as, but not limited to, primary amines, secondary amines, alcohols or thiols to further encompass compounds of Formula (25) or (26). See March, J., *Advanced Organic Chemistry*, copyright 1985, John Wiley and Sons, Inc., pp 255-446.

As shown in step v, alcohol containing compounds of Formula (26) may be oxidized to give compounds of Formula (27) by techniques that are well known to the skilled artisan, as described in Scheme 1, step c. For example, the alcohol may be oxidized by reaction with a combination of DMSO, oxalyl chloride, and triethylamine in CH₂Cl₂. These and other oxidizing conditions are described in Larock, R. C., *Comprehensive Organic Transformations*, 2ⁿᵈ ed., Wiley-VCH: New York, 1999, pp 1234-1246. A skilled artisan could also use an acetal group, instead of the hydroxy group of Formula (26), to produce aldehydes of Formula (27) by treating the acetal containing compound under aqueous acidic conditions.

Compounds of Formula (I) in which both Q¹ and Q² are nitrogen may be prepared from aldehydes of Formula (27), in which Rˣ is a bond, by conditions well known in the art. Specifically, hydrazine is added to an aldehyde of Formula (27) in a suitable solvent, such as acetic acid. Other suitable solvents include MeOH and EtOH. The product of Formula (I) may be isolated and purified by techniques well known in the art, such as flash chromatography.

The skilled artisan will appreciate that when Q¹ is nitrogen and Q² is CR⁸, the compound of Formula (I) may be prepared from the corresponding aldehyde of Formula (27) (wherein Rˣ is a methylene) by treatment with an appropriate source of ammonia, such as ammonium acetate or ammonia, in an appropriate solvent, such as acetic acid methanol or ethanol. The product may be isolated and purified by techniques that are well known in the art.

Route 2

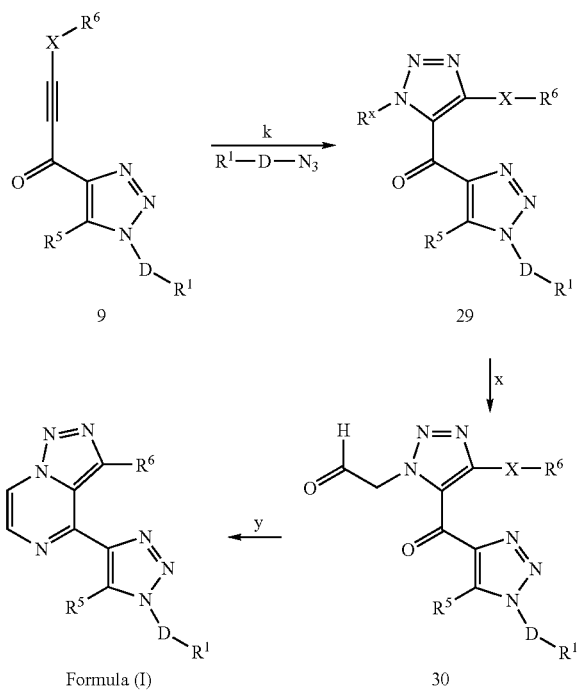

Compounds of Formula (I) in which R⁴ is a bicyclic radical of Formula (IF) may be prepared as shown in Route 2. In each of compounds of Formula (9), (29), and (30), X is a bond. The keto aldehyde of Formula (30) can be prepared from compounds of Formula (29) by a number of reaction conditions well known to the skilled artisan. When $R^x$ is 2,2-dimethoxy-ethyl or 2,2-diethoxy-ethyl, the acetal is dissolved in a mixture of acetone/water, and a suitable acid, such as p-TsOH, CSA, or HCl, is added. Alternatively, as the skilled artisan will recognize, the reaction may be carried out in a pressure vessel in a mixture of acetic acid and water mixture. The product of Formula (30) is isolated and purified by techniques well known in the art, and as described above.

$R^x$ may also be an alcohol protected with a suitable protecting group, such as THP or trimethylsilane. For such compounds of Formula (29), the protected alcohol is de-protected and further oxidized substantially by steps u and v, discussed above in Route 1. Compounds of Formula (29) can be synthesized by a reaction involving compounds of Formula (9) and azides of Formula (I) by the reaction conditions previously described in Scheme 3, step k.

The aldehyde of Formula (30) may be transformed to a compound of Formula (I) in which R⁴ is a radical of Formula (IF), as shown in step y. An appropriate source of ammonia, such as ammonium acetate or ammonia, is added to a solution of the aldehyde of Formula (30) in an appropriate solvent, such as acetic acid. Other suitable solvents are well known in the art and include anhydrous MeOH, EtOH, or THF. The compound of Formula (I) may be isolated and purified by techniques well known in the art.

Scheme 7

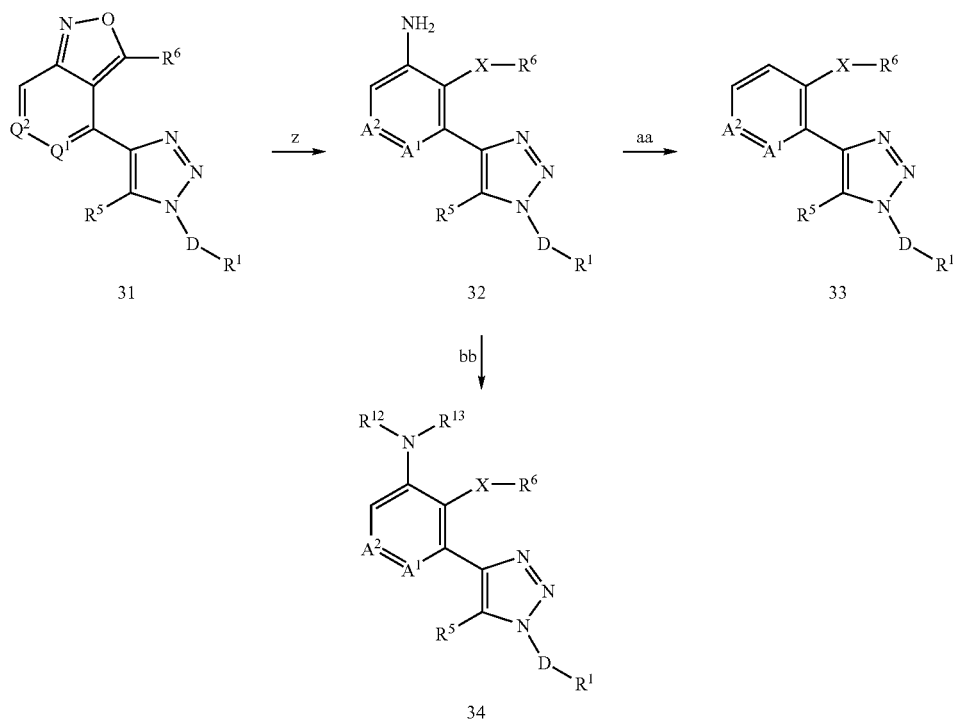

Scheme 7 demonstrates that compounds of Formula (I), as depicted by the compounds of Formula (31)-(34), can be farther transformed to encompass the invention. The skilled artisan will recognize that bicyclic compounds of Formula (32) may undergo an N—O bond cleavage to give compounds of Formula (31) in which $R^4$ is a radical of Formula (IA) and in which $A^3$ is —CH— and $A^4$ is $CR^8$—, wherein $R^8$ is $NH_2$. Such a reaction is depicted in Scheme 7, step z. Specifically, the bicyclic isoxazole is dissolved in a suitable solvent, such as acetonitrile. To the reaction, is added molybdenum hexacarbonyl and water. The skilled artisan will recognize that the solution may be heated for the reaction to proceed. The product of Formula (32) is purified by techniques well known in the art, such as silica gel chromatography or recrystallization. Such reactions have been described in the art. See Nitta et al., *J. Chem. Soc., Chem. Commun.* (1982) 877. Alternatively, the N—O bond cleavage may be carried out using $H_2$/Pt—C in a pressure sealed vessel.

As shown in step aa, the amino-substituted compound of Formula (32) may undergo deamination to give a compound in which $A^3$ and $A^4$ are both —CH—. The amine is dissolved in a suitable solvent, such as THF, and a nitrite compound, such as isoamylnitrite or tert-butylnitrite, is added to the solution. The reaction product is concentrated and purified by techniques well known in the art.

Alternatively, the amine of Formula (32) may be further substituted, as shown in step bb. The amine is dissolved in pyridine and an acylating agent, such as acetic anhydride or acetyl chloride is added. Other suitable co-solvents include $CH_2Cl_2$, THF, and ether. The reaction product can be isolated and purified by techniques well known to the skilled artisan, including silica gel chromatography. The reaction is well known in the art, as described in Greene et al., *Protective Groups in Organic Synthesis*, New York: John Wiley and Sons (1981) 251-253.

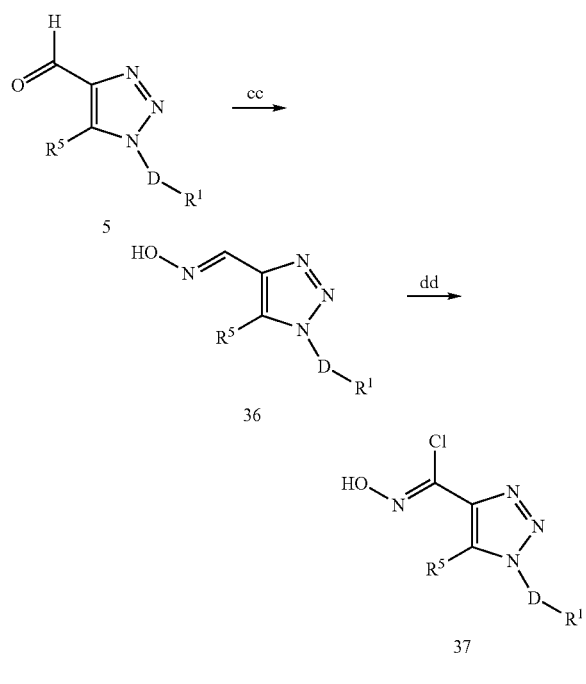

Scheme 8

In scheme 8, aldehydes of Formula (5) (described in Scheme 1) may be treated with hydroxylamine hydrochloride and a carboxylate salt such as sodium acetate in a convenient solvent such as methanol to provide compounds of Formula (36). Such reactions are well known in the art. See Bousquet, E. W.; *Org Syn* 1943, II, 313.

Compounds of Formula (36) may be treated with a chlorinating agent such as N-chlorosuccinimide in a suitable solvent such as dimethylformamide to provide hydroxyimidoyl chlorides of Formula (37). This reaction is also well known in the art. see Torssell, K. B. G. *Nitriles Oxides, Nitrones and Nitronates in Organic Synthesis*; VCH: Weinheim, 1998. Compounds of Formula (37) are useful in the preparation of Compounds of Formula (I) in which $R^4$ is a radical of Formula (IB), as discussed below in Scheme 10.

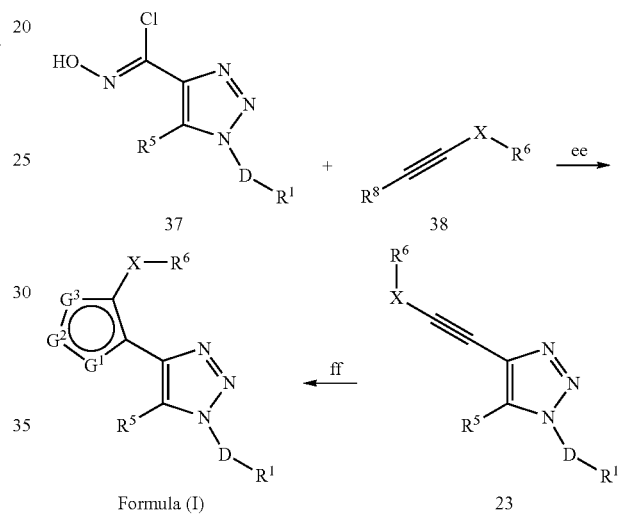

Scheme 10

In scheme 10, compounds of Formula (I) may be treated with a nitroalkyl or substituted nitroalkyl compound, and an isocyanate, such as 1,4-phenyl-diisocyanate, in the presence of a suitable base such as triethylamine. The reaction is conveniently carried out in a suitable solvent such as toluene or benzene to obtain compounds of Formula (I) in which -$G^1$-$G^2$-$G^3$- is either —O—N—$CR^8$—, or —$CR^8$—N—O—. For compounds of Formula (I), in which R5 is a halide, such as chloride, it is also recognized that one can perform a nucleophilic displacement as described in Scheme 6, to further encompass the invention for the radicals represented by $R^5$.

When compounds of Formula (I) contain a hydroxy protecting group, the protecting group may be cleaved by subsequent treatment of the reaction product with a suitable acid such as para-toluene sulfonic acid, CSA, or HCl, in a solvent such as methanol, ethanol, or THF. The products maybe purified by techniques known to the skilled artisan, such as column chromatography.

Nitroalkanes and substituted nitroalkanes are well known in the art. Such compounds are commercially available or can be readily prepared by reaction of nitromethane with a carbonyl compound, or alternatively, by displacement of a halide using silver nitrite or sodium nitrite. See Simoni, D. et al., Tetrahedron Lett., 1997, 38 (15) 2749-2752; Simoni, D., et al., Tetrahedron Lett., 2000,41 (10), 1607-1610; Dauben, H. J. Jr., Org Synth., 1963, IV, 221.

Compounds in which -G$^1$-G$^2$-G$^3$- is —CH—N—NH— may be prepared by treating compounds of Formula (23) with a diazomethane agent such as trimethylsilyldiazomethane in a suitable solvent such as toluene. The reaction is conveniently carried out in a sealed reaction pressure vessel to allow for heating. The pyrazole product can be concentrated and purified by techniques well known in the art.

A mixture of tautomeric forms of a compound of Formula (I) in which -G$^1$-G$^2$-G$^3$- is —N—N—NH— and —NH—N—N— are prepared by combining compounds of Formula (23) with trimethylsilylazide in a suitable solvent such as toluene. The reaction is conveniently carried out in a sealed reaction pressure vessel to allow for heating. The mixture may be purified by purification techniques known to the skilled artisan, such as column chromatography.

Alternatively, compounds of Formula I, in which -G$^1$-G$^2$-G$^3$- is —N—O—CR$^8$— may be prepared by treating compounds of Formula (37) with alkynes of Formula (38), step ee. The reaction is conveniently carried out in the presence of a base such as triethylamine in a suitable solvent such as ethyl acetate or ether. See Hussein, A., et al., *J. Heterocycl. Chem.* (1983), 20(2), 301-4.

Compounds of Formula (38) may be prepared from conditions recognized by the skilled artisan, such as the addition of an appropriate alkynyl anion to a N-methyl-N-methoxyamide derivative or to the appropriate aldehyde followed by an oxidation of the intermediate alcohol. See for example the procedures outlined in Suzuki, K. et al. *J. Org. Chem.*, 1987, 52, 2929. Conditions for this reaction have been described previously.

Compounds of Formula (I) in which X is —C(O)— can be reduced to give compounds in which X is a —CH(OH)— or a methylene moiety. This reduction can be accomplished by reaction of the ketone with a hydride source such as lithium aluminum hydride, in a suitable solvent such as THF, to give the alcohol. The alcohol can be further reduced by treatment with triethylsilane and an acid such as acetic acid or trifluoroacetic acid. A suitable solvent such as methylene chloride is used. The products of these reactions can be isolated and purified using techniques well know in the art. For other reduction methods, see Larock, R. C., Comprehensive Organic Transformations, 2$^{nd}$ ed., Wiley-VCH: New York, 1999, pp 44-46).

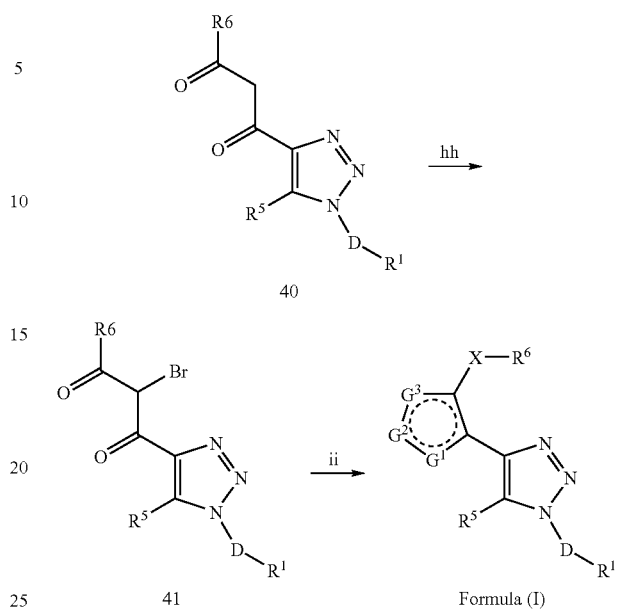

Compounds of Formula (I) in which -G$^1$-G$^2$-G$^3$- is —N—CR$^5$—S— may be prepared from a compound of Formula 10, which is described in Scheme 2.

Specifically, a compound of Formula (10) maybe treated with an enolate prepared from a ketone such as 1-(2-chlorophenyl)ethanone and a base such as lithium diisopropylamide in a suitable solvent such as tetrahydrofuran to provide a compound of Formula (40). A compound of Formula (40) may be treated with a halogenating agent such bromine in a suitable solvent such as a mixture of methylene chloride and water to provide a compound of Formula (41) A c h of Formula (I) may be prepared by treating a compound of Formula (41) with a suitable condensing agent such as thioamide or thiourea in the presence of a dehydrating agent such as molecular sieves. Convenient solvents include ethanol, acetone, MeOH, CH$_2$Cl$_2$, THF, or ether.

A compound of Formula (I) in which R$^8$ is —NH$_2$ may be deaminated, as described above (See Scheme 7). Furthermore, the —X— linker of Formula (I) may undergo reduction as previously described.

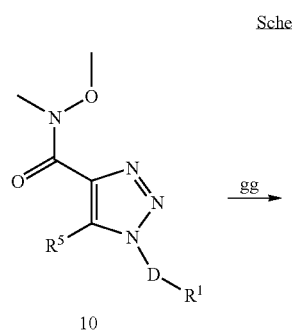

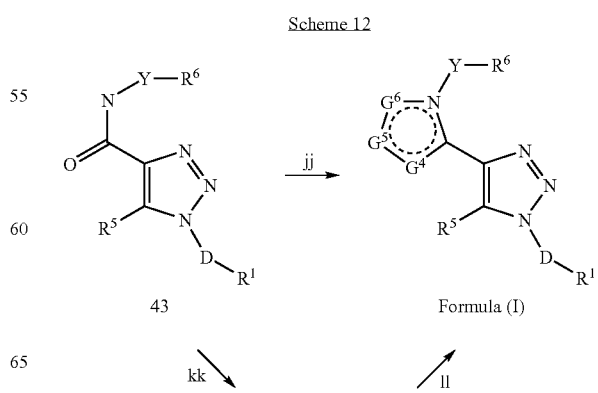

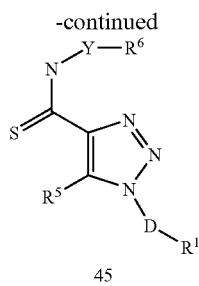

45

Compounds of Formula (I) in which -G$^4$-G$^5$-G$^6$- is —N—N—N— may be prepared by treating compounds of Formula (43) with phosphorus pentachloride in a suitable solvent such as methylene chloride. After complete removal of the solvent, the resulting residue is treated with an azide agent such as sodium azide in a suitable solvent such as dimethylformamide. Transformations of the type depicted in Scheme 12 are well known in the art. For example, see Butler, R. N. *Advances in Heterocyclic Chemistry*; Katritzky, A. R.; Boulton A. J., Eds.; Academic: New York, 1977; Vol 21, p. 378, Thomas, E.; *Synthesis*, 1993, 767 and references therein.

Compounds of Formula (I) in which -G$^4$-G$^5$-G$^6$- is —N—N—CR$^8$— may also be prepared from a compound of Formula (43). More specifically, compounds of Formula (43) are treated with phosphorous pentachloride followed by the appropriate hydrazide in a suitable solvent such as dichloroethane or toluene. Ried, W., Peters, B.; *Liebigs Ann. Chem.*, 1969, p. 124. Phosphorous oxychloride may be used in place of phosphorous pentachloride (see Amer, A. et al. *J. Heterocyclic Chem.*, 1994, p. 549).

Alternatively, compounds of Formula (I) in which -G$^4$-G$^5$-G$^6$- is —N—N—CR$^8$— may be prepared from compounds of Formula (45), which in turn may be prepared from compounds of Formula (43). More specifically, compounds of Formula (43) may be treated with a thiolating agent such as Lawesson's reagent [2,4-bis(4-methoxyphenyl)-1,3-dithia-2,4-diphosphetane-2,4-disulfide] in a suitable solvent such as toluene to provide compounds of Formula (45). Tanaka, H., Nakao, T.; *J. Heterocyclic Chem.*, 1997, 34, p. 921. The skilled artisan will recognize that Lawesson's reagent can be replaced with other thiolating agents such as phosphorous pentasulfide (Schwartz, G.; *Org. Synth.*, 1955, III, p. 322).

Compounds of Formula (45) may be treated with hydrazine and an acylating agent such as an acyl halide, anhydride, or an orthoester in a suitable solvent such as pyridine. Subsequent treatment with an acid such as para-toluene sulfonic acid provides compounds of Formula (I). Nagaoka, H., Mase, T.; *Heterocycles*, 1990, 31 p. 1241 and Santus, M.; *Liebigs Ann;. Chem.*, 1988, p. 179.

Scheme 13

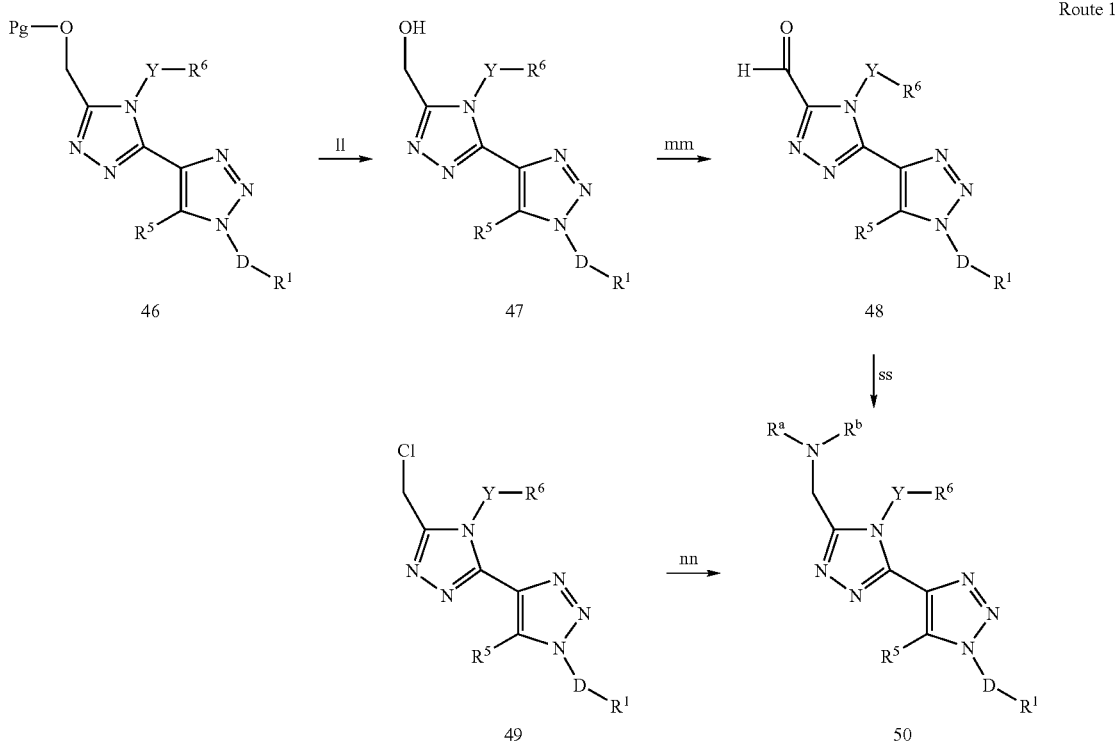

Scheme 13 depicts further transformations of the R$^8$ substituent on 1,2,4-triazoles in which R$^8$ is a substituted alkyl. The skilled artisan will recognize that similar transformations can be carried out for any R$^8$ substituent on radicals of Formula (IA), (IB), or (IC).

Compounds of Formula (47), which are encompassed in Formula (I), can be prepared by the deprotection of the protected primary alcohol of Formula (46). A protecting group such as TIPS can be utilized. Such alcohol protections and deprotections are readily accomplished by methods well known in the art. (Protecting Groups in Organic Synthesis, Theodora Greene (Wiley-Interscience)).

Compounds of Formula (48), which are encompassed in Formula (I), can be prepared by the oxidation of the appropriate alcohol compounds of Formula (47). Oxidation conditions may include the use of sulfur trioxide pyridine complex with the addition of a base such as triethylamine. The reaction is carried out in an appropriate solvent such as dimethylsulfoxide. Other oxidizing conditions can be found in a leading reference such as Larock, R. C., Comprehensive Organic Transformations, $2^{nd}$ ed., Wiley-VCH: New York, 1999, pp 1234-1246.

Compounds of Formula (50), which are encompassed in Formula (I), can also be prepared by the reductive amination of aldehydes of Formula (48) with an appropriate amine. Suitable reducing agents may include are triacetylsodium borohydride, sodium cyanobohydride and sodium borohydride. Appropriate solvents may include methanol, 1,2-dichloroethane or ethanol. Reductive amination reactions are well appreciated in the art. A leading reference is Larock, R. C., Comprehensive Organic Transformations, $2^{nd}$ ed., Wiley-VCH: New York, 1999, pp 835-846. The product of the reaction can be isolated and purified using techniques well know in the art.

Compounds of Formula (50) can be prepared from a halogen displacement by the amine. The halogen displacement can be accomplished by reacting the chloromethylene derivative and an appropriate amine. The product of the reaction can be isolated and purified using techniques well know in the art. These techniques include extraction, evaporation, chromatography, and recrystallization.

Route 2

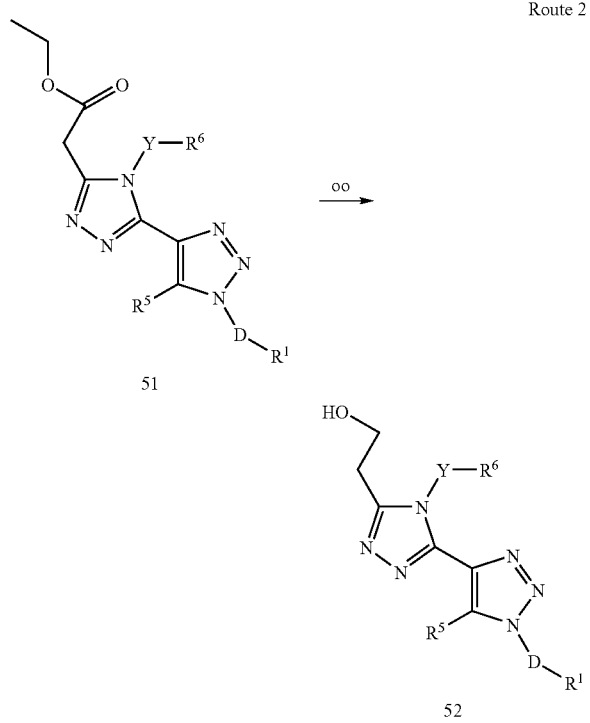

In Route 2, compounds of Formula (52), which are encompassed in Formula (I), can be synthesized by the reduction of the appropriate ester to the alcohol. The ester is dissolved in tetrahydrofuran or another appropriate solvent such as ethanol or methanol and a reducing agent such as lithium borohydride, sodium borohydride, or lithium aluminum hydride is added. The product of the reaction can be isolated and purified using techniques well know in the art. Other reducing conditions can be found in a leading reference such as Larock, R. C., Comprehensive Organic Transformations, $2^{nd}$ ed., Wiley-VCH: New York, 1999.

Scheme 14

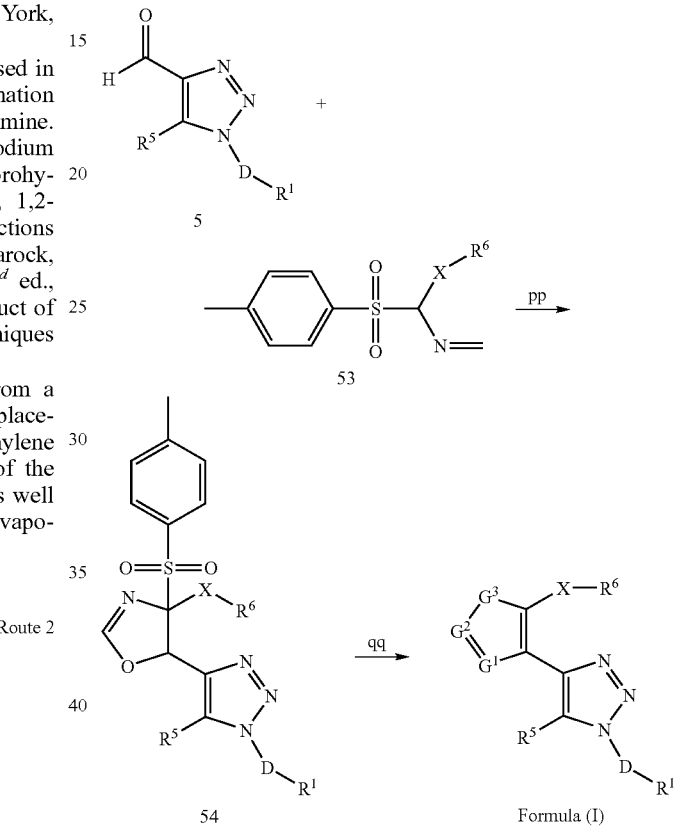

One skilled in the art would also appreciate the formation of the compounds of Formula (I) in which -$G^1$-$G^2$-$G^3$- is —N—$CR^8$—NH—. A representative example of this formation is shown in Scheme 13. Step pp depicts the condensation of the aldehydes of Formula (5) with a methylene-(toluene-4-sulfonylmethyl)-amine intermediate of Formula (53) in the presence of sodium cyanide in a suitable solvent such as N,N-dimethylformamide or ethanol. The corresponding 4-(toluene-4-sulfonyl)-4,5-dihydro-oxazole intermediate, Formula (54), can be transformed to the imidazole compounds of Formula (I), by heating with a mixture of an ammonia alcohol solution in a high boiling solvent such as xylenes, chlorobenzene or toluene. The transformation to the imidazole is well known and appreciated in the art. See Buchi, G. Heterocycles, 1994, pg. 139; Van Leusen, A. M. Tetrahedron Lett. 1972, pg. 2369. The appropriate methylene-(toluene-4-sulfonylmethyl)-amine intermediate of Formula (53) can be synthesized by an alkylation reaction of the tosylmethyl isocyanide with the appropriate alkyl halide and base, such as potassium hydride or sodium hydride.

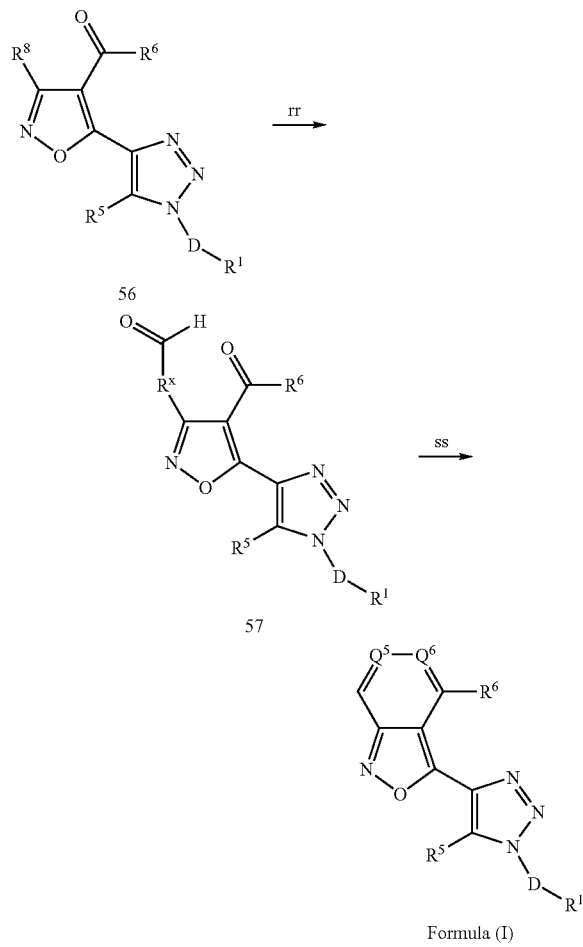

Scheme 15 dimethoxy-acetal is reacted under aqueous acidic conditions to give a compound of Formula (57) in which $R^8$ is an aldehyde or an acetaldehyde. Compounds of Formula (I) can be synthesized by reacting the appropriate aldehyde-containing compound of Formula (57) with ammonium acetate or hydrazine under acidic conditions such acetic acid. When $R^x$ is a methylene group, ammonium acetate is the reactant, to provide compounds of Formula (I) in which $Q^5$ is —$CR^8$— and $Q^6$ is nitrogen are achieved or with hydrazine as the reactant, when $R^x$ is a bond, compounds of Formula (I) in which $Q^5$ and $Q^6$ are nitrogen are achieved.

Compounds of Formula (56), which are encompassed in Formula (I), in which $R^8$ is hydroxy methyl or hydroxy ethyl, can be prepared by deprotection of the protected alcohol, have been described previously. Such deprotections are readily accomplished by methods well known in the art. (Protecting Groups in Organic Synthesis, Theodora Greene (Wiley-Interscience)).

The skilled artisan will recognize that the resulting hydroxyl group of R8 can be oxidized to give compounds of Formula (57), which are encompassed in Formula (I), where $R^x$ is a bond or a methylene group, and in which $R^8$ is an oxo-substituted alkyl. The alcohol can be oxidized by many different oxidizing reagents such as under Dess-Martin periodinane oxidizing conditions or using combination of DMSO and triethylamine with oxalyl chloride. Such oxidations are readily accomplished by methods well known in the art. (Larock, R. C., Comprehensive Organic Transformations, $2^{nd}$ ed., Wiley-VCH: New York, 1999, pp 1234-1246). The product of the reaction can be isolated and purified using techniques well know in the art.

Compounds of Formula (57) in which $R^8$ is an oxo-substituted alkyl group can also be made by deprotection of the appropriate acetal. Such deprotections are readily accomplished by methods well known in the art. (Protecting Groups in Organic Synthesis, Theodora Greene (Wiley-Interscience)). For example, a compound in which $R^8$ is Route 1 of Scheme 16 depicts the formation of compounds of Formula (63), which are encompassed in Formula (I), by the reaction of a diamine of the Formula (60) and esters of the Formula (3). It is understood that this reaction can occur when $R^x$ is either a bond or methylene, to give compounds of Formula (I) in which $R^4$ is a radical of Formula (IG) or (IH), respectively. The reaction can be carried out in the presence of an appropriate solvent such as toluene or benzene. A solution of the diamine in toluene is treated with trimethylaluminum and then the appropriate ester is added as a solution in the appropriate solvent such as toluene or benzene. The reaction is heated until the reaction is complete. The product of the reaction can be isolated and purified using techniques well know in the art. These techniques include extraction, evaporation, chromatography, and recrystallization. The compounds of Formula (60) can be prepared by reductive amination reactions, generally by combining a N-protected-amino-aldehyde with an appropriate amine, or alternatively, one skilled in the art could combine a mono-protected diamine with an appropriate aldehyde, and a suitable reducing agent such as triacetoxysodium borohydride, sodium cyanobohydride or sodium borohydride. Appropriate solvents may include methanol, 1,2-dichloroethane or ethanol. A leading reference that can be consulted for reaction conditions is Larock, R.

C., Comprehensive Organic Transformations, 2nd ed., Wiley-VCH: New York, 1999, pp 835-846. This may be followed by deprotection of the protecting groups.

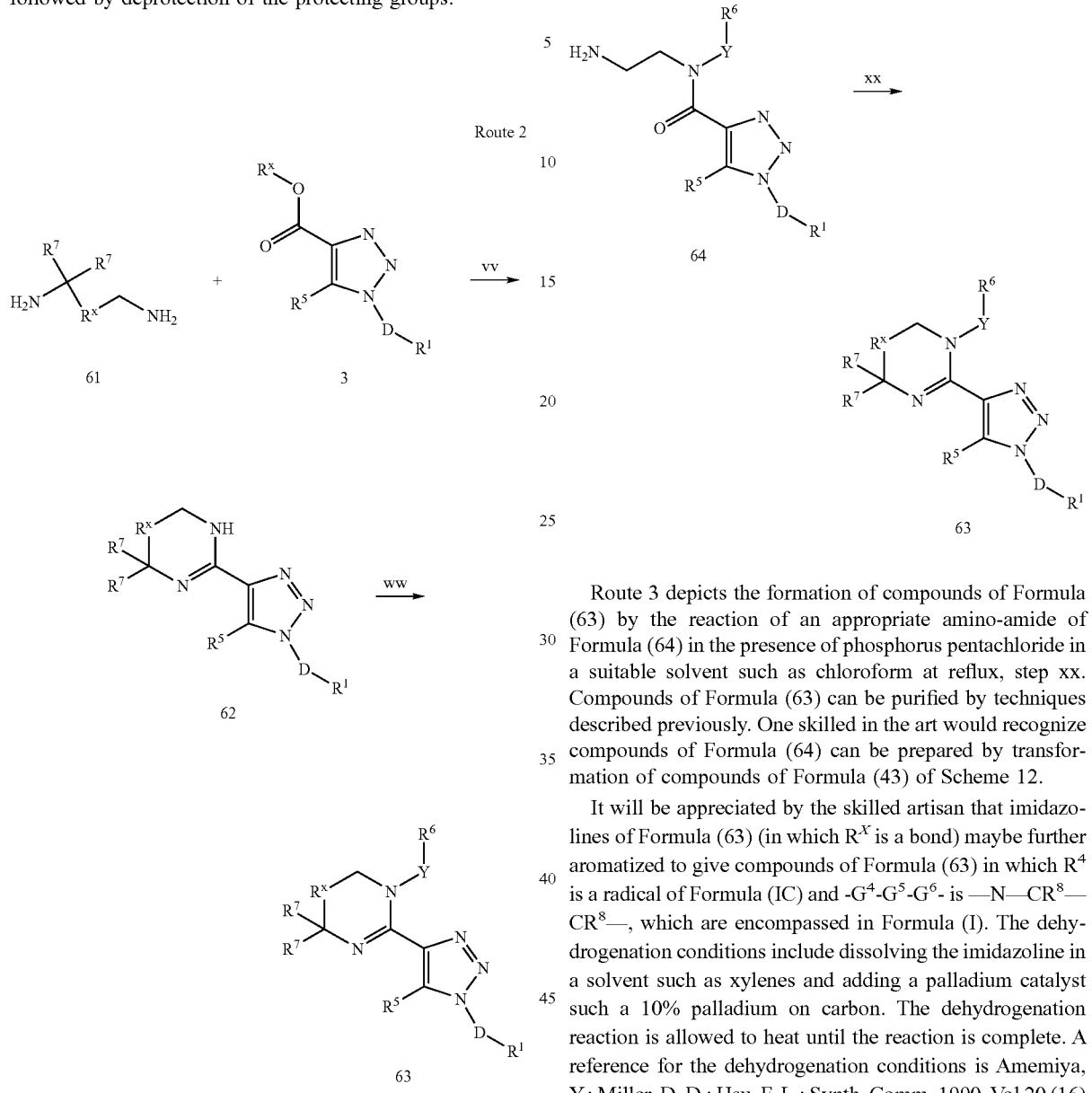

Alternatively, Route 2 shows compounds of Formula (63), which are encompassed in Formula (I), can be prepared by the alkylation of compounds of Formula (62). Alkylations of this type are well known in the literature. An appropriate solvent for such reactions is dimethylformamide. A suitable non-nucleophilic base may include potassium carbonate. Sodium iodide is added in a catalytic amount.

Compounds of Formula (62) are conveniently prepared by the reaction of the esters of Formula (3) and commercially available diamines in the presence of trimethylaluminum. Products can be purified by techniques previously described.

Route 3 depicts the formation of compounds of Formula (63) by the reaction of an appropriate amino-amide of Formula (64) in the presence of phosphorus pentachloride in a suitable solvent such as chloroform at reflux, step xx. Compounds of Formula (63) can be purified by techniques described previously. One skilled in the art would recognize compounds of Formula (64) can be prepared by transformation of compounds of Formula (43) of Scheme 12.

It will be appreciated by the skilled artisan that imidazolines of Formula (63) (in which $R^X$ is a bond) maybe further aromatized to give compounds of Formula (63) in which $R^4$ is a radical of Formula (IC) and -$G^4$-$G^5$-$G^6$- is —N—$CR^8$—$CR^8$—, which are encompassed in Formula (I). The dehydrogenation conditions include dissolving the imidazoline in a solvent such as xylenes and adding a palladium catalyst such a 10% palladium on carbon. The dehydrogenation reaction is allowed to heat until the reaction is complete. A reference for the dehydrogenation conditions is Amemiya, Y.; Miller, D. D.; Hsu, F. L.; Synth. Comm. 1990, Vol 20 (16) 2483-2489. The product of the reaction can be isolated and purified using techniques well know in the art. These techniques include extraction, evaporation, chromatography, and recrystallization.

General Preparation A

Combine the appropriate commercially available halide (1 eq) and sodium azide (3 eq)in DMSO/water (10:1, ca. 10 mL/g $NaN_3$). Stir for 2-12 hours at RT, then add water and extract with ether. Wash the organic layer with water (2×) and brine. Dry ($Na_2SO_4$), filter and concentrate to dryness to give the desired compound. May be used without further purification. By a method similar to General Preparation A, the following compounds can be prepared and isolated:

| Prep. # | Product | Physical Data |
|---|---|---|
| 1 | 1-azidomethyl-3-trifluoromethoxy-benzene | TLC $R_f$=0.70(20% EtOAc/hexanes) |
| 2 | 2-azidomethyl-1,4-bis-trifluoromethyl-benzene | TLC $R_f$=0.90(20% EtOAc/hexanes) |
| 3 | 1-azidomethyl-3-fluoro-5-trifluoromethylbenzene | TLC $R_f$=0.78(20% EtOAc/hexanes) |
| 4 | 1-azidomethyl-5-fluoro-2-trifluoromethylbenzene | TLC $R_f$=0.76(20% EtOAc/hexanes) |
| 5 | 1-azidomethyl-2-fluoro-5-trifluoromethylbenzene | TLC $R_f$=0.78(20% EtOAc/hexanes) |
| 6 | 1-azidomethyl-3-trifluoromethyl-benzene | TLC $R_f$=0.70(20% EtOAc/hexanes) |
| 7 | 4-azidomethyl-1-fluoro-2-trifluoromethylbenzene | TLC $R_f$=0.89(20% EtOAc/hexanes) |
| 8 | 1-azidomethyl-2,5-difluorobenzene | TLC $R_f$=0.83(20% EtOAc/hexanes) |
| 9 | 1-azidomethyl-2,4-difluorobenzene | TLC $R_f$=0.78(20% EtOAc/hexanes) |
| 10 | 1-azidomethyl-3,4-difluorobenzene | TLC $R_f$=0.50(20% EtOAc/hexanes) |
| 11 | 1-azidomethyl-2,6-difluorobenzene | TLC $R_f$=0.71(20% EtOAc/hexanes) |
| 12 | 1-azidomethyl-3,5-difluorobenzene | TLC $R_f$=0.66(20% EtOAc/hexanes) |
| 13 | 1-azidomethyl-4-trifluoromethyl-benzene | TLC $R_f$=0.61(20% EtOAc/hexanes) |
| 14 | 1-azidomethyl-2-chloro-4-fluoro-benzene | $^1$H NMR(400MHz, CDCl$_3$): 4.46(s, 2H); 7.01(t, 1H, J=7.8Hz); 7.18(d, 1H, J=8.8Hz); 7.38(t, 1H, J=7.8Hz). |
| 15 | 1-azidomethyl-3,5-dichlorobenzene | TLC $R_f$=0.57(20:1 hex/EtOAc) $^1$H NMR(CDCl$_3$, 250MHz) δ 7.36(m, 1H), 7.25(s, 2H), 4.36(s, 2H). |
| 16 | 1-azidomethyl-3,5-dimethylbenzene | TLC $R_f$=0.68(20:1 hex/EtOAc) $^1$H NMR(CDCl$_3$, 250MHz) δ 7.03(s, 1H), 6.96(s, 2H), 4.30(s, 2H), 2.37(s, 6H). |
| 17 | 1-azidomethyl-3,5-bis-trifluoromethyl-benzene | TLC $R_f$=0.42(20:1 hex/EtOAc) $^1$H NMR(CDCl$_3$, 250MHz) δ 7.95(s, 1H), 7.82(s, 2H), 4.58(s, 2H); IR: 2105cm$^{-1}$ |
| 18 | 2-Azidomethyl-[1,3]dioxolane | $^1$H NMR(CDCl$_3$): δ 5.12(t, J=3.5Hz, 1H), 4.02(m, 4H), 3.36(d, J=3.5Hz, 2H). |
| 19 | 2-Azido-1,1-dimethoxy-ethane | $^1$H NMR(CDCl$_3$): δ 4.57(t, J=5.8Hz, 1H), 3.42(s, 6H), 3.39(d, J=5.5Hz, 2H). |

Preparation 20

(2-Bromo-pyridin-3-yl)-(2-chlorophenyl)-methanol

Add LDA (400 mL, 0.8 mol) to 2-bromopyridine (105 g, 0.667 mol) in THF (3.2 L) at −78° C. and stir. After 2 hours, add 2-chlorobenzaldehyde (103 g, 0.733 mol) in THF (300 mL) and allow the reaction mixture to gradually warm to ambient temperature. Treat the reaction mixture with 1 M HCl (1.7 L) and extract with diethyl ether. Combine the organic layers and wash with water and brine. Dry over sodium sulfate, filter, and concentrate under reduced pressure. Purification by flash chromatography, eluting with hexane:ethyl acetate (10:1 to 1:1) gives the title compound: $^1$H NMR (300 MHz, CDCl$_3$), δ8.28(dd, 1H, J=1.83, 4.73), 7.67 (dd, 1H, J=1.83, 7.63), 7.48-7.19 (m, 5H), 6.41 (s, 1H), 3.10 (bs, 1H); MS (IS) m/z 298.0 (M+1), 300.0 (M+1); Analysis for C$_{12}$H$_9$BrClNO: calcd: C, 48.27; H, 3.04; N, 4.69; found: C, 49.06; H, 3.18; N, 4.64. $R_f$=0.29 heptane:ethyl acetate, 2:1).

By a method analogous to Preparation 20, using the appropriate starting materials, the following compounds may be prepared and isolated.

| Prep. | Product | Physical Data |
|---|---|---|
| 21 | (2-Bromo-pyridin-3-yl)-phenyl-methanol | MS(IS) 264.1(M+1); TLC(25% ether in hexanes): Rf=0.1. |
| 22 | (2-Bromo-pyridin-3-yl)-o-tolyl-methanol | MS(IS) 278.0(M+1); TLC(33% ether in hexanes): Rf=0.1. |
| 23 | (2-Bromo-pyridin-3-yl)-(2-methoxy-phenyl)-methanol | MS(IS) 294.0(M+1); TLC(33% ether in hexanes): Rf=0.1. |
| 24 | (2-Bromo-pyridin-3-yl)-(2-trifluoromethyl-phenyl)-methanol | MS(IS) 332.0(M+1); TLC(33% ether in hexanes): Rf=0.1. |
| 25 | (2-Bromo-pyridin-3-yl)-(2-fluoro-phenyl)-methanol | MS(IS) 281.9(M+1); TLC(33% ether in hexanes): Rf=0.1. |
| 26 | (2-Bromo-pyridin-3-yl)-(3-chloro-phenyl)-methanol | MS(IS) 300.0(M+1); TLC(25% ether in hexanes): Rf=0.1. |
| 27 | (2-Bromo-pyridin-3-yl)-(4-chloro-phenyl)-methanol | MS(IS) 300.0(M+1); TLC(25% ether in hexanes): Rf=0.1. |
| 28 | (2-chloro-phenyl)-(3-iodo-pyrazin-2-yl)-methanol | MS(IS) 330(M$^+$+1-H$_2$O) TLC(35% EtOAc/hexanes) $R_f$=0.29. |

Preparation 29

(3-bromo-pyridin-4-yl)-(2-chloro-phenyl)-methanol

Add n-BuLi (48.2 mL, 77.1 mmol, 1.6N in hexane) to a −70° C. solution of diisopropylamine (10.8 mL, 77.1 mmol) in THF (130 mL) in a flame-dried flask. After 30 minutes add 3-bromo-pyridine (2.48 mL, 25.7 mmol) dropwise and stir the mixture at −70° C. After 4 hours, add 2-chloro-benzaldehyde (2.95 mL, 26.2 mmol) dropwise, stir at −70° C. After 1 hour, warm reaction to RT, quench reaction with dropwise addition of 60 mL saturated $NH_4Cl$ solution. Extract with $Et_2O$ (3×), wash with brine, dry the combined organic layers over $MgSO_4$ and concentrate. Purify the residue by flash chromatography on silica gel eluting with 0-40% EtOAc/hexane to afford the title compound: MS(IS) 299 (M+1); TLC (50% EtOAc/hexanes) $R_f$=0.23.

Preparation 30

(5-Bromo-pyrimidin-4-yl)-(2-chloro-phenyl)-methanol

Slowly add freshly prepared lithium diisopropylamide (0.5 M in ether) to a refluxing solution of 5-bromopyrimidine (4.03 g, 25.3 mmol) and 2-chloro-benzaldehyde (3.55 g, 25.2 mmol) in ether (100 mL). After addition is complete, stir at reflux for an additional 2 hours, then quench with 2N HCl (50 mL). Wash the organic layer with water (4×50 mL), dry, filter, and concentrate. Purify the crude material by flash chromatography using a linear gradient of 100% hexanes to 50% EtOAc/hexanes to give the title compound: MS (IS) 298.9 (M+1); $^1H$ NMR (400 MHz, $CDCl_3$) δ 9.19 (s, 1H), 8.77 (s, 1H), 7.40 (dd, 1H, J=1.4, 8.4), 7.23 (dt, 1H, J=1.9, 7.9), 7.15 (dt, 1H, J=1.4, 7.7), 6.92 (dd, 1H, J=1.5,7.9), 6.34 (d, 1H, J=6.4), 4.75 (d, 1H, J=6.7).

Preparation 31

{2-[(2-chloro-phenyl)-hydroxy-methyl]-phenyl}-carbamic acid tert-butyl ester Add TMEDA (8.3 mL, 55.0 mmol) to a solution of phenyl-carbamic acid tert-butyl ester (4.83 g, 25.0 mmol) in THF (50 mL) at −40° C. in a flame dried flask. After 5 min., add s-BuLi (43 mL, 55.0 mmol, 1.3 M in cyclohexane) dropwise over 10 min. Allow solution to warm to RT. After 30 min., add saturated aqueous $NH_4Cl$ solution (approx. 15 mL) and stir for 30 min. Concentrate, partition between 20% i-PrOH/$CHCl_3$ and saturated aqueous $NaHCO_3$ solution and separate. Wash organic layer with brine, dry over $MgSO_4$, and concentrate. Purify the residue by flash chromatography on silica gel eluting with 0-20% ethyl acetate/hexanes to afford the title compound: TLC (10% ethyl acetate/hexanes) $R_f$=0.20.

Preparation 32

(2-Bromopyridin-3-yl)-(2-chlorophenyl)-methanone

Add 85% manganese(IV) oxide (500 g, 5.75 mol) to a slurry of (2-bromopyridine)-(2-chlorophenyl)-methanol (392 g, 1.131 mol) in toluene (2.5 L), heat to a reflux and stir. After one hour cool to ambient temperature and filter through Celite®. Concentrate the solution under reduced pressure. Purify by recrystallization from MTBE: heptane (2:1) to give title compound 312.4 g (80%). $^1H$ NMR (300 MHz, $CDCl_3$), δ 8.50 (dd, 1H, J=1.83, 4.73), 7.78 (dd, 1H, J=1.83, 7.63), 7.60 (dd, 1H, J=1.53, 7.63), 7.53-7.34 (m, 4H); MS (IS) m/z 296.0 (M+1), 298.0 (M+1); m.p.=76.3° C.; Analysis for $C_{12}H_7BrClNO$: calcd: C, 48.60; H, 2.38; N, 4.72; found: C, 48.71; H, 2.48; N, 4.61; $R_f$=0.40 (hexane: ethyl acetate 2:1).

By a method similar to Preparation 32, the following compounds can be prepared and are isolated by crystallization or chromatography.

| Prep. # | Product | Physical Data |
|---|---|---|
| 33 | (2-Bromo-pyridin-3-yl)-phenyl-methanone | MS(IS) 261.1(M+1); TLC(20% ether in hexanes): Rf=0.1. |
| 34 | (2-Bromo-pyridin-3-yl)-o-tolyl-methanone | MS(IS) 275.9(M+1); TLC(25% ether in hexanes): Rf=0.1. |
| 35 | (2-Bromo-pyridin-3-yl)-(2-methoxy-phenyl)-methanone | MS(IS) 291.9(M+1); TLC(25% ether in hexanes): Rf=0.1. |
| 36 | (2-Bromo-pyridin-3-yl)-(2-trifluoromethyl-phenyl)-methanone | MS(IS) 329.9(M+1); TLC(25% ether in hexanes): Rf=0.1. |
| 37 | (2-Bromo-pyridin-3-yl)-(2-fluoro-phenyl)-methanone | MS(IS) 279.9(M+1); TLC(25% ether in hexanes): Rf=0.1. |
| 38 | (2-Bromo-pyridin-3-yl)-(3-chloro-phenyl)-methanone | MS(IS) 295.9(M+1); TLC(25% ether in hexanes): Rf=0.1. |
| 39 | (2-Bromo-pyridin-3-yl)-(4-chloro-phenyl)-methanone | MS(IS) 295.9(M+1); TLC(25% ether in hexanes): Rf=0.1. |
| 40 | (3-bromo-pyridin-4-yl)-(2-chloro-phenyl)-methanone | MS(IS) 297(M+1). TLC(5% MeOH/$CH_2Cl_2$) $R_f$=0.57. |
| 41 | [2-(2-chloro-benzoyl)-phenyl]-carbamic acid tert-butyl ester | TLC(10% EtOAc/hexanes) $R_f$=0.32. |
| 42 | (5-Bromo-pyrimidin-4-yl)-(2-chloro-phenyl)-methanone | MS(IS) 296.9(75%), 298.9(100%)(M+1) $^1H$ N MR(400MHz, $CDCl_3$) δ 9.11(s, 1H), 8.99(s, 1H), 7.77(dd, 1H, J=1.9, 7.3), 7.51(dt, 1H, J=1.5, 7.9), 7.41(m, 2H). |
| 43 | (2-chloro-phenyl)-(3-iodo-pyrazin-2-yl)-methanone | MS(IS) 344.9($M^+$+1) TLC: Rf=0.41(35% EtOAc/hexanes) |

Preparation 44

(2-amino-phenyl)-(2-chloro-phenyl)-methanone

Dissolve [2-(2-chloro-benzoyl)-phenyl]-carbamic acid tert-butyl ester (850 mg, 2.6 mmol) in a saturated HCl in AcOH solution (10 mL, ~3N in HCl), stir at room temperature for 3 hours. Concentrate, add CHCl$_3$ and concentrate (3×) to remove remaining AcOH. Dissolve the residue in 20% i-PrOH/CHCl$_3$, wash with saturated NaHCO$_3$ solution (2×) and brine. Dry the combined organic layers over MgSO$_4$ and concentrate to afford the title compound (495 mg, 83%): MS(IS) 232 (M+1).

Preparation 45

(2-chloro-phenyl)-(2-iodo-phenyl)-methanone

Add concentrated HCl (0.5 mL) to a solution of (2-amino-phenyl)-(2-chloro-phenyl)-methanone (495 mg, 2.14 mmol) in glacial AcOH (1.1 mL). Cool solution to 10° C.; add a solution of sodium nitrite (156 mg, 2.26 mmol) in water (1 mL) dropwise over 30 min. After an additional 30 min., add water (4° C., 2 mL) and EtOAc (4° C., 4 mL). Add a solution of KI (425 mg, 2.56 mmol) and I$_2$ (319 mg, 1.25 mmol) in water (2 mL) dropwise over 25 min. Stir at 5-15° C. for 2.5 hours under N$_2$. Extract with EtOAc (×3), wash with 1N aqueous Na$_2$S$_2$O$_3$ solution (×3), saturated aqueous NaHCO$_3$ solution (×3) and brine. Dry the combined organic layers over Na$_2$SO$_4$ and concentrate. Purify the residue by flash chromatography on silica gel eluting with 0-10% EtOAc/hexanes to afford the title compound (498 mg, 68%): MS(IS) 343 (M+1); TLC (10% EtOAc/hexanes) R$_f$=0.39.

Preparation 46

4,5-Dihydro-2H-pyridazin-3-one

Dilute succinic semialdehyde (15% wt/H$_2$O, 1 eq) in a mixture of acetic acid/H$_2$O (1.5/1), add hydrazine (2.5 eq) by syringe. Attach a reflux condensor and set in 120° C. bath, stir. After 2 hours., neutralize with saturated aqueous NaHCO$_3$, extract with EtOAc, dry over MgSO$_4$, filter and remove solvent under vacuum to give the title compound: $^1$H NMR (CDCl$_3$): δ 8.56 (br s, 1H), 7.15 (s, 1H), 2.53 (m, 4H).

General Preparation B

Combine the appropriate dihydropyridazinone (1 eq) in a solution of 5% KOH/EtOH and the appropriate benzaldehyde. Attach a reflux condensor and heat to 60° C., with stirring. After 1 hour, add concentrated aqueous HCl to pH 3, extract with EtOAc, dry over MgSO$_4$ and remove solvent under vacuum. Purify by chomatography on silica gel to give the title compound.

By an analogous method to General Preparation B, the following compounds may be prepared and isolated:

| Prep. | Product | Physical Data |
|---|---|---|
| 47 | 4-(2-Chloro-benzyl)-pyridazin-3-ol | $^1$H NMR(CDCl$_3$): δ 8.56(brs, 1H), 7.15(s, 1H), 2.53(m, 4H) |
| 48 | 4-(2-Chloro-benzyl)-6-methyl-pyridazin-3-ol | $^1$H NMR(CDCl$_3$): δ 10.5(brs, 1H), 7.48-7.25(m, 5H), 4.06(s, 2H), 2.26(s, 3H). |

General Preparation C

In a sealed vessel, combine the appropriate benzyl-pyridazine (1 eq) in a solution of acetic acid and sodium dichromate (2 eq). Heat to 125° C., with stirring. After 24 hours, concentrate, neutralize with saturated aqueous NaHCO$_3$, extract with EtOAc, dry over MgSO$_4$, filter and concentrate. Purify by chomatography on silica gel to give the title compound.

By a method similar to General Preparation C, the following compounds may be prepared and isolated.

| Prep. | Product | Physical Data |
|---|---|---|
| 49 | (2-Chloro-phenyl)-(3-hydroxy-pyridazin-4-yl)-methanone | MS(IS) 235.0(M+1), $^1$H NMR(CDCl$_3$): δ 11.64(brs, 1H), 7.98(d, J=4.0Hz, 1H), 7.69-7.23(m, 5H). |
| 50 | (2-Chloro-phenyl)-(3-hydroxy-6-methyl-pyridazin-4-yl)-methanone | MS(IS) 249.0(M+1), $^1$H NMR(CDCl$_3$): δ 12.11(brs, 1H), 7.47(m, 1H), 7.39-7.20(m, 3H), 7.14(m, 1H), 2.29(s, 3H). |

General Preparation D

Combine the appropriate hydroxy-pyridazine (1 eq) and phosphorous oxybromide, neat, heat to 100° C., and stir. After 1 hour, pour the hot mixture into ice, add 5N NaOH to pH 10, extract with EtOAc. Dry over MgSO$_4$, filter and concentrate. Purify by chomatography on silica gel to give the title compound.

By a method similar to General Preparation D, the following compounds may be prepared and isolated.

| Prep. | Product | Physical Data |
|---|---|---|
| 51 | (3-Bromo-pyridazin-4-yl)-(2-chloro-phenyl)-methanone | MS(IS)297.0(M+1), $^1$H NMR(CDCl$_3$): δ 9.34(apd, 1H), 7.71(m, 1H), 7.58(m, 1H), 7.51-7.43(m, 3H). |
| 52 | (3-Bromo-6-methyl-pyridazin-4-yl)-(2-chloro-phenyl)-methanone | MS(IS) 313.0(M+1), $^1$H NMR(CDCl$_3$): δ 7.68(m, 1H), 7.57(m, 1H), 7.52-7.40(m, 2H), 7.33(s, 1H), 2.77(s, 3H). |

Preparation 53

4-Ethynyl-pyridine

Add K$_2$CO$_3$ (3.32 g, 24.0 mmol) to a solution of 4-trimethylsilanylethynyl-pyridine (3.51 g, 20.0 mmol) in MeOH (40 mL). After 10 min, add saturated aqueous NH$_4$Cl solution (approx. 10 mL) and stir. After 10 min., add MgSO$_4$, filter and concentrate at RT. Purify by Kugelrohr distillation (50-55° C.) to afford the title compound (1.31 g, 64%): MS(IS) 104 (M+1). $^1$H NMR (400 MHz, CDCl$_3$): 3.29 (s, 1H); 7.34 (d, 2H, J=5.9 Hz); 8.59 (d, 2H, J=5.9 Hz).

Preparation 54

5-Trimethylsilanylethynyl-pyrimidine

Dissolve 5-bromopyrimidine (50.0 g, 314.4 mmol) in triethylamine (400 mL), add copper (I) iodide (1.20 g, 6.2 mmol) and stir mixture under nitrogen. After 15 minutes, add trimethylsilyl acetylene (53.3 mL, 377.3 mmol), followed by dichlorobis(triphenylphosphine) palladium (II) (8.82 g, 12.5 mmol) and stir at room temperature. After 3 hours, filter the solution through Celite®, rinsing with ether. Concentrate the filtrate under reduced pressure. Purification by flash chromatography on silica gel eluting first with hexanes (100%), then with hexanes:ethyl acetate (3:1) gives the title compound: $^1$H NMR (CDCl$_3$) δ 9.10 (s, 1H), 8.77 (s, 2H), 0.27 (s, 9H).

Preparation 55

4-Trimethylsilanylethynyl-pyridine

Heat a mixture of 4-bromopyridine hydrochloride (1.0 eq), ethynyl-trimethyl-silane (2.0 eq), PdCl$_2$(PPh$_3$)$_2$ (0.1 eq), CuI (0.2 eq) and diisopropyl ethyl amine (10 eq) in DMF at 70° C. for 18 hours. Dilute with methylene chloride, and wash with water. Dry over MgSO$_4$, filter and concentrate in vacuo. Purify the residue by flash chromatography on silica gel to give the title compound. MS (IS) 176.0 (M+1); TLC (20% ether in hexanes): Rf=0.1.

By a method similar to Preparation 55, using 2-iodopyrazine, the following compound may be prepared and isolated.

| Prep. | Product | Physical Data |
|---|---|---|
| 56 | 2-Trimethylsilanylethynyl-pyrazine | $^1$H NMR(CDCl$_3$) δ 8.65-8.71(m, 1H), 8.52-8.55(m, 1H), 8.45-8.48(m, 1H), 0.30(s, 9H) |

Preparation 57

2-Tributylstannanylethynyl-pyridine

Dissolve 2-ethynylpyridine (7.14 g, 69.23 mmol) in THF (350 mL) and cool the solution to −10° C. (ice/methanol) under nitrogen. Add n-butyllithium (1.6 M in hexanes, 47.6 mL, 76.16 mmol) dropwise and stir the mixture. After 15 minutes, add tributyltin chloride (20.7 mL, 76.2 mL) dropwise. Warm the mixture to room temperature overnight. Quench the reaction with water, dilute with ether, and wash with saturated ammonium chloride, then brine. Dry over sodium sulfate, filter and concentrate. No further purification necessary to give the title compound: $^1$H NMR (CDCl$_3$) δ 8.50-8.54 (m, 1H), 7.51-7.59 (m, 1H), 7.35-7.43 (m, 1H), 7.11-7.18 (m, 1H), 1.59-1.64 (m, 6H), 1.32-1.42 (m, 6H), 1.05-1.10 (m, 6H), 0.88-0.94 (m, 9H).

Preparation 58

Tributyl-cyclopropylethynyl-stannane

To a solution of n-butyllithium (2.5M in hexanes, 159 mL, 0.398 mol) in THF (800 mL) at −10° C. under nitrogen, add 5-chloropentyne (20 g, 0.195 mol) dropwise, keeping the temperature below 10° C. After the addition is complete, allow the reaction to warm to room temperature and stir for 6 hours, then add tributyltin chloride (70 g, 0.215 mol) and stir overnight. Pour the reaction mixture into hexanes (500 mL), wash with saturated sodium bicarbonate (300 mL) and brine (300 mL), dry with sodium sulfate, filter, and concentrate to afford the title compound (70 g, 100%) which can be used without further purification: mass spectrum (m/e): 357 (M+H$^+$); $^1$H NMR (CDCl$_3$) δ 1.70-1.49 (m, 6H), 1.49-1.24 (m, 7H), 1.10-0.65 (m, 19H).

Preparation 59

4-[3-(3,5-bis-trifluoromethyl-benzyl)-5-tributylstannanyl-3H-[1,2,3]triazol-4-yl]-morpholine Add 1-azidomethyl-3,5-bis-trifluoromethyl-benzene (1.21 g, 4.5 mmol) to a solution of 4-tributylstannanylethynyl-morpholine in toluene (5 mL) (1.20 g, 3.0 mmol). See Berger, D., et al., *Helv. Chim. Acta* (1996) 79(I): 179-91. Flush with N$_2$, seal in reaction vessel, and heat at 100° C. overnight. Concentrate, dissolve residue in CHCl$_3$, dry over MgSO$_4$, concentrate. Purify by flash chromatography on silica gel eluting with 0-30% EtOAc/hexanes to afford the title compound (710 mg, 66%); MS(IS) 669 (M+1); TLC: Rf=0.53 (25% EtOAc/hexanes).

Preparation 60

4-[3-(3,5-bis(trifluoromethyl)benzyl)-5-tributylstannanyl-3H-[1,2,3]triazol-4-yl]-pyridine Add potassium trimethylsilanolate (0.651 g, 4.56 mmol, 90% purity) in one portion to a solution of 4-[(trimethylsilanyl)ethynyl]pyridine (40.0 g, 228 mmol, Ziessel, R., et al. *J. Org. Chem.* 1996, 61, 6535) and bis(tributyltin) oxide (95.2 g, 160 mmol) in THF (400 mL) while keeping the temperature between 25-30° C. with a water bath. After approximately 1 hour, concentrate the solution by rotary evaporation (50° C.) to give an oil containing 78-85% 4-[(tributylstannanyl)ethynyl]pyridine, 15-22% 4-ethynylpyridine and excess bis(tributyltin) oxide. Add 1-azidomethyl-3,5-bis(trifluoromethyl)benzene (73.7 g, 274 mmol) to the oil and heat at 110° C., distilling off any volatiles required to achieve the desired temperature. Heat the solution until the reaction is complete by $^1$H-NMR analysis (approximately 22 h). After cooling to 50° C., dilute the reaction mixture with heptane (600 mL) and stir at room temperature. Filter the mixture to remove the solids. Purify the mixture by pouring the heptane solution on a silica gel column (810 g silica gel in a 2 L fritted-glass funnel) and elute sequentially with heptane (5.2 L), 1:10 EtOAc:heptane (5.1 L), and 1:3 EtOAc:heptane (12.6 L). Combine the fractions containing product and concentrate by rotary evaporation to give 124 g (82% yield) of the title compound; mp 61.9-63.1° C.; Analysis for C$_{28}$H$_{36}$F$_6$N$_4$Sn: Calcd: C, 50.86; H, 5.49; N, 8.47. Found: C, 51.08, H, 5.61; N, 8.50.

Using the method similar to Preparation 60, with the appropriate starting materials, the following compounds may be prepared and isolated.

| Prep. | Product | Physical Data |
|---|---|---|
| 61 | 5-[3-(3,5-bis-trifluoromethyl-benzyl)-5-tributylstannanyl-3H-[1,2,3]triazol-4-yl]-pyrimidine | m.p.=65-68° C.; TLC: $R_f$=0.46(2:1 Ethyl Acetate: Methylene Chloride); mass spectrum(m/e): 664(M+H$^+$); |
| 62 | 2-[3-(3,5-bis-trifluoromethyl-benzyl)-5-tributylstannanyl-3H-[1,2,3]triazol-4-yl]-pyrazine | mass spectrum(m/e): 664(M+H$^+$); $^1$H NMR(CDCl$_3$) δ 8.66-8.72(m, 1H), 8.62-8.65(m, 1H), 8.55-8.61(m, 1H), 7.76(s, 1H), 7.65(s, 2H), 5.96(s, 2H), 1.37-1.52(m, 6H), 1.16-1.33(m, 6H), 1.06-1.15(m, 6H), 0.76-0.87(m, 9H); TLC(Silica, 5:1 Hexanes:Ethyl Acetate)$R_f$ 0.48. |
| 63 | 3-[3-(3,5-bis-trifluoromethyl-benzyl)-5-tributylstannanyl-3H-[1,2,3]triazole-4-yl]-pyridine | TLC: $R_f$=0.39(25% EtOAc/hexanes); MS(IS): 661(M+1). |

General Preparation E

Heat a mixture of the appropriate ethynylstannane (1.0 eq) and the appropriate benzyl azide (1.0 eq) in toluene until reaction is complete. Concentrate to remove the solvent in vacuo. Purify the residue by flash chromatography on silica gel to give the desired product.

By a method similar to General Preparation E, the following compounds may be prepared and isolated.

| Prep. | Product | Physical Data |
|---|---|---|
| 64 | 1-(3,5-bis-trifluoromethyl-benzyl)-4-(tri-n-butylstannanyl)-5-phenyl-1H-[1,2,3]triazole | MS(IS)660.1(M+1); TLC(17% ether in hexanes): Rf=0.1. |
| 65 | 2-[3-(3,5-bis-trifluoromethyl-benzyl)-5-tributylstannanyl-3H-[1,2,3]triazole-4-yl]-pyridine | m.p.=47-50° C.; mass spectrum(m/e): 663(M+H$^+$); TLC: $R_f$=0.34(5:1 Hexanes:Ethyl Acetate) |
| 66 | 1-(3,5-bis-trifluoromethyl-benzyl)-5-methyl-4-tributylstannanyl-1H-[1,2,3]triazole | MS(m/e): 598(M–H)$^-$; TLC: $R_f$=0.57(3:1 Hexanes:Ethyl Acetate) $^1$H NMR(CDCl$_3$) δ 7.83(s, 1H), 7.56(s, 2H), 5.61(s, 2H), 2.20(s, 3H), 1.49-1.62(m, 6H), 1.28-1.40(m, 6H), 1.15-1.24(m, 6H), 0.87(t, J=7.3Hz, 9H) |
| 67 | 1-(3,5-bis-trifluoromethyl-benzyl)-5-isopropyl-4-tributylstannanyl-1H-[1,2,3]triazole | mass spectrum(m/e): 626(M–H)$^-$; TLC(Silica, 4:1 Hexanes:Ethyl Acetate) $R_f$ 0.52 |
| 68 | 1-(3,5-bis-trifluoromethyl-benzyl)-5-cyclopropyl-4-tributylstannanyl-1H-[1,2,3]triazole | mass spectrum(m/e): 626(M+H$^+$); TLC(Silica, 4:1 Hexanes:Ethyl Acetate) $R_f$ 0.44 |

Preparation 69

3-Oxo-3-pyrimidin-5-yl-propionic acid methyl ester

Add a 25 wt % solution of sodium methoxide in methanol (4.5 mL, 19.8 mmol) to toluene (40 mL) and heat to 85° C. under N$_2$. Dissolve pyrimidine-5-carboxylic acid ethyl ester (2.0 g, 13.2 mmol) in methyl acetate (2.1 mL) and add dropwise to the toluene solution. Heat the reaction mixture for 1 hour and add a suspension of sodium methoxide (715 mg, 13.2 mmol) in methyl acetate (15 mL) dropwise. Heat the reaction mixture at 85° C. overnight, cool to room temperature, and pour into a solution of glacial acetic acid (12 mL) and water (150 mL). After stirring for 1 hour at room temperature, extract with ethyl acetate (3×100 mL), wash the organic phase with brine (200 mL), dry over sodium sulfate, filter, and concentrate under reduced pressure to give the title compound as a mixture of tautomers: $^1$H NMR (CDCl$_3$) enol form δ 12.43 (s, 1H), 9.26 (s, 1), 9.10 (s, 2H), 5.76 (s, 1H), 3.86 (s, 3H); keto form δ 9.42 (s, 1H), 9.30 (s, 2H), 4.06 (s, 3H), 3.74 (s, 2H).

Preparation 70

3-Oxo-3-pyrazin-2-yl-propionic acid methyl ester

Dissolve NaOMe (1.5 eq) in toluene and heat 90° C. Add a solution of 2-pyrazine methylester (1.0 eq) and methylacetate (2.0 eq) in toluene dropwise and heat at 90° C. After 20 hours, conc. in vacuo at RT. Slurry in excess methyl acetate and reflux 20 hours. Cool to RT. Add water. Extract with EtOAc, dry (Na$_2$SO$_4$), filter and conc. in vacuo to give the title compound: TLC $R_f$=0.58 (1:1 EtOAc/hexanes)

Preparation 71

1-(3,5-bis-trifluoromethyl-benzyl)-5-pyridin-4-yl-1H-[1,2,3]triazole-4-carboxylic acid ethyl ester Treat a solution of ethyl isonicotinoylacetate (2.52 g, 13.0 mmol) and 3,5-bis-trifluourobenzyl azide (3.54 g, 13.1 mmol) in DMSO (20 mL) with milled K₂CO₃ (5.72 g, 41.4 mmol). Warm mixture to 40° C. and stir for 18 hours, then dilute with H₂O and treat with 1N HCl until mixture reaches pH=7. Extract mixture with EtOAc (2×50 mL). Combine organic phases and wash with H₂O (2×50 mL) and brine (50 mL), then dry, filter, and concentrate organic layer. Triturate crude material with hexanes then recrystallize solid from 40% EtOAc/hexanes to give the title compound (2.80 g, 48%).) MS(EI+)445.2 (M+H); $^1$H NMR (400 MHz, CDCl₃): δ 8.74 (dd, 2H, J=1.5, 4.4), 7.80 (s, 1H), 7.45 (s, 2H), 7.13 (dd, 2H, J=2.0, 4.4), 5.56 (s, 2H), 4.27 (q, 2H, J=7.3), 1.28 (t, 3H, J=7.3). Analytical ($C_{19}H_{14}F_6N_4O_2$): Calculated C, 51.36; H, 3.18; N, 12.61. Found C, 51.35; H, 3.21; N, 12.52.

By a method similar to Preparation 71, the following compounds may be prepared and isolated.

| Prep | Product | Physical Data |
| --- | --- | --- |
| 72 | 1-(3,5-bis-trifluoromethyl-benzyl)-5-methyl-1H-[1,2,3]triazole-4-carboxylic acid ethyl ester | MS(IS) 382.1(M+1), MS(ES−) 380.0(M−1). $^1$H NMR(400MHz, CDCl₃) δ 7.86(s, 1H), 7.64(s, 2H), 5.62(s, 2H), 4.42(q, 2H, J=7.4), 2.50(s, 3H), 1.41(t, 3H, J=7.4). |
| 73 | 1-(3,5-bis-trifluoromethyl-benzyl)-5-pyridin-3-yl-1H-[1,2,3]triazole-4-carboxylic acid methyl ester | MS(IS) 431.1(M+H). $^1$H NMR(400MHz, CDCl₃): δ 8.76(s, 1H), 8.49(s, 1H), 7.79(s, 1H), 7.51(m, 1H), 7.41(s, 2H), 7.40(m, 1H), 5.59(s, 2H), 3.83(s, 3H). |
| 74 | 1-(3,5-bis-trifluoromethyl-benzyl)-5-phenyl-1H-[1,2,3]triazole-4-carboxylic acid methyl ester | Rf=0.42(2:1 hexanes/EtOAc); MS(IS): 444.1(M+1); $^1$H NMR(CDCl₃, 250MHz) δ 7.82(s, 1H), 7.4-7.6(m, 5H), 7.20(m, 2H), 5.58(s, 2H), 4.35(q, 2H), 1.27(t, 3H). |
| 75 | 1-(3,5-bis-trifluoromethyl-benzyl)-5-pyrazin-2-yl-1H-[1,2,3]triazole-4-carboxylic acid methyl ester | MS(IS) 431.29(M+1); TLC R$_f$=0.29(1:1 EtOAc/hexanes) |
| 76 | 1-(3,5-bis-trifluoromethyl-benzyl)-5-pyrimidin-5-yl-1H-[1,2,3]triazole-4-carboxylic acid methyl ester | $^1$H NMR(CDCl₃) δ 9.34(s, 1H), 8.62(s, 2H), 7.82(s, 1H), 7.48(s, 2H), 5.63(s, 2H), 3.91(s, 3H) |
| 77 | 1-(3,5-Dichloro-benzyl)-5-pyridin-4-yl-1H-[1,2,3]triazole-4-carboxylic acid ethyl ester | MS(IS) 377.0, 379.0(M+1); TLC R$_f$=0.50 (7% MeOH/CH₂Cl₂). |

Preparation 78

1-(3,5-bis-trifluoromethyl-benzyl)-5-hydroxy-1H-[1,2,3]triazole-4-carboxylic acid ethyl ester Combine a solution of sodium ethoxide (5.5 mL, 21 wt % in ethanol) and diethyl malonate (2.50 mL, 16.5 mmol) in ethanol (26 mL) with a solution of 1-azidomethyl-3,5-bis-trifluoromethyl-benzene (4.40 g, 16.3 mmol) in ethanol (6 mL) and heat to 80° C. After 7 hours, cool to RT. Concentrate mixture in vacuo and dissolve the viscous oil in H₂O (20 mL). Add aqueous 1N HCl until solution reaches pH 2-3. Collect the white precipitate by filtration and dry under reduced pressure to give the title compound: MS (IS) 384.0 (M+H), MS (ES−) 382.1 (M−H); $^1$H NMR (400 MHz, CDCl₃) δ 8.05 (s, 1H), 7.92 (s, 2H), 5.41 (s, 2H), 4.15 (q, 2H, J=7.3), 1.22 (t, 3H, J=7.3).

Preparation 79

1-(3,5-bis-trifluoromethyl-benzyl)-5-chloro-1H-[1,2,3]triazole-4-carboxylic acid ethyl ester Combine PCl₅ (5.73 g, 27.5 mmol) with a solution of 1-(3,5-bis-trifluoromethyl-benzyl)-5-hydroxy-1H-[1,2,3]triazole-4-carboxylic acid ethyl ester (5.30 g, 13.8 mmol) in toluene (150 mL) and heat to 50° C. After 2 hours, cool to RT, concentrate solution and dissolve crude material in ether (100 mL). Wash the organic solution with saturated NaHCO₃ (2×100 mL) and brine (100 mL), dry, filter, and concentrate. Purify the crude material by passing through a short plug of silica gel using a linear gradient of 50% to 80% EtOAc/hexanes then recrystallize from 1:1 diethyl ether:petroleum ether (150 mL). MS (IS) 402.0 (M+H). $^1$H NMR (400 MHz, CDCl₃) δ 7.88 (s, 1H), 7.76 (s, 2H), 5.67 (s, 2H), 4.43 (q, 2H, J=7.0), 1.40 (t, 3H, J=7.0).

General Preparation F

Add a solution of LiOH.H₂O (10 eq) in water to a solution of the appropriate ester (1 eq) in dioxane. Stir under N₂ overnight. Acidify to a pH of 1-2 with 5N HCl solution and filter out the precipitate. Dry the material in vacuo to afford the desired product.

By a method similar to General Preparation F, using the appropriate starting materials, the following compounds may be prepared and isolated.

| Prep | Product | Data |
| --- | --- | --- |
| 80 | 1-(3,5-bis-trifluoromethyl-benzyl)-5-chloro-1H-[1,2,3]triazole-4-carboxylic acid | MS(IS) 372(M⁺−1); $^1$H NMR(400MHz, DMSO): 5.89(s, 2H); 8.03(s, 2H); 8.15(s, 1H) |

-continued

| Prep | Product | Data |
|---|---|---|
| 81 | 1-(3,5-bis-trifluoromethyl-benzyl)-5-pyridin-4-yl-1H-[1,2,3]triazole-4-carboxylic acid | MS(IS) 415(M$^+$−1); $^1$H NMR(400MHz, DMSO): 5.76(s, 2H); 7.43(d, 2H, J=5.9Hz); 7.70(s, 2H); 8.04(s, 1H); 8.66(d, 2H, J=5.9Hz) |
| 82 | 1-(3,5-bis-trifluoromethyl-benzyl)-5-pyrazin-2-yl-1H-[1,2,3]triazole-4-carboxylic acid | MS(IS) 418.1(M+1) |
| 83 | 1-(3,5-Dichloro-benzyl)-5-pyridin-4-yl-1H-[1,2,3]triazole-4-carboxylic acid | MS(IS) 349.0, 351.0(M+1) |
| 84 | 5-Chloro-1-(3,5-Dichloro-benzyl)-1H-[1,2,3]triazole-4-carboxylic acid | MS(FAB) 305.9 M$^+$; TLC R$_f$ =0.05(7% MeOH/CH$_2$Cl$_2$) |
| 85 | 1-(3,5-bis-trifluoromethyl-benzyl)-5-pyridin-3-yl-1H-[1,2,3]triazole-4-carboxylic acid | MS(ES−) 415.1(M−H); $^1$H NMR(400MHz, DMSO-d6): δ 13.05(br s, 1H), 8.66(m, 1H), 8.56(d, 1H, J=1.5), 8.05(s, 1H), 7.85(dt, 1H, J=2.0, 7.8), 7.71(s, 2H), 7.48(dd, 1H, J=4.9, 7.8), 5.79(s, 2H). |
| 86 | 1-(3,5-bis-trifluoromethyl-benzyl)-5-methyl-1H-[1,2,3]triazole-4-carboxylic acid | MS(ES−) 352.1(M−H); $^1$H NMR(400MHz, DMSO-d6) δ 7.31(s, 1H), 7.14(s, 2H), 5.00(s, 2H), 2.50(s, 3H). |
| 87 | 1-(3,5-bis-trifluoromethyl-benzyl)-5-phenyl-1H-[1,2,3]triazole-4-carboxylic acid | R$_f$ =0.40(2:1 CHCl$_3$/MeOH); MS(IS): 416.1(M+1) |
| 88 | 1-(3,5-bis-trifluoromethyl-benzyl)-5-pyrimidin-5-yl-1H-[1,2,3]triazole-4-carboxylic acid | $^1$H NMR(CDCl$_3$) δ 9.27(s, 1H), 8.64(s, 2H), 7.84(s, 1H), 7.50(s, 2H), 5.69(s, 2H) |

General Preparation G

Add N,O-dimethyl-hydroxylamine (1.3 eq), EDCI (1.3 eq), and DMAP (0.6-1.3 eq) to a solution of the appropriate carboxylic acid (1 eq) in CH$_2$Cl$_2$ (0.3 M). Stir the solution at RT for 5-24 hours, then dilute with CH$_2$Cl$_2$ and wash with water, saturated NaHCO$_3$, and brine. Dry, filter, and concentrate the organic solution and purify the crude material by flash chromatography or recrystallization. By a method similar to General Preparation G, the following compounds may be prepared and isolated.

| Prep | Product | Physical Data |
|---|---|---|
| 89 | 1-(3,5-bis-trifluoromethyl-benzyl)-5-pyridin-3-yl-1H-[1,2,3]triazole-4-carboxylic acid methoxy-N-methyl-amide | Recrystallized from iPrOH/hexanes MS(IS) 460.1(M−H), MS(ES$^−$) 458.1(M−H): $^1$H NMR(400MHz, CDCl$_3$) δ 8.72(s, 1H), 8.50(s, 1H), 7.80(s, 1H), 7.58(d, 1H, J=7.6), 7.43(s, 2H), 7.36(dd, 1H, J=4.8, 7.7), 5.57(s, 2H), 3.86(s, 3H), 3.33(br s, 3H). |
| 90 | 1-(3,5-bis-trifluoromethyl-benzyl)-5-methyl-1H-[1,2,3]triazole-4-carboxylic acid methoxy-N-methyl-amide | MS(IS) 397.1(M+H), MS(ES−)395.1(M−H); $^1$H NMR(400MHz, CDCl$_3$) δ 7.86(s, 1H), 7.67(s, 2H), 5.60(s, 2H), 3.89(s, 3H), 3.45(brs, 3H), 2.46(s, 3H) |
| 91 | 1-(3,5-bis-trifluoromethyl-benzyl)-5-pyrazin-2-yl-1H-[1,2,3]triazole-4-carboxylic acid methoxy-N-methyl-amide | MS(IS) 461.2(M+1); TLC Rf=0.47(5% MeOH/CHCl$_3$) |
| 92 | 1-(3,5-bis-trifluoromethyl-benzyl)-5-chloro-1H-[1,2,3]triazole-4-carboxylic acid methoxy-N-methyl-amide | MS(IS) 417.0(M+H). $^1$H NMR(400MHz, CDCl$_3$) δ 7.88(s, 1H), 7.78(s, 2H), 5.64(s, 2H), 3.86(s, 3H), 3.40(br s, 3H). |
| 93 | 1-(3,5-bis-trifluoromethyl benzyl)-5-pyrimidin-5-yl-1H-[1,2,3]triazole-4-carboxylic acid methoxy-N-methyl-amide | $^1$H NMR(CDCl$_3$) δ 9.30(s, 1H), 8.63(s, 2H), 7.84(s, 1H), 7.47(s, 2H), 5.58(s, 2H), 3.90(s, 3H), 3.38(br s, 3H). |
| 94 | 1-(3,5-bis-trifluoromethyl-benzyl)-5-pyridin-4-yl-1H-[1,2,3]triazole-4-carboxylic acid methoxy-N-methyl-amide | $^1$H NMR(500MHz, CDCl$_3$) δ 8.75(d, J=5.7Hz, 2 H), 7.85(s, 1 H), 7.50(s, 2 H), 7.21(d, J=5.7Hz, 2 H), 5.57(s, 2 H), 3.87(s, 3 H), 3.32(s, 3H); Mass spectrum(m/e): 460.1(M+H$^+$). |
| 95 | 1-(3,5-bis-trifluoromethylbenzyl)-5-phenyl-1H-[1,2,3]triazole-4-carboxylic acid methoxy-N-methyl amide | $^1$H NMR(500MHz, CDCl$_3$) δ 7.79(s, 1 H), 7.52-7.44(m, 5 H), 7.24-7.22(m, 2 H), 5.55(s, 2 H), 3.83(s, 3 H), 3.33(s, 3 H). Mass spectrum(m/e): 459.1(M+H$^+$). |

Preparation 96

[1-(3,5-bis-trifluoromethyl-benzyl)-5-pyridin-3-yl-1H-[1,2,3]triazol-4-yl]-methanol Dissolve 1-(3,5-bis-trifluoromethyl-benzyl)-5-pyridin-3-yl-1H-[1,2,3]triazole-4-carboxylic acid methyl ester in MeOH. Add NaBH$_4$ (2.64 g, 3 eq) and warm to reflux overnight (70° C.). Cool to RT and slowly pour into a separatory funnel containing an equal volume of water. Extract with CH$_2$Cl$_2$. Concentrate and recrystallize from EtOAc/Hexanes to give the 7.0 g (75%) of the title compound. MS (IS) 403.2 (M+1); $^1$H NMR: (400 MHz, CD$_3$OD) δ: 8.65 (dd, J=5.2, 1.6 Hz, 1H) 8.53-8.52 (m, 1H), 7.89 (s, 1H), 7.86-7.83 (m, 1H), 7.60 (s, 2H), 7.56-7.53 (m, 1H), 5.83 (s, 2H), 4.59 (s, 2H).

Preparation 97

1-(3,5-bis-trifluoromethyl-benzyl)-5-chloro-1H-[1,2,3]triazole-4-carbaldehyde Add a solution of LiBH$_4$ (65 mL, 2M in THF) to a solution of 1-(3,5-bis-trifluoromethyl-benzyl)-5-chloro-1H-[1,2,3]triazole-4-carboxylic acid ethyl ester (15.0 g, 37.3 mmol) in THF (150 mL) at 0° C. After addition is complete, stir solution at RT for 6 hours, then cool again to 0° C. Carefully quench with slow addition of 5N HCl (50 mL). Stir at RT for 30 min., then neutralize with 5N NaOH. Dilute mixture with water (100 mL) and extract with EtOAc (2×50 mL). Combine the organic phases and wash with water (100 mL), and brine (100 mL) then dry, filter, and concentrate to give the alcohol that was used in the next reaction without further purification.

Add Dess-Martin periodinane (19.0 g, 44.8 mmol) to a 0° C. solution of the above alcohol in CH$_2$Cl$_2$ (100 mL). Stir solution at 0° C. for 15 min., then at RT for 2 hours. Add additional Dess-Martin periodinane (1.7 g, 4.0 mmol) and stir at RT for 1 hour. Pour solution into cold 5N NaOH (70 mL) and extract with ether (3×150 mL). Combine the organic phases and wash with 1N NaOH (100 mL), water (100 mL), and brine (100 mL), then dry, filter, and concentrate. Purify the crude material by flash chromatography to give the title compound. MS (IS) 358.1(M+H). $^1$H NMR (400 MHz, CDCl$_3$) δ 10.13 (s, 1H), 7.90 (s, 1H), 7.76 (s, 2H), 5.67 (s, 2H).

Using the method similar to Preparation 97, using the appropriate ester, the following compound is prepared and isolated.

| Prep | Product | Physical Data |
| --- | --- | --- |
| 98 | 1-(3,5-bis-trifluoromethyl-benzyl)-5-pyridin-4-yl-1H-[1,2,3]triazole-4-carbaldehyde | MS(IS) 401.1(M+1). $^1$H NMR(CDCl$_3$): δ 10.14(s, 1H), 8.75(d, J=5.7Hz, 2H), 7.80(s, 1H), 7.47(s, 1H), 7.13(dd, J=4.0, 1.7Hz, 2H), 5.55(s, 2H). |

Preparation 99

1-[1-(3,5-bis-trifluoromethyl-benzyl)-5-chloro-1H-[1,2,3]triazol-4-yl]-3-(2-chloro-phenyl)-prop-2-yn-1-ol Dissolve 1-chloro-2-ethynyl-benzene (22.1 g, 162 mmol) in THF (300 mL) and slowly add methyl magnesium bromide (50 mL, 3.0 M in ether). Stir solution at RT for 40 min, then add a solution of 1-(3,5-bis-trifluoromethyl-benzyl)-5-chloro-1H-[1,2,3]triazole-4-carbaldehyde (29.6 g, 82.8 mmol) in THF (160 ml). Stir resulting solution at RT for 2 h then pour into cold water (500 mL) and 1N HCl (150 mL) and extract with EtOAc (3×200 mL). Combine the organic phases and wash with saturated NaHCO$_3$ (200 mL) and brine (200 mL) then dry, filter, and concentrate. Purify the crude material by triturating with 30% ether/hexanes to give the title compound. MS (IS) 494.0 (M+1), MS (ES−) 492.0 (M−1); $^1$H NMR (400 MHz, CDCl$_3$) δ 7.87 (s, 1H), 7.79 (s, 2H), 7.47 (dd, 1H, J=1.9, 7.3), 7.37 (dd, 1H, J=1.4, 7.9), 7.25 (dt, 1H, J=2.0, 7.3), 7.19 (dt, 1H, J=1.5, 7.3), 5.92 (d, 1H, J=6.7), 5.62 (s, 2H), 2.79 (d, 1H, J=6.4).

Using a method similar to Preparation 99, using the appropriate aldehyde, the following compound may be prepared and isolated.

| Prep | Product | Physical Data |
| --- | --- | --- |
| 100 | 1-[1-(3,5-bis-trifluorormethyl-benzyl)-5-phenyl-1H-[1,2,3]triazol-4-yl]-3-(2-chloro-phenyl)-prop-2-yn-1-ol | MS(IS) 536.0(M+1); $^1$H NMR(CDCl$_3$): δ 7.82(s, 1H), 7.56-7.12(m, 11H), 5.85(s, 1H), 5.59(s, 2H). |

Preparation 101

1-[1-(3,5-bis-trifluoromethyl-benzyl)-5-chloro-1H-[1,2,3]triazol-4-yl]-3-(2-chloro-phenyl)-propynone Dissolve 1-[1-(3,5-bis-trifluoromethyl-benzyl)-5-chloro-1H-[1,2,3]triazol-4-yl]-3-(2-chloro-phenyl)-prop-2-yn-1-ol (33.5 g, 67.8 mmol) in CH$_2$Cl$_2$ (300 mL) and treat with MnO$_2$ (50.0 g, 556 mmol). Stir mixture at RT overnight then filter through a pad of Celite® and concentrate the filtrate. Purify the crude material by triturating with 30% ether/hexanes. MS (IS) 492.1 (M+1). $^1$H NMR (400 MHz, CDCl$_3$) δ 7.89 (s, 1H), 7.81 (s, 2H), 7.47 (dd, 1H, J=1.5, 7.8), 7.46 (dd, 1H, J=1.4, 7.8), 7.40 (dt, 1H, J=1.5, 7.4), 7.29 (dt, 1H, J=1.5, 7.4), 5.68 (s, 2H).

Preparation 102

1-[1-(3,5-bis-trifluoromethyl-benzyl)-5-phenyl-1H-[1,2,3]triazol-4-yl]-3-(2-chloro-phenyl)-propynone Chill a solution of 1-chloro-2-ethynylbenzene 4.0 mL, 32.8 mmol) in anhydrous THF (25 mL) under nitrogen to 0° C. Add by syringe ethylmagnesium bromide, 3.0 M in ether (9.7 mL, 29.3 mmol) with stirring. After 30 minutes, remove from ice-bath and add by syringe a solution of 1-(3,5-bis-trifluoromethyl-benzyl)-5-phenyl-1H-[1,2,3]triazole-4-carboxylic acid methoxy-N-methyl-amide (10.73 g, 23.4 mmol) in THF (35 mL). After 2 hours, quench with saturated aqueous NH$_4$Cl and extract with ethyl acetate, dry over MgSO$_4$, filter and concentrate under vacuum. Purify by chromatography (silica gel, hexanes/ethyl acetate gradient) to give the title compound: MS (IS) 534.0 (M+1), $^1$H NMR (CDCl$_3$): δ 7.82 (s, 1H), 7.56-7.12 (m, 11H), 5.59 (s, 2H).

Using the method similar to Preparation 102, using the appropriate starting materials, the following compounds are prepared and isolated.

| Prep | Product | Physical Data |
| --- | --- | --- |
| 103 | 1-[1-(3,5-bis-trifluoromethyl-benzyl)-5-methyl-1H-[1,2,3]triazole-4-yl]-3-(2-chloro-phenyl)-propynone | MS(IS) 472.1(M+H), 470.1(M−H); $^1$H NMR(400MHz, CDCl$_3$) δ 7.90(s, 1H), 7.75(dd, 1H, J=7.9, 1.6), 7.71(s, 2H), 7.47(dd, 1H, J=8.2, 1.3), 7.41(dt, 1H, J=7.9, 1.6), 7.31(dt, 1H, J=8.2, 1.3), 5.66(s, 2H), 2.61(s, 3H) |
| 104 | 1-[1-(3,5-bis-trifluoromethyl-benzyl)-5-pyridin-4-yl-1H-[1,2,3]triazole-4-yl]-3-(2-chloro-phenyl)-propynone | m.p.=50-54° C.; MS(m/e): 535(M+H$^+$); TLC: R$_f$=0.34(2:1 Ethyl Acetate:Hexanes) |
| 105 | 1-[1-(3,5-bis-trifluoromethyl-benzyl)-5-pyridin-3-yl-1H-[1,2,3]triazol-4-yl]-3-(2-chloro-phenyl)-propynone | m.p.=100-101° C.; MS(m/e): 535(M+H$^+$); TLC: R$_f$=0.12(1:1 Ethyl Acetate:Hexanes). |
| 106 | 1-[1-(3,5-bis-trifluoromethyl-benzyl)-5-pyrimidin-5-yl-1H-[1,2,3]triazol-4-yl]-3-(2-chloro-phenyl)-propynone | m.p.=168-169° C.; MS(m/e): 536(M+H$^+$); TLC: R$_f$=0.27(Silica, 1:1 Ethyl Acetate:Hexanes). |

Preparation 107

[1-(3,5-bis-trifluoromethyl-benzyl)-5-phenyl-1H-[1,2,3]triazol-4-yl]-[5-(2-chloro-phenyl)-3-(2,2-dimethoxy-ethyl)-isoxazol-4-yl]-methanone Combine 1-[1-(3,5-bis-trifluoromethyl-benzyl)-5-phenyl-1H-[1,2,3]triazol-4-yl]-3-(2-chloro-phenyl)-propynone (600 mg, 1.126 mmol) and 40 mL of benzene, add 1,1 dimethoxy-3-nitroproprane (253.2 mg, 0.225 mL, 1.689 mmol), 1,4-phenylene diisocyanate and 30 drops of triethylamine (~0.25 mL). Heat the mixture to reflux. After 8 hours, add another 500 mg of 1,4-phenylene diisocyanate and 200 mg of 1,1 dimethoxy-3-nitroproprane followed by 20 drops of triethyl amine. Continue heating for another 20 h and then cool to RT. Dilute the mixture with 1 mL of water, stir for 10 min. and pour the mixture through a plug of Celite® (1 cm) and extract 3 times with CH$_2$Cl$_2$ (100 mL each) and once with EtOAc (50 mL). Dry the combined organics over MgSO$_4$, filter, and concentrate. Purification by chromatography (silica gel, hexanes/ethyl acetate gradient) provides 550 mg of the title compound. MS (aspci): m/z=633.9 (M+1 (—OMe)), 635.1 (M−1); $^1$H NMR (250 MHz, CDCl$_3$) δ 7.72 (s, 1H), 7.59 (dd, J=6.2, 2.7 Hz, 1H), 7.48-7.10 (m, 10H), 5.37 (s, 2H), 4.70 (t, J=6.2 Hz, 1H), 3.41 (s, 6H), 3.70 (q, J=6.25 Hz, 2H), 3.21 (s, 6H), 3.1-3.2 (m, 2H).

By a method analogous to Preparation 107, using the appropriate starting materials, the following compounds may be prepared and isolated.

| Prep | Product | Physical Data |
| --- | --- | --- |
| 108 | [1-(3,5-bis-trifluoromethyl-benzyl)-5-pyridin-3-yl-1H[1,2,3]triazol-4-yl]-{5-(2-chloro-phenyl)-3-[2-(tetrahydro-pyran-2-yloxy)-ethyl]-isoxazol-4-yl}-methanone | $^1$H NMR(CDCl$_3$) δ 1.34-1.70(m, 5H), 3.23(td, 2H, J=6.84, 1.70Hz), 3.41-3.51(m, 1H), 3.72-3.79(m, 2H), 4.59(m, 1H), 5.47(s, 2H), 7.2-7.45(m, 7H), 7.59-7.62(m, 1H), 7.70-7.72(dd, 1H, J=7.55, 1.65Hz), 7.83(s, 1H), 8.50(d, 1H, J=1.46Hz), 8.78(dd, 1H, J=4.87, 1.47Hz). |
| 109 | [1-(3,5-bis-trifluoromethyl-benzyl)-5-pyridin-4-yl-1H-[1,2,3]triazol-4-yl]-[5-(2-chloro-phenyl)-3-(tetrahydro-pyran-2-yloxymethyl)-isoxazol-4-yl]-methanone | Exact Mass 691.14; mass spectrum(ESI) 714.1 m/z(M+Na); $^1$H NMR(CDCl$_3$) δ1.38-1.80(m, 6H), 3.48(m, 1H) 3.78(m, 1H), 4.69(m, 1H), 4.93(ABq, 2H, J=13.31Hz, Δv=64.63Hz) 5.47(s, 2H), 7.16(m, 2H), 7.24(m, 1H), 7.33-7.43(m, 4H), 7.70(dd, 1H, J=7.51, 2.04Hz), 7.86(s, 1H), 8.78(m, 2H). |
| 110 | [1-(3,5-bis-trifluoromethyl-benzyl)-5-pyridin-3-yl-1H-[1,2,3]triazol-4-yl]-[5-(2-chloro-phenyl)-3-(tetrahydro-pyran-2-yloxymethyl)-isoxazol-4-yl]-methanone | $^1$H NMR(CDCl$_3$) δ 1.40-1.63(m, 6H), 1.66-1.72(m, 1H), 3.45-3.50(m, 1H), 3.75-3.81(m, 1H), 4.69(t, 1H, J=3.23Hz), 4.94(ABq, 2H, J=13.19, Δv=66.43Hz), 5.51(s, 2H), 7.25-7.30(m, 1H), 7.35-7.44(m, 5H), 7.57-7.60(m, 1H), 7.69-7.71(m, 1H), 7.84(s, 1H), 8.48(d, 1H, J=2.1Hz), 8.76(dd, 1H, J=4.86, 1.67Hz); TLC R$_f$=0.3(10% ether/dichloromethane). |
| 111 | [1-(3,5-bis-trifluoromethyl-benzyl)-5-pyridin-4-yl-1H-[1,2,3]triazol-4-yl]-{5-(2-chloro-phenyl)-3-[2-(tetrahydro-pyran-2- | $^1$H NMR(CDCl$_3$) δ 1.32-1.72(m, 6H), 3.23(td, 2H, J=6.75, 1.39Hz) 3.44(m, 1H), 3.76(m, 2H), 4.07(dt, 1H, J=9.76, 6.83Hz), 4.60(bt, 1H, J=3.32Hz) 5.43(s, |

-continued

| Prep | Product | Physical Data |
|---|---|---|
| | yloxy)-ethyl]-isoxazol-4-yl}-methanone | 2H), 7.17-7.20(m, 3H), 7.32-7.43(m, 4H), 7.72(dd, 1H, J=7.71, 1.66Hz), 7.86(s, 1H), 8.80(m, 2H). |
| 112 | [1-(3,5-bis-trifluoromethyl-benzyl)-5-phenyl-1H-[1,2,3]triazol-4-yl]-[5-(2-chloro-phenyl)-3-(tetrahydro-pyran-2-yloxymethyl)-isoxazol-4-yl]-methanone | MS(IS) 691.2(M+1), $^1$H NMR(CDCl$_3$): δ 7.84(s, 1H), 7.72-7.18(m, 11H), 5.48(s, 2H), 4.96(m, 2H), 4.73(m, 1H), 3.81(m, 1H), 3.50(m, 1H), 1.80-1.37(m, 6H). |
| 113 | [1-(3,5-bis-trifluoromethyl-benzyl)-5-phenyl-1H-[1,2,3]triazol-4-yl]-[5-(2-chloro-phenyl)-3-[1,3]dioxolan-2-ylmethyl-isoxazol-4-yl]-methanone | MS(IS) 663.1(M+1), $^1$H NMR(CDCl$_3$): δ 7.80(s, 1H), 7.67(dd, J=7.8Hz, 1.7Hz, 1H), 7.56-7.16(m, 10H), 5.44(s, 2H), 5.29(t, J=4.2Hz, 1H), 3.84-3.74(m, 4H), 3.33(d, J=4.4Hz, 2H). |
| 114 | [1-(3,5-bis-trifluoromethyl-benzyl)-5-pyrazin-2-yl-1H-[1,2,3]triazol-4-yl]-[5-(2-chlorophenyl)-3-(2,2-dimethoxy-ethyl)-isoxazol-4-yl]-methanone | $^1$H NMR(CDCl$_3$): δ 9.18(d, J=1.3Hz, 1H), 8.68(m, 2H), 7.80(s, 1H), 7.68(m, 1H), 7.59(s, 2H), 7.38-7.24(m, 2H), 7.19(m, 1H), 5.84(s, 2H), 5.27(t, J=4.1Hz, 1H), 3.78(m, 4H), 3.38(d, J=4.1Hz, 2H). TLC(50% EtOAc/Hexane), R$_f$=0.13 |
| 115 | [1-(3,5-bis-trifluoromethyl-benzyl)-5-phenyl-1H-[1,2,3]triazol-4-yl]-{5-(2-chloro-phenyl)-3-[2-(tetrahydro-pyran-2-yloxy)-ethyl]-isoxazol-4-yl}-methanone | MS(IS) 705.5(M+1), TLC(30% EtOAc/Hexane), Rf=0.15 |
| 116 | [1-(3,5-bis-trifluoromethyl-benzyl)-5-pyrazin-2-yl-1H-[1,2,3]triazol-4-yl]-[5-(2-chloro-phenyl)-3-(tetrahydro-pyran-2-yloxymethyl)-isoxazol-4-yl]-methanone | MS(IS) 693.2(M+1) TLC Rf=0.50(10% CH$_3$CN/CH$_2$Cl$_2$) |

General Preparation H

Dissolve appropriate alkyne (1 eq) in toluene (0.1 M) and treat the solution with the appropriate nitroalkoxy-tetrahydropyran (5 eq), 1,4-diisocyanato-benzene (5 eq), and triethylamine (5 eq). Heat the solution at 110° C. overnight, add water and filter through a pad of Celite®. Wash the solid with EtOAc and wash the filtrate with brine. Dry, filter, and concentrate the organic solution and use the material without further purification. Dissolve the above material in MeOH (0.1M) and treat with AcOH or p-TsOH.H$_2$O (2 eq). Stir the solution at RT for 18 hours. Concentrate the solution and re-dissolve the crude material in EtOAc. Wash the organic solution with saturated NaHCO$_3$, then dry, filter, and concentrate. Purify the crude material by flash chromatography to give the title compound.

By a method similar to general preparation H, the following compounds are prepared and isolated.

| Prep | Product | Physical Data |
|---|---|---|
| 117 | [1-(3,5-bis-trifluoromethyl-benzyl)-5-chloro-1H-[1,2,3]triazol-4-yl]-[5-(2-chloro-phenyl)-3-hydroxymethyl-isoxazol-4-yl]-methanone | MS(IS) 565.0(M+1). $^1$HNMR(400MHz, CDCl$_3$) δ 7.91(s, 1H), 7.65(s, 2H), 7.63(dd, 1H, J=1.8, 8.0), 7.36(dt, 1H, J=1.5, 7.3), 7.31(dt, 1H, J=1.9, 7.8), 7.11(dd, 1H, J=1.5, 7.8), 5.55(s, 2H), 4.84(d, 2H, J=7.4), 3.74(t, 1H, J=7.4). |
| 118 | [1-(3,5-bis-trifluoromethyl-benzyl)-5-chloro-1H-[1,2,3]triazol-4-yl]-[5-(2-chloro-phenyl)-3-(2-hydroxy-ethyl)-isoxazol-4-yl]-methanone | MS(IS) 579.0(M+1); $^1$HNMR(400MHz, CDCl$_3$) δ 7.90(s, 1H), 7.64(s, 2H), 7.63(m, 1H), 7.33(dt, 1H, J=1.0, 7.3), 7.27(dt, 1H, J=1.5, 7.8), 7.12(dd, 1H, J=1.0, 7.8), 5.53(s, 2H), 4.05(t, 2H, J=5.9), 3.19(t, 2H, J=5.9), 2.35(br s, 1H). |
| 119 | [1-(3,5-bis-trifluoromethyl-benzyl)-5-methyl-1H-[1,2,3]triazol-4-yl]-[5-(2-chloro-phenyl)-3-hydroxymethyl-isoxazol-4-yl]-methanone | MS(IS) 545.1(M+H), 543.1(M−H). $^1$H NMR(400MHz, CDCl$_3$) δ 7.90(s, 1H), 7.69(dd, 1H, J=7.6, 2.2), 7.55(s, 2H), 7.35-7.40(m, 2H), 7.22(dd, 1H, J=8.0, 1.6), 5.53(s, 2H), 4.85(d, 2H, J=7.6), 4.08(t, 1H, J=7.6), 2.55(s, 3H). |
| 120 | [1-(3,5-bis-trifluoromethyl-benzyl)-5-methyl-1H [1,2,3]triazol-4-yl]-[5-(2-chloro- | MS(IS) 558.9(M+1)$^+$, MS(ES−) 556.9(M−1)$^-$. $^1$HNMR(400MHz, CDCl$_3$) δ 7.87(s, 1H), 7.67(dd, 1H, J=2.0, 7.3), 7.51(s, |

| Prep | Product | Physical Data |
|---|---|---|
| | phenyl)-3-(2-hydroxy-ethyl)-isoxazol-4-yl]-methanone | 2H), 7.36(dt, 1H, J=1.5, 7.3), 7.30(dt, 1H, J=2.0, 7.8), 7.18(dd, 1H, J=1.5, 7.8), 5.49(s, 2H), 4.05(t, 2H, J=5.4), 3.17(t, 2H, J=5.4), 2.51(s, 3H), 1.70(br s, 1H). |
| 121 | [1-(3,5-bis-trifluoromethyl-benzyl)-5-pyrimidin-5-yl-1H-[1,2,3]triazol-4-yl]-[5-(2-chloro-phenyl)-3-(2-hydroxy-methyl)-isoxazol-4-yl]-methanone | $^1$H NMR(400MHz, CDCl$_3$) δ 3.59(t, J=7.2Hz, 2H), 4.82(d, J=6Hz, 2H), 5.52(s, 2H), 7.26(d, J=0.8Hz, 1H), 7.35-7.40(m, 3H), 7.42(t, J=6Hz, 1H), 7.76(d, J=4Hz, 1H), 7.89(s, 1H), 8.66(s, 2H), 9.38(s, 1H); mass spectrum(apci) m/z 609.0(M+1) |
| 122 | [1-(3,5-bis-trifluoromethyl-benzyl)-5-pyridin-3-yl-1H-[1,2,3]triazol-4-yl]-[5-(2-chloro-phenyl)-3-(2-hydroxy-ethyl)-isoxazol-4-yl]-methanone | $^1$H NMR(CDCl$_3$) δ 3.15(t, J=5.93Hz, 2H), 4.02(t, J=5.86Hz, 2H), 5.47(s, 2H), 7.21-7.45(m, 6H), 7.61(m, 1H), 7.72(dd, J=7.59, 1.87Hz, 1H), 7.84(s, 1H), 8.51(d, J=1.63Hz, 1H), 8.78(m, 1H); mass spectrum(ESI) m/z 604.1(M-OH). |

General Preparation J

Dissolve the appropriate 5-chlorotriazole (1 eq) in the appropriate amine, (20-120 eq) and stir at 80-110° C. The amine may be in solution in a suitable solvent, such as MeOH or THF. After 2-20 hours, dilute the solution with EtOAc (25 mL) and wash with 1N HCl (20 mL), water (20 mL), and saturated NaHCO$_3$ (20 mL). Dry, filter, and concentrate the organic phase then purify the crude material by flash chromatography.

By a method similar to General Preparation J, the following compounds are prepared and isolated.

| Prep | Product | Physical Data |
|---|---|---|
| 123 | [1-(3,5-bis-trifluoromethyl-benzyl)-5-morpholin-4-yl-1H-[1,2,3]triazol-4-yl]-[5-(2-chloro-phenyl)-3-hydroxymethyl-isoxazol-4-yl]-methanone | MS(IS) 616.1(M+1), MS(ES−) 614.1(M−1); $^1$HNMR(400MHz, CDCl$_3$) δ 7.87(s, 1H), 7.67(dd, 1H, J=1.5, 7.8), 7.62(s, 2H), 7.37(dt, 1H, J=1.4, 7.4), 7.29(dt, 1H, J=1.4, 7.8), 7.12(dd, 1H, J=1.0, 7.8), 5.43(s, 2H), 4.82(d, 2H, J=6.8), 4.03(t, 1H, J=7.6), 3.74(m, 4H), 3.00(m, 4H). |
| 124 | [1-(3,5-bis-trifluoromethyl-benzyl)-5-morpholin-4-yl-1H-[1,2,3]triazol-4-yl]-[5-(2-chloro-phenyl)-3-(2-hydroxy-ethyl)-isoxazol-4-yl]-methanone | MS(IS) 630.1(M+1), MS(ES−) 628.0(M−1); $^1$HNMR(400MHz, CDCl$_3$) δ 7.86(s, 1H), 7.66(dd, 1H, J=1.4, 7.8), 7.62(s, 2H), 7.34(dt, 1H, J=1.0, 7.4), 7.26(dt, 1H, J=2.0, 7.9), 7.12(dd, 1H, J=1.0, 7.9), 5.42(s, 2H), 4.07(t, 2H, J=6.0), 3.73(m, 4H), 3.18(t, 2H, J=6.0), 3.00(m, 4H), 2.24(br s, 1H). |
| 125 | [1-(3,5-bis-trifluoromethyl-benzyl)-5-dimethylamino-1H-[1,2,3]triazol-4-yl]-[5-(2-chloro-phenyl)-3-hydroxymethyl-isoxazol-4-yl]-methanone | MS(IS) 574.3(M+H); $^1$H NMR(400MHz, CDCl$_3$) δ 7.88(s, 1H), 7.67(dd, 1H, J=7.7, 1.9) 7.60(s, 2H), 7.35(dt, 1H, J=8.0, 1.7), 7.29(dt, 1H, J=7.7, 2.0), 7.15(dd, 1H, J=8.0, 1.3), 5.42(s, 2H), 4.83(brs, 2H), 4.22(brs, 1H), 2.78(s, 6H). |
| 126 | [1-(3,5-bis-trifluoromethyl-benzyl)-5-dimethylamino-1H-[1,2,3]triazol-4-yl]-[5-(2-chloro-phenyl)-3-(2-hydroxy-ethyl)-isoxazol-4-yl]-methanone | MS(IS) 588.1(M+H), 586.1(M−H); $^1$H NMR(400MHz, CDCl$_3$) δ 7.87(s, 1H), 7.67(dd, 1H, J=7.8, 1.8), 7.60(s, 2H), 7.33(dt, 1H, J=7.9, 1.5), 7.27(dt, 1H, J=8.3, 1.8), 7.16(dd, 1H, J=8.3, 1.1), 5.41(s, 2H), 4.07(dt, 2H, J=6.7, 6.1), 3.20(t, 2H, J=6.1), 2.78(t, 1H, J=6.7), 2.76(s, 6H). |
| 127 | [1-(3,5-bis-trifluoromethyl-benzyl)-5-(thiomorpholin-4-yl)-1H-[1,2,3]triazol-4-yl]-[5-(2-chloro-phenyl)-3-(2-hydroxy-ethyl)-isoxazol-4-yl]-methanone | MS(IS) 646.1(M+H); $^1$H NMR(400MHz, CDCl$_3$) δ 7.88(s, 1H), 7.68(dd, 1H, J=7.7, 1.8), 7.62(s, 2H), 7.36 dt, 1H, J=8.0, 1.5), 7.28(dt, 1H, J=7.7, 1.1), 7.15(dd, 1H, J=8.0, 1.1), 5.40(s, 2H), 4.09(m, 2H), 3.25(m, 4H), 3.19(t, 2H, J=6.3), 2.69(m, 4H). |

General Preparation K

Dissolve the appropriate protected alcohol (1 eq) in THF, water and HOAc and heat at 60° C. Stir 5-24 hours, concentrate in vacuo, extract with EtOAc, wash with water, saturated aqueous NaHCO$_3$, brine, dry (Na$_2$SO4), filter and concentrate in vacuo. Purify by chromatography to give the title compound.

By a method similar to General Preparation K, the following compounds are prepared and isolated.

| Prep. | Product | Physical Data |
|---|---|---|
| 128 | [1-(3,5-bis-trifluoromethyl-benzyl)-5-pyrazin-2-yl-1H-[1,2,3]triazol-4-yl]-[5-(2-chloro-phenyl)-3-hydroxymethyl-isoxazol-4-yl]-methanone | MS(IS) 609.1(M+1); TLC Rf=0.50 (20% $CH_3CN/CH_2Cl_2$) |
| 129 | [1-(3,5-bis-trifluoromethyl-benzyl)-5-phenyl-1H-[1,2,3]triazol-4-yl]-[5-(2-chloro-phenyl)-3-hydroxymethyl-isoxazol-4-yl]-methanone | MS(IS) 607.0(M+1); $^1$H NMR ($CDCl_3$): δ 7.85(s, 1H), 7.74(d, J=7.4Hz, 1H), 7.62-7.37(m, 5H), 7.35(s, 2H), 7.27-7.20(m, 3H), 5.45(s, 2H), 4.83(d, J=7.2Hz, 2H), 3.85(t, J=7.2Hz, 1H). |
| 130 | [1-(3,5-bis-trifluoromethyl-benzyl)-5-phenyl-1H-[1,2,3]triazol-4-yl]-[5-(2-chloro-phenyl)-3-(2-hydroxy-ethyl)-isoxazol-4-yl]-methanone | MS(IS) 620.1(M+1); $^1$H NMR ($CDCl_3$): δ 7.74(s, 1H), 7.63(dd, J=7.5, 1.9Hz, 1H), 7.50-7.09(m, 10H), 5.34(s, 2H), 3.94(t, J=6.0Hz, 2H), 3.08(t, J=6.0Hz, 2H). |
| 131 | [1-(3,5-bis-trifluoromethyl-benzyl)-5-pyrimidin-5-yl-1H-[1,2,3]triazol-4-yl]-[5-(2-chloro-phenyl)-3-hydroxymethyl-isoxazol-4-yl]-methanone | Exact Mass 608.08; mass spectrum (apci): m/z=609.0(M+1); $^1$H NMR (400MHz, $CDCl_3$): δ 9.38(s, 1H), 8.67(s, 2H), 7.89(s, 1H), 7.76(d, J=7.6Hz, 1H), 7.47(t, J=7.6Hz, 1H), 7.44(d, J=7.6Hz, 1H), 7.42(s, 2H), 7.24(d, J=8Hz, 1H), 5.51(s, 2H), 4.82(d, J=7.2Hz, 2H), 3.58(t, J=7.2Hz, 1H). |
| 132 | [1-(3,5-bis-trifluoromethyl-benzyl)-5-pyridin-3-yl-1H-[1,2,3]triazol-4-yl]-[5-2-chloro-phenyl)-3-hydroxymethyl-isoxazol-4-yl]-methanone | MS(APCI) m/z 608(M+1); $^1$H NMR($CDCl_3$) δ 4.81(d, J=7.26Hz, 2H), 5.48(s, 2H), 7.23(d, J=7.82Hz 1H), 7.34-7.46(m, 5H), 7.58-7.61(m, 1H), 7.73(dd, J=7.65, 1.72Hz, 1H), 7.85(s, 1H), 8.52(d, J=1.84Hz, 1H), 8.80(m, 1H). |
| 133 | [1-(3,5-bis-trifluoromethyl-benzyl)-5-pyridin-4-yl-1H-[1,2,3]triazol-4-yl]-[5-(2-chloro-phenyl)-3-hydroxymethyl-isoxazol-4-yl]-methanone | MS(ESI)m/z 608.1(M+1); $^1$H NMR($CDCl_3$) δ3.64(bs, 2H), 4.81(s, 2H), 5.45(s, 2H), 7.20(m, 3H), 7.38-7.47(m, 4H), 7.74(dd, J=7.61, 1.76Hz, 2H), 7.87(s, 1H), 8.82(br s, 2H); |

Preparation 134

[1-(3,5-bis-trifluoromethyl-benzyl)-5-(1,1-dioxo-1λ$^6$-thiomorpholin-4-yl)-1H-[1,2,3]triazol-4-yl]-[5-(2-chloro-phenyl)-3-(2-hydroxy-ethyl)-isoxazol-4-yl]-methanone Combine [1-(3,5-bis-trifluoromethyl-benzyl)-5-(thiomorpholin-4-yl)-1H-[1,2,3]triazol-4-yl]-[5-(2-chloro-phenyl)-3-hydroxymethyl-isoxazol-4-yl]-methanone (0.17 g, 0.26 mmol) in dichloromethane (3.0 mL), add 3-chloroperoxybenzoic acid (0.12 g, 0.50 mmol) and stir at RT. After 2 hours, dilute with EtOAc, wash with 1N NaOH, water and brine, dry, filter, and concentrate. Purify by flash chromatography using a linear gradient of 50% to 80% EtOAc in hexane to give the title compound. MS (IS) 678.0 (M+H). $^1$H NMR (400 MHz, $CD_3COCD_3$) δ 8.09(s, 1H), 7.99 (s, 2H), 7.65 (m, 1H), 7.42 (m, 2H), 7.35 (m, 1H), 5.86 (s, 2H), 3.89 (m, 3H), 3.62 (m, 4H), 3.26 (m, 4H), 3.14 (m, 2H).

General Preparation L

Add Dess-Martin periodinane (1.5 eq) to a solution of the appropriate alcohol (1 eq) in dichloromethane (0.05M-0.5M). Stir at 0° C. for 30 min., then at RT for 1-5 hours. Dilute with ether and wash with cold 0.1N NaOH, water, and brine. Dry, filter, and concentrate the organic phase and purify the crude material by flash chromatography to give the title compound.

Alternatively, under $N_2$, charge an oven-dried flask with oxalyl chloride (2M in $CH_2Cl_2$, 1.2 eq) and chill in a dry ice/acetone slush. Add DMSO (3 eq,) slowly by syringe and stir 15 minutes. Add the alcohol of interest (1 eq) in anhydrous $CH_2Cl_2$ (0.4 M) slowly by syringe and stir 1 hour. Add TEA (5 eq) slowly by syringe and stir 2 hours while bath is allowed to expire. Quench $H_2O$, extract with ether, dry over $MgSO_4$, filter and concentrate under vacuum to give the title compound.

Using methods similar to General Preparation L, the following compounds are prepared and isolated.

| Prep | Product | Physical Data |
|---|---|---|
| 135 | 4-[1-(3,5-bis-trifluoromethyl-benzyl)-5-morpholin-4-yl-1H-[1,2,3]triazole-4-carbonyl]-5-(2-chloro-phenyl)-isoxazole-3-carbaldehyde | MS(IS) 614.0(M+1), MS(ES−) 612.0(M−1); $^1$H NMR(400MHz, CDCl$_3$) δ 10.15(s, 1H), 7.87(s, 1H), 7.69(s, 2H), 7.67(m, 1H), 7.41(m, 3H), 5.54(s, 2H), 3.72(m, 4H), 3.01(m, 4H). |
| 136 | [4-[1-(3,5-bis-trifluoromethyl-benzyl)-5-morpholin-4-yl-1H-[1,2,3]triazole-4-carbonyl]-5-(2-chloro-phenyl)-isoxazol-3-yl]-acetaldehyde | MS(IS) 628.1(M+1), MS(ES−) 626.0(M−1); $^1$H NMR(400MHz, CDCl$_3$) δ 9.82(t, 1H, J=1.0), 7.86(s, 1H), 7.70(dd, 1H, J=1.9, 7.8), 7.63(s, 2H), 7.38(dt, 1H, J=1.3, 7.8), 7.31(dt, 1H, J=1.9, 7.8), 7.16(dd, 1H, J=1.0, 7.8), 5.43(s, 2H), 4.10(d, 2H, J=1.0), 3.72(m, 4H), 2.97(m, 4H). |
| 137 | 4-[1-(3,5-bis-trifluoromethyl-benzyl)-5-dimethylamino-1H-[1,2,3]triazole-4-carbonyl]-5-(2-chloro-phenyl)-isoxazole-3-carbaldehyde | MS(IS) 572.1(M+H), 570.1(M−H); $^1$H NMR(400MHz, CDCl$_3$) δ 10.21(s, 1H), 7.89(s, 1H), 7.68(m, 1H), 7.60(s, 2H), 7.38-7.46(m, 3H), 5.52(s, 2H), 3.44(s, 6H). |
| 138 | [4-[1-(3,5-bis-trifluoromethyl-benzyl)-5-(1,1-dioxo-1λ$^6$-thiomorpholin-4-yl)-1H-[1,2,3]triazole-4-carbonyl]-5-(2-chloro-phenyl)-isoxazol-3-yl]-acetaldehyde | MS(IS) 572.1(M+H), 570.1(M−H); $^1$H NMR(400MHz, CDCl$_3$) δ 9.81(s, 1H), 7.92(s, 1H), 7.74(dd, 1H, J=7.8, 1.5), 7.60(s, 2H), 7.45(dt, 1H, J=7.8, 1.5), 7.38(dt, 1H, 7.8, 1.5), 7.21(dd, 1H, 7.8, 1.5), 5.48(s, 2H), 4.18(s, 2H), 3.53(m, 4H), 3.12(m, 4H). |
| 139 | 4-[1-(3,5-bis-trifluoromethyl-benzyl)-5-methyl-1H-[1,2,3]triazole-4-carbonyl]-5-(2-chloro-phenyl)-isoxazole-3-carbaldehyde | MS(IS) 543.0(M+H), 541.0(M−H); $^1$H NMR(400MHz, CDCl$_3$) δ 10.21(s, 1H), 7.89(s, 1H), 7.68(m, 1H), 7.60(s, 2H), 7.38-7.46(m, 3H), 5.60(s, 2H), 2.58(s, 3H). |
| 140 | [4-[1-(3,5-bis-trifluoromethyl-benzyl)-5-methyl-1H-[1,2,3]triazole-4-carbonyl]-5-(2-chloro-phenyl)-isoxazol-3-yl]-acetaldehyde | MS(IS) 556.9(M+1), MS(ES−) 554.9(M−1); $^1$H NMR(400MHz, CDCl$_3$) δ 9.83(s, 1H), 7.87(s, 1H), 7.70(dd, 1H, J=2.0, 7.8), 7.52(s, 2H), 7.36(m, 2H), 7.22(m, 1H), 5.50(s, 2H), 4.08(s, 2H), 2.49(s, 3H). |
| 141 | 4-[1-(3,5-bis-trifluoromethyl-benzyl)-5-pyridin-4-yl-1H-[1,2,3]triazole-4-carbonyl]-5-(2-chloro-phenyl)-isoxazole-3-carbaldehyde | MS(IS) 606.0(M+1); $^1$H NMR(400MHz, CDCl$_3$) δ 10.17(s, 1H), 8.74(m, 2H), 7.84(s, 1H), 7.65(m, 1H), 7.44(s, 2H), 7.42(m, 1H), 7.38(m, 2H), 7.21(m, 2H), 5.56(s, 2H). |
| 142 | 4-[1-(3,5-bis-trifluoromethyl-benzyl)-5-phenyl-1H-[1,2,3]triazole-4-carbonyl]-5-(2-chloro-phenyl)-isoxazole-3-carbaldehyde | MS(IS) 605.0(M+1); $^1$H NMR(CDCl$_3$): δ 10.11(s, 1H), 7.74(s, 1H), 7.62-7.10(m, 11H), 5.48(s, 2 H). |
| 143 | 5-[1-(3,5-bis-trifluoromethyl-benzyl)-5-pyridin-4-yl-1H-[1,2,3]triazol-4-yl]-4-(2-chloro-benzoyl)-isoxazole-3-carbaldehyde | $^1$H NMR(CDCl$_3$): δ 10.11(s, 1H), 8.78(ap d, 2H). 7.86(s, 1H), 7.75(dd, J=7.5, 1.8Hz, 1H), 7.45-6.88(m, 7H), 5.54(s, 2H) |
| 144 | 4-[1-(3,5-bis-trifluoromethyl-benzyl)-5-pyrazin-2-yl-1H-[1,2,3]triazole-4-carbonyl]-5-(2-chloro-phenyl)-isoxazole-3-carbaldehyde | TLC R$_f$ 0.54(EtOAc); $^1$H NMR (CDCl$_3$): δ 10.20(s, 1H), 9.07(s, 1H), 8.67(m, 2H), 7.81(s, 1H), 7.67(m, 3H), 7.43(m, 3H), 5.93(s, 2H). |

General Preparation M

In a pressure vessel, dilute the acetal of interest (1 eq), with acetic acid/H$_2$O (2:1, 0.1 M). Seal and heat at 125° C. for 48 hours. Concentrate, neutralize with saturated aqueous NaHCO$_3$, extract with ethyl acetate, dry over MgSO4, filter and concentrate under vacuum. By a method similar to General Preparation M, using the appropriate starting materials, the following compounds are prepared and isolated.

| Prep | Product | Physical Data |
|---|---|---|
| 145 | [4-[1-(3,5-bis-trifluoromethyl-benzyl)-5-phenyl-1H-[1,2,3]triazole-4-carbonyl]-5-(2-chloro-phenyl)-isoxazol-3-yl]-acetaldehyde | MS(IS) 619.0(M+1), $^1$H NMR(CDCl$_3$): δ 9.82(s, 1H), 7.84(s, 1H), 7.76(m, 1H), 7.59-7.19(m, 10H), 5.45(s, 2H), 4.10(d, J=1.3Hz, 2H). |
| 146 | [5-[1-(3,5-bis-trifluoromethyl-benzyl)-5-phenyl-1H- | MS(IS) 619.0(M+1), $^1$H NMR(CDCl$_3$): δ 9.70(s, 1H), 7.87-7.07(m, 12H), |

| Prep | Product | Physcial Data |
|------|---------|---------------|
|  | [1,2,3]triazole-4-carbonyl]-4-(2-chloro-phenyl)-[1,2,3]triazol-1-yl]-acetaldehyde | 5.49(s, 2H), 5.43(s, 2H), 2.10(s, 2H). |
| 147 | [5-[1-(3,5-bis-trifluoromethyl-benzyl)-5-pyridin-3-yl-1H-[1,2,3]triazole-4-carbonyl]-4-(2-chloro-phenyl)-[1,2,3]triazol-1-yl]-acetaldehyde | TLC $R_f$ 0.04(75% EtOAc/Hexane), $^1$H NMR(CDCl$_3$): δ 9.60(s, 1H) indicates aldehyde |
| 148 | [5-[1-(3,5-bis-trifluoromethyl-benzyl)-5-pyridin-4-yl-1H-[1,2,3]triazole-4-carbonyl]-4-(2-chloro-phenyl)-[1,2,3]triazol-1-yl]-acetaldehyde | TLC $R_f$ 0.07(75% EtOAc/Hexane), $^1$H NMR(CDCl$_3$): δ 9.61(s, 1H) indicates aldehyde |
| 149 | [5-[1-(3,5-bis-trifluoromethyl-benzyl)-5-pyrazin-2-yl-1H-[1,2,3]triazole-4-carbonyl]-4-(2-chloro-phenyl)-[1,2,3]triazol-1-yl]-acetaldehyde | TLC $R_f$ 0.07(50% EtOAc/Hexane), $^1$H NMR(CDCl$_3$): δ 9.75(s, 1H) indicates aldehyde |
| 150 | [4-[1-(3,5-bis-trifluoromethyl-benzyl)-5-pyrazin-2-yl-1H-[1,2,3]triazole-4-carbonyl]-5-(2-chloro-phenyl)-isoxazol-3-yl]-acetaldehyde | MS(IS) 621.1(M+1), TLC(50% EtOAc/Hexane×3), $R_f$=0.30. |
| 151 | [5-[1-(3,5-bis-trifluoromethyl-benzyl)-5-pyridin-4-yl-1H-[1,2,3]triazol-4-yl]-4-(2-chloro-benzoyl)-isoxazol-3-yl]-acetaldehyde | $^1$H NMR(CDCl$_3$): δ 9.84(s, 1H), 8.78(app t, 2H), 7.87(br s, 2H), 7.59-7.06(m, 7H), 5.46(s, 2H), 4.10(s, 2H) |

General Preparation N

Add dichlorobis(triphenylphosphine)palladium (II) (0.16 g, 0.2 mmol) to a degassed mixture of (2-bromo-pyridin-3-yl)-(2-chloro-phenyl)-methanone (1 eq), the acetylene of interest (1.1 eq), CuI (0.11 g, 0.6 mmol), and triethylamine. Heat the mixture to reflux under N$_2$ for 1-2 hours. Concentrate, dissolve the residue in 20% i-PrOH/CHCl$_3$, wash with saturated aqueous NaHCO$_3$ solution and back extract (2×). Wash with brine, dry the combined organic layers over MgSO$_4$ and concentrate. Purify the residue by flash chromatography to give the title compound.

By a method similar to General Preparation N, using the appropriate starting materials, the following compounds may be prepared and isolated.

| Prep | Product | Physical Data |
|------|---------|---------------|
| 152 | (2-chloro-phenyl)-(2-pyridin-4-ylethynyl-pyridin-3-yl)-methanone | MS(IS) 319(M+1); TLC: $R_f$=0.16(10% ACN/Et$_2$O) |
| 153 | (2-chloro-phenyl)-(2-pyridin-2-ylethynyl-pyridin-3-yl)-methanone | MS(IS) 319(M+1); TLC: $R_f$=0.25(10% ACN/Et$_2$O) |
| 154 | (2-Chloro-phenyl)-(2-pyridin-3-ylethynyl-pyridin-3-yl)-methanone | mass spectrum(m/e): 319(M + H$^+$); $^1$H NMR(CDCl$_3$) δ 8.78-8.80(m, 1H), 8.50-8.60(m, 1H), 8.42-8.43(m, 1H), 8.01-8.05(m, 1H), 7.59-7.61(m, 2H), 7.25-7.45(m, 4H), 7.15-7.25(m, 1H); HPLC 98.1%; TLC(Silica, 2:1 Hexanes:Ethyl Acetate) $R_f$ 0.14 |
| 155 | (2-Chloro-phenyl)-[2-(3-methyl-but-1-ynyl)-pyridin-3-yl]methanone | mass spectrum(m/e): 284(M+H$^+$); $^1$H NMR(CDCl$_3$) δ 8.69-8.70(m, 1H), 7.93-7.97(m, 1H), 7.31-7.51(m, 5H), 2.41-2.51(m, 1H), 0.97(d, J=6.91Hz, 6H); TLC(Silica, 2:1 Ethyl Acetate:Methylene Chloride) $R_f$ 0.29 |
| 156 | (2-Chloro-phenyl)-(2-pyrimidin-5-ylethynyl-pyridin-3-yl)-methanone | m.p.=111-112° C.; mass spectrum(m/e): 320(M+H$^+$); $^1$H NMR(CDCl$_3$) δ 9.13(s, 1H), 8.81-8.85(m, 1H), 8.60(s, 2H), 8.03-8.07(m, 1H), 7.58-7.63(m, 1H), 7.26-7.49(m, 4H); HPLC >99%; TLC(Silica, 8:1.5:0.5 Methylene Chloride:Ethyl Acetate:Methanol) $R_f$ 0.23 |

-continued

| Prep | Product | Physical Data |
|---|---|---|
| 157 | (2-Chloro-phenyl)-(2-pyridin-4-ylethynyl-pyridin-3-yl)-methanone | mass spectrum(m/e): 319(M+H+); $^1$H NMR(CD$_3$OD) δ 8.74-8.82(m, 1H), 8.44-8.57(m, 2H), 8.09-8.17(m, 1H), 7.58-7.69(m, 2H), 7.41-7.53(m, 3H), 7.22-7.30(m, 2H); TLC(Silica, Dichloromethane) R$_f$0.28 |

Preparation 158

(2-Chloro-phenyl)-(2-prop-1-ynyl-pyridin-3-yl)-methanone

Dissolve (2-bromo-pyridin-3-yl)-(2-chloro-phenyl)-methanone (18.0 g, 60.8 mmol) in toluene (600 mL) and purge the solution with nitrogen. After 10 minutes., add tributyl(1-propynyl)tin (22.2 mL, 72.9 mmol) followed by tetrakis(triphenylphosphine)palladium (2.10 g, 1.82 mmol) and heat the mixture to reflux temperature. After 2 hours, cool the mixture to room temperature and concentrate. Purification by flash chromatography on silica gel eluting with hexanes:ethyl acetate (5:1 to 2:1) gives the title compound: m.p.=45-49° C.; mass spectrum (m/e): 256 (M+H+); $^1$H NMR (CDCl$_3$) δ 8.67-8.68 (m, 1H), 7.95-7.98 (m, 1H), 7.32-7.55 (m, 5H), 1.74 (s, 3H); HPLC 98.4%; TLC (Silica, 2:1 Hexanes:Ethyl Acetate) R$_f$ 0.20.

By a method similar to Preparation 158, the following compound may prepared in an analogous fashion.

| Prep | Product | Physical Data |
|---|---|---|
| 159 | (2-Chloro-phenyl)-(2-cyclopropylethynyl-pyridin-3-yl)-methanone | Purification by reverse phase(C18) prep. HPLC eluting with acetonitrile:water m.p.=70-71° C.; mass spectrum(m/e): 282(M+H+); $^1$H NMR(CDCl$_3$) δ 8.67-8.69(m, 1H), 7.94-7.97(m, 1H), 7.30-7.53(m, 5H), 1.12-1.21(m, 1H), 0.70-0.78(m, 2H), 0.50-0.56(m, 2H); HPLC 97.8%; TLC(Silica, 1:1 Ethyl Acetate:Hexanes) R$_f$0.36. |

General Preparation O

Combine tert-butyl-dimethyl-prop-2-ynyloxy-silane (3.0 eq) in THF and cool to 0° C. Add ethylmagnesium bromide (3.0 eq) and stir the mixture at 0° C. After 0.5 hour, add a solution of the appropriate aldehyde (1.0 eq) as a soln.in THF into the above mixture in a dropwise fashion and stir the mixture at 0° C. and room temperature for 0.5 hour. Pour the mixture into saturated aqueous ammonium chloride solution, extract with ether, dry the combined organic layer with MgSO$_4$, filter and concentrate in vacuo. Purify the residue by flash chromatography on silica gel to give the title compound.

By a method similar to General Preparation O, using the appropriate starting materials, the following compounds are prepared and isolated.

| Prep | Product | Physical Data |
|---|---|---|
| 160 | 1-[1-(3,5-bis-trifluoromethyl-benzyl)-5-chloro-1H-[1,2,3]triazol-4-yl]-4-(tert-butyl-dimethyl-silanyloxy)-but-2-yn-1-ol | MS(IS) 528.1(M+1); TLC(50% Et2O in hexanes): R$_f$=0.2. |
| 161 | 1-[1-(3,5-bis-trifluoromethyl-benzyl)-5-phenyl-1H-[1,2,3]triazol-4-yl]-4-(tert-butyl-dimethyl-silanyloxy)-but-2-yn-1-ol | MS(IS) 570.1(M+1); TLC(50% Et2O in hexanes): R$_f$=0.1. |

General Preparation P

Combine the appropriate alcohol (1.0 eq) in dichloromethane, add 4 Å molecular sieves(powder) and stir the mixture. After 10 min., add N-methyl morpholine N-oxide (2.0 eq) into the above mixture and stir. After 10 min., add TPAP (0.1 eq) to the mixture and stir at room temperature. After 20 min., filter the mixture through a pad of silica gel and concentrate the filtrate in vacuo. Purify the residue by flash chromatography on silica gel to give the title compound.

By a method similar to General Preparation P, using the appropriate starting materials, the following compounds are prepared and isolated.

| Prep | Product | Physical Data |
|---|---|---|
| 162 | 1-[1-(3,5-bis-trifluoromethyl-benzyl)-5-chloro-1H-[1,2,3]triazol-4-yl]-4-(tert-butyl-dimethyl-silanyloxy)-but-2-yn-1-one | MS(IS) 526.1(M+1); TLC(30% Et$_2$O in hexanes): R$_f$=0.2. |
| 163 | 1-[1-(3,5-bis-trifluoromethyl-benzyl)-5-phenyl-1H-[1,2,3]triazol-4-yl]-4-(tert-butyl-dimethyl-silanyloxy)-but-2-yn-1-one | MS(IS) 568.1(M+1); TLC(50% Et2O in hexanes): R$_f$=0.3. |

General Preparation Q

Combine 2-chlorophenylhydroximimoyl acid chloride (2.0 eq, See: Hussein, A Q. et al, *J. Heterocycl. Chem.* 1983, 20(2), 301-304.) and appropriate isoxazole (1.0 eq) in EtOAc (3.0 mL), add triethylamine (2.5 eq) and stir the mixture at room temperature for 2 hours, and 50° C. for 18 hours. Treat the reaction mixture with saturated sodium bicarbonate solution, extract it with ether, dry the combined organic layers with MgSO$_4$, filter and concentrate in vacuo. Purify the residue by flash chromatography on silica gel to give the title compound. By a method similar to General Preparation Q, using the appropriate starting materials, the following compounds are prepared and isolated.

| Prep | Product | Physical Data |
|---|---|---|
| 164 | [1-(3,5-bis-trifluoromethyl-benzyl)-5-chloro-1H-[1,2,3]triazol-4-yl]-[5-(tert-butyl-dimethyl-silanyloxymethyl)-3-(2-chloro-phenyl)-isoxazol-4-yl]-methanone | MS(IS) 679.1(M+1); TLC(50% Et$_2$O in hexanes): Rf=0.3. |
| 165 | [1-(3,5-bis-trifluoromethyl-benzyl)-5-phenyl-1H-[1,2,3]triazol-4-yl]-[5-(tert-butyl-dimethyl-silanyloxymethyl)-3-(2-chloro-phenyl)-isoxazol-4-yl]-methanone | MS(IS) 721.2(M+1); TLC(50% Et$_2$O in hexanes): R$_f$=0.2. |

General Preparation R

Combine the appropriate protected alcohol(1.0 eq) in methanol, add toluenesulfonic acid (1.3 eq) and allow the mixture to stir at room temperature. After 18 hours, concentrate it in vacuo, dilute the residue in ether, wash the resulting organic solution with aqueous saturated sodium bicarbonate solution, dry, filter and concentrate in vacuo. Purify the residue by flash chromatography on silica gel to give the title compound.

By a method similar to general preparation R, using the appropriate starting materials, the following compounds are prepared and isolated.

| Prep | Product | Physical Data |
|---|---|---|
| 166 | [1-(3,5-bis-trifluoromethyl-benzyl)-5-chloro-1H-[1,2,3]triazol-4-yl]-[3-(2-chloro-phenyl)-5-hydroxymethyl-isoxazol-4-yl]-methanone | MS(IS) 564.9(M+1); TLC(30% hexanes in Et2O): R$_f$=0.1. |
| 167 | [1-(3,5-bis-trifluoromethyl-benzyl)-5-phenyl-1H-[1,2,3]triazol-4-yl]-[3-(2-chloro-phenyl)-5-hydroxymethyl-isoxazol-4-yl]-methanone | MS(IS) 607.0(M+1); TLC(20% ether in hexanes): Rf=0.1. |

Preparation 168

[1-(3,5-bis-trifluoromethyl-benzyl)-5-morpholin-4-yl-1H-[1,2,3]triazol-4-yl]-[3-(2-chloro-phenyl)-5-hydroxymethyl-isoxazol-4-yl]-methanone Combine[1-(3,5-bis-trifluoromethyl-benzyl)-5-chloro-1H-[1,2,3]triazol-4-yl]-[3-(2-chloro-phenyl)-5-hydroxymethyl-isoxazol-4-yl]-methanone (1.0 eq) and morpholine (3.0 eq) and heat at 50° C. After 18 hours, dilute the mixture with dichloromethane and wash with water, dry the organic layer with MgSO$_4$, filter and concentrate in vacuo. Purify the residue by flash chromatography on silica gel to give the title compound. MS (IS) 616.0 (M+1); TLC (50% EtOAc in hexanes): R$_f$=0.1.

General Preparation S

Combine the appropriate alcohol (1.0 eq) in dichloromethane, add Dess-Martin periodinane (2.0 eq) and allow the mixture to stir at room temperature. After 1 hour, concentrate in vacuo and dilute the residue with ether and wash with saturated aqueous sodium bicarbonate solution, dry the organic layer with anhydrous MgSO$_4$, filter and concentrate in vacuo. Purify by chromatography on silica gel to give the title compound.

By a method similar to General Preparation S, using the appropriate starting materials, the following compounds are prepared and isolated.

| Prep | Product | Physical Data |
|---|---|---|
| 169 | 4-[1-(3,5-bis-trifluoromethyl-benzyl)-5-morpholin-4-yl-1H-[1,2,3]triazole-4-carbonyl]-3-(2-chloro-phenyl)-isoxazole-5-carbaldehyde | MS(IS) 614.1(M+1); TLC(50% ether in hexanes): Rf=0.1. |
| 170 | 4-[1-(3,5-bis-trifluoromethyl-benzyl)-5-phenyl-1H-[1,2,3]triazole-4-carbonyl]-3-(2-chloro-phenyl)-isoxazole-5-carbaldehyde | MS(IS) 605.0(M+1); TLC(33% EtOAc in hexanes): Rf=0.1. |

Preparation 171

5-Chloro-1-(3,5-Dichloro-benzyl)-1H-[1,2,3]triazole-4-carboxylic acid ethyl ester Combine 1-(3,5-Dichloro-benzyl)-5-hydroxy-1H-[1,2,3]triazole-4-carboxylic acid ethyl ester (1 eq) with PCl$_5$ (2 eq) in toluene and heat at 40-50° C. until reaction is complete. Concentrate the mixture, treat with aqueous NaHCO$_3$, and extract with Et$_2$O. Dry the combined extracts over Na$_2$SO$_4$, concentrate, and purify by chromatography on silica gel. MS (IS) 334.0, 336.0 (M+1).

Preparation 172

2-chloro-4-fluoro-benzylamine

Add triphenylphosphine (129.9 g, 495 mmol) to a solution of 1-azidomethyl-2-chloro-4-fluoro-benzene (61.2 g, 330 mmol) in THF (500 mL) and water (30 mL). Stir at RT until no more N$_2$ is evolved. Add 100 mL MeOH and stir at RT overnight. Concentrate; acidify to pH 1 with 1N HCl solution, wash with CH$_2$Cl$_2$ (3 times). Basify aqueous layer with 5N NaOH solution, extract with CH$_2$Cl$_2$ (3 times), dry over MgSO$_4$. Concentrate to afford the title compound (38.5 g, 73%) as a clear liquid. MS(IS) 160 (M+1). $^1$H NMR (400 MHz, CDCl$_3$): 3.90 (s, 2H); 6.96 (t, 1H, J=6.4 Hz); 7.11 (d, 1H, J=8.3 Hz); 7.36 (t, 1H, J=6.4 Hz).

Preparation 173

[2-(2-Chloro-4-fluoro-benzylamino)-ethyl]-carbamic acid tert-butyl ester

To a solution of 2-chloro-4-fluoro-benzaldehyde (742 mg, 4.68 mmol) in MeOH (16 mL), add N-(2-aminoethyl)carbamic acid tert-butyl ester (500 mg, 3.12 mmol) and stir at RT for 4 hours. Cool reaction to 0° C. and slowly add NaBH$_4$ (1.42 g, 37.4 mmol). Allow reaction to slowly warm to RT and stir for 12 hours. Quench reaction with 1N NaOH (80 mL) and extract with CH$_2$Cl$_2$ (40 mL). Dry organic layer over Na$_2$SO$_4$ and concentrate to afford the title compound. Quantitative yield. MS (IS) 303.1 (M+1).

By a method similar to Preparation 173, the following compounds may be prepared and isolated using the appropriate starting materials.

| Prep. # | Product (Chemical Name) | Physical Data |
|---|---|---|
| 174 | [3-(2-Chloro-benzylamino)-propyl]-carbamic acid tert-butyl ester | Rf=0.47 20:1 CHCl$_3$/MeOH |

-continued

| Prep. # | Product (Chemical Name) | Physical Data |
|---|---|---|
| 175 | $N^1$-(2-Chloro-benzyl)-2-methyl-propane-1,2-diamine | MS(IS) 213.1(M+1) |
| 176 | [2-(4-Methyl-benzylamino)-ethyl]-carbamic acid tert-butyl ester | Rf=0.51 20:1 CHCl$_3$/MeOH |
| 177 | R-[2-(1-Phenyl-ethylamino)-ethyl]-carbamic acid tert-butyl ester | Rf=0.77 20:1 CHCl$_3$/MeOH For starting amine see: Polniaszek et al, Syn. Comm., 1992, 22(1), 171-178 |
| 178 | S-[2-(1-Phenyl-ethylamino)-ethyl]-carbamic acid tert-butyl ester | Rf=0.77 20:1 CHCl$_3$/MeOH |
| 179 | [2-(2,3-Dichloro-benzylamino)-ethyl]-carbamic acid tert-butyl ester | MS(IS) 319.0(M+1) |
| 180 | [2-(2-Trifluoromethyl-benzylamino)-ethyl]-carbamic acid tert-butyl ester | MS(IS) 319.1(M+1) |
| 181 | [2-(2-Methyl-benzylamino)-ethyl]-carbamic acid tert-butyl ester | MS(IS) 265.1(M+1) |

General Preparation T

Dissolve N-(2-aminoethyl) carbamic acid t-butyl ester (1.2 eq) in MeOH and add an appropriate aldehyde or ketone (1 eq), NaCNBH$_3$ (2.0 eq), and HOAc (catalytic). Stir 72 h at RT. Quench with water and dissolve in 20% iPrOH/CHCl$_3$. Wash with saturated aqueous NaHCO$_3$ and brine. Dry (Na$_2$SO$_4$), filter and concentrate in vacuo. Purify by chromatography to give the title compound.

By a method similar to General Preparation T, the following compounds may be prepared and isolated.

| Prep. # | Product | Physical Data |
|---|---|---|
| 182 | [2-(2-Chloro-benzylamino)-ethyl]-carbamic acid tert-butyl ester | MS(IS) 287.1(M+1) TLC R$_f$=0.28(1:1 EtOAc/hexanes) |
| 183 | {2-[1-(2-chloro-phenyl)-ethylamino]-ethyl}-carbamic acid tert-butyl ester | MS(IS) 299.1(M+1) TLC R$_f$=0.34(1:1 EtOAc/hexanes) |

General Preparation U

Combine the appropriate acid (1 eq), the appropriate amine (1.5 eq), EDCI (1.1 eq), HOAt or HOBt (1.1 eq), TEA (1.1 eq) and DMAP (cat.) in DMF or CH$_2$Cl$_2$ and stir overnight at RT. Concentrate to dryness and dissolve in 20% iPrOH/CHCl$_3$. Wash with saturated aqeous NaHCO$_3$ and brine. Dry (Na$_2$SO$_4$), filter and concentrate to dryness. Purify by crystallization or chromatography to give the title compound.

By a method similar to General Preparation U, the following compounds may be prepared and isolated.

| Prep. # | Product | Physical Data |
|---|---|---|
| 184 | {2-[[1-(3,5-bis-trifluoromethyl-benzyl)-5-pyridin-4-yl-1H-[1,2,3]triazole-4-carbonyl]-(2-chloro-benzyl)-amino]-ethyl}-carbamic acid tert-butyl ester | MS(IS) 683.06(M+1) TLC Rf=0.29(10% MeOH/CHCl$_3$) |
| 185 | {2-[[1-(3,5-bis-trifluoromethyl-benzyl)-5-chloro-1H-[1,2,3]triazole-4-carbonyl]-(2-chloro-benzyl)-amino]-ethyl}-carbamic acid tert-butyl ester | MS(IS) 640.0(M+1) TLC Rf=0.60(1:1 EtOAc/hexanes) |
| 186 | (2-{[1-(3,5-bis-trifluoromethyl-benzyl)-5-chloro-1H-[1,2,3]triazole-4-carbonyl]-[1-(2-chloro-phenyl)-ethyl]-amino}-ethyl)-carbamic acid tert-butyl ester | MS(IS) 654.0(M+1); TLC R$_f$=0.60(1:1 EtOAc/hexanes) |
| 187 | (2-{[1-(3,5-bis-trifluoromethyl-benzyl)-5-pyridin-4-yl-1H-[1,2,3]triazole-4-carbonyl]-[1-(2-chloro-phenyl)-ethyl]-amino}-ethyl)-carbamic acid tert-butyl ester | MS(IS) 697.0(M+1) TLC Rf=0.50(10% MeOH/CHCl$_3$) |
| 188 | 1-(3,5-bis-trifluoromethyl-benzyl)-5-chloro-1H-[1,2,3]triazole-4-carboxylic acid 2-chloro-benzylamide | MS(IS) 497(M+1) $^1$H NMR(400MHz, CDCl$_3$): 4.72(d, 2H, J=6.6Hz); 5.65(s, 2H); 7.25(m, 2H); 7.38(m, 1H); 7.46(m, 1H); 7.56(bs, 1H); 7.78(s, 2H); 7.89(s, 1H) |
| 189 | 1-(3,5-bis-trifluoromethyl-benzyl)-5-pyridin-4-yl-1H-[1,2,3]triazole-4-carboxylic acid 2-chloro-benzylamide | MS(IS) 540(M+1) $^1$H NMR(400MHz, CDCl$_3$): 4.67(d, 2H, J=6.4Hz); 5.56(s, 2H); 7.24(m, 4H); 7.40(m, 2H); 7.49(m, 2H); 7.70(bs, 1H); 7.85(s, 1H); 8.76(s, 2H) |
| 190 | 1-(3,5-bis-trifluoromethyl-benzyl)-5-pyridin-3-yl-1H-[1,2,3]triazole-4-carboxylic acid 2-chloro-benzylamide | MS(IS) 540(M+1) $^1$H NMR(400MHz, CDCl$_3$): 4.67(d, 2H, J=6.4Hz); 5.60(s, 2H); 7.24(m, 2H); 7.40(m, 2H); 7.45(m, 2H); 7.62(m, 1H); 7.70(m, 1H); 7.82(s, 1H); 8.53(s, 1H); 8.74(s, 1H) |

-continued

| Prep. # | Product | Physical Data |
|---|---|---|
| 191 | (R)-1-(3,5-bis-trifluoromethyl-benzyl)-5-pyridin-4-yl-1H-[1,2,3]triazole-4-carboxylic acid [1-(2-chloro-phenyl)-ethyl]-amide | MS(IS) 554(M+1) TLC: $R_f$=0.43(3% MeOH/CHCl$_3$) |
| 192 | (R)-1-(3,5-bis-trifluoromethyl-benzyl)-5-chloro-1H-[1,2,3]triazole-4-carboxylic acid [1-(2-chloro-phenyl)-ethyl]-amide | MS(IS) 511(M+1) TLC: $R_f$=0.59(50% EtOAc/hexanes) |
| 193 | 1-(3,5-bis-trifluoromethyl-benzyl)-5-chloro-1H-[1,2,3]triazole-4-carboxylic acid 2-chloro-4-fluoro-benzylamide | MS(IS) 515(M+1) TLC: $R_f$=0.58(3% MeOH/CHCl$_3$) |
| 194 | 1-(3,5-bis-trifluoromethyl-benzyl)-5-pyridin-3-yl-1H-[1,2,3]triazole-4-carboxylic acid [1-(2-chloro-phenyl)-ethyl]-amide | MS(IS) 554(M+1) TLC: $R_f$=0.39(3% MeOH/CHCl$_3$) |
| 195 | 1-(3,5-bis-trifluoromethyl-benzyl)-5-pyridin-4-yl-1H-[1,2,3]triazole-4-carboxylic acid 2-chloro-4-fluoro-benzylamide | MS(IS) 558(M+1) TLC: $R_f$=0.21(3% MeOH/CHCl$_3$) |
| 196 | 1-(3,5-Dichloro-benzyl)-5-pyridin-4-yl-1H-[1,2,3]triazole-4-carboxylic acid-2-chloro-benzylamide | MS(IS)472.1, 474.1(M+1) TLC $R_f$=0.43(7% MeOH/CH$_2$Cl$_2$) |
| 197 | 5-Chloro-1-(3,5-dichloro-benzyl)-1H-[1,2,3]triazole-4-carboxylic acid-2-chloro-benzylamide | MS(FAB) 429.0, 431.0 M$^+$. Rf=0.37(CH$_2$Cl$_2$). |
| 198 | 1-(3,5-bis-trifluoromethyl-benzyl)-5-pyrazin-2-yl-1H-[1,2,3]triazole-4-carboxylic acid 2-chloro-benzylamide | MS(IS) 536.0(M+1); TLC $R_f$=0.62(1:1 EtOAc/hexanes) |
| 199 | 1-(3,5-bis-trifluoromethyl-benzyl)-5-phenyl-1H-[1,2,3]triazole-4-carboxylic acid 2-chloro-benzylamide | MS(IS) 537.2(M−1) Rf=0.24(1:1 hexanes:EtOAc) |
| 200 | 1-(3,5-bis-trifluoromethyl-benzyl)-5-phenyl-1H-[1,2,3]triazole-4-carboxylic acid benzylamide | MS(IS) 505.2(M+1) Rf=0.13(3:1 hexanes:EtOAc) |
| 201 | 1-(3,5-bis-trifluoromethyl-benzyl)-5-phenyl-1H-[1,2,3]triazole-4-carboxylic acid 2-methyl-benzylamide | MS(IS) 519.1(M+1) Rf=0.21(3:1 hexanes:EtOAc) |
| 202 | 1-(3,5-bis-trifluoromethyl-benzyl)-5-phenyl-1H-[1,2,3]triazole-4-carboxylic acid 2-trifluoromethyl-benzylamide | MS(IS) 573.1(M+1) Rf=0.29(3:1 hexanes:EtOAc) |
| 203 | 1-(3,5-bis-trifluoromethyl-benzyl)-5-phenyl-1H-[1,2,3]triazole-4-carboxylic acid 2-bromo-benzylamide | MS(IS) 585.1(M+1) Rf=0.24(3:1 hexanes:EtOAc) |
| 204 | 1-(3,5-bis-trifluoromethyl-benzyl)-5-phenyl-1H-[1,2,3]triazole-4-carboxylic acid 4-fluoro-benzylamide | MS(IS) 523.1(M+1) Rf=0.14(3:1 hexanes:EtOAc) |
| 205 | 1-(3,5-bis-trifluoromethyl-benzyl)-5-phenyl-1H-[1,2,3]triazole-4-carboxylic acid 2,3-dichloro-benzylamide | MS(IS) 573.0(M+1) Rf=0.18(3:1 hexanes:EtOAc) |
| 206 | 1-(3,5-bis-trifluoromethyl-benzyl)-5-phenyl-1H-[1,2,3]triazole-4-carboxylic acid 2-chloro-4-fluoro-benzylamide | MS(IS) 557.1(M+1) Rf=0.20(3:1 hexanes:EtOAc) |
| 207 | 1-(3,5-bis-trifluoromethyl-benzyl)-5-phenyl-1H-[1,2,3]triazole-4-carboxylic acid p-tolylamide | MS(IS) 505.0(M+1) Rf=0.26(3:1 hexanes:EtOAc) |
| 208 | 1-(3,5-bis-trifluoromethyl-benzyl)-5-phenyl-1H-[1,2,3]triazole-4-carboxylic acid(2-chloro-phenyl)-amide | MS(IS) 525.1(M+1) Rf=0.44(3:1 hexanes:EtOAc) |
| 209 | 1-(3,5-bis-trifluoromethyl-benzyl)-5-phenyl-1H-[1,2,3]triazole-4-carboxylic acid [1-(4-fluoro-phenyl)-ethyl]-amide | MS(IS) 537.2(M+1) Rf=0.20(3:1 hexanes:EtOAc) |
| 210 | 1-(3,5-bis-trifluoromethyl-benzyl)-5-phenyl-1H-[1,2,3]triazole-4-carboxylic acid((S)-1-phenyl-ethyl)-amide | MS(IS) 519.2(M+1) Rf=0.18(3:1 hexanes:EtOAc) |
| 211 | 1-(3,5-bis-trifluoromethyl-benzyl)-5-phenyl-1H-[1,2,3]triazole-4-carboxylic acid phenylamide | MS(IS) 491.2(M+1) Rf=0.17(4:1 hexanes:EtOAc) |
| 212 | 1-(3,5-bis-trifluoromethyl-benzyl)-5-phenyl-1H-[1,2,3]triazole-4-carboxylic acid(2-chloro-4-methyl-phenyl)-amide | MS(IS) 539.0(M+1) Rf=0.38(3:1 hexanes:EtOAc) |
| 213 | 1-(3,5-bis-trifluoromethyl-benzyl)-5-phenyl-1H-[1,2,3]triazole-4-carboxylic acid(3,4-dichloro-phenyl)-amide | MS(IS) 559.0(M+1) Rf=0.42(3:1 hexanes:EtOAc) |
| 214 | 1-(3,5-bis-trifluoromethyl-benzyl)-5-phenyl-1H-[1,2,3]triazole-4-carboxylic acid(2,4-dichloro-phenyl)-amide | MS(IS) 557.0(M−1) Rf=0.34(3:1 hexanes:EtOAc) |

-continued

| Prep. # | Product | Physical Data |
|---|---|---|
| 215 | 1-(3,5-bis-trifluoromethyl-benzyl)-5-phenyl-1H-[1,2,3]triazole-4-carboxylic acid((R)-1-phenyl-ethyl)-amide | MS(IS) 519.1(M+1)<br>Rf=0.14(3:1 hexanes:EtOAc) |
| 216 | 1-(3,5-bis-trifluoromethyl-benzyl)-5-phenyl-1H-[1,2,3]triazole-4-carboxylic acid [1-(R)-(2-chloro-phenyl)-ethyl]-amide | MS(IS) 553.0(M+1)<br>Rf=0.31(3:1 hexanes:EtOAc) |
| 217 | 1-(3,5-bis-trifluoromethyl-benzyl)-5-phenyl-1H-[1,2,3]triazole-4-carboxylic acid(2-chloro-4-fluoro-phenyl)-amide | MS(IS) 543.0(M+1)<br>Rf=0.35(3:1 hexanes:EtOAc) |

General Preparation V

Combine the appropriate chloro-triazole (1 eq) and the appropriate amine (excess) and heat to 100° C. in a sealed tube, under $N_2$, overnight. Concentrate, dissolve the residue in 20% i-PrOH/CHCl$_3$, wash with saturated NaHCO$_3$ solution and brine. Dry the combined organic layers over MgSO$_4$, filter, and concentrate. Purify the residue by flash chromatography or by silica gel, hexanes/EtOAc 6:1 to 2:1 gradient, to give the title compound.

By a method similar to General Preparation V, the compounds listed below may be prepared and isolated.

| Prep. # | Product | Physical Data |
|---|---|---|
| 218 | 1-(3,5-bis-trifluoromethyl-benzyl)-5-morpholin-4-yl-1H-[1,2,3]triazole-4-carboxylic acid 2-chloro-benzylamide | MS(IS) 548(M+1)<br>$^1$H NMR(400MHz, CDCl$_3$): 3.06(t, 4H, J=4.7Hz); 3.75(t, 4H, J=4.7Hz); 4.72(d, 2H, J=6.4Hz); 5.57(s, 1H); 7.25(m, 2H); 7.39(m, 1H); 7.43(m, 1H); 7.68(bs, 1H); 7.83(s, 2H); 7.87(s, 1H) |
| 219 | 1-(3,5-bis-trifluoromethyl-benzyl)-5-dimethylamino-1H-[1,2,3]triazole-4-carboxylic acid 2-chloro-benzylamide | MS(IS) 506(M+1)<br>TLC: R$_f$=0.48(35% EtOAc/hexanes) |
| 220 | 1-(3,5-bis-trifluoromethyl-benzyl)-5-(4-methyl-piperazin-1-yl)-1H-[1,2,3]triazole-4-carboxylic acid 2-chloro-benzylamide | MS(IS) 561(M+1)<br>TLC: R$_f$=0.26(5% MeOH/CHCl$_3$) |
| 221 | 1-(3,5-bis-trifluoromethyl-benzyl)-5-thiomorpholin-4-yl-1H-[1,2,3]triazole-4-carboxylic acid 2-chloro-benzylamide | MS(IS) 564(M+1)<br>TLC: R$_f$=0.61(50% EtOAc/hexanes) |
| 222 | (R)-1-(3,5-bis-trifluoromethyl-benzyl)-5-morpholin-4-yl-1H-[1,2,3]triazole-4-carboxylic acid [1-(2-chloro-phenyl)-ethyl]-amide | MS(IS) 562(M+1)<br>TLC: R$_f$=0.44(3% MeOH/CHCl$_3$) |
| 223 | (R)-1-(3,5-bis-trifluoromethyl-benzyl)-5-(4-methyl-piperazin-1-yl)-1H-[1,2,3]triazole-4-carboxylic acid [1-(2-chloro-phenyl)-ethyl]-amide | MS(IS) 575(M+1)<br>TLC: R$_f$=0.17(3% MeOH/CHCl$_3$) |
| 224 | 1-(3,5-bis-trifluoromethyl-benzyl)-5-morpholin-4-yl-1H-[1,2,3]triazole-4-carboxylic acid 2-chloro-4-fluoro-benzylamide | MS(IS) 566(M+1)<br>TLC: R$_f$=0.34(50% EtOAc/hexanes) |
| 225 | 1-(3,5-bis-trifluoromethyl-benzyl)-5-(4-methyl-piperazin-1-yl)-1H-[1,2,3]triazole-4-carboxylic acid 2-chloro-4-fluoro-benzylamide | MS(IS) 579(M+1)<br>TLC: R$_f$=0.31(3% MeOH/CHCl$_3$) |
| 226 | 1-(3,5-bis-trifluoromethyl-benzyl)-5-dimethylamino-1H-[1,2,3]triazole-4-carboxylic acid 2-chloro-4-fluoro-benzylamide | MS(IS) 524(M+1)<br>TLC: R$_f$=0.43(1% MeOH/CHCl$_3$) |
| 227 | 3-[1-(3,5-bis-trifluoromethyl-benzyl)-5-chloro-1H-[1,2,3]triazol-4-yl]-5-(tert-butyl-dimethyl-silanyloxymethyl)-isoxazol-4-yl]-(2-morpholin-4-yl-phenyl)-methanone | TLC: R$_f$=0.65(2:1 hexanes/EtOAc)<br>MS/ES: 730.0(M+1) |

-continued

| Prep. # | Product | Physical Data |
|---|---|---|
| 228 | (±)-[3-[1-(3,5-bis-trifluoromethyl-benzyl)-5-chloro-1H-[1,2,3]triazol-4-yl]-5-(1-tert-butoxy-ethyl)-isoxazol-4-yl]-(2-morpholin-4-yl-phenyl)-methanone | TLC: $R_f$=0.54(2:1 hexanes/EtOAc)<br>MS/ES: 685.9(M+1) |
| 229 | 1-(3,5-dichloro-benzyl)-5-morpholin-4yl-1H-[1,2,3]triazole-4-carboxylic acid 2-chloro-benzylamide | MS(IS)502.0587[(M+Na)$^+$]<br>Rf=0.10(CH$_2$Cl$_2$). |
| 230 | {2-[[1-(3,5-bis-trifluoromethyl-benzyl)-5-morpholin-4-yl-1H-[1,2,3]triazole-4-carbonyl]-(2-chloro-benzyl)-amino]-ethyl}-carbamic acid tert-butyl ester | MS(IS) 691.1(M+1)<br>TLC $R_f$=0.40(1:1 EtOAc/hexanes) |
| 231 | (2-{[1-(3,5-bis-trifluoromethyl-benzyl)-5-morpholin-4-yl-1H-[1,2,3]triazole-4-carbonyl]-[1-(2-chloro-phenyl)-ethyl]-amino}-ethyl)-carbamic acid tert-butyl ester | MS(IS) 705.0(M+1)<br>TLC $R_f$=0.50(1:1 EtOAc/hexanes) |

Preparation 232

[1-(3,5-bis-trifluoromethyl-benzyl)-5-morpholin-4-yl-1H-[1,2,3]triazol-4-yl]-morpholin-4-yl-methanone Dissolve 1-(3,5-bis-trifluoromethyl-benzyl)-5-chloro-1H-[1,2,3]triazole-4-carboxylic acid ethyl ester in morpholine (20 eq). Stir at 70° C. overnight then increase temp to 80° C. and continue stirring for another 60 hours. Cool to RT, pour into separatory funnel with EtOAc and 1N HCl. Separate layers and wash organic layer with 1N HCl and then with brine. Dry over MgSO$_4$, filter, and concentrate. Purify via silica gel chromatography using a gradient of 1:1 to 1:5 hexanes:EtOAc to give the desired product. MS (IS) 494.2 (M+1). Rf=0.16 (1:1 Hexanes:EtOAc)

General Preparation W

Dissolve the N-Boc-protected amine of choice (1 eq) in HCl HOAc and stir at RT until the reaction is complete. Concentrate to dryness to achieve the title compound.

By a method analogous to General Preparation W, the following compounds may be prepared and isolated.

| Prep. # | Product | Physical Data |
|---|---|---|
| 233 | 1-(3,5-bis-trifluoromethyl-benzyl)-5-pyridin-4-yl-1H-[1,2,3]triazole-4-carboxylic acid(2-amino-ethyl)-(2-chloro-benzyl)-amide dihydrochloride | MS(IS) 583.1(M+1);<br>Anal Calcd for<br>C$_{26}$H$_{21}$ClF$_6$N$_6$0.2HCl:<br>C, 47.61; H, 3.53;<br>N, 12.81. Found:<br>C, 47.25; H, 3.42;<br>N, 12.44. |
| 234 | 1-(3,5-bis-trifluoromethyl-benzyl)-5-morpholin-4-yl-1H-[1,2,3]triazole-4-carboxylic acid(2-amino-ethyl)-(2-chloro-benzyl)-amide hydrochloride | MS(IS) 591.1(M+1);<br>HPLC trace(100%) |
| 235 | 1-(3,5-bis-trifluoromethyl-benzyl)-5-morpholin-4-yl-1H-[1,2,3]triazole-4-carboxylic acid(2-amino-ethyl)-[1-(2-chloro-phenyl)-ethyl]-amide dihydrochloride | MS(IS) 605.2(M+;<br>Anal. Calc'd for<br>C$_{26}$H$_{27}$ClF$_6$N$_6$O$_2$2.5HCl:<br>C, 44.86; H, 4.27;<br>N, 12.07. Found: C,<br>44.82; H, 4.51; N, 11.60. |

-continued

| Prep. # | Product | Physical Data |
|---|---|---|
| 236 | 1-(3,5-bis-trifluoromethyl-benzyl)-5-pyridyl-4-yl-1H-[1,2,3]triazole-4-carboxylic acid(2-amino-ethyl)-[1-(2-chloro-phenyl)-ethyl]-amide dihydrochloride | MS(IS) 598.1(M+1);<br>HPLC trace(98%) |

Preparation 237

N$^1$-(2-Chloro-4-fluoro-benzyl)-ethane-1,2-diamine

To a solution of [2-(2-Chloro-4-fluoro-benzylamino)-ethyl]-carbamic acid tert-tert-butyl ester (500 mg, 1.65 mmol) and anisole (538 μL, 4.95 mmol) in CH$_2$Cl$_2$ (8.25 mL), add TFA (1.39 mL, 18 mmol) and stir at RT for 12 hours. Pour the solution into separatory funnel and add 1N HCl until solution is acidic. Extract with CH$_2$Cl$_2$ (20 mL×2). To the aqueous portion, add 5N NaOH until solution is basic, and extract with CH$_2$Cl$_2$ (20 mL×2). Dry over Na$_2$SO$_4$ and concentrate to afford the title compound (196 mg, 59%). MS (IS) 203.1

By a method similar to Preparation 237, the following compounds may be prepared and isolated.

| Prep. # | Product | Physical Data |
|---|---|---|
| 238 | N$^1$-(2,3-Dichloro-benzyl)-ethane-1,2-diamine | 182 mg crude, 51%<br>MS(IS) 219.1(M+1) |
| 239 | N$^1$-(2-Trifluoromethyl-benzyl)-ethane-1,2-diamine | 123 mg crude, 35%<br>MS(IS) 219.0(M+1) |
| 240 | N$^1$-(2-methyl-benzyl)-ethane-1,2-diamine | 128 mg crude, 47%<br>MS(IS) 165.1(M+1) |
| 241 | N$^1$-p-tolyl-ethane-1,2-diamine | Quantative yield<br>MS(IS) 151.1(M+1)<br>Rf=0.11<br>100% MeOH |
| 242 | R-N$^1$-(1-Phenyl-ethyl)-ethane-1,2-diamine | 1.01 g crude, 81%<br>MS(IS) 165.2(M+1) |

-continued

| Prep. # | Product | Physical Data |
|---|---|---|
| 243 | S-N¹-(1-Phenyl-ethyl)-ethane-1,2-diamine | 1.08 g crude, 87% MS(IS) 165.2(M+1) |
| 244 | N1-(2-Chloro-benzyl)-propane-1,3-diamine | MS(IS) 199.2(M+1) |

Preparation 245

1-(3,5-bis-trifluoromethyl-benzyl)-4-(4,5-dihydro-1H-imidazol-2-yl)-5-phenyl-1H-[1,2,3]triazole To a solution of Me$_3$Al (1.36 mL, 2M soln in toluene) at 0° C. under N$_2$, add ethylenediamine (185 μL, 0.36 mmol) and stir for several minutes warming to RT. Add 1-(3,5-bis-trifluoromethyl-benzyl)-5-phenyl-1H-[1,2,3]triazole-4-carboxylic acid methyl ester (750 mg, 1.69 mmol) dissolved in toluene to this solution. Reflux reaction for 3.5 hours at 110° C. Cool to RT and stir for 12 hours. Quench reaction with MeOH (2 mL), add H$_2$O (2 mL) and extract with CH$_2$Cl$_2$ (4 mL×2). Dry over Na$_2$SO$_4$ and concentrate to afford title compound (30 mg, 4%). MS (IS) 440.1 (M+1).

Preparation 246

(4-methoxy-benzyloxy)-acetic acid methyl ester

Add sodium hydride (5.20 g, 130.0 mmol) to a stirred solution of bromoacetic acid (7.23 g, 52.0 mmol) in THF (150 mL). Stir reaction at RT until H$_2$ evolution ceases. Add a solution of p-methoxybenzyl alcohol (6.5 mL, 52.5 mmol) in THF (150 mL) to the reaction dropwise over 10 minutes at 0° C. Allow the reaction to warm to RT. After 30 minutes, add tetrabutylammonium bromide (0.97 g, 3.0 mmol) and heat to reflux for 4 hours. Cool reaction to 0° C., quench with EtOH (15 mL, absolute) and concentrate to get white solids. Partition between Et$_2$O and saturated NaHCO$_3$ solution and separate. Extract from organic layer with saturated sodium bicarbonate solution (2 times) and acidify combined aqueous layers with 10% H$_2$SO$_4$ solution. Extract from aqueous layer with Et$_2$O (3 times), dry the combined organic layers over MgSO$_4$, filter, and concentrate to afford 10.66 g of yellow oil. Add MeOH (200 mL) and p-toluene-sulfonic acid (50 mg, 0.26 mmol) to residue and heat to 60° C. for 4 hours. Allow to cool to RT under N$_2$ overnight. Concentrate, and then purify the residue by flash chromatography on silica gel, eluting with 0-25% EtOAc/hexanes to afford the title compound (8.05 g, 74%) as clear oil. TLC: R$_f$=0.29 (25% EtOAc/hexanes). $^1$H NMR (400 MHz, CDCl$_3$) δ 3.76 (s, 3H); 3.81 (s, 3H); 4.07 (s, 2H); 4.57 (s, 2H); 6.88 (d, 2H, J=8.3 Hz); 7.29 (d, 2H, J=8.3 Hz).

Preparation 247

(4-methoxy-benzyloxy)-acetic acid hydrazide

Add hydrazine hydrate (2.1 mL, 42.1 mmol) and pyridine (0.3 mL, 3.8 mmol) to a solution of (4-methoxy-benzyloxy)-acetic acid methyl ester (8.05 g, 38.3 mmol) in ethanol (100 mL, absolute). Heat the reaction to reflux under N$_2$ overnight. Concentrate; add toluene and concentrate (2 times). Purify the residue by flash chromatography on silica gel eluting with 0-40% ACN/CH$_2$Cl$_2$ to afford the title compound (6.42 g, 80%) as clear oil. $^1$H NMR (400 MHz, DMSO) δ 3.73 (s, 3H); 3.84 (s, 2H); 4.24 (bs, 2H); 4.42 (s, 2H); 6.89 (d, 2H, J=8.3 Hz); 7.27 (d, 2H, J=8.3 Hz); 9.00 (bs, 1H). MS(IS) 209 (M⁻).

Preparation 248

Triisopropylsilanyloxy-acetic acid hydrazide

Add 4.1 g imidazole (3 eq) to a solution of 1.8 g methyl glycolate (HOCH$_2$CO$_2$Me; 1 eq) in 30 ml DMF. Next, add 6.4 ml (1.5 eq) of triisopropylsilylchloride and stir overnight at RT. Pour into 30 ml saturated NaHCO$_3$ and extract with Et$_2$O (2×35 ml). Wash the combined organic layers with 1N HCl, water, and brine (25 ml each). Remove the solvent to give the silyl protected methyl glycolate, which is then dissolved in 20 ml THF. To this solution, add 1.6 ml NH$_2$NH$_2$ (2.5 eq). Heat the reaction to reflux overnight. Cool to RT, then pour into saturated NaHCO$_3$ (30 ml) and extract with Et$_2$O (3×20 ml). Remove the solvent to give the crude hydrazide, which was purified by recrystallizing from EtOAc/hexanes to give 2.85 g (58% yield) of the desired product. MS (IS) 247.1 (M+1); Rf=0.11 (2:1 hexanes: EtOAc).

General Preparation X

Dissolve 1 eq of the appropriate starting amide in 1,2-dichloroethane (0.05-0.21M). Add PCl$_5$ (1 eq) and stir at RT for 30 min. Next, add 1.8 to 3 eq of the desired hydrazide. Stir at 70° C. overnight. Pour into aqeous NaHCO$_3$ and extract with CH$_2$Cl$_2$. Wash the organic layer with 1N HCl and then with brine. Dry with Na$_2$SO$_4$ and concentrate. Purify via radial chromatography using a gradient of 1:1 to 1:5 hexanes: EtOAc.

By a method similar to General Procedure X, the following compounds may be prepared and isolated.

| Prep # | Product | Physical Data |
|---|---|---|
| 249 | 1-(3,5-bis-trifluoromethyl-benzyl)-4-[4-(2-chloro-benzyl)-5-triisopropylsilanyloxymethyl-4H-[1,2,4]triazol-3-yl]-5-phenyl-1H-[1,2,3]triazole | MS(IS) 749.2(M+1) Rf=0.37 (1:1 hexanes:EtOAc) |
| 250 | {3-(3,5-bis-trifluoromethyl-benzyl)-5-[4-(2-chloro-benzyl)-triisopropylsilanyloxymethyl-4H-[1,2,4]triazol-3-yl]-3H-[1,2,3]triazol-4-yl}-dimethylamine | MS(IS) 716.3(M+1) Rf=0.64 (1:1 hexanes:EtOAc) |

General Preparation Y

Dissolve the appropriate amide in toluene (0.04M-0.1M). Add 0.8 eq Lawesson's reagent. Heat reaction to 110° C. for 12-24 hours or until reaction is complete, as indicated by TLC. Cool to RT, pour into 20 ml water and extract with Et$_2$O. Wash combined organic layers with brine, dry with Na$_2$SO$_4$ and purify via radial chromatography using 4:1 hexanes:EtOAc to give the title compound.

By a method analogous to General Preparation Y, the following compounds may be prepared and isolated.

| Prep # | Product | Physical Data |
|---|---|---|
| 251 | 1-(3,5-bis-trifluoromethyl-benzyl)-5-phenyl-1H-[1,2,3]triazole-4-carbothioic acid 2-chloro-benzylamide | MS(IS) 555.0(M+1) Rf=0.34(3:1 Hexanes:EtOAc) |
| 252 | 1-(3,5-bis-trifluoromethyl-benzyl)-5-phenyl-1H-[1,2,3]triazole-4-carbothioic acid p-tolylamide | MS(IS) 555.0(M+1) |
| 253 | 1-(3,5-bis-trifluoromethyl-benzyl)-5-phenyl-1H-[1,2,3]triazole-4-carbothioic acid((S)-1-phenyl-ethyl)-amide | MS(IS) 535.2(M+1) Rf=0.38(3:1 Hexanes:EtOAc) |
| 254 | 1-(3,5-bis-trifluoromethyl-benzyl)-5-phenyl-1H-[1,2,3]triazole-4-carbothioic acid(2-chloro-phenyl)-amide | MS(IS) 541.0(M+1) Rf=0.37(4:1 Hexanes:EtOAc) |
| 255 | 1-(3,5-bis-trifluoromethyl-benzyl)-5-phenyl-1H-[1,2,3]triazole-4-carbothioic acid(3,4-dichloro-phenyl)-amide | MS(IS) 577.0(M+1) Rf=0.32(3:1 Hexanes:EtOAc) |

Preparation 256

(3,5-bis-trifluoromethyl-benzyl)-5-phenyl-1H-[1,2,3]triazole-4-carbaldehyde

Add sodium borohydride (1.70 g, 0.045 mol) to a solution of 1-(3,5-bis-trifluoromethylbenzyl)-5-phenyl-1H-[1,2,3]triazole-4-carboxylic acid ethyl ester (5.0 g, 0.011 mol) in EtOH (70 mL). Heat to reflux and stir for 2 hours. Cool to room temperature. Add the reaction mixture to 0.5 N HCl (200 mL) and methylene chloride (200 mL). Separate layers and extract aqueous layer with methylene chloride (50 mL). Combine organic layers, dry (magnesium sulfate), filter and concentrate to give [1-(3,5-bis-trifluoromethyl-benzyl)-5-phenyl-1H-[1,2,3]triazol-4-yl]-methanol. Dissolve [1-(3,5-bis-trifluoromethyl-benzyl)-5-phenyl-1H-[1,2,3]triazol-4-yl]-methanol (3.90 g, 0.0097 mol) in DMSO (30 mL) and add N,N-diispropylethylamine (6.77 mL, 0.039 mol). To this solution add sulfur trioxide pyridine complex (3.09 g, 0.019 mol) in DMSO (30 mL). Stir for 2 hours. Add the reaction mixture to ethyl acetate (150 mL) and 0.5 N HCl (200 mL), and separate layers. Extract aqueous layer with ethyl acetate (50 mL). Combine organic layers and wash with saturated, aqueous sodium bicarbonate (100 mL) and 1.0 N HCl (100 mL). Dry organic layers (magnesium sulfate), filter and concentrate to give the title compound: $^1$H NMR (500 MHz, DMSO) δ 9.91 (s, 1H), 8.02 (s, 1H), 7.69 (s, 2H), 7.55-7.49 (m, 5 H), 5.86 (s, 2 H); Mass spectrum (m/e): 400 (M$^+$1).

Preparation 257

1-(3,5-bis-trifluoromethyl-benzyl)-5-morpholin-4-yl-1H-[1,2,3]triazole-4-carbaldehyde Dissolve [1-(3,5-bis-trifluoromethyl-benzyl)-5-morpholin-4-yl-1H-[1,2,3]triazol-4-yl]-morpholin-4-yl-methanone in THF. Cool to −78° C., slowly add 28.3 ml (4 eq) of 1M diisobutyl aluminum hydride in toluene, and stir 2.5 hours. Move to 0° C. ice bath and allow reaction to slowly warm while stirring overnight. Slowly quench by adding ~5 ml 1N HCl while still at 0° C. then warming to RT. Pour into 50 ml 1N NaOH. Extract with EtOAc, then wash organic layer with 1N HCl. Concentrate organic layer to give the desired aldehyde, which can be used without further purification. MS (IS) 409.2 (M+1). Rf=0.61 (1:1 Hexanes:EtOAc)

General Preparation Z

Add 2 eq of hydroxylamine hydrochloride to a mixture of the appropriate aldehyde in MeOH. Next, add 2 eq of NaOAc and stir at RT until aldehyde is consumed, as indicated by TLC. Pour the reaction into NaHCO$_3$ and extract with EtOAc, dry over MgSO$_4$, filter, and concentrate. Recrystallize by dissolving in a minimal amount of warm EtOAc, adding twice as much hexane and cooling to −40° C. to give the desired oxime.

By a method similar to General Preparation Z, the following compounds may be prepared and isolated.

| Prep # | Product | Physical Data |
|---|---|---|
| 258 | 1-(3,5-bis-trifluoromethyl-benzyl)-5-morpholin-4-yl-1H-[1,2,3]triazole-4-carbaldehyde oxime | MS(IS) 424.2(M+1) Rf=0.43(1:1 hexanes:EtOAc) |
| 259 | 1-(3,5-bis-trifluoromethyl-benzyl)-5-phenyl-1H-[1,2,3]triazole-4-carbaldehyde oxime | MS(IS) 413.0(M−1) Rf=0.32(1:1 hexanes:EtOAc) |
| 260 | 1-(3,5-bis-trifluoromethyl-benzyl)-5-pyridin-4-yl-1H-[1,2,3]triazole-4-carbaldehyde oxime | MS(IS) 416.0(M+1) Rf=0.05(1:1 hexanes:EtOAc) |
| 261 | 1-(3,5-bis-trifluoromethyl-benzyl)-5-chloro-1H-[1,2,3]triazole-4-carbaldehyde oxime | m.p. 140° C. TLC: R$_f$=0.35(2:1 hexanes/EtOAc) MS(IS): 373.0(M+1) |

Preparation 262

1-(3,5-bis-trifluoromethyl-benzyl)-5-pyridin-3-yl-1H-[1,2,3]triazole-4-carbaldehyde oxime Add 3 eq sulfur trioxide pyridine complex (Aldrich) to a solution of [1-(3,5-bis-trifluoromethyl-benzyl)-5-pyridin-3-yl-1H-[1,2,3]triazol-4-yl]-methanol in DMSO, then add 10 eq TEA. Stir for 6 hours, pour into 15 ml 1N HCl and extract with EtOAc (2×20 ml). Remove solvent and dissolve the crude aldehyde in MeOH. Add 1.5 eq of hydroxyl amine hydrochloride and stir for 6 hours. Pour into 50 ml water and extract with EtOAc. Purify via radial chromatography 1:1 hexanes:EtOAc to give the title compound. MS (IS) 416.1 (M+1). Rf=0.16 (1:1 hexanes:EtOAc).

General Preparation AA

Add NCS (1 eq) in two portions to a solution of the appropriate oxime in DMF. Heat briefly with heat gun to help initiate reaction. Stir overnight, add another eq NCS and stir 5 hours. Dilute with CH$_2$Cl$_2$ then wash with water and brine. Recrystallize from EtOAc/hexanes to give the desired chlorooxime.

By a method similar to General Preparation AA, the following compounds may be prepared and isolated.

| Prep # | Product | Physical Data |
|---|---|---|
| 263 | 1-(3,5-bis-trifluoromethyl-benzyl)-5-phenyl-1H-[1,2,3]triazole-4-hydroxyimidoyl chloride | $^1$H NMR:(400MHz, CDCl$_3$) δ: 8.10(s, 1H), 7.82(s, 1H), 7.59-7.45(m, 5H), 7.19-7.16(m, 2H), 5.54(s, 2H). Rf=0.16(1:1 hexanes:EtOAc) |

-continued

| Prep # | Product | Physical Data |
|---|---|---|
| 264 | 1-(3,5-bis-trifluoromethyl-benzyl)-5-chloro-1H-[1,2,3]triazole-4-hydroxyimidoyl chloride | m.p. 150-155° C.(decomp.) TLC: $R_f$=0.55(2:1 hexanes/EtOAc) |

Preparation 265

1-(3,5-bis-trifluoromethyl-benzyl)-4-ethynyl-5-phenyl-1H-[1,2,3]triazole

To sodium hydride (188 mg of a 60% solution in mineral oil, 113 mg clean, 4.70 mmol) in 14 mL of benzene and 2.5 mL of tetrahydrofuran, add the (2-Oxo-propyl)-phosphonic acid dimethyl ester (743 mg, 618 μL, 4.48 mmol) as a solution in 5 mL of benzene at 0° C. dropwise. The mix remains white and produces some gas. After 1 h at 0° C., add tosyl azide (940 mg, 4.70 mmol) as a solution in 2.5 mL of benzene and remove the bath. After 2.3 hours, pour the mix through a plug of Celite® with tetrahydrofuran, benzene and ether. Concentrate and apply to a 4 mm chromatotron plate and elute with 100 mL of Hexanes, and then 200 mL of 20:80 EtOAc/Hexanes, 30:70 EtOAc/Hexanes, 50:50 Hexanes/EtOAc, 85:15 EtOAc/Hexanes and 250 ml of EtOAc to provide 794 mg of (1-Diazo-2-oxo-propyl)-phosphonic acid dimethyl ester as a yellow solid. This material may be used directly. Exact Mass 192.03: mass spectrum (aspci): m/z=165.0 (M+1 (—$N_2$).

To the (1-Diazo-2-oxo-propyl)-phosphonic acid dimethyl ester (794, 4.20 mmol) in 70 mL of methanol, add 1-(3,5-bis-trifluoromethyl-benzyl)-5-phenyl-1H-[1,2,3]triazole-4-carbaldehyde (1.44 g, 3.60 mmol) as a solution in 5 mL of methanol. To this mix, add (995 mg, 7.20 mmol) of potassium carbonate and mix the solution for 18 hours. Dilute with ether, saturated $NaHCO_3$ and extract with ether 3 times, wash the organics again with saturated $NaHCO_3$, and dry the combined organics with $MgSO_4$. Filter and concentrate. Purify by chromatography (silica gel, hexanes/EtOAc gradient) to provide 764 mg of the title compound. Exact Mass 395.09 spectrum (aspci): m/z=396.1 (M+1), 394.0 (M−1); $^1$H NMR (250 MHz, $CDCl_3$) δ 7.73 (s, 1H), 7.55-7.40 (m, 3H), 7.42-7.30 (m, 3H), 5.52 (s, 2H), 3.21 (s, H).

By a method analogous to Preparation 265, the following compounds may be prepared and isolated.

| Prep # | Product | Physical Data |
|---|---|---|
| 266 | 4-[3-(3,5-bis-trifluoromethyl-benzyl)-5-ethynyl-3H-[1,2,3]triazol-4-yl]-pyridine | Exact Mass 396.08 spectrum(aspci): m/z=397.1(M+1), 395.1(M−1); $^1$H NMR(250MHz, $CDCl_3$) δ 8.72(d, J=6.0Hz, 2H), 7.77(s, 1H), 7.48(s, 2H), 7.22(d, J=6.0Hz, 2H), 5.64(s, 2H), 3.22(s, 1H). |
| 267 | 1-(3,5-bis-trifluoromethyl-benzyl)-5-chloro-4-ethynyl-1H-[1,2,3]triazole | MS(IS) 353.9(M+1). $^1$HNMR(400MHz, $CDCl_3$) δ 7.88(s, 1H), 7.76(s, 2H), 5.61(s, 2H), 3.42(s, 1H). |

General Preparation BB

Dissolve the appropriate alkyne (9.76 mmol) in THF (50 mL) and cool to −78° C. Add a solution of MeMgBr (3 eq, 3.0M in ether) and stir at −78° C. for 1.5 hours, then add 2-chlorobenzaldehyde (3 eq). Stir solution at −78° C. for 1 hour, then at RT for 2 hours. Dilute the solution with ether (100 mL) and wash with 1N HCl (30 mL), saturated $NaHCO_3$ (50 mL), and brine (50 mL). Dry, filter, and concentrate the organic phase then purify the crude material by flash chromatography (silica gel, hexanes/EtOAc gradient) to give the title compound.

By a method similar to General Preparation BB, the following compounds may be prepared and isolated.

| Prep # | Product | Physical Data |
|---|---|---|
| 268 | 3-[1-(3,5-bis-trifluoromethyl-benzyl)-5-chloro-1H-[1,2,3]triazol-4-yl]-1-(2-chloro-phenyl)-prop-2-yn-1-ol | MS(IS) 493.9(M+1). $^1$HNMR(400MHz, $CDCl_3$) δ 7.87(s, 1H), 7.79(dd, 1H, J=2.0, 7.8), 7.75(s, 2H), 7.38(dd, 1H, J=1.5, 7.3), 7.30(m, 2H), 6.05(s, 1H), 5.60(s, 2H), 2.60(br s, 1H). |
| 269 | 3-[1-(3,5-bis-trifluoromethyl-benzyl)-5-phenyl-1H-[1,2,3]triazol-4-yl]-1-(2-chloro-phenyl)-prop-2-yn-1-ol | MS(IS) 536.0(M+1); $^1$H NMR(250MHz, $CDCl_3$) δ 7.71(s, 1H), 7.56(m, 1H), 7.43(s, 2H), 7.35-7.48(m, 3H), 7.09-7.34(m, 5H), 5.90(s, 1H), 5.57(s, 2H). |
| 270 | 3-[1-(3,5-bis-trifluoromethyl-benzyl)-5-pyridin-4-yl-1H-[1,2,3]triazol-4-yl]-1-(2-chloro-phenyl)-prop-2-yn-1-ol | MS(IS) 537.0(M+1) 535.0(M−1); $^1$H NMR(250MHz, $CDCl_3$) δ 8.65(d, J=6.25Hz, 2H), 7.77(s, 1H), 7.60(m, 1H), 7.48(s, 2H), 7.10-7.35(m, 5H), 5.92(s, 1H), 5.63(s, 2H). |

General Preparation CC

Under $N_2$, charge an oven-dried flask with oxalyl chloride (2M in $CH_2Cl_2$, 1.2 eq) and chill in a dry ice/acetone slush. Add DMSO (3 eq) slowly by syringe and stir 45 minutes. Add the alcohol of interest (1 eq) in anhydrous $CH_2Cl_2$ (0.4 M) slowly by syringe and stir 1 hour. Add TEA (5 eq) slowly by syringe and stir 90 minutes while warming to room temp. Quench with saturated aqueous $NH_4Cl$ and $H_2O$, extract with ether, wash combined organics with brine, dry over $MgSO_4$, filter and concentrate under vacuum. Purify by flash chromatography (silica gel, EtOAc/Hexane gradient) to give the title compound.

By a method similar to General Preparation CC, the following compounds may be prepared and isolated.

| Prep. # | Product | Physical Data |
|---|---|---|
| 271 | 3-[1-(3,5-bis-trifluoromethyl-benzyl)-5-phenyl-1H-[1,2,3]triazol-4-yl]-1-(2-chloro-phenyl)-propynone | MS(IS) 534.0(M+1), $^1$H NMR(CDCl3): δ 8.03(m, 1H), 7.86(s, 1H), 7.63-7.30(m, 10H), 5.70(s, 2H). |
| 272 | 3-[1-(3,5-bis-trifluoromethyl-benzyl)-5-pyridin-4-yl-1H-[1,2,3]triazol-4-yl]-1-(2-chloro-phenyl)-propynone | MS(IS) 534.9(M+1), $^1$H NMR(300MHz, CDCl3): δ 8.86(d, J=6.0Hz, 2H), 8.02(ap d, 1H), 7.90(s, 1H), 7.60(s, 2H), 7.56-7.31(m, 5H), 5.74(s, 2H). |

Preparation 273

3-[1-(3,5-bis-trifluoromethyl-benzyl)-5-chloro-1H-[1,2,3]triazol-4-yl]-1-(2-chloro-phenyl)-propynone Dissolve 3-[1-(3,5-bis-trifluoromethyl-benzyl)-5-chloro-1H-[1,2,3]triazol-4-yl]-1-(2-chloro-phenyl)-prop-2-yn-1-ol (1 eq) in CH$_2$Cl$_2$ (50 mL) and add Dess-Martin periodinane (1.3 eq). Stir at RT for 3 h and dilute with EtOAc (100 mL). Wash the organic solution with 1N NaOH (50 mL) and saturated NaHCO$_3$ (50 mL), then dry, filter, and concentrate. Purify the crude material by flash chromatography to give the title compound. MS (IS) 491.8 (M+1). $^1$H NMR (400 MHz, CDCl$_3$) δ 8.11 (m, 1H), 7.90 (s, 1H), 7.78 (s, 2H), 7.48 (m, 2H), 7.40 (m, 1H), 5.65 (s, 2H).

General Preparation DD

Dissolve 1.1 eq of an appropriate alkyne in THF. Cool to 0° C. and slowly add 1.5 eq LDA (1.5M in cyclohexane) and stir 30 min. Add an appropriate aldehyde (1 eq). Stir 20 min. then move to RT and stir overnight. Pour into 1N HCl and extract with EtOAc. Dry, filter, and concentrate. Then, redissolve the crude alcohol in toluene or CH$_2$Cl$_2$ and add 5 eq of MnO$_2$. Sonicate the reaction mixture for 5-10 min, then stir overnight, heating if necessary. Filter reaction mixture through a plug of Celite® and silica gel. Purify via chromatography using a gradient of 10:1 to 6:1 to 3:1 hexanes:EtOAc to give the desired compound.

By a method analogous to General Preparation DD, the following compounds may be prepared and isolated.

| Prep # | Product | Physical Data |
|---|---|---|
| 274 | 1-(2-Chloro-phenyl)-4,4-diethoxy-but-2-yn-1-one | $^1$H NMR:(400MHz, CDCl$_3$) δ: 8.03, d(J=7Hz), 1H; 7.47-7.45. m, 2H; 7.40-7.36, m, 1H; 5.47, s, 1H; 3.83-3.75, m, 2H; 3.70-3.63, m, 2H; 1.26, t(J=7Hz), 6H Rf=0.32(10:1 hexanes:EtOAc) |
| 275 | 1-(2-Chloro-phenyl)-4-methyl-4-trimethylsilanyloxy-pent-2-yn-1-one | $^1$H NMR:(400MHz, CDCl$_3$) δ: 7.76, d(J=7.9Hz), 1H; 7.25, d(J=3.6Hz), 2H; 7.20-7.15, m, 1H; 1.39, s, 6H; 0.00, s, 9H. Rf=0.74(6:1 hexanes:EtOAc). |
| 276 | (±)-4-tert-Butoxy-1-(2-chloro-phenyl)-pent-2-yn-1-one | TLC: R$_f$=0.57(hexanes/EtOAc) MS/ES: 208.9[M−C(CH$_3$)$_3$]$^+$ |
| 277 | 4-(tert-Butyl-dimethyl-silanyloxy)-1-(2-chloro-phenyl)-but-2-yn-1-one | TLC: R$_f$=0.67(5:1 hexanes/EtOAc) MS/ES: 309.1(M+1) |
| 278 | 1-(2-Chlorophenyl)-but-2-yn-1-one | m.p. 35° C. TLC: R$_f$=0.50(5:1 hexanes/EtOAc) MS/ES: 178.9(M+1). Prepared using butynylmagnesium bromide(Aldrich). |
| 279 | 1-(2-Chloro-4-fluoro-phenyl)-but-2-yn-1-one | m.p. 91-93° C. TLC: R$_f$=0.51(5:1 hexanes/EtOAc) MS/ES: 196.9(M+1). Prepared using butynylmagnesium bromide(Aldrich). |
| 280 | 4-(tert-Butyl-dimethyl-silanyloxy)-1-(2-chloro-4-fluoro-phenyl)-but-2-yn-1-one | TLC: R$_f$=0.70(5:1 hexanes/EtOAc) MS/ES: 327.0(M+1) |

Preparation 281

1-(2-Chloro-phenyl)-4-hydroxy-4-methyl-pent-2-yn-1-one

Add 1.5 eq N,O-dimethylhydroxylamine hydrochloride to a solution of 2-chlorobenzoyl chloride in CH$_2$Cl$_2$. Cool to 0° C., then slowly add 2 eq pyridine and stir overnight while slowly warming to RT. Pour into 100 ml water and extract with CH$_2$Cl$_2$. Dry organic layer with Na$_2$SO$_4$, filter and concentrate. Redissolve the crude amide in THF. In a separate flask, cool a solution of 1.2 eq [(1,1-dimethyl-2-propynyl)oxy]trimethylsilane in THF to −78° C. Slowly add 1.2 eq LDA (1.5 M in cyclohexane), stir 10 min., then warm to 0° C. Stir at 0° C. for 40 min., then transfer via cannula into the amide solution (also at 0° C.). Let reaction stir overnight while warming to RT. Pour into saturated NH$_4$Cl and extract with EtOAc. Purify via radial chromatography using a gradient of 6:1 to 3:1 hexanes:EtOAc to give the free alkynyl alcohol. $^1$H NMR (400 MHz, CDCl$_3$) δ 7.98-7.97, m, 1H, 7.44-7.33, m, 3H, 1.62, s, 6H. Rf=14 (4:1 hexanes: EtOAc).

Preparation 282

1-(2-Chloro-phenyl)-3-(N-methoxy-N-methyl-amino)-2-propenone

Treat a solution of 2-chloro-N-methoxy-N-methyl-benzamide (1.0 eq) in THF with ethynylmagnesium bromide (2.0 eq) at 0° C. Stir the mixture for 2 hours, then warm to room temperature. Add aqueous saturated NH$_4$Cl solution slowly. Extract with ether. Dry the combined organic layers with anhydrous MgSO$_4$, filter and concentrate in vacuo. Purify by chromatography on silica gel to give the desired compound. MS (IS) 226.1 (M+1); TLC (50% EtOAc in hexanes): Rf=0.1.

Preparation 283

(1,1-Dimethyl-2-nitro-ethoxy)-trimethyl-silane

To a solution of nitromethane (100 g, 1.64 mmol) and acetone (5 mL), add a catalytic amount of tetramethylguanidine. Using a syringe pump, add acetone (115 mL, 1.64 mmol) over a period of 72 hours to the stirred solution at RT. Separately, combine chlorotrimethylsilane (206 mL, 1.64 mmol) and imidazole (123 g, 1.8 mmol) at 0° C. Transfer the nitromethane/acetone mixture into the silyl-imidazole mixture and allow this new solution to stir 18 hours at RT. Then cool the reaction to 0° C., dilute with cold ether (450 mL) and wash with cold 1N HCl (200 mL×2). Wash the organic layer with brine (300 mL). Carefully concentrate the crude material in vacuo without heating. Purify by distillation to provide the title compound. R$_t$=3.85 (GC Initial Temp 100° C.(5 min), 20°/min, Final Temp 180° C. (5 min)).

General Preparation EE

Combine a solution of the appropriate alkyne (1 eq) and (1,1-Dimethyl-2-nitro-ethoxy)-trimethyl-silane (1.5 eq) in benzene or toluene (0.25 M). Add 1,4-phenylene diisocyanate (3 eq) and stir at RT for 10 min. Add a catalytic amount of triethylamine and bring the solution to reflux. After 18 hours, add an additional 1.5 eq of the nitro compound, and 1,4-phenylene diisocyanate (2 eq), and more triethylamine (catalytic). Repeat the previous step as needed until the alkyne is consumed. While still warm, quench the reaction with H$_2$O and stir for 30 min, allowing the reaction to cool. Dilute with CH$_2$Cl$_2$, add 1N HCl, and pass solution through Varian ChemElute® drying cartridge. Wash the drying cartridge with CH$_2$Cl$_2$ several times, then concentrate the organic layer. Purify the residue by chromatography (silica gel, hexanes/EtOAc gradient) to provide the desired compound.

By a method similar to General Preparation EE, the following compounds are prepared and isolated.

| Prep # | Product (Chemical Name) | Physical Data |
| --- | --- | --- |
| 284 | [4-[1-(3,5-bis-trifluoromethyl-benzyl)-5-pyridin-4-yl-1H-[1,2,3]triazol-4-yl]-3-(1-methyl-1-trimethylsilanyloxy-ethyl)-isoxazol-5-yl]-(2-chloro-phenyl)-methanone | Rf=0.23 2:1 Hex/EtOAc MS(IS) 708.2(M+1) |
| 285 | [4-[1-(3,5-bis-trifluoromethyl-benzyl)-5-phenyl-1H-[1,2,3]triazol-4-yl]-3-(1-methyl-1-trimethylsilanyloxy-ethyl)-isoxazol-5-yl]-(2-chloro-phenyl)-methanone | Rf=0.70 2:1 Hex/EtOAc MS(IS) 707.2(M+1) |

General Preparation FF

Combine the alkyne of interest (1 eq) in benzene or toluene (0.1 M), with the appropriate nitro compound (1.5 eq), 1,4-phenylene diisocyanate (3 eq) and TEA (10 drops/mmol A). Attach a reflux condensor and heat to reflux. After 20 hours, add additional nitro compound (0.5 eq), 1,4-phenylene diisocyanate (1 eq) and TEA, stir 6 hours. Remove from heat, add H$_2$O and stir 20 min. Filter through Celite®, remove H$_2$O, dry over MgSO$_4$, filter and concentrate under vacuum. Purify by chromatography on silica gel to give the title compound.

By a method similar to General Preparation FF, the following compounds may be prepared and isolated.

| Prep. # | Product | Physical Data |
| --- | --- | --- |
| 286 | [5-[1-(3,5-bis-trifluoromethyl-benzyl)-5-phenyl-1H-[1,2,3]triazol-4-yl]-3-(tetrahydro-pyran-2-yloxymethyl)-isoxazol-4-yl]-(2-chloro-phenyl)-methanone | TLC(30% EtOAc/Hexenex2), Rf=0.30. |
| 287 | [5-[1-(3,5-bis-trifluoromethyl-benzyl)-5-pyridin-4-yl-1H-[1,2,3]triazol-4-yl]-3-(tetrahydro-pyran-2-yloxymethyl)-isoxazol-4-yl]-(2-chloro-phenyl)-methanone | TLC(3% MeOH/CH$_2$Cl$_2$), Rf=0.53. |
| 288 | [5-[1-(3,5-bis-trifluoromethyl-benzyl)-5-phenyl-1H-[1,2,3]triazol-4-yl]-3-(2,2-dimethoxy-ethyl)-isoxazol-4-yl]-(2-chloro-phenyl)-methanone | MS(IS) 665.0(M+1); TLC(30% EtOAc/Hexane), Rf=0.42. |
| 289 | [5-[1-(3,5-bis-trifluoromethyl-benzyl)-5-pyridin-4-yl-1H-[1,2,3]triazol-4-yl]- | MS(IS) 665.9(M+1); TLC(30% EtOAc/Hexane), Rf=0.16. |

-continued

| Prep. # | Product | Physical Data |
|---|---|---|
| 290 | 3-(2,2-dimethoxy-ethyl)-isoxazol-4-yl]-(2-chloro-phenyl)-methanone {5-[1-(3,5-bis-trifluoromethyl-benzyl)-5-phenyl-1H-[1,2,3]triazol-4-yl]-3-[2-(tetrahydro-pyran-2-yloxy)-ethyl]-isoxazol-4-yl}-(2-chloro-phenyl)-methanone | MS(IS) 621.0(M+1); TLC(30% EtOAc/Hexane), Rf=0.22. |
| 291 | {4-[1-(3,5-bis-trifluoromethyl-benzyl)-5-phenyl-1H-[1,2,3]triazol-4-yl]-3-[2-(tetrahydro-pyran-2-yloxy)-ethyl]-isoxazol-5-yl}-(2-chloro-phenyl)-methanone | MS(IS) 621.0(M+1), TLC(30% EtOAc/Hexane), Rf=0.19 |
| 292 | {5-[1-(3,5-bis-trifluoromethyl-benzyl)-5-pyridin-4-yl-1H-[1,2,3]triazol-4-yl]-3-[2-(tetrahydro-pyran-2-yloxy)-ethyl]-isoxazol-4-yl}-(2-chloro-phenyl)-methanone | MS(IS) 621.9(M+1), TLC(50% EtOAc/Hexanex2), Rf=0.15, 0.24 |

General Preparation GG

Dissolve an appropriate chloro-oxime (1 eq) and the desired alkyne (2 eq) in EtOAc (0.5 M). Add triethylamine (1.2 eq) as a 1 M solution in EtOAc dropwise over 15 min. After 18 hours, dilute with EtOAc (10 mL), wash with 1N HCl (5 mL) and brine (5 mL). Dry ($MgSO_4$), filter, and concentrate. Purify the residue by chromatography (silica gel, hexanes/EtOAc gradient) to give the title compound.

By a method analogous to General Preparation GG, the following compounds may be prepared and isolated.

| Prep. # | Product | Physical Data |
|---|---|---|
| 293 | (R,S)-[3-[1-(3,5-bis-trifluoromethyl-benzyl)-5-chloro-1H-[1,2,3]triazol-4-yl]-5-(1-tert-butoxy-ethyl)-isoxazol-4-yl]-(2-chloro-phenyl)-methanone | TLC: $R_f$=0.71(2:1 hexanes/EtOAc) MS/ES: 634.9(M+1), 578.8[M−C(CH$_3$)$_3$] |
| 294 | {3-[1-(3,5-bis-trifluoromethyl-benzyl)-5-chloro-1H-[1,2,3]triazol-4-yl]-5-(tert-butyl-dimethyl-silanyloxymethyl)-isoxazol-4-yl]}-(2-chloro-phenyl)-methanone | TLC: $R_f$=0.77(2:1 hexanes/EtOAc) MS/ES: 678.9(M+1) |

Preparation 295

1-[1-(3,5-bis-trifluoromethyl-benzyl)-5-pyridin-3-yl-1H-[1,2,3]triazol-4-yl]-3-(2-chloro-phenyl)-propane-1,3-dione Add lithium diisopropylamide (6 mL, 1.0 M in THF) to a solution of 1-(2-chloro-phenyl)-ethanone (0.929 g, 6.01 mmol) in THF (10 mL) at −78° C. and stir for 30 min. To the above enolate solution at −78° C., add a solution of 1-(3,5-bis-trifluoromethyl-benzyl)-5-pyridin-3-yl-1H-[1,2,3]triazole-4-carboxylic acid methoxy-N-methyl-amide (1.29 g, 2.81 mmol) in THF (15 mL) via cannula. Warm solution to 70° C. and stir for 4 hours, than add 1N HCl (6 mL) and stir for an additional 30 min. Concentrate the mixture in vacuo to ¼ volume, dilute with EtOAc (60 mL) and wash with water (30 mL), saturated $NaHCO_3$ (30 mL), and brine (30 mL). Dry, filter, and concentrate the organic phase and purify the crude material by flash chromatography using a linear gradient of 20% to 80% EtOAc/hexanes to give the title compound (1.07 g, 69%) as an orange foam. MS (IS) 553.2 (M+1), MS (ES−) 551.2 (M−1). $^1$H NMR (400 MHz, $CDCl_3$): δ 15.5 (m, 1H), 7.78 (dd, 1H, J=1.3, 4.8), 8.54 (d, 1H, J=2.2), 7.81 (s, 1H), 7.64 (dd, 1H, J=2.0, 7.7), 7.57 (dt, 1H, J=2.0, 7.9), 7.44 (m, 4H), 7.38 (dt, 1H, J=1.8, 7.5), 7.33 (dt, 1H, J=1.5, 7.5), 7.19 (s, 1H), 5.59 (s, 2H).

Preparation 296

1-[1-(3,5-bis-trifluoromethyl-benzyl)-5-pyridin-3-yl-1H-[1,2,3]triazol-4-yl]-2-bromo-3-(2-chloro-phenyl)-propane-1,3-dione Add bromine (28 μL, 0.54 mmol) to a mixture of 1-[1-(3,5-bis-trifluoromethyl-benzyl)-5-pyridin-3-yl-1H-[1,2,3]triazol-4-yl]-3-(2-chloro-phenyl)-propane-1,3-dione (256 mg, 0.463 mmol) in 1:1 $CH_2Cl_2$:$H_2O$ (4 mL). Stir mixture at RT for 30 min, then dilute with additional $CH_2Cl_2$ (20 mL) and wash with $NaHCO_3$ (20 mL). Dry, filter, and concentrate the organic layer to give the title compound (287 mg, 98%). MS (IS) 553.2 (M+1), MS (ES−) 551.2 (M−1). $^1$HNMR (400 MHz, $CDCl_3$): δ 7.80 (m, 1H), 8.53 (m, 1H), 7.85 (m, 2H), 7.63 (m, 1H), 7.46 (m, 7H), 7.04 (s, 1H), 5.60 (m, 2H).

Preparation 297

[1-(3,5-bis-trifluoromethyl-benzyl)-5-phenyl-1H-[1,2,3]triazol-4-yl]-[5-(2-chloro-phenyl)-3-[1,3]dioxolan-2-ylmethyl-3H-[1,2,3]triazol-4-yl]-methanone In a pressure vessel, combine 1-[1-(3,5-bis-trifluoromethyl-benzyl)-5-phenyl-1H-[1,2,3]triazol-4-yl]-3-(2-chloro-phenyl)-propynone (1 eq) in toluene (0.1 M), and 2-azidomethyl-[1,3]dioxolane (2 eq). Heat in a 120° C. bath for 48 hours. Then concentrate and purify by chromatography on silica gel to give the title compound. MS (IS) 663.6 (M+1), $^1$H NMR ($CDCl_3$): δ 7.85 (br s, 1H), 7.78 (dd, J=7.7, 1.6 Hz, 1H), 7.61-7.49 (m, 3H), 7.41-7.10 (m, 7H), 5.46 (s, 2H), 5.32 (t, J=3.0 Hz, 1H), 4.97 (d, J=3.0 Hz, 2H), 3.70 (m, 4H).

Preparation 298

Trifluoro-methanesulfonic acid 2-(2-chloro-benzoyl)-pyridin-3-yl ester

Add diisopropylethylamine (0.09 mL, 0.52 mmol) to a 0° C. solution of (2-chloro-phenyl)-(3-hydroxy-pyridin-2-yl)-methanone (102 mg, 0.44 mmol) in $CH_2Cl_2$ (3 mL). Add triflic anhydride (0.09 mL, 0.52 mmol) dropwise and allow reaction to warm slowly to RT. Dilute with 20% i-PrOH/CHCl$_3$, wash with 0.1N HCl (2×) and saturated NaHCO$_3$ solution. Dry the combined organic layers over MgSO$_4$ and concentrate. Purify the residue by flash chromatography on silica gel eluting with 0-50% Et$_2$O/hexanes to afford the title compound (149 mg, 93%) as yellow oil. MS(IS) 366 (M+1). TLC: R$_f$=0.30 (50% Et$_2$O/hexanes).

Preparation 299

(2-chloro-phenyl)-(3-hydroxy-pyridin-2-yl)-methanone

Add trifluoroacetic acid (5 mL) to a solution of (2-chloro-phenyl)-[3-(2-trimethylsilanyl-ethoxymethoxy)-pyridin-2-yl]-methanone (195 mg, 0.54 mmol) in CH$_2$Cl$_2$ (3 mL), stir for 30 minutes. Concentrate; dissolve in 20% i-PrOH/CHCl$_3$, wash with saturated NaHCO$_3$ solution (×2). Dry the combined organic layers over MgSO$_4$ and concentrate. Purify the residue by flash chromatography on silica gel eluting with 0-30% Et$_2$O/hexanes to afford the title compound (102 mg, 82%) as white solid. MS(IS) 233.9 (M+1). TLC: R$_f$=0.20 (25% Et$_2$O/hexanes).

Preparation 300

(2-chloro-phenyl)-[3-(2-trimethylsilanyl-ethoxymethoxy)-pyridin-2-yl]-methanone

Add manganese oxide (II) (463 mg, 5.33 mmol) to a solution of (2-chloro-phenyl)-[3-(2-trimethylsilanyl-ethoxymethoxy)-pyridin-2-yl]-methanol (390 mg, 1.07 mmol) in toluene (20 mL), heat to reflux overnight. Filter mixture through Celite® and concentrate. Purify the residue by flash chromatography on silica gel eluting with 0-20% EtOAc/hexanes to afford the title compound (195 mg, 49%) as pink oil. MS(IS) 364 (M+1). TLC: R$_f$=0.45 (35% EtOAc/hexanes).

Preparation 301

(2-chloro-phenyl)-[3-(2-trimethylsilanyl-ethoxymethoxy)-pyridin-2-yl]-methanol

Add t-BuLi dropwise to a cooled (−78° C.) solution of 4trimethylsilanyl-3-(2-trimethylsilanyl-ethoxymethoxy)-pyridine (1.57 g, 5.3 mmol) in Et$_2$O (15 mL, freshly distilled over Na$^0$). After 1 hour, add 2-chloro-benzaldehyde (0.71 mL, 6.3 mmol) dropwise and allow reaction to warm slowly to RT. After 2 hours, quench reaction with dropwise addition of water (5 mL). Wash with saturated NaHCO$_3$ solution and brine. Dry the combined organic layers over MgSO$_4$ and concentrate. Purify the residue by flash chromatography on silica gel eluting with 0-20% EtOAc/hexanes to afford the silyl protected intermediate (1.61 g). Dissolve the residue in tetrabutylammoniumfluoride solution (20 mL, 1.0 M in THF), and stir for 1 hour. Concentrate and dissolve the residue in EtOAc. Wash with 1N HCl (3×), saturated NaHCO$_3$ solution, and brine. Dry the combined organic layers over MgSO$_4$ and concentrate. Purify the residue by flash chromatography on silica gel eluting with 0-25% EtOAc/hexanes to afford the title compound (394 mg, 20%) as clear oil. MS(IS) 366 (M+1). TLC: R$_f$=0.37 (30% Et$_2$O/hexanes).

Preparation 302

4-trimethylsilanyl-3-(2-trimethylsilanyl-ethoxymethoxy)-pyridine

Add t-BuLi dropwise to a −78° C. solution of 3-(2-trimethylsilanyl-ethoxymethoxy)-pyridine (1.98 g, 8,8 mmol) in Et$_2$O (25 mL, freshly distilled over Na$^0$). After 1 hour, add chlorotrimethylsilane (1.33 mL, 10.5 mmol) dropwise and allow reaction to warm slowly to RT. After 1.5 hours, add water (5 mL) dropwise to quench. Wash with saturated NaHCO$_3$ solution and brine. Dry the combined organic layers over MgSO$_4$ and concentrate. Purify the residue by flash chromatography on silica gel eluting with 0-30% EtOAc/hexanes to afford the title compound (1.57 g, 60%) as yellow oil. MS(IS) 298 (M+1). TLC: R$_f$=0.38 (35% EtOAc/hexanes).

Preparation 303

3-(2-trimethylsilanyl-ethoxymethoxy)-pyridine

Add potassium tert-butoxide (2.69 g, 24 mmol) to a 0° C. solution of 3-hydroxy-pyridine (1.90 g, 20 mmol) in DMF (30 mL) and THF (30 mL) stirring under N$_2$. Add 2-(trimethylsilyl)ethoxy-methyl chloride (3.72 mL, 21 mmol) dropwise and allow to warm slowly to RT overnight. Add water to quench, stir for 5 minutes and concentrate. Dissolve in 20% i-PrOH/CHCl$_3$, wash with saturated NaHCO$_3$ solution (2×) and brine. Dry the combined organic layers over MgSO$_4$ and concentrate. Purify the residue by flash chromatography on silica gel eluting with 0-50% EtOAc/hexanes to afford the title compound (3.14 g, 70%) as yellow liquid. MS(IS) 226 (M+1). TLC: R$_f$=0.43 (50% EtOAc/hexanes).

EXAMPLES

Example 1

{2-[1-(3,5-bis-trifluoromethyl-benzyl)-5-methyl-1H-[1,2,3]triazol-4-yl]-pyridin-3-yl}-(2-chloro-phenyl)-methanone

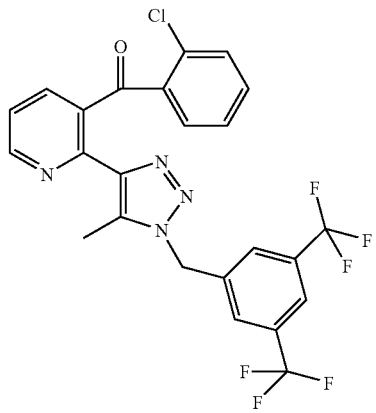

Dissolve (2-bromo-pyridin-3-yl)-(2-chloro-phenyl)-methanone (148 mg, 0.50 mmol) and 1-(3,5-bis-trifluoromethyl-benzyl)-5-methyl-4-tributylstannanyl-1H-[1,2,3]triazole (449 mg, 0.75 mmol) in DMF (5 mL) and degass, then add dichlorobis(triphenylphosphine) palladium (70 mg, 0.10 mmol). Seal the mixture under N$_2$ and heat at 80° C. for 24 hours. Concentrate, dissolve in CHCl$_3$, wash with saturated potassium fluoride solution (2×), saturated potassium bicarbonate solution, brine, dry over MgSO$_4$ and concentrate. Purify the residue by flash chromatography on silica gel eluting with 0-40% EtOAc/hexane followed by recrystallization from EtOAc/hexane to afford the title compound (142 mg, 54%). MS(IS) 525 (M+1); TLC (60% EtOAc/hexane) R$_f$=0.30.

Using a method similar to Example 1, using the appropriate starting materials and catalyst, the title compounds are prepared and isolated.

| Ex # | Product | Physical Data |
|---|---|---|
| 2 | {2-[1-(3,5-bis-trifluoromethyl-benzyl)-5-phenyl-1H-[1,2,3]triazol-4-yl]-pyridin-3-yl}-(2-chloro-phenyl)-methanone | MS(IS) 587(M+1); TLC: R$_f$=0.18(5% ACN/CH$_2$Cl$_2$) |
| 3 | {2-[1-(3,5-bis-trifluoromethyl-benzyl)-5-pyridin-3-yl-1H-[1,2,3]triazol-4-yl]-pyridin-3-yl}-(2-chloro-phenyl)-methanone | MS(IS) 588(M+1); TLC: R$_f$=0.30(20% ACN/CH$_2$Cl$_2$) |
| 4 | {2-[1-(3,5-bis-trifluoromethyl-benzyl)-5-morpholin-4-yl-1H-[1,2,3]triazol-4-yl]-pyridin-3-yl}-(2-chloro-phenyl)-methanone | MS(IS) 596(M+1); TLC: R$_f$=0.46(20% ACN/CH$_2$Cl$_2$) |
| 5 | {2-[1-(3,5-bis-trifluoromethyl-benzyl)-5-pyrimidin-5-yl-1H-[1,2,3]triazol-4-yl]-pyridin-3-yl}-(2-chloro-phenyl)-methanone | MS(IS) 589(M+1); TLC: R$_f$=0.48(10% ACN/Et$_2$O) |
| 6 | {2-[1-(3,5-bis-trifluoromethyl-benzyl)-5-pyrazin-2-yl-1H-[1,2,3]triazol-4-yl]-pyridin-3-yl}-(2-chloro-phenyl)-methanone | MS(IS) 589(M+1); TLC: R$_f$=0.60(10% ACN/Et$_2$O) |
| 7 | {2-[1-(3,5-bis-trifluoromethyl-benzyl)-5-cyclopropyl-1H-[1,2,3]triazol-4-yl]-pyridin-3-yl}-(2-chloro-phenyl)-methanone | MS(IS) 551.0(M+1); TLC: R$_f$=0.50(10% MeOH/CHCl$_3$) |
| 8 | {2-[1-(3,5-bis-trifluoromethyl-benzyl)-5-pyridin-4-yl-1H-[1,2,3]triazol-4-yl]-phenyl}-(2-chloro-phenyl)-methanone | MS(IS) 587(M+1); TLC: R$_f$=0.29(75% EtOAc/hexane) |
| 9 | {3-[1-(3,5-bis-trifluoromethyl-benzyl)-5-pyridin-3-yl-1H-[1,2,3]triazol-4-yl]-pyridin-4-yl}-(2-chloro-phenyl)-methanone | MS(IS) 588(M+1); TLC: R$_f$=0.24(5% MeOH/CH$_2$Cl$_2$) |
| 10 | {3-[1-(3,5-bis-trifluoromethyl-benzyl)-5-morpholin-4-yl-1H-[1,2,3]triazol-4-yl]-pyridin-4-yl}-(2-chloro-phenyl)-methanone | MS(IS) 596(M+1); TLC: R$_f$=0.18(10% ACN/Et$_2$O) |
| 11 | {3-[1-(3,5-bis-trifluoromethyl-benzyl)-5-methyl-1H-[1,2,3]triazol-4-yl]-pyridin-4-yl}-(2-chloro-phenyl)-methanone | MS(IS) 525(M+1); TLC: R$_f$=0.38(10% ACN/Et$_2$O) |
| 12 | {3-[1-(3,5-bis-trifluoromethyl-benzyl)-5-pyrimidin-5-yl-1H-[1,2,3]triazol-4-yl]-pyridin-4-yl}-(2-chloro-phenyl)-methanone | MS(IS) 589(M+1); TLC: R$_f$=0.17(10% ACN/Et$_2$O) |
| 13 | {3-[1-(3,5-bis-trifluoromethyl-benzyl)-5-pyrazin-2-yl-1H-[1,2,3]triazol-4-yl]-pyridin-4-yl}-(2-chloro-phenyl)-methanone | MS(IS) 589(M+1); TLC: R$_f$=0.35(10% ACN/Et$_2$O) |
| 14 | {3-[1-(3,5-bis-trifluoromethyl-benzyl)-5-pyridin-4-yl-1H-[1,2,3]triazol-4-yl]-pyridin-4-yl}-(2-chloro-phenyl)-methanone | MS(IS) 588(M+1); TLC: R$_f$=0.17(20% ACN/Et$_2$O) |
| 15 | {3-[1-(3,5-bis-trifluoromethyl-benzyl)-5-pyridin-2-yl-1H-[1,2,3]triazol-4-yl]-pyridin-4-yl}-(2-chloro-phenyl)-methanone | MS(IS) 588(M+1); TLC: R$_f$=0.28(5% ACN/Et$_2$O) |
| 16 | {3-[1-(3,5-bis-trifluoromethyl-benzyl)-5-cyclopropyl-1H-[1,2,3]triazol-4-yl]-6-methyl-pyridazin-4-yl}-(2-chloro-phenyl)-methanone | Exact Mass 565.11; mass spectrum(IS): m/z=568.1(M+1), 566.1(M−1); $^1$H NMR(300MHz, CDCl$_3$) δ 7.80(s, 1H), 7.61(s, 2H), 7.43(s, 1H), 7.20-7.06(m, 4H), 5.53(s, 2H), 2.80(s, 3H), 1.67(m, 1H), 1.02-0.91(m, 2H), 0.56-0.48(m, 2H). |

-continued

| Ex # | Product | Physical Data |
|---|---|---|
| 17 | 3-[1-(3,5-bis-trifluoromethyl-benzyl)-5-cyclopropyl-1H-[1,2,3]triazol-4-yl]-4-(2-chloro-benzyl)-6-methyl-pyridazine | Exact Mass 551.13; mass spectrum(IS): m/z=554.1(M+1), 552.0(M−1); $^1$H NMR(300MHz, CDCl$_3$) δ 7.77(s, 1H), 7.70(s, 2H), 7.62-7.48(m, 2H), 7.45-6.88(m, 3H), 6.83(s, 1H), 5.65(s, 2H), 4.15(s, 2H), 2.53(s, 3H), 1.60(m, 1H), 0.85-0.71(m, 2H), 0.22-0.11(m, 2H). |
| 18 | {3-[1-(3,5-bis-trifluoromethyl-benzyl)-5-pyridin-3-yl-1H-[1,2,3]triazol-4-yl]-6-methyl-pyridazin-4-yl}-(2-chloro-phenyl)-methanone | Exact Mass 602.11: mass spectrum(IS): m/z=605.1(M+1), 603.1(M−1); $^1$H NMR(300MHz, CDCl$_3$) δ 8.25-8.70(m, 3H), 7.73(s, 1H), 7.70(m, 1H), 7.51-7.65(m, 3H), 7.08-7.50(m, 4H), 5.42(s, 2H), 2.71(s, 3H). |
| 19 | 3-[1-(3,5-bis-trifluoromethyl-benzyl)-5-pyridin-3-yl-1H-[1,2,3]triazol-4-yl]-4-(2-chloro-benzyl)-6-methyl-pyridazine | Exact Mass 588.13: mass spectrum(IS): m/z=591.1(M+1), 589.1(M−1); $^1$H NMR(300MHz, CDCl$_3$) δ 8.47(dd, J=6.5, 0.2Hz, 1H), 8.16(d, J=0.2Hz, 1H), 7.78(m, 1H), 7.62(s, 1H), 7.48(m, 2H), 7.33(s, 2H), 6.80-7.24(m, 4H), 6.73(s, 1H), 5.40(s, 2H), 4.28(s, 2H), 2.40(s, 3H). |
| 20 | {3-[1-(3,5-bis-trifluoromethyl-benzyl)-5-pyrimidin-5-yl-1H-[1,2,3]triazol-4-yl]-6-methyl-pyridazin-4-yl}-(2-chloro-phenyl)-methanone | Exact Mass 603.10: mass spectrum(IS): m/z=604.1(M+1), 602.1(M−1); $^1$H NMR(300MHz, CDCl$_3$) δ 9.30-9.11(m, 1H), 8.50-8.72(m, 2H), 7.77(s, 2H), 7.67(dd, J=7.2, 0.8Hz, 1H), 7.53-7.65(m, 2H), 7.33-7.52(m, 2H), 7.10-7.32(m, 2H), 5.44(s, 2H), 2.74(s, 3H). |
| 21 | {3-[1-(3,5-bis-trifluoromethyl-benzyl)-5-pyridin-4-yl-1H-[1,2,3]triazol-4-yl]-6-methyl-pyridazin-4-yl}-(2-chloro-phenyl)-methanone | Exact Mass 603.1: mass spectrum(IS): m/z=603.1(M+1), 601.1(M−1); $^1$H NMR(300MHz, CDCl$_3$) δ 8.67(bd, J=6.8Hz, 2H), 7.82(s, 1H), 7.62(m, 1H), 7.42(m, 1H), 7.37(s, 2H), 7.10-7.25(m, 5H), 5.41(s, 2H), 2.71(s, 3H). |
| 22 | {3-[1-(3,5-bis-trifluoromethyl-benzyl)-5-isopropyl-1H-[1,2,3]triazol-4-yl]-6-methyl-pyridazin-4-yl}-(2-chloro-phenyl)-methanone | Exact Mass 601.1: mass spectrum(IS): m/z=570.1(M+1), 568.1(M−1); $^1$H NMR(300MHz, CDCl$_3$) δ 7.77(s, 1H), 7.60(dd, J=7.5, 2.5Hz, 1H), 7.52(s, 1H), 7.47(s, 2H), 7.25-7.10(m, 3H), 5.53(s, 2H), 2.76(s, 3H), 1.60(m, 1H), 1.25(d, J=7.5Hz, 6H). |
| 23 | 3-[1-(3,5-bis-trifluoromethyl-benzyl)-5-isopropyl-1H-[1,2,3]triazol-4-yl]-4-(2-chloro-benzyl)-6-methyl-pyridazine | Exact Mass 553.15: mass spectrum(IS): m/z=556.1(M+1), 554.1(M−1); $^1$H NMR(300MHz, CDCl$_3$) δ 7.82(s, 1H), 7.64(s, 2H), 7.26(bd, J=7.5Hz, 1H), 7.00-7.23(m, 3H), 6.75(s, 1H), 5.67(s, 2H), 4.27(s, 2H), 2.60(s, 1H), 1.58(m, 1H), 1.10(d, J=7.5Hz, 6H). |
| 24 | {3-[1-(3,5-bis-trifluoromethyl-benzyl)-5-phenyl-1H-[1,2,3]triazol-4-yl]-6-methyl-pyridazin-4-yl}-(2-chloro-phenyl)-methanone | Exact Mass 601.11: mass spectrum(IS): m/z=602.1(M+1), 600.1(M−1); $^1$H NMR(300MHz, CDCl$_3$) δ 7.22(s, 1H), 7.57(m, 1H), 7.43-7.29(m, 7H), 7.10-7.22(m, 5H), 5.36(s, 2H), 2.70(s, 3H). |
| 25 | {3-[1-(3,5-bis-trifluoromethyl-benzyl)-5-methyl-1H-[1,2,3]triazol-4-yl]-6-methyl-pyridazin-4-yl}-(2-chloro-phenyl)-methanone | Exact Mass 539.09: mass spectrum(IS): m/z=540.1(M+1), 538.0(M−1); $^1$H NMR(300MHz, CDCl$_3$) δ 7.78(s, 1H), 7.69(m, 1H), 7.52(s, 2H), 7.42(m, 1H), 7.10-7.31(m, 4H), 5.45(s, 2H), 2.78(s, 3H), 2.57(s, 3H). |
| 26 | {3-[1-(3,5-bis-trifluoromethyl-benzyl)-5-pyrazin-2-yl-1H-[1,2,3]triazol-4-yl]-6-methyl-pyridazin-4-yl}-(2-chloro-phenyl)-methanone | Exact Mass 603.1: mass spectrum(IS): m/z=604.1(M+1), 602.0(M−1); $^1$H NMR(300MHz, CDCl$_3$) δ 9.45(m, 1H), 8.69(m, 1H), 8.62(m, 1H), 7.81(s, 1H), 7.71(m, 1H), 7.70(s, 2H), 7.57(s, 1H), 7.10-7.29(m, 3H), 5.83(s, 2H), 2.75(s, 3H). |
| 27 | 2-{2-[1-(3,5-bis-trifluoromethyl-benzyl)-5-phenyl-1H-[1,2,3]triazol-4-yl]-benzoyl}-benzonitrile | Exact Mass 576.1: mass spectrum(IS): m/z=577.1(M+1); $^1$H NMR(250MHz, CDCl$_3$) δ7.80-7.10(m, 1H), 6.95(m, 1H), 6.68(m, 1H), 6.37-6.48(m, 2H), 5.70(d, J=7.0Hz, 1H), 5.35(s, 1H). |
| 28 | {3-[1-(3,5-bis-trifluoromethyl-benzyl)-5-pyridin-4-yl-1H-[1,2,3]triazol-4-yl]-pyridazin-4-yl}-(2-chloro-phenyl)-methanone | MS(IS) 589.1(M+1), $^1$H NMR(CDCl$_3$): 9.29(d, J=5.1Hz, 1H), 8.74(br s, 2H), 7.84(s, 1H), 7.76(m, 1H), 7,.62(d, J=5.1Hz, 1H), 7.45(s, 2H), 7.34-7.23(m, 5H), 5.48(s, 2H). |

-continued

| Ex # | Product | Physical Data |
|---|---|---|
| 29 | {3-[1-(3,5-bis-trifluoromethyl-benzyl)-5-methyl-1H-[1,2,3]triazol-4-yl]-pyridazin-4-yl}-(2-chloro-phenyl)-methanone | MS(IS) 526.0(M+1), $^1$H NMR(CDCl$_3$): 9.31(d, J=5.1Hz, 1H), 7.87(s, 1H), 7.79(dd, J=7.4, 2.0Hz, 1H), 7.61(m, 3H), 7.34-7.25(m, 3H), 5.54(s, 2H). |
| 30 | {3-[1-(3,5-bis-trifluoromethyl-benzyl)-5-pyridin-3-yl-1H-[1,2,3]triazol-4-yl]-pyridazin-4-yl}-(2-chloro-phenyl)-methanone | MS(IS) 589.0(M+1), $^1$H NMR(CDCl$_3$): 9.28(d, J=5.0Hz, 1H), 8.73(br s, 1H), 8.46(br s, 1H), 7.85-7.25(m, 10H), 5.49(s, 2H). |
| 31 | {3-[1-(3,5-bis-trifluoromethyl-benzyl)-5-pyrazin-2-yl-1H-[1,2,3]triazol-4-yl]-pyridazin-4-yl}-(2-chloro-phenyl)-methanone | MS(IS) 590.0(M+1), $^1$H NMR(CDCl$_3$): 9.38(d, J=5.2Hz, 1H), 9.03(s, 1H), 8.66(m, 2H), 7.80(s, 1H), 7.75-7.71(m, 2H), 7.67(s, 2H), 7.27-7.14(m, 3H), 5.85(s, 2H). |
| 32 | {3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone | MS(IS) 590.0(M+1), $^1$H NMR(CDCl$_3$): 9.30(m, 1H), 8.71(s, 1H), 7.85(s, 1H), 7.83-7.26(m, 9H), 5.52(s, 2H). |
| 33 | {2-[1-(3,5-bis-trifluoromethyl-benzyl)-5-phenyl-1H-[1,2,3]triazol-4-yl]-phenyl}-phenyl-methanone | MS(IS) 552.0(M+1) TLC Rf=0.1(6% acetone in hexanes) |
| 34 | {2-[1-(3,5-bis-trifluoromethyl-benzyl)-5-pyridin-4-yl-1H-[1,2,3]triazol-4-yl]-pyridin-3-yl}-phenyl-methanone | MS(IS) 554.1(M+1) TLC Rf=0.1(20% ether in hexanes) |
| 35 | {2-[1-(3,5-bis-trifluoromethyl-benzyl)-5-pyridin-4-yl-1H-[1,2,3]triazol-4-yl]-pyridin-3-yl}-o-tolyl-methanone | MS(IS) 568.0(M+1); TLC(50% acetone in hexanes): Rf=0.3. |
| 36 | {2-[1-(3,5-bis-trifluoromethyl-benzyl)-5-pyridin-4-yl-1H-[1,2,3]triazol-4-yl]-pyridin-3-yl}-(2-methoxy-phenyl)-methanone | MS(IS) 584.0(M+1); TLC(50% acetone in hexanes): Rf=0.3. |
| 37 | {2-[1-(3,5-bis-trifluoromethyl-benzyl)-5-pyridin-4-yl-1H-[1,2,3]triazol-4-yl]-pyridin-3-yl}-(2-trifluoromethyl-phenyl)-methanone | MS(IS) 622.0(M+1); TLC(50% acetone in hexanes): Rf=0.3. |
| 38 | {2-[1-(3,5-bis-trifluoromethyl-benzyl)-5-pyridin-4-yl-1H-[1,2,3]triazol-4-yl]-pyridin-3-yl}-(2-fluoro-phenyl)-methanone | MS(IS) 572.0(M+1); TLC(50% acetone in hexanes): Rf=0.3. |
| 39 | {2-[1-(3,5-bis-trifluoromethyl-benzyl)-5-pyridin-4-yl-1H-[1,2,3]triazol-4-yl]-pyridin-3-yl}-(3-chloro-phenyl)-methanone | MS(IS) 588.0(M+1); TLC(50% acetone in hexanes): Rf=0.3. |
| 40 | {2-[1-(3,5-bis-trifluoromethyl-benzyl)-5-pyridin-4-yl-1H-[1,2,3]triazol-4-yl]-pyridin-3-yl}-(4-chloro-phenyl)-methanone | MS(IS) 588.0(M+1); TLC(50% acetone in hexanes): Rf=0.3. |
| 41 | {5-[1-(3,5-bis-trifluoromethyl-benzyl)-5-pyridin-4-yl-1H-[1,2,3]triazol-4-yl]-pyrimidin-4-yl}-(2-chloro-phenyl)-methanone | MS(IS) 589.0(M+1), MS(ES−) 587.1(M−1). $^1$HNMR(400MHz, CDCl$_3$) δ 9.21(s, 1H), 8.74(s, 1H), 8.65(m, 2H), 7.84(s, 1H), 7.64(dd, 1H, J=1.4, 7.8), 7.52(s, 2H), 7.45(m, 1H), 7.36(m, 1H), 7.34(m, 1H), 7.07(m, 2H), 5.58(s, 2H). |
| 42 | {5-[1-(3,5-bis-trifluoromethyl-benzyl)-5-pyridin-3-yl-1H-[1,2,3]triazol-4-yl]-pyrimidin-4-yl}-(2-chloro-phenyl)-methanone | MS(IS) 5 89.0(M+1), MS(ES−) 587.1(M−1). $^1$HNMR(400MHz, CDCl$_3$) δ 9.19(s, 1H), 8.78(s, 1H), 8.64(m, 1H), 8.42(s, 1H), 7.81(s, 1H), 7.63(dd, 1H, J=1.5, 7.3), 7.47(s, 2H), 7.42(m, 2H), 7.34(m, 2H), 7.27(m, 1H), 5.56(s, 2H). |
| 43 | {5-[1-(3,5-bis-trifluoromethyl-benzyl)-5-pyrimidin-5-yl-1H-[1,2,3]triazol-4-yl]-pyrimidin-4-yl}-(2-chloro-phenyl)-methanone | MS(IS) 590.0(M+1), MS(ES−) 588.1(M−1). $^1$HNMR(400MHz, CDCl$_3$) δ 9.22(s, 1H), 9.17(s, 1H), 8.88(s, 1H), 8.50(s, 2H), 7.84(s, 1H), 7.59(dd, 1H, J=1.5, 7.6), 7.49(s, 2H), 7.45(m, 1H), 7.34(m, 2H), 5.61(s, 2H). |
| 44 | {5-[1-(3,5-bis-trifluoromethyl-benzyl)-5-cyclopropyl-1H-[1,2,3]triazol-4-yl]-pyrimidin-4-yl}-(2-chloro-phenyl)-methanone | MS(IS) 552.0(M+1), MS(ES−) 550.1(M−1). $^1$HNMR(400MHz, CDCl$_3$) 89.28(s, 1H), 9.03(s, 1H), 7.87(s, 1H), 7.74(s, 2H), 7.70(dd, 1H, J=1.5, 7.8), 7.40(m, 1H), 7.31(m, 1H), 7.29(m, 1H), 5.67(s, 2H), 1.61(m, 1H), 1.01(m, 2H), 0.46(m, 2H). |

-continued

| Ex # | Product | Physical Data |
|---|---|---|
| 45 | 3-[1-(3,5-bis-trifluoromethyl-benzyl)-5-pyridin-4-yl-1H-[1,2,3]triazol-4-yl]-4-(2-chloro-benzyl)-6-methyl-pyridazine | Rf 0.166(85% EtOAc/15% Hex); $^1$H NMR(300MHz, CDCl$_3$) δ 8.77(bd, J=7.5Hz, 2H), 7.87(s, 1H), 7.40-7.61(m, 5H), 7.20-7.35 7.35(m, 3H), 5.73(s, 2H), 5.52(s, 2H), 2.72(s, 3H). |
| 46 | 4-(2-Benzyl-phenyl)-1-(3,5-bis-trifluoromethyl-benzyl)-5-phenyl-1H-[1,2,3]triazole | Exact Mass 537.5: mass spectrum(aspci): m/z=538.1(M+1), 536.1(M−1); $^1$H NMR(250MHz, CDCl$_3$) δ 7.76(s, 1H), 7.82-7.68(m, 4H), 7.51(s, 2H), 7.35-7.5(m, 4H), 7.22-7.33(m, 2H), 6.9-7.15(m, 3H), 6.75-6.83(m, 2H), 6.60-6.69(m, 2H), 5.56(s, 2H), 4.14(s, 2H). |
| 47 | {3-[1-(3,5-bis-trifluoromethyl-benzyl)-5-pyridin-4-yl-1H-[1,2,3]triazol-4-yl]-pyrazin-2-yl}-(2-chloro-phenyl)-methanone | MS(IS) 589(M$^+$+1) TLC: R$_f$=0.41(10% ACN/Et$_2$O) |

Example 48

(2-chloro-phenyl)-{2-[5-pyridin-4-yl-1-(3-trifluoromethyl-benzyl)-1H-[1,2,3]triazol-4-yl]-pyridin-3-yl}-methanone

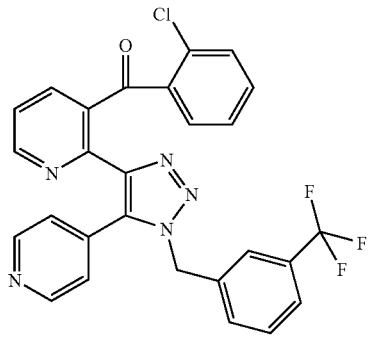

Add 1-azidomethyl-3-trifluoromethyl-benzene (152 mg, 0.75 mmol), (2-chloro-phenyl)-(2-pyridin-4-ylethynyl-pyridin-3-yl)-methanone (200 mg, 0.63 mmol), and toluene (2 mL) to a sealed tube. Flush with nitrogen, seal, and heat at 150° C. overnight. Concentrate to dryness and triturate with diethyl ether to afford the title compound (66 mg, 20%) as a pink solid: MS(IS) 520(M+1); TLC (5% MeOH/dichloromethane) R$_f$=0.48.

By using a method similar to Example 48, with the appropriate starting materials, the following compounds are prepared and isolated.

| Ex. # | Product | Physical Data |
|---|---|---|
| 49 | (2-chloro-phenyl)-{2-[1-(3-fluoro-5-trifluoromethyl-benzyl)-5-pyridin-3-yl-1H-[1,2,3]triazol-4-yl]-pyridin-3-yl}-methanone | MS(IS) 538(M+1); TLC: R$_f$=0.46(5% MeOH/CH$_2$Cl$_2$) |
| 50 | (2-chloro-phenyl)-{2-[1-(2-fluoro-5-trifluoromethyl-benzyl)-5-pyridin-3-yl-1H-[1,2,3]triazol-4-yl]-pyridin-3-y1}-methanone | MS(IS) 538(M+1); TLC: R$_f$=0.40(5% MeOH/CH$_2$Cl$_2$) |
| 51 | (2-chloro-phenyl)-{2-[1-(4-fluoro-3-trifluoromethyl-benzyl)-5-pyridin-3-yl-1H-[1,2,3]triazol-4-yl]-pyridin-3-yl}-methanone | MS(IS) 538(M+1); TLC: R$_f$=0.42(5% MeOH/CH$_2$Cl$_2$) |
| 52 | (2-chloro-phenyl)-{2-[1-(2-fluoro-5-trifluoromethyl-benzyl)-5-pyridin-4-yl-1H-[1,2,3]triazol-4-yl]-pyridin-3-yl}-methanone | MS(IS) 538(M+1); TLC: R$_f$=0.46(5% MeOH/CH$_2$Cl$_2$) |
| 53 | (2-chloro-phenyl)-{2-[5-pyridin-4-yl-1-(3-trifluoromethyl-benzyl)-1H-[1,2,3]triazol-4-yl]-pyridin-3-yl}-methanone | MS(IS) 520(M+1); TLC: R$_f$=0.48(5% MeOH/CH$_2$Cl$_2$) |
| 54 | (2-chloro-phenyl)-{2-[5-pyridin-4-yl-1-(3-trifluoromethoxy-benzyl)-1H-[1,2,3]triazol-4-yl]-pyridin-3-yl}-methanone | MS(IS) 536(M+1); TLC: R$_f$=0.47(5% MeOH/CH$_2$Cl$_2$) |

-continued

| Ex. # | Product | Physical Data |
|---|---|---|
| 55 | {2-[1-(2,5-bis-trifluoromethyl-benzyl)-5-pyridin-4-yl-1H-[1,2,3]triazol-4-yl]-pyridin-3-yl}-(2-chloro-phenyl)-methanone | MS(IS) 589(M+1); TLC: R$_f$=0.42(5% MeOH/CHCl$_3$) |
| 56 | (2-chloro-phenyl)-{2-[1-(4-fluoro-3-trifluoromethyl-benzyl)-5-pyridin-4-yl-1H-[1,2,3]triazol-4-yl]-pyridin-3-yl}-methanone | MS(IS) 538(M+1); TLC: R$_f$=0.35(5% MeOH/CH$_2$Cl$_2$) |
| 57 | {2-[1-(3,5-bis-trifluoromethyl-benzyl)-5-pyridin-2-yl-1H-[1,2,3]triazol-4-yl]-pyridin-3-yl}-(2-chloro-phenyl)-methanone | MS(IS) 588(M+1); TLC(5% MeOH/CH$_2$Cl$_2$) R$_f$=0.59 |
| 58 | (2-Chloro-phenyl)-{2-[1(3-fluoro-5-trifluoromethyl-benzyl)-5-isopropyl-1H-[1,2,3]triazol-4-yl]-pyridin-3-yl}-methanone | R$_f$=0.47 1:1 Hex/EtOAc MS(IS) 503.1(M+1) |
| 59 | {2-[1-(3,5-bis-trifluoromethyl-benzyl)-5-isopropyl-1H-[1,2,3]triazol-4-yl]-pyridin-3-yl}-(2-chloro-phenyl)-methanone | MS(IS) 553.1(M+1) R$_f$=0.49 1:1 Hex/EtOAc |
| 60 | (2-Chloro-phenyl)-{2-[5-pyridin-3-yl-1-(3-trifluoromethyl-benzyl)-1H-[1,2,3]triazole-4-yl]-pyridin-3-yl}-methanone | MS(IS)520.1, 522.2(M+1), R$_f$=0.19(50% EtOAc/CH$_2$Cl$_2$ |
| 61 | (2-chloro-phenyl)-{2-[1-(3,5-dichloro-benzyl)-5-pyridin-3-yl-1H-[1,2,3]triazol-4-yl]-pyridin-3-yl}-methanone | MS(IS) 520.1(M+1); TLC R$_f$=0.41(10% MeOH/CHCl$_3$) |
| 62 | (2-chloro-phenyl)-{2-[1-(3,5-dimethyl-benzyl)-5-pyridin-3-yl-1H-[1,2,3]triazol-4-yl]-pyridin-3-yl}-methanone | MS(IS) 480.2(M+1); TLC R$_f$=0.43(10% MeOH/CHCl$_3$) |
| 63 | {2-[1-(2,5-bis-trifluoromethyl-benzyl)-5-pyridin-3-yl-1H-[1,2,3]triazol-4-yl]-pyridin-3-yl}-(2-chloro-phenyl)-methanone | MS(IS) 588.2(M+1); TLC R$_f$=0.46(10% MeOH/CHCl$_3$) |
| 64 | (2-chloro-phenyl)-{2-[1-(3-fluoro-5-trifluoromethyl-benzyl)-5-pyridin-4-yl-1H-[1,2,3]triazol-4-yl]-pyridin-3-yl}-methanone | MS(IS) 538.2(M+1); TLC R$_f$=0.33 0.33(10% MeOH/CHCl$_3$) |
| 65 | (2-chloro-phenyl)-{2-[1-(3,5-dichloro-benzyl)-5-pyridin-4-yl-1H-[1,2,3]triazol-4-yl]-pyridin-3-yl}-methanone | MS(IS) 520.1(M+1);TLC R$_f$=0.45(10% MeOH/CHCl$_3$) |
| 66 | (2-chloro-phenyl)-{2-[1-(3,5-dimethyl-benzyl)-5-pyridin-4-yl-1H-[1,2,3]triazol-4-yl]-pyridin-3-yl}-methanone | MS(IS) 480.1(M+1); TLC R$_f$=0.51(10% MeOH/CHCl$_3$) |
| 67 | (2-chloro-phenyl)-{2-[1-(3-fluoro-5-trifluoromethyl-benzyl)-5-pyrimidin-5-yl-1H-[1,2,3]triazol-4-yl]-pyridin-3-yl}-methanone | MS(IS) 539.1(M+1); TLC R$_f$=0.40(10% MeOH/CHCl$_3$) |
| 68 | (2-chloro-phenyl)-{2-[5-pyrimidin-5-yl-1-(3-trifluoromethyl-benzyl)-1H-[1,2,3]triazol-4-yl]-pyridin-3-yl}-methanone | MS(IS) 521.0(M+1); TLC R$_f$=0.26(10% MeOH/CHCl$_3$) |
| 69 | (2-chloro-phenyl)-{2-[1-(4-fluoro-3-trifluoromethyl-benzyl)-5-pyrimidin-5-yl-1H-[1,2,3]triazol-4-yl]-pyridin-3-yl}-methanone | MS(IS) 539.1(M+1); TLC R$_f$=0.26(10% MeOH/CHCl$_3$) |
| 70 | (2-chloro-phenyl)-{2-[1-(2-fluoro-5-trifluoromethyl-benzyl)-5-pyrimidin-5-yl-1H-[1,2,3]triazol-4-yl]-pyridin-3-yl}-methanone | MS(IS) 539.2(M+1); TLC R$_f$=0.51(10% MeOH/CHCl$_3$) |
| 71 | (2-chloro-phenyl)-{2-[5-pyrimidin-5-yl-1-(3-trifluoromethoxy-benzyl)-1H-[1,2,3]triazol-4-yl]-pyridin-3-yl}-methanone | MS(IS) 537.1(M+1); TLC R$_f$=0.55(10% MeOH/CHCl$_3$) |
| 72 | {2-[1-(2,5-bis-trifluoromethyl-benzyl)-5-pyrimidin-5-yl1H-[1,2,3]triazol-4-yl]-pyridin-3-yl}-(2-chloro-phenyl)-methanone | MS(IS) 589.1(M+1); TLC R$_f$=0.66(10% MeOH/CHCl$_3$) |
| 73 | (2-chloro-phenyl)-{2-[5-pyridin-3-yl-1-(3-trifluoromethoxy-benzyl)-1H-[1,2,3]triazol-4-yl]-pyridin-3-yl}-methanone | MS(IS) 539.2(M+1) |
| 74 | (2-Chloro-phenyl)-{2-[1-(3-fluoro-5-trifluoromethyl-benzyl)-5-methyl-1H-[1,2,3]triazol-4-yl]-pyridin-3-yl}-methanone | MS(IS) 475.1(M+1); TLC R$_f$=0.33(85% EtOAc/Hexane) |

-continued

| Ex. # | Product | Physical Data |
|---|---|---|
| 75 | (2-Chloro-phenyl)-{2-[1-(2-fluoro-5-trifluoromethyl-benzyl)-5-methyl-1H-[1,2,3]triazol-4-yl]-pyridin-3-yl}-methanone | MS(IS) 475.1(M+1); TLC $R_f$=0.30(85% EtOAc/Hexane) |
| 76 | (2-Chloro-phenyl)-{2-[5-methyl-1-(3-trifluoromethyl-benzyl)-1H-[1,2,3]triazol-4-yl]-pyridin-3yl}-methanone | MS(IS) 457.2(M+1), TLC $R_f$=0.33(85% EtOAc/Hexane) |
| 77 | (2-Chloro-phenyl)-{2-[1-(4-fluoro-3-trifluoromethyl-benzyl)-5-methyl-1H-[1,2,3]triazol-4-yl]-pyridin-3-yl}-methanone | MS(IS) 475.2(M+1), TLC $R_f$=0.28(85% EtOAc/Hexane) |
| 78 | {2-[1-(2,5-bis-trifluoromethyl-benzyl)-5-methyl-1H-[1,2,3]triazol-4-yl]-pyridin-3-yl}-(2-chloro-phenyl)-methanone | MS(IS) 525.1(M+1), TLC $R_f$=0.75(85% EtOAc/Hexane) |
| 79 | (2-Chloro-phenyl)-{2-[5-methyl-1-(3-trifluoromethoxy-benzyl)-1H-[1,2,3]triazol-4-yl]-pyridin-3-yl}-methanone | MS(IS) 473.1(M+1), TLC $R_f$=0.45(85% EtOAc/Hexane) |
| 80 | (2-Chloro-phenyl)-{2-[1-(3,5-difluoro-benzyl)-5-methyl-1H-[1,2,3]triazol-4-yl]-pyridin-3-yl}-methanone | MS(IS) 425.2(M+1), TLC $R_f$=0.39(85% EtOAc/Hexane) |
| 81 | (2-Chloro-phenyl)-{2-[1-(3,5-dichloro-benzyl)-5-methyl-1H-[1,2,3]triazol-4-yl]-pyridin-3-yl}-methanone | MS(IS) 457.0(M+1), TLC $R_f$=0.16(50% EtOAc/Hexane) |

Example 82

{2-[1-(3,5-bis-trifluoromethyl-benzyl)-5-pyridin-4-yl-1H-[1,2,3]triazol-4-yl]-pyridin-3-yl}-(2-chloro-phenyl)-methanol

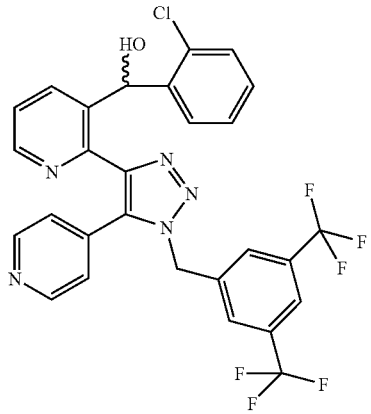

Add LiAlH$_4$ (2.6 mL, 2.6 mmol, 1.0 M in THF) dropwise to a stirred solution of {2-[1-(3,5-bis-trifluoromethyl-benzyl)-5-pyridin-4-yl-1H-[1,2,3]triazol-4-yl]-pyridin-3-yl}-(2-chloro-phenyl)-methanone (1.28 g, 2.18 mmol) in THF (20 mL, anhydrous) at RT. After 15 min, add water (2.6 mL) dropwise with rapid stirring to quench. Add 1N NaOH solution (2.6 mL) dropwise, followed by dropwise addition of water (7.8 mL). Filter out solids and rinse with THF. Concentrate, dissolve in CH$_2$Cl$_2$, wash with saturated NaHCO$_3$ solution (2×), dry over MgSO$_4$ and concentrate. Purify the solid by flash chromatography on silica gel eluting with 0-15% ACN/Et$_2$O to afford the title compound (882 mg, 69%); MS(IS) 590 (M+1); TLC: $R_f$=0.32 (7.5% EtOH/CHCl$_3$).

General Example A

Combine the appropriate keto-aldehyde (1 eq) in AcOH, then add hydrazine (1-3 eq) and stir at 25-80° C. After 1-4 hours, concentrate the solution and dissolve the crude material in EtOAc and wash with saturated NaHCO$_3$ and brine. Dry, filter, and concentrate the organic phase and purify the crude material by flash chromatography (silica gel) to give the title compound.

By using a method analogous to General Example A, using the appropriate starting materials, the title compounds are prepared and isolated.

| Ex # | Product | Physical Data |
|---|---|---|
| 83 | 4-[1-(3,5-bis-trifluoromethyl-benzyl)-5-phenyl-1H-[1,2,3]triazol-4-yl]-3-(2-chloro-phenyl)-isoxazolo[3,4-d]pyridazine | MS(IS) 601.3(M+1), $^1$H NMR(CDCl$_3$): δ 9.42(s, 1H), 7.77(s, 1H), 7.64-7.17(m, 11H), 5.47(s, 2H). |
| 84 | 4-[1-(3,5-bis-trifluoromethyl-benzyl)-5-morpholin-4-yl-1H-[1,2,3]triazol-4-yl]-3-(2-chloro-phenyl)-isoxazolo[4,5-d]pyridazine | MS(IS) 610.0(M+1); TLC(50% EtOAc in hexanes): Rf=0.2. |

-continued

| Ex # | Product | Physical Data |
| --- | --- | --- |
| 85 | 4-[1-(3,5-bis-trifluoromethyl-benzyl)-5-phenyl-1H-[1,2,3]triazol-4-yl]-3-(2-chloro-phenyl)-isoxazolo[4,5-d]pyridazine | MS(IS) 601.0(M+1); TLC(33% EtOAc in hexanes): Rf=0.1. |
| 86 | 4-[1-(3,5-bis-trifluoromethyl-benzyl)-5-morpholin-4-yl-1H-[1,2,3]triazol-4-yl]-3-(2-chloro-phenyl)-isoxazolo[3,4-d]pyridazine | MS(IS) 612.8(M+1), MS(ES−) 610.9(M−1); $^1$HNMR(400MHz, CDCl$_3$) δ 9.55(s, 1H), 7.88(s, 1H), 7.75(s, 2H), 7.68(m, 1H), 7.47(m, 2H), 7.21(m, 1H), 5.53(s, 2H), 3.72(m, 4H), 3.12(m, 4H). |
| 87 | {3-(3,5-bis-trifluoromethyl-benzyl)-5-[3-(2-chloro-phenyl)-isoxazolo[3,4-d]pyridazin-4-yl]-3H-[1,2,3]triazol-4-yl}-dimethyl-amine | LC/MS(IS) 568.0(M+H). $^1$H NMR(400MHz, CDCl$_3$) δ 9.56(s, 1H), 7.89(s, 1H), 7.74(s, 2H) 7.68(m, 1H), 7.46-7.49(m, 2H), 7.22(dd, 1H, J=7.9, 2.0), 5.52(s, 2H), 2.81(s, 6H). |
| 88 | 4-[1-(3,5-bis-trifluoromethyl-benzyl)-5-methyl-1H-[1,2,3]triazol-4-yl]-3-(2-chloro-phenyl)-isoxazolo[3,4-d]pyridazine | LC/MS(IS) 539.0(M+H). $^1$H NMR(400MHz, CDCl$_3$) δ 9.56(s, 1H), 7.89(s, 1H), 7.68(dd, 1H, J=7.8, 1.8), 7.64(s, 2H), 7.56(dt, 1H, J=7.4, 1.8), 7.49(dt, 1H, J=7.8, 1.1), 7.39(dd, 1H, J=7.4, 1.1), 5.63(s, 2H), 2.69(s, 3H). |
| 89 | 4-[1-(3,5-bis-trifluoromethyl-benzyl)-5-pyrazin-2-yl-1H-[1,2,3]triazol-4-yl]-3-(2-chloro-phenyl)-isoxazolo[3,4-d]pyridazine | MS(IS) 602.1(M+1), $^1$H NMR(CDCl$_3$): δ 8.92(d, J=1.6Hz, 1H), 8.65(dd, J=2.6, 1.6Hz 1H), 8.59(dd, J=2.6Hz, 1H), 8.22(d, J=6.5Hz, 1H), 7.82(s, 1H), 7.72(s, 2H), 7.55(m, 1H), 7.51(d, J=6.5Hz, 1H), 7.39(m, 2H), 7.19(m, 1H), 5.92(s, 2H). |
| 90 | 3-[1-(3,5-bis-trifluoromethyl-benzyl)-5-phenyl-1H-[1,2,3]triazol-4-yl]-4-(2-chloro-phenyl)-isoxazolo[3,4-d]pyridazine | MS(IS) 601.1(M+1), $^1$H NMR(CDCl$_3$): δ 9.59(s, 1H), 7.87(s, 1H), 7.75-7.15(m, 11H), 5.56(s, 2H). |
| 91 | 3-[1-(3,5-bis-trifluoromethyl-benzyl)-5-pyridin-4-yl-1H-[1,2,3]triazol-4-yl]-4-(2-chloro-phenyl)-isoxazolo[3,4-d]pyridazine | MS(IS) 601.9(M+1), TLC Rf 0.15(50% EtOAc/Hexane×2). |

General Example B

Dissolve the hydroxymethyl isoxazole of interest (1 eq) in CH$_2$Cl$_2$ (0.025 M), then add Dess-Martin Periodinane (1-2 eq), and stir at RT for 2.5 hours. Purify by elution through Florisil column to give the aldehyde intermediate. Dissolve the material in acetic acid, add anhydrous hydrazine (1.5 eq), and stir at RT until complete by TLC. Concentrate, neutralize with saturated aqueous NaHCO$_3$, extract with EtOAc, dry over MgSO$_4$, filter and concentrate. Purify by chromatography on silica gel to give the title compound.

By using a method similar to General Example B, using the appropriate starting materials, the title compounds may be prepared and isolated.

General Example C

Dissolve the hydroxyethyl isoxazole of interest (1 eq) and CH$_2$Cl$_2$ (0.025 M), then add Dess-Martin Periodinane (1 eq), and stir at RT for 1 hour. Purify by elution through Florisil column to give the aldehyde intermediate. Combine the acetaldehyde in acetic acid (0.2 M), add ammonium acetate (5 eq), and stir 2 hours at 60° C. Concentrate under vacuum, neutralize with saturated aqueous NaHCO$_3$, extract with ether, dry over MgSO$_4$, filter and purify by chromatography on silica gel to give the title compound.

By using a method similar to General Example C, using the appropriate starting materials, the title compounds can be prepared and isolated.

| Ex # | Product | Physical Data |
| --- | --- | --- |
| 92 | 4-[1-(3,5-bis-trifluoromethyl-benzyl)-5-pyridin-4-yl-1H-[1,2,3]triazol-4-yl]-3-(2-chloro-phenyl)-isoxazolo[3,4-d]pyridazine | MS(IS) 602.2(M+1), $^1$H NMR(CDCl$_3$): δ 9.52(s, 1H), 8.75(m, 2H), 7.88(s, 1H), 7.73(dd, J=7.1, 2.3Hz, 1H), 7.59-7.50(m, 4H), 7.34(dd, J=7.8, 1.4Hz, 1H), 7.26(m, 1H), 5.57(s, 2H). |
| 93 | 4-[1-(3,5-bis-trifluoromethyl-benzyl)-5-pyrimidin-5-yl-1H-[1,2,3]triazol-4-yl]-3-(2-chloro-phenyl)-isoxazolo[3,4-d]pyridazine | MS(IS) 603.1(M+1), $^1$H NMR(CDCl$_3$): δ 9.52(s, 1H), 9.32(s, 2H), 8.74(m, 2H), 7.89(s, 1H), 7.77(m, 1H), 7.59(m, 2H), 7.49(s 2H), 7.40(m, 1H), 5.61(s, 2H). |

| Ex # | Product | Physical Data |
|---|---|---|
| 94 | 4-[1-(3,5-bis-trifluoromethyl-benzyl)-5-pyridin-4-yl-1H-[1,2,3]triazol-4-yl]-3-(2-chloro-phenyl)-isoxazolo[4,3-c]pyridine | MS(IS) 601.1(M+1), $^1$H NMR(CDCl$_3$): δ 8.71(d, J=5.3Hz, 2H), 8.09(dd, J=6.6, 1.2Hz, 1H), 7.87(s, 1H), 7.65(m, 1H), 7.50-7.45(m, 4H), 7.42(d, J=6.7Hz, 2H), 7.24(m, 1H), 7.16(dd, J=4.3, 1.4Hz, 2H), 5.55(s, 2H). |
| 95 | 4-[1-(3,5-bis-trifluoromethyl-benzyl)-5-pyridin-3-yl-1H-[1,2,3]triazol-4-yl]-3-(2-chloro-phenyl)-isoxazolo[4,3-c]pyridine | MS(IS) 601.1(M+1), $^1$H NMR(CDCl$_3$): δ 8.71(m, 1H), 8.52(m, 1H), 8.08(d, J=6.5, 1H), 7.84(s, 1H), 7.67-7.64(m, 1H), 7.52-7.29(m, 8H), 7.42(d, J=6.7Hz, 2H), 5.55(s, 2H) |
| 96 | 4-[1-(3,5-bis-trifluoromethyl-benzyl)-5-pyrimidin-5-yl-1H-[1,2,3]triazol-4-yl]-3-(2-chloro-phenyl)-isoxazolo[4,3-c]pyridine | MS(IS) 602.1(M+1), $^1$H NMR(CDCl$_3$): δ 9.30(s, 1H), 8.70(s, 2H), 8.08(ap d, 1H), 7.88(s, 1H), 7.70(m, 1H), 7.52-7.33(m, 6H), 5.55(s, 2H) |
| 97 | 3-[1-(3,5-bis-trifluoromethyl-benzyl)-5-phenyl-1H-[1,2,3]triazol-4-yl]-4-(2-chloro-phenyl)-isoxazolo[4,3-c]pyridine | MS(IS) 600.1(M+1), $^1$H NMR(CDCl$_3$): δ 8.35(d, J=6.5Hz, 1H), 7.84(s, 1H), 7.58-7.13(m, 12H), 5.52(s, 2H). |
| 98 | 3-[1-(3,5-bis-trifluoromethyl-benzyl)-5-pyridin-4-yl-1H-[1,2,3]triazol-4-yl]-4-(2-chloro-phenyl)-isoxazolo[4,3-c]pyridine | MS(IS) ) 600.9(M+1), $^1$H NMR(CDCl$_3$): δ 8.76(br s, 2H), 8.38(d, J=6.7Hz, 1H), 7.89(s, 1H), 7.57(dd, J=7.5, 1.9Hz, 1H), 7.50(s, 2H), 7.47-7.36(m, 4H), 7.12(m, 3H), 5.56(ap d, 2H). |
| 99 | 4-[1-(3,5-bis-trifluoromethyl-benzyl)-5-pyrazin-2-yl-1H-[1,2,3]triazol-4-yl]-3-(2-chloro-phenyl)-isoxazolo[4,3-c]pyridine | MS(IS) 602.1(M+1), $^1$H NMR(CDCl$_3$): δ 8.92(d, J=1.6Hz, 1H), 8.65(dd, J=2.6, 1.6Hz, 1H), 8.59(dd, J=2.6Hz, 1H), 8.22(d, J=6.5Hz, 1H), 7.82(s, 1H), 7.72(s, 2H), 7.55(m, 1H), 7.51(d, J=6.5Hz, 1H), 7.39(m, 2H), 7.19(m, 1H), 5.92(s, 2H). |

Example 100

4-[1-(3,5-bis-trifluoromethyl-benzyl)-5-phenyl-1H-[1,2,3]triazol-4-yl]-3-(2-chloro-phenyl)-isoxazolo[4,3-c]pyridine

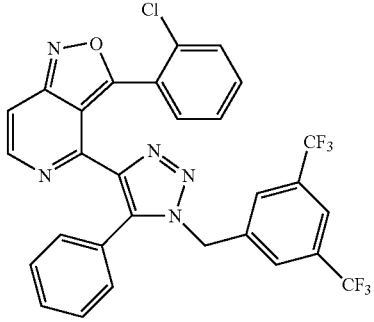

Combine [4-[1-(3,5-bis-trifluoromethyl-benzyl)-5-phenyl-1H-[1,2,3]triazole-4-carbonyl]-5-(2-chloro-phenyl)-isoxazol-3-yl]-acetaldehyde (0.401 g, 0.65 mmol) and acetic acid (4.5 mL), add ammonium acetate (0.25 g, 3.2 mmol) and stir at 65° C. for 90 minutes. Concentrate, neutralize with saturated aqeous NaHCO$_3$, extract with ether, dry over MgSO$_4$, filter and concentrate under vacuum. Purify on chromatotron, using EtOAc/Hexane (10%-85%) to give the title compound: Exact mass 599.1, MS (IS) 600.1 (M+1), $^1$H NMR (CDCl$_3$): δ 8.15 (d, J=6.6 Hz, 1H), 7.85 (s, 1H), 7.60 (m, 1H), 7.52-7.38 (m, 8H), 7.17 (m, 2H), 5.54 (s, 2H).

By using a method similar to Example 100, using the appropriate starting materials, the title compounds can be prepared and isolated.

| Ex # | Product | Physical Data |
|---|---|---|
| 101 | 4-[1-(3,5-bis-trifluoromethyl-benzyl)-5-methyl-1H-[1,2,3]triazol-4-yl]-3-(2-chloro-phenyl)-isoxazolo[4,3-c]pyridine | MS(IS) 537.9(M+1), MS(ES−)535.9(M−1). $^1$H NMR(400MHz, CDCl$_3$) δ 8.33(d, 1H, J=6.8), 7.87(s, 1H), 7.63(s, 2H), 7.61(m, 1H), 7.43(m, 3H), 7.30(m, 1H), 5.56(s, 2H), 2.54(s, 3H). |
| 102 | 4-[1-(3,5-bis-trifluoromethyl-benzyl)-5-morpholin-4-yl-1H-[1,2,3]triazol-4-yl]-3-(2-chloro-phenyl)-isoxazolo[4,3-c]pyridine | MS(IS) 609.0(M+1), MS(ES−)607.0(M−1). $^1$H NMR(400MHz, CDCl$_3$) δ 8.33(m, 1H), 7.87(s, 1H), 7.75(s, 2H), 7.64(m, 1H), 7.42(m, 3H), 7.14(m, 1H), 5.49(s, 2H), 3.70(m, 4H), 3.05(m, 4H). |
| 103 | 4-[1-(3,5-bis-trifluoromethyl-benzyl)-5-(1,1-dioxo-1λ$^6$- | MS(IS) 657.0(M+H). $^1$H NMR(400MHz, CDCl$_3$) 8.37(d, 1H, J=6.8), 7.92(s, 1H), |

-continued

| Ex # | Product | Physical Data |
|---|---|---|
|  | thiomorpholin-4-yl)-1H-[1,2,3]triazol-4-yl]-3-(2-chloro-phenyl)-isoxazolo[4,3-c]pyridine | 7.72(m, 3H), 7.47-7.50(m, 3H), 7.24(m, 1H), 5.55(s, 2H), 3.61(m, 4H), 3.09(m, 4H) |
| 104 | 3-[1-(3,5-bis-trifluoromethyl-benzyl)-5-phenyl-1H-[1,2,3]triazol-4-yl]-4-(2-chloro-phenyl)-isoxazolo[4,3-c]pyridine | MS(IS)) 600.1(M+1), $^1$H NMR(CDCl$_3$): δ 8.35(d, J=6.5Hz, 1H), 7.84(s, 1H), 7.58-7.13(m, 12H), 5.52(s, 2H). |
| 105 | 3-[1-(3,5-bis-trifluoromethyl-benzyl)-5-pyridin-4-yl-1H-[1,2,3]triazol-4-yl]-4-(2-chloro-phenyl)-isoxazolo[4,3-c]pyridine | MS(IS) 600.9(M+1), $^1$H NMR(CDCl$_3$): δ 8.76(br s, 2H), 8.38(d, J=6.7Hz, 1H), 7.89(s, 1H), 7.57(dd, J=7.5, 1.9Hz, 1H), 7.50(s, 2H), 7.47-7.36(m, 4H), 7.12(m, 3H), 5.56(ap d, 2H). |

Example 106

{5-Amino-3-[1-(3,5-bis-trifluoromethyl-benzyl)-5-phenyl-1H-[1,2,3]triazol-4-yl]-pyridazin-4-yl}-(2-chloro-phenyl)-methanone

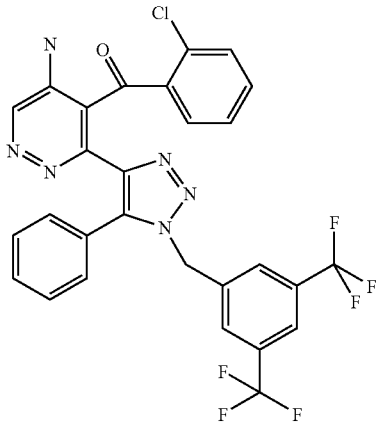

Combine 4-[1-(3,5-bis-trifluoromethyl-benzyl)-5-phenyl-1H-[1,2,3]triazol-4-yl]-3-(2-chloro-phenyl)-isoxazolo[3,4-d]pyridazine (79 mg, 0.1314 mmol), acetonitrile (2.5 mL), water (131 μL), and molybdenum hexacarbonyl (17.4 mg, 0.066 mmol), and heat to 73° C. After 4 hours, cool to RT. Pour the mixture through a plug of Celite® (1 cm) and silica gel (2 cm). Concentrate the dark liquid to 1.5 mL and apply to a 2 mm chromatotron plate with CH$_2$Cl$_2$ and EtOAc and elute with a EtOAc/hexanes gradient to provide 70 mg of a pink solid. Exact Mass 602.1: mass spectrum (IS): m/z=603.0 (M+1), 601.0 (M−1). $^1$H NMR (250 MHz, CDCl$_3$) δ 8.62 (s, 1H), 7.75 (s, 1H), 7.45-7.32 (m, 3H), 7.28-7.10 (m, 3H), 7.00-6.80 (m, 3H), 6.10 (s, 2H).

Using a method similar to Example 106, with the appropriate starting materials, the title compounds can be prepared and isolated.

| Ex. # | Product | Physical Data |
|---|---|---|
| 107 | {5-Amino-3-[1-(3,5-bis-trifluoromethyl-benzyl)-5-phenyl-1H-[1,2,3]triazol-4-yl]-pyridazin-4-yl}-(2-chloro-phenyl)-methanone | Exact Mass 602.1: mass spectrum(IS): m/z=603.0(M+1), 601.0(M−1). $^1$H NMR(250MHz, CDCl$_3$) δ 8.62(s, 1H), 7.75(s, 1H), 7.45-7.32(m, 3H), 7.28-7.10(m, 3H), 7.00-6.80(m, 3H), 6.10(s, 2H). |
| 108 | {5-Amino-3-[1-(3,5-bis-trifluoromethyl-benzyl)-5-morpholin-4-yl-1H-[1,2,3]triazol-4-yl]-pyridazin-4-yl}-(2-chloro-phenyl)-methanone | Exact Mass 611.1: mass spectrum(IS): m/z=611.9(M+1), 610.1(M−1); $^1$H NMR(300MHz, CDCl$_3$) δ 8.72(s, 1H), 7.33(s, 1H), 7.70(s, 2H), 7.25(m, 1H), 6.85(m, 1H), 6.82-6.70(m, 2H), 5.89(bs, 1H), 5.28(s, 2H), 3.71-3.62(m, 4H), 3.03-2.95(m, 4H) |
| 109 | {4-Amino-2-[1-(3,5-bis-trifluoromethyl-benzyl)-5-(1,1-dioxo-1λ$^6$-thiomorpholin-4-yl)-1H-[1,2,3]triazol-4-yl]-pyridin-3-yl}-(2-chloro-phenyl)-methanone | Exact Mass 658.1: mass spectrum(IS): m/z 658.9(m=1), 656.8(M−1); $^1$H NMR(300MHz, CDCl$_3$) δ 8.22(d, J=5.6Hz, 1H), 7.84(s, 1H), 7.61(s, 1H), 7.50(s, 1H), 7.31(s, 1H), 6.91(m, 1H), 6.84-6.76(m, 2H), 6.57(d, J=5.6Hz, 1H), 6.64(s, 2H), 5.22(s, 2H), 3.55-3.40(m, 4H), 3.10-2.96(m, 4H). |
| 110 | {4-Amino-2-[1-(3,5-bis-trifluoromethyl-benzyl)-5-pyridin-4-yl-1H-[1,2,3]triazol-4-yl]- | Exact Mass 602.1: mass spectrum(IS): m/z 602.9(m=1), 601.0(M−1); $^1$H NMR(300MHz, CDCl$_3$) δ 8.65(bs, 2H), 8.01(d, |

-continued

| Ex. # | Product | Physical Data |
|---|---|---|
| | pyridin-3-yl}-(2-chloro-phenyl)-methanone | J=7.0Hz, 1H), 7.77(s, 1H), 7.38(s, 2H), 7.26(m, 1H), 7.15-7.05(m, 2H), 6.96(m, 1H), 6.91-6.80(m, 2H), 6.52(d, J=7.0Hz, 1H), 5.77(s, 2H), 5.25(s, 2H). |
| 111 | {4-Amino-2-[1-(3,5-bis-trifluoromethyl-benzyl)-5-morpholin-4-yl-1H-[1,2,3]triazol-4-yl]-pyridin-3-yl}-(2-chloro-phenyl)-methanone | Exact Mass 609.1: mass spectrum(IS): m/z=609.9(M+1), 608.0(M−1); $^1$H NMR(300MHz, CDCl$_3$) δ 7.82(s, 1H), 7.72(s, 2H), 6.84(m, 1H), 6.62-6.78(m, 2H), 6.53(d, J=3.3Hz, 1H), 5.64(s, 2H), 5.25(s, 2H), 3.60-3.69(m, 4H), 76(m, 4h). |
| 112 | {4-Amino-2-[1-(3,5-bis-trifluoromethyl-benzyl)-5-methyl-1H-[1,2,3]triazol-4-yl]-pyridin-3-yl}-(2-chloro-phenyl)-methanone | Exact Mass 539.1: mass spectrum(IS): m/z 539.9(m=1), 538.0(M−1); $^1$H NMR(300MHz, CDCl$_3$) δ 8.19(d, J=7.0Hz, 1H), 7.81(s, 1H), 7.60(s, 2H), 7.25(dd, J=7.5, 3.0Hz, 1H), 6.94-6.78(m, 3H), 5.80(s, 2H), 5.22(s, 2H), 2.26(s, 3H) |
| 113 | {5-Amino-3-[1-(3,5-bis-trifluoromethyl-benzyl)-5-pyridin-4-yl-1H-[1,2,3]triazol-4-yl]-pyridazin-4-yl}-(2-chloro-phenyl)-methanone | Exact Mass 603.1: mass spectrum(IS): m/z=604.1(M+1), 602.1(M−1); $^1$H NMR(300MHz, CDCl$_3$) δ 8.68(s, 2H), 7.80(s, 1H), 7.39(s, 2H), 7.30(d, J=7.8Hz, 1H), 7.37-7.10(m, 2H), 7.03-6.81(m, 3H), 6.02(bs, 2H), 5.28(s, 2H). |
| 114 | {5-Amino-3-[1-(3,5-bis-trifluoromethyl-benzyl)-5-methyl-1H-[1,2,3]triazol-4-yl]-pyridazin-4-yl}-(2-chloro-phenyl)-methanone | Exact Mass 540.1: mass spectrum(IS): m/z=541.1(M+1), 539.0(M−1); $^1$H NMR(300MHz, CDCl$_3$) δ 9.01(s, 1H), 7.92(s, 1H), 7.66(s, 2H), 7.41(dd, J=4.2, 0.9Hz, 1H), 7.07-6.88(m, 3H), 6.89-6.65(bs, 2H), 5.36(s, 2H), 2.52(s, 3H) |
| 115 | {4-Amino-2-[1-(3,5-bis-trifluoromethyl-benzyl)-5-pyrimidin-5-yl-1H-[1,2,3]triazol-4-yl]-pyridin-3-yl}-(2-chloro-phenyl)-methanone | Exact Mass 603.1: mass spectrum(IS): m/z=604.1(M+1); $^1$H NMR(250MHz, CDCl$_3$) δ 9.19(s, 1H), 8.56(s, 2H), 7.98(d, J=5.9Hz, 1H), 7.81(s, 1H), 7.37(s, 2H), 7.25(m, 1H), 7.17(s, 2H), 7.01-6.88(m, 3H), 6.59(bs, 1H), 5.81(bs, 1H), 5.26(s, 2H). |
| 116 | {5-Amino-3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone | Exact Mass 604.1: mass spectrum(IS): m/z=605.1(M+1); $^1$H NMR(250MHz, CDCl$_3$) δ 9.23(s, 1H), 8.61(s, 2H), 7.81(s, 1H), 7.55-7.40(m, 1H), 7.37(s, 2H), 7.31-7.11(m, 2H), 6.99(s, 2H), 5.31(s, 2H), 5.26(s, 2H). |
| 117 | {5-Amino-3-[1-(3,5-bis-trifluoromethyl-benzyl)-5-dimethylamino-1H-[1,2,3]triazol-4-yl]-pyridazin-4-yl}-(2-chloro-phenyl)-methanone | Exact Mass 569.1: mass spectrum(IS): m/z 567.9(M−1); $^1$H NMR(300MHz, CDCl$_3$) δ 7.77(s, 1H), 7.68(s, 2H), 7.21(m, 1H), 6.87(m, 1H), 6.78-6.70(m, 2H), 5.87(bs, 2H), 5.43(s, 2H). |
| 118 | {4-Amino-2-[1-(3,5-bis-trifluoromethyl-benzyl)-5-pyrazin-2-yl-1H-[1,2,3]triazol-4-yl]-pyridin-3-yl}-(2-chloro-phenyl)-methanone | Exact Mass 603.1: mass spectrum(IS): m/z=604.3(M+1), m/z=602.3(M−1); $^1$H NMR(300MHz, CDCl$_3$) δ 9.08(s, 1H), 8.52(d, J=14.7Hz, 1H), 7.74(s, 1H), 7.68(s, 2H), 7.19(s, 2H), 6.74(s, 3H), 6.59(d, J=6.0Hz, 1H), 5.88(bs, 2H), 5.70(s, 2H). |
| 119 | {4-Amino-2-[1-(3,5-bis-trifluoromethyl-benzyl)-5-pyridin-4-yl-1H-[1,2,3]triazol-4-yl]-pyridin-3-yl}-(2-chloro-phenyl)-methanone | Exact Mass 602.0, mass spectrum(ESI) m/z 603.1(M+1), 601.1(M−1); $^1$H NMR(300 CDCl$_3$) δ 8.62(d, J=3.8Hz, 2H), 7.92(d, J=7.2Hz, 1H), 7.76(s, 1H), 7.36(s, 2H), 7.22(m, 1H), 7.07(d, J=3.8Hz, 2H), 6.93(m, 1H), 6.77-6.80(m, 2H), 6.50(d, J=7.2Hz, 2H), 5.82(bs, 2H), 5.27(s, 2H). |
| 120 | {4-Amino-2-[1-(3,5-bis-trifluoromethyl-benzyl)-5-pyridin-3-yl-1H-[1,2,3]triazol-4-yl]-pyridin-3-yl}-(2-chloro-phenyl)-methanone | Exact Mass 639.4: mass spectrum(aspci): m/z=603.1(M+1), 601.2(M−1); $^1$H NMR(250MHz, CDCl$_3$) δ 8.62(bd, J=6.0Hz, 1H), 8.27(s, 1H), 8.0(d, J=6.9Hz, 1H), 7.75(s, 1H), 7.58(m, 1H), 7.35(s, 2H), 7.30(m, 1H), 7.20(m, 1H), 6.98(m, 1H), 6.85-6.92(m, 2H), 6.50(d, J=6.8Hz, 1H), 5.77(s, 2H), 5.27(s, 2H). |

Example 121

{2-[1-(3,5-bis-trifluoromethyl-benzyl)-5-phenyl-1H-[1,2,3]triazol-4-yl]-pyridin-3-yl}-(2-chloro-phenyl)-methanone

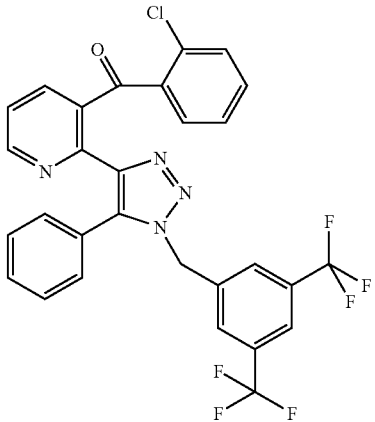

Dissolve {4-amino-2-[1-(3,5-bis-trifluoromethyl-benzyl)-5-phenyl-1H-[1,2,3]triazol-4-yl]-pyridin-3-yl}-(2-chloro-phenyl)-methanone (40.0 mg, 0.067 mmol) in THF (2 mL), add isoamylnitrite (12.0 mg, 13.8 µL, 0.101 mmol) and heat 72° C. for 0.5 h, then cool to RT. Pour the mixture through a plug of Celite® 1 cm and silica gel 2 cm. Concentrate the clear liquid to 1.5 mL and apply to a 2 mm chromatotron plate with $CH_2Cl_2$ and EtOAc and elute with a EtOAc/hexane gradient to provide 24 mg of the title compound. Exact Mass 586.1: MS (IS): m/z=586.9 (M+1); $^1$H NMR (300 MHz, $CDCl_3$) δ 8.53 (bs, 1H), 7.87 (d, J=7.4 Hz, 1H), 7.72 (s, 1H), 7.45-7.00 (m, 9H), 5.37 (s, 2H).

By using a method similar to Example 121, using the appropriate starting materials, the title compounds can be prepared and isolated.

| Ex. # | Product | Physical Data |
|---|---|---|
| 122 | {3-[1-(3,5-bis-trifluoromethyl-benzyl)-5-phenyl-1H-[1,2,3]triazol-4-yl]-pyridazin-4-yl}-(2-chloro-phenyl)-methanone | Exact Mass 587.1: mass spectrum(IS): m/z=587.9(M+1); $^1$H NMR(300MHz, $CDCl_3$) δ 9.22(bs, 1H), 7.75(s, 1H), 7.67-7.52(m, 2H), 7.51-7.05(m, 10H), 5.37(s, 2H) |
| 123 | {2-[1-(3,5-bis-trifluoromethyl-benzyl)-5-pyrimidin-5-yl-1H-[1,2,3]triazol-4-yl]-pyridin-3-yl}-(2-chloro-phenyl)-methanone | Exact Mass 588.1: mass spectrum(IS): m/z=589.1(M+1), 587.1(M−1); $^1$H NMR(300MHz, $CDCl_3$) δ 9.22(s, 1H), 8.61(s, 2H), 8.48(dd, J=2.5, 0.8Hz, 1H), 7.78(dd, J=3.6, 0.9Hz, 1H), 7.77(s, 1H), 7.57(m, 1H), 7.37(s, 2H), 7.27(dd, J=4.2, 3.0Hz, 1H), 7.23-7.10(m, 3H), 5.42(s, 2H). |
| 124 | {3-[1-(3,5-bis-trifluoromethyl-benzyl)-5-pyridin-4-yl-1H-[1,2,3]triazol-4-yl]-pyridazin-4-yl}-(2-chloro-phenyl)-methanone | Exact Mass 588.1: mass spectrum(IS): m/z=589.0(M+1), 587.0(M−1); $^1$H NMR(300MHz, $CDCl_3$) δ 9.08(d, J=6.9, 1H), 8.52(bs, 2H), 7.66(s, 1H), 7.54(m, 1H), 7.42(d, J=6.6Hz, 1H), 7.23(s, 2H), 6.90-7.14(m, 4H), 5.42(s, 2H). |
| 125 | {2-[1-(3,5-bis-trifluoromethyl-benzyl)-5-pyrazin-2-yl-1H-[1,2,3]triazol-4-yl]-pyridin-3-yl}-(2-chloro-phenyl)-methanone | Exact Mass 588.1: mass spectrum(IS): m/z=589.2(M+1), 587.2(M−1); $^1$H NMR(300MHz, $CDCl_3$) δ 8.89(bs, 1H), 8.61(bs, 2H), 8.51(bs, 1H), 7.98(dd, J=8.4, 1.2Hz, 1H), 7.72(s, 1H), 7.65(s, 2H), 7.51(m, 1H), 7.41(m, 1H), 6.99-7.09(m, 3H), 5.78(s, 2H). |

General Example D

Combine the acetaldehyde of interest(1 eq) and acetic acid (0.03 M) with ammonium acetate (10 eq) and stir at 60° C. until complete by TLC. Concentrate under vacuum, neutralize with saturated aqueous NaHCO$_3$, and extract with EtOAc. Dry over MgSO$_4$, filter and purify by chromatography on silica gel.

By using a method similar to General Example D, with the appropriate starting materials, the title compounds can be prepared and isolated.

pyrone (28.2 mg, 24 μL, 0.282 mmol) and heat to 130° C. After 22 hours, add additional pyrone (20 μL, 0.240 mmol) and heat. After 26 hours, cool to RT. And pour the mixture through a plug of Celite® (1 cm) and silica gel (1 cm). Concentrate the clear liquid to 1.5 mL and apply to a 2 mm chromatotron plate and elute with EtOAc/hexanes gradient to provide 32 mg of the title compound: Exact Mass 585.1: mass spectrum (IS): m/z=586.0 (M+1); $^1$H NMR (300 MHz, CDCl3) δ 8.91 (bd, J=7.5 Hz, 1H), 7.76 (s, 1H), 7.51-7.05 (m, 14H), 6.99 (m, 1H), 5.60 (s, 2H).

| Ex # | Product | Physical Data |
|---|---|---|
| 126 | 4-[1-(3,5-bis-trifluoromethyl-benzyl)-5-phenyl-1H-[1,2,3]triazol-4-yl]-3-(2-chloro-phenyl)-[1,2,3]triazolo[1,5-a]pyrazine | MS(IS) 600.0(M+1), $^1$H NMR(CDCl$_3$): δ 8.57(d, J=4.8Hz, 1H), 7.91(d, J=4.8Hz, 1H), 7.82(s, 1H), 7.66(dd, J=7.4, 2.0Hz, 1H), 7.51-7.32(m, 7H), 7.19(m, 2H), 7.12(dd, J=7.8, 1.2Hz, 1H), 5.51(s, 2H). |
| 127 | 4-[1-(3,5-bis-trifluoromethyl-benzyl)-5-pyridin-3-yl-1H-[1,2,3]triazol-4-yl]-3-(2-chloro-phenyl)-[1,2,3]triazolo[1,5-a]pyrazine | MS(IS) 601.0(M+1), $^1$H NMR(CDCl$_3$): δ 8.73(dd, J=5.0, 1.4Hz, 1H), 8.60(d, J=4.4Hz, 1H), 8.57(ap d, 1H), 7.90(d, J=4.8Hz, 1H), 7.86(s, 1H), 7.73(dd, J=7.6, 1.7Hz, 1H), 7.56-7.34(m, 6H), 7.17(dd, J=7.6, 1.2Hz, 1H), 5.56(br s, 2H). |
| 128 | 4-[1-(3,5-bis-trifluoromethyl-benzyl)-5-pyridin-4-yl-1H-[1,2,3]triazol-4-yl]-3-(2-chloro-phenyl)-[1,2,3]triazolo[1,5-a]pyrazine | MS(IS) 601.0(M+1), $^1$H NMR(CDCl$_3$): δ 8.73(d, J=5.2Hz, 2H), 8.61(d, J=4.8Hz, 1H), 7.90(d, J=4.8Hz, 1H), 7.88(s, 1H), 7.73(dd, J=7.4, 1.7Hz, 1H), 7.51(s, 2H), 7.48-7.35(m, 2H), 7.22-7.11(m, 3H), 5.56(br s, 2H). |
| 129 | 4-[1-(3,5-bis-trifluoromethyl-benzyl)-5-pyrazin-2-yl-1H-[1,2,3]triazol-4-yl]-3-(2-chloro-phenyl)-[1,2,3]triazolo[1,5-a]pyrazine | MS(IS) 602.0(M+1), $^1$H NMR(CDCl$_3$): δ 8.82(d, J=1.5Hz, 1H), 8.70(d, J=4.4Hz, 1H), 8.68(m, 1H), 8.61(d, J=2.4Hz, 1H), 8.04(d, J=4.4Hz, 1H), 7.83(s, 1H), 7.74(s, 2H), 7.60(dd, J=7.7, 1.7Hz, 1H), 7.36(m, 1H), 7.29(dd, J=7.8, 1.8Hz, 1H), 7.04(dd, J=7.8, 0.3Hz, 1H), 5.94(s, 2H). |

Example 130

{2-[1-(3,5-bis-trifluoromethyl-benzyl)-5-phenyl-1H-[1,2,3]triazol-4-yl]-phenyl}-(2-chloro-phenyl)-methanone

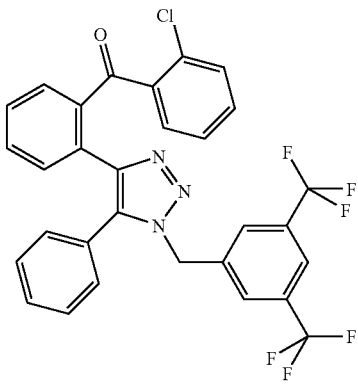

Dissolve 3-[1-(3,5-bis-trifluoromethyl-benzyl)-5-phenyl-1H-[1,2,3]triazol-4-yl]-1-(2-chloro-phenyl)-propynone (100.0 mg, 0.188 mmol), chlorobenzene (2 mL) and add

Example 131

N-[2-[1-(3,5-bis-trifluoromethyl-benzyl)-5-phenyl-1H-[1,2,3]triazol-4-yl]-3-(2-chloro-benzoyl)-pyridin-4-yl]-acetamide

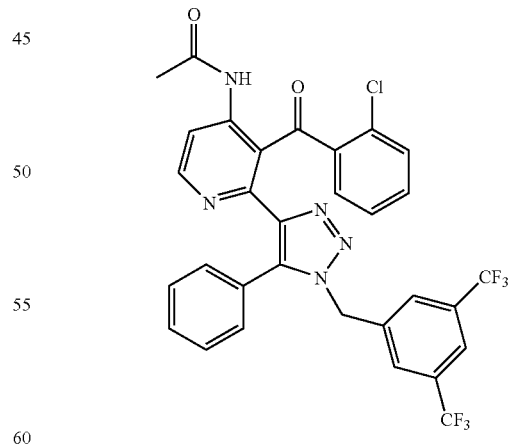

Combine {4-amino-2-[1-(3,5-bis-trifluoromethyl-benzyl)-5-phenyl-1H-[1,2,3]triazol-4-yl]-pyridin-3-yl}-(2-chloro-phenyl)-methanone (840 mg, 0.067 mmol) and 2.0 ml of acetic anhydride and sodium acetate (18.2 mg, 0.134 mmol). Seal the reaction mixture in a pyrex tube and heat to 80° C. After 13 hours, cool to RT. Pour the mixture through a plug of Celite® (1 cm) and silica gel (2 cm). Concentrate the clear liquid to 1.0 mL and apply to a 2 mm chromatotron plate and elute with a EtOAc/hexane gradient to provide 26 mg of the title compound: Exact Mass 643.1; mass spectrum (IS): m/z=643.9 (M+1), m/z=641.8 (M−1); $^1$H NMR (250 MHz, CDCl$_3$) δ9.69 (s, 0.6H), 8.39 (s, 1H), 7.74 (s, 1H), 7.15-7.49 (m, 5H), 7.27 (s, 2H), 6.80-7.05 (m, 5H), 5.26 (s, 2H), 2.16 (s, 3H).

Example 132

{2-[1-(3,5-bistrifluoromethylbenzyl)-5-pyridin-4-yl-1H-[1,2,3]triazol-4-yl]-pyridin-3-yl}-(2-chlorophenyl)-methanone

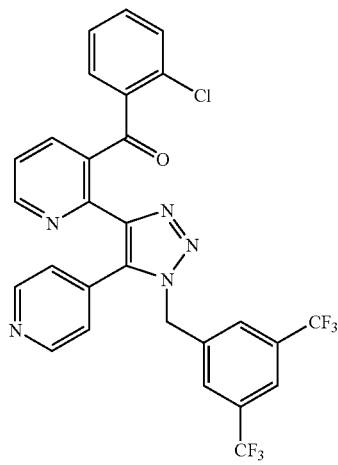

Combine 4-[3-(3,5-bistrifluoromethylbenzyl)-5-tributylstannanyl-3H-[1,2,3]triazol-4-yl]-pyridine (489 g, 740 mmol) and toluene (1 L), add (2-bromopyridin-3-yl)-(2-chlorophenyl)-methanone (240 g, 810 mmol) in toluene (500 mL). Next, add tris(dibenzylideneacetone)dipalladium (16.95 g, 18.5 mmol) and toluene (300 mL). Add tri-2-furylphosphine (17.35 g, 74 mmol) in toluene (200 mL) and heat the reaction mixture to reflux (113° C.). Upon completion of the reaction, remove the solvent by rotary evaporation and purify the crude product by flash column chromatography (dichloromethane/ethyl acetate gradient). Treat the material with activated charcoal in ethyl acetate, wash with 5% aqueous trithiocyanuric acid trisodium salt solution, and recrystallize (ethyl acetate/hexane) to give the title compound. MS(IS) 588 (M+1). TLC (3% MeOH/CH$_2$Cl$_2$) R$_f$=0.17. $^1$H NMR (400 MHz, CDCl$_3$): 5.46 (s, 2H); 7.19 (m, 5H); 7.36 (dd, 1H, J=4.9, 7.8); 7.45 (s, 2H); 7.59 (m, 1H); 7.83 (s, 1H); 7.93 (dd, 1H, J=1.5, 7.8); 8.56 (dd, 1H, J=1.5, 4.9); 8.70 (d, 2H, J=5.9).

Example 133

4-[1-(3,5-bistrifluoromethylbenzyl)-5-phenyl-1H-[1,2,3]triazol-4-yl]-3-(2-chlorophenyl)-isoxazolo[4,3-c]pyridine

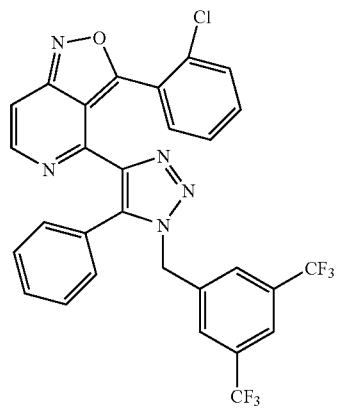

Heat a mixture of ammonium chloride (200 g, 3.74 mol) and [1-(3,5-bistrifluoromethylbenzyl)-5-phenyl-1H-[1,2,3]triazol-4-yl]-[5-(2-chlorophenyl)-3-[1,3]dioxolan-2-yl methylisoxazol-4-yl]-methanone (500 g, 0.754 mol) in acetic acid (4.0 L) and water (800 mL) for 2 hours. While cooling to room temperature, add 5% NaOH solution (4.0 L) dropwise. When the reaction mixture cools to room temperature, filter and dry to give the title compound.: $^1$H NMR (500 MHz, CDCl$_3$) δ 8.12 (d, J=6.6 Hz, 1H), 7.82 (s, 1H), 7.57 (dd, J=7.3, 0.83 Hz, 1H), 7.50-7.38 (m, 8H), 7.25 (m, 1H), 7.14 (d, J=7.7 Hz, 2H), 5.51 (s, 2H). TLC eluting with 95:5 methylene chloride:methanol: R$_f$=0.51.

Example 134

{4-Amino-2-[1-(3,5-bis-trifluoromethyl-benzyl)-5-phenyl-1H-[1,2,3]triazol-4-yl]-pyridin-3-yl}-(2-chloro-phenyl)-methanone

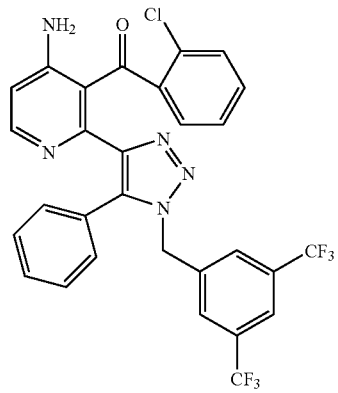

Stir a mixture of 4-[1-(3,5-bistrifluoromethylbenzyl)-5-phenyl-1H-[1,2,3]triazol-4-yl]-3-(2-chlorophenyl)-isoxazolo[4,3-c]pyridine (350 g, 0.583 mol) and 5% Pt—C (35 g) in ethyl acetate (3.5 L) under a H$_2$ (~5 psi) atmosphere for 20 hours. Filter through hyflo, wash with ethyl acetate (3.5

L) and concentrate to a solid. Dissolve in ethyl acetate (7 L) and add Darco® (600 g). Stir for 2 hours then filter through hyflo. Rinse filter cake with ethyl acetate (3.5 L) and concentrate filtrates to give the title compound. Exact Mass 601.1: mass spectrum (IS): m/z=602.0 (M+1); $^1$H NMR (250 MHz, CDCl$_3$) δ8.0 (d, J=6.0 Hz, 1H), 7.23 (s, 1H), 7.45-7.29 (m, 5H), 7.22 (m, 1H), 7.13-7.03 (m, 2H), 6.96 (m, 1H), 6.90-6.80 (m, 2H), 6.48 (d, J=6.0 Hz, 1H), 7.79 (bs, 2H), 5.31 (s, 2H).

The crystalline form of the title compound may be prepared as follows. Dissolve {4-Amino-2-[1-(3,5-bistrifluoromethylbenzyl)-5-phenyl-1H-[1,2,3]triazol-4-yl]-pyridin-3-yl}-(2-chlorophenyl)-methanone (42.2 g, 70.1 mmol) in ethyl acetate (100 mL). Remove 25 mL of ethyl acetate by distillation on rotary evaporator. Add hexanes (50 mL) dropwise at room temperature. Stir for 30 minutes, filter and dry to give the title compound as a crystalline solid. M.P.=156° C.

General Example E

Dissolve the appropriate hydroxyimidoylchloride (1 eq) and appropriate alkyne (2 eq) in EtOAc (0.5M). Add triethylamine (1.2 eq) as a 1 M solution in EtOAc dropwise over 15 min. After 18 hours, dilute with EtOAc (10 mL), wash with 1N HCl (5 mL) and brine (5 mL). Dry (MgSO4), filter, and concentrate. Purify the residue by chromatography (silica gel, hexanes/EtOAc gradient) to give the title compound.

Using a method similar to General Example E, with the appropriate starting materials, the title compounds are prepared and isolated.

| Ex. # | Product | Physical Data |
|---|---|---|
| 135 | {3-[1-(3,5-bis-trifluoromethyl-benzyl)-5-phenyl-1H-[1,2,3]triazol-4-yl]-5-methyl-isoxazol-4-yl}-(2-chloro-4-fluoro-phenyl)-methanone | TLC: R$_f$=0.2(4:1 hexanes/EtOAc)MS(IS): 609.0(M+1) |
| 136 | {3-[1-(3,5-bis-trifluoromethyl-benzyl)-5-chloro-1H-[1,2,3]triazol-4-yl]-5-methyl-isoxazol-4-yl}-(2-chloro-phenyl)-methanone | m.p. 140-141° C. TLC: R$_f$=0.17(4:1 hexanes/EtOAc)MS(IS): 548.8(M+1) |

General Example F

Combine the appropriate hydroxyimidoylchloride (1 eq), EtOAc, and the appropriate alkyne (2 eq). Slowly add TEA (1.5 eq) via syringe pump over 2-7 hours and stir an additional 2-12 hours. Quench with water. Separate layers and extract from aqueous layer with EtOAc. Chromatograph crude product on silica gel (15-35% EtOAc/hexanes) to give the protected isoxazole. Dissolve the residue in MeOH. Add TsOH (2 eq), and stir for 4 hours. Pour into 10 ml aqueous NaHCO$_3$ and extract with EtOAc. Chromatography using the same solvent system described above gives the desired isoxazole.

Using a method analogous to General Example F, with the appropriate starting materials, the title compounds are prepared and isolated.

| Ex | Product | Physical Data |
|---|---|---|
| 137 | {3-[1-(3,5-bis-trifluoromethyl-benzyl)-5-phenyl-1H-[1,2,3]triazol-4-yl]-5-hydroxymethyl-isoxazol-4-yl}-(2-chloro-phenyl)-methanone | MS(IS) 606.9(M+1) Rf=0.58(1:1 hexanes:EtOAc) |
| 138 | {3-[1-(3,5-bis-trifluoromethyl-benzyl)-5-phenyl-1H-[1,2,3]triazol-4-yl]-5-hydroxymethyl-isoxazol-4-yl}-(2-chloro-4-fluoro-phenyl)-methanone | MS(IS) 624.9(M+1) Rf=0.54(1:1 hexanes:EtOAc) |
| 139 | {3-[1-(3,5-bis-trifluoromethyl-benzyl)-5-phenyl-1H-[1,2,3]triazol-4-yl]-5-diethoxymethyl-isoxazol-4-yl}-(2-chloro-phenyl)-methanone | MS(IS) 676.9(M−1) Rf=0.28(3:1 hexanes:EtOAc) |
| 140 | [3-[1-(3,5-bis-trifluoromethyl-benzyl)-5-phenyl-1H-[1,2,3]triazol-4-yl]-5-(1-hydroxy-1-methyl-ethyl)-isoxazol-4-yl]-(2-chloro-phenyl)-methanone | MS(IS) 634.9(M+1) Rf=0.10(4:1 hexanes:EtOAc) |
| 141 | {3-[1-(3,5-bis-trifluoromethyl-benzyl)-5-chloro-1H-[1,2,3]triazol-4-yl]-5-methyl-isoxazol-4-yl}-(2-chloro-4-fluoro-phenyl)-methanone | m.p. 144° C.; TLC: R$_f$=0.24 (5:1 hexanes/EtOAc); MS/ES:566.9(M+1). |

General Example G

Combine appropriate oxime and DMF, add 1.5 eq of N-chlorosuccinimide and stir at RT until oxime is consumed (monitor by TLC (5-10 h)). Pour into water and extract with Et$_2$O. Concentrate to give the crude hydroxyimidoylchloride. Dissolve this intermediate in EtOAc. Add appropriate alkyne then slowly add TEA via syringe pump over 6-7 h while stirring overnight. Pour into 1N HCl and extract with EtOAc. Purify via radial chromatography to give the silyl protected isoxazole. Dissolve in THF, cool to 0° C., and add 1 eq of TBAF (optional). Let the reaction slowly warm to RT overnight. Pour into saturated aqueous NaHCO$_3$ and extract with EtOAc. Purify via radial chromatography to give the desired product.

By using a method similar to General Example G, the title compounds may be prepared and isolated.

| Ex | Product | Physical Data |
|---|---|---|
| 142 | [3-[1-(3,5-bis-trifluoromethyl-benzyl)-5-pyridin-4-yl-1H-[1,2,3]triazol-4-yl]-5-(1-hydroxy-1-methyl-ethyl)-isoxazol-4-yl]-(2-chloro-phenyl)-methanone | MS(IS) 636.1(M+1) Rf=0.16(1:1 hexanes:EtOAc) |
| 143 | [3-[1-(3,5-bis-trifluoromethyl-benzyl)-5-morpholin-4-yl-1H-[1,2,3]triazol-4-yl]-5-(1-hydroxy-1-methyl-ethyl)-isoxazol-4-yl]-(2-chloro-phenyl)-methanone | MS(IS) 644.2(M+1) Rf=0.55(1:1 hexanes:EtOAc) |
| 144 | [3-[1-(3,5-bis-trifluoromethyl-benzyl)-5-pyridin-3-yl-1H-[1,2,3]triazol-4-yl]-5-(1-hydroxy-1-methyl-ethyl)-isoxazol-4-yl]-(2-chloro-phenyl)-methanone | MS(IS) 636.2(M+1) Rf=0.28(1:1 hexanes:EtOAc) |
| 145 | {3-[1-(3,5-bis-trifluoromethyl-benzyl)-5-pyridin-3-yl-1H-[1,2,3]triazol-4-yl]-isoxazol-4-yl}-(2-chloro-phenyl)-methanone | TLC(50% EtOAc in hexanes): Rf=0.3. |

General Example H

Dilute the THP-protected alcohol of interest (1 eq) in a solution of acetic acid/H$_2$O/THF (2/1/1). Attach a reflux condenser, place in 60° C. bath, and stir 24 hours. Purify by chromatography on silica gel to give the title compound.

Using a method similar to General Example H, with the appropriate starting materials, the title compounds are prepared and isolated.

| Ex# | Product | Physical Data |
|---|---|---|
| 146 | {5-[1-(3,5-bis-trifluoromethyl-benzyl)-5-phenyl-1H-[1,2,3]triazol-4-yl]-3-hydroxymethyl-isoxazol-4-yl}-(2-chloro-phenyl)-methanone | MS(IS) 607.0(M+1), $^1$H NMR(CDCl$_3$): δ 7.88(s, 1H), 7.63-7.46(m, 4H), 7.41(s, 2H), 7.29-7.08(m, 5H), 5.46(s, 2H), 4.87(d, J=7.3Hz, 2H), 3.86(t, J=7.3Hz, 1H) |
| 147 | {4-[1-(3,5-bis-trifluoromethyl-benzyl)-5-phenyl-1H-[1,2,3]triazol-4-yl]-3-hydroxymethyl-isoxazol-5-yl}-(2-chloro-phenyl)-methanone | MS(IS) 607.0(M+1), $^1$H NMR(CDCl$_3$): δ 7.85(s, 1H), 7.54(s, 2H), 7.45-7.11(m, 9H), 5.68(s, 2H), 4.86(ap s, 2H). |
| 148 | {5-[1-(3,5-bis-trifluoromethyl-benzyl)-5-phenyl-1H-[1,2,3]triazol-4-yl]-3-(2-hydroxy-ethyl)-isoxazol-4-yl]-(2-chloro-phenyl)-methanone | MS(IS) 621.0(M+1), $^1$H NMR(CDCl$_3$): δ 7.86(s, 1H), 7.62-7.45(m, 4H), 7.40(s, 2H), 7.29-7.11(m, 5H), 5.45(s, 2H), 4.05(t, J=5.9Hz, 2H), 3.19(t, J=5.9Hz, 2H). |
| 149 | [4-[1-(3,5-bis-trifluoromethyl-benzyl)-5-phenyl-1H-[1,2,3]triazol-4-yl]-3-(2-hydroxy-ethyl)-isoxazol-5-yl]-(2-chloro-phenyl)-methanone | MS(IS) 621.0(M+1), $^1$H NMR(CDCl$_3$): δ 7.84(s, 1H), 7.52(s, 2H), 7.44-7.07(m, 9H), 5.66(s, 2H), 4.03(t, J=6.0Hz, 2H), 3.10(t, J=6.0Hz, 2H). |
| 150 | {5-[1-(3,5-bis-trifluoromethyl-benzyl)-5-pyridin-4-yl-1H-[1,2,3]triazol-4-yl]-3-hydroxymethyl-isoxazol-4-yl}-(2-chloro-phenyl)-methanone | MS(IS) 607.9(M+1), $^1$H NMR(CDCl$_3$): δ 8.78(dd, J=4.3, 1.8Hz, 2H), 7.89(s, 1H), 7.53(dd, J=7.6, 2.2Hz, 1H), 7.43(s, 2H), 7.33-7.27(m, 2H), 7.12(dd, J=4.5, 1.8Hz, 2H), 7.07(dd, J=7.6, 1.9Hz, 1H), 5.46(s, 2H), 4.85(s, 2H). |
| 151 | {5-[1-(3,5-bis-trifluoromethyl-benzyl)-5-pyridin-4-yl-1H-[1,2,3]triazol-4-yl]-isoxazol-3-yl}-methanol | MS(IS) 470.0(M+1), $^1$H NMR(CDCl$_3$): δ 8.81(ap d, 2H), 7.85(s, 1H), 7.52(s, 2H), 7.21(d, 1=5.5Hz, 2H), 6.76(s, 1H), 5.60(s, 2H), 4.77(s, 2H). |
| 152 | [5-[1-(3,5-bis-trifluoromethyl-benzyl)-5-pyridin-4-yl-1H-[1,2,3]triazol-4-yl]-3-(2-hydroxy-ethyl)-isoxazol-4-yl]-(2-chloro-phenyl)-methanone | MS(IS) 621.9(M+1), $^1$H NMR(CDCl$_3$): δ 8.79(br s, 2H), 7.87(s, 1H), 7.53(m, 1H), 7.42(s, 2H), 7.26(m, 3H), 7.12(m, 3H), 5.46(s, 2H), 4.01(t, J=5.9Hz, 2H), 3.14(t, J=5.9Hz, 2H). |
| 153 | [4-[1-(3,5-bis-trifluoromethyl-benzyl)-5-pyridin-4-yl-1H-[1,2,3]triazol-4-yl]-3-(2-hydroxy-ethyl)-isoxazol-5-yl]-(2-chloro-phenyl)-methanone | MS(IS) 621.9(M+1), $^1$H NMR(CDCl$_3$): δ 8.66(br s, 2H), 7.86(s, 1H), 7.54(s, 2H), 7.44-7.21(m, 4H), 7.11(d, J=4.5Hz, 2H), 5.70(s, 2H), 4.03(t, J=5.9Hz, 2H), 3.17(t, J=5.9Hz, 2H). |

Example 154

4-[1-(3,5-bis-trifluoromethyl-benzyl)-5-pyridin-4-yl-1H-[1,2,3]triazol-4-yl]-3-(1-hydroxy-1-methyl-ethyl)-isoxazol-5-yl]-(2-chloro-phenyl)-methanone

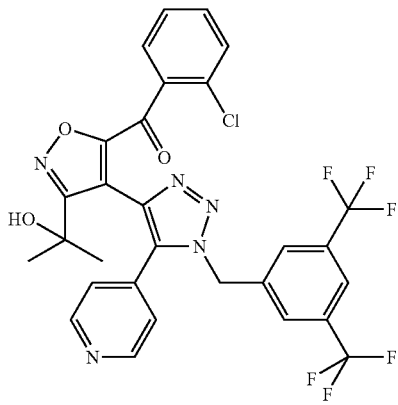

Combine [4-[1-(3,5-bis-trifluoromethyl-benzyl)-5-pyridin-4-yl-1H-[1,2,3]triazol-4-yl]-3-(1-methyl-1-trimethylsilanyloxy-ethyl)-isoxazol-5-yl]-(2-chloro-phenyl)-methanone (43 mg, 0.06 mmol) and THF (0.60 mL) at 0° C. under N$_2$ and slowly add TBAF (0.07 mL, 1M in THF). After 1 h quench with H$_2$O (1 mL) and dilute with EtOAc (2 mL). Wash solution with 1N HCl (3 mL×3), saturated aqueous NaHCO$_3$ (3 mL). Dry and concentrate then purify the crude material by silica gel chromatography using an EtOAc/hexanes gradient to afford title compound: Rf=0.32 (2:1 Hex/EtOAc); MS (IS) 636.2 (M+1).

By using a method similar to Example 154 and the appropriate starting materials, the following compound is prepared and isolated.

| Ex | Compound | Data |
|---|---|---|
| 155 | 4-[1-(3,5-bis-trifluoromethyl-benzyl)-5-phenyl-1H-[1,2,3]triazol-4-yl]-3-(1-hydroxy-1-methyl-ethyl)-isoxazol-5-yl]-(2-chloro-phenyl)-methanone | Rf=0.62 2:1 hex/EtOAc; MS(IS)635.2(M+1) |

General Example J

Dissolve appropriate silyl ether in methanol and add p-toluenesulfonic acid (1.5 eq). Stir at RT overnight, then dilute with EtOAc, and wash with 1N NaOH, and brine. Dry ($MgSO_4$), filter, and concentrate. Purify the residue by chromatography (silica gel, hexanes/EtOAc gradient) to give the title compound.

By using a method similar to General Example J, the title compounds are prepared and isolated.

| Ex # | Product | Physical Data |
|---|---|---|
| 156 | {3-[1-(3,5-bis-trifluoromethyl-benzyl)-5-chloro-1H-[1,2,3]triazol-4-yl]-5-hydroxymethyl-isoxazol-4-yl}-(2-chloro-phenyl)-methanone | m.p. 150° C. TLC: $R_f$=0.24(2:1 hexanes/EtOAc)MS/ES: 564.9(M+1) |
| 157 | {3-[1-(3,5-bis-trifluoromethyl-benzyl)-5-chloro-1H-[1,2,3]triazol-4-yl]-5-hydroxymethyl-isoxazol-4-yl}-(2-morpholin-4-yl-phenyl)-methanone | m.p. 193° C. TLC: $R_f$=0.17(2:1 hexanes/EtOAc)MS/ES: 615.9(M+1) MS/ES: 615.9(M+1) |

General Example K

Add trifluoroacetic acid (Aldrich, 0.5 mL) to the appropriate t-butyl ether and stir at RT. After 18 hours, dilute with EtOAc (10 mL) and add 1N NaOH until the solution is basic (pH 10). Separate the layers and wash the organic layer with brine (5 mL). Dry ($MgSO_4$), filter, and concentrate. Purify the residue by chromatography (silica gel, hexanes/EtOAc gradient) or by recrystallization to give the title compound.

By using a method analogous to General Example K, the title compounds may be prepared and isolated.

| Ex # | Product | Physical Data |
|---|---|---|
| 158 | (R,S)-[3-[1-(3,5-bis-trifluoromethyl-benzyl)-5-chloro-1H-[1,2,3]triazol-4-yl]-5-(1-hydroxy-ethyl)-isoxazol-4-yl]-(2-chloro-phenyl)-methanone | m.p. 131-133° C. TLC: $R_f$=0.34(2:1 hexanes/EtOAc) MS/ES: 580.8(M+1) |
| 159 | (R,S)-[3-[1-(3,5-bis-trifluoromethyl-benzyl)-5-chloro-1H-[1,2,3]triazol-4-yl]-5-(1-hydroxy-ethyl)-isoxazol-4-yl]-(2-morpholin-4-yl-phenyl)-methanone | m.p. 193° C. TLC: $R_f$=0.28(2:1 hexanes/EtOAc) MS/ES: 629.9(M+1) |

Example 160

[5-[1-(3,5-bis-trifluoromethyl-benzyl)-5-phenyl-1H-[1,2,3]triazol-4-yl]-4-(2-chloro-benzoyl)-isoxazol-3-yl]-acetaldehyde

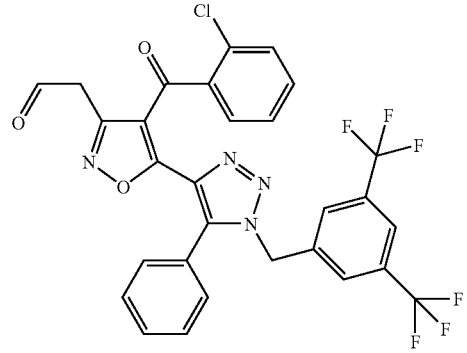

Combine [5-[1-(3,5-bis-trifluoromethyl-benzyl)-5-phenyl-1H-[1,2,3]triazol-4-yl]-3-(2,2-dimethoxy-ethyl)-isoxazol-4-yl]-(2-chloro-phenyl)-methanone (1 eq) in acetone/$H_2O$ (4:1) and p-toluenesulfonic acid (1 eq) with stirring. Attach a reflux condensor and stir overnight in a 60° C. oil bath. Neutralize with saturated aqueous $NaHCO_3$, extract with ethyl acetate, dry over $MgSO_4$, filter, and concentrate under vacuum. $^1$H NMR ($CDCl_3$): δ 9.84 (s, 1H), 7.83 (s, 1H), 7.56-7.09 (m, 11H), 5.43 (s, 2H), 4.09 (s, 2H).

General Example L

Under $N_2$, charge an oven-dried flask with oxalyl chloride (2M in $CH_2Cl_2$, 1.2 eq) and chill in a dry ice/acetone slush. Add DMSO (3 eq) slowly by syringe and stir 15 minutes. Add the hydroxymethyl isoxazole of interest (1 eq) in anhydrous $CH_2Cl_2$ (0.4 M) slowly by syringe and stir 1 hour. Add TEA (5 eq) slowly by syringe and stir 2 hours and allow to warm to RT. Quench with $H_2O$, extract with ether, dry over $MgSO_4$, filter and concentrate under vacuum.

By using a method similar to General Example L, the title compounds are prepared and isolated.

| Ex # | Product | Physical Data |
|---|---|---|
| 161 | 5-[1-(3,5-bis-trifluoromethyl-benzyl)-5-phenyl-1H-[1,2,3]triazol-4-yl]-4-(2-chloro-benzoyl)-isoxazole-3-carbaldehyde | MS(IS) 605.1(M+1), $^1$H NMR($CDCl_3$): δ 10.06(s, 1H), 7.75(s, 1H), 7.63(dd, J=7.5, 1.8Hz, 1H), 7.48-6.97(m, 10H), 5.43(s, 2H). |
| 162 | 4-[1-(3,5-bis-trifluoromethyl-benzyl)-5-phenyl-1H-[1,2,3]triazol-4-yl]-5-(2-chloro-benzoyl)-isoxazole-3-carbaldehyde | MS(IS) 605.1(M+1), TLC Rf=0.47(50% EtOAc/Hexane×2) |

Example 163

[5-[1-(3,5-bis-trifluoromethyl-benzyl)-5-phenyl-1H-[1,2,3]triazol-4-yl]-3-(2-hydroxy-ethyl)-isoxazol-4-yl]-(2-chloro-phenyl)-methanone oxime

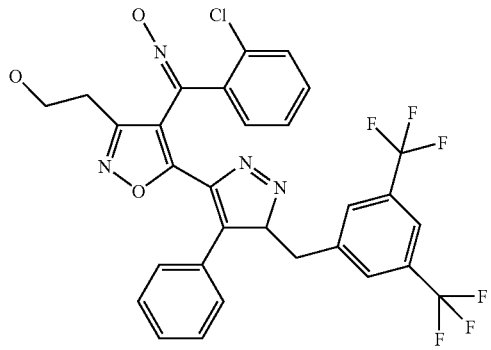

To a solution of [5-[1-(3,5-bis-trifluoromethyl-benzyl)-5-phenyl-1H-[1,2,3]triazol-4-yl]-3-(2-hydroxy-ethyl)-isoxazol-4-yl]-(2-chloro-phenyl)-methanone (1 eq) in pyridine. Add hydroxylamine HCl (10 eq) and reflux and stir overnight. Quench with $H_2O$, extract with ethyl acetate, and concentrate. Remove remaining pyridine by azeotrope with heptane (2×) in vacuo. Dissolve in $CH_2Cl_2$, dry over $MgSO_4$, filter and concentrate under vacuum. Purify by radial chromatography on silica gel to give the title compound. MS (IS) 635.96 (M+1), $^1$H NMR (CD$_3$Cl): δ 9.59 (br s, 1H), 7.76 (s, 1H), 7.49-6.90 (m, 11H), 5.34 (s, 2H), 3.94 (t, J=5.6 Hz, 2H), 3.07 (t, J=5.6 Hz, 2H).

Example 164

[1'-(3,5-bis-trifluoromethyl-benzyl)-5'-phenyl-1H,1'H-[4,4']bi[[1,2,3]triazolyl]-5-yl]-(2-chloro-phenyl)-methanone

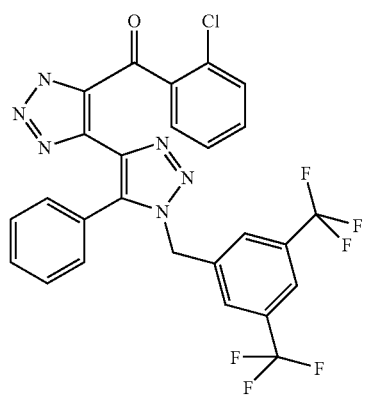

Combine 3-[1-(3,5-bis-trifluoromethyl-benzyl)-5-phenyl-1H-[1,2,3]triazol-4-yl]-1-(2-chloro-phenyl)-propynone (42 mg, 0.079 mmol), 1.0 mL of toluene, and (18.2 mg, 21.0 μL, 0.158 mmol) of trimenthylsilylazide. The mixture was heated to 120° C. for 19 h in a sealed tube and was then cooled to RT. Concentrate to 1.0 mL and apply to a 1 mm chromatotron plate with $CH_2Cl_2$ and EtOAc and elute with a 100 mL of hexanes, and 200 mL each of 20:80 EtOAc/hexanes, 30:70 EtOAc/hexanes, 50:50 hexanes/EtOAc, 85:15 EtOAc/hexanes to provide 29.0 mg of the title compound as a clear, colorless liquid. Exact Mass 576.1: mass spectrum (IS): m/z=577.0 (M+1), 575.0 (M−1); $^1$H NMR (300 MHz, CDCl$_3$) δ7.93 (s, 1H), 7.62 (s, 2H), 7.52-7.22 (m, 9H), 5.75 (s, 2H).

Example 165

{4-[1-(3,5-bis-trifluoromethyl-benzyl)-5-phenyl-1H-[1,2,3]triazol-4-yl]-2H-pyrazol-3-yl}-(2-chloro-phenyl)-methanone

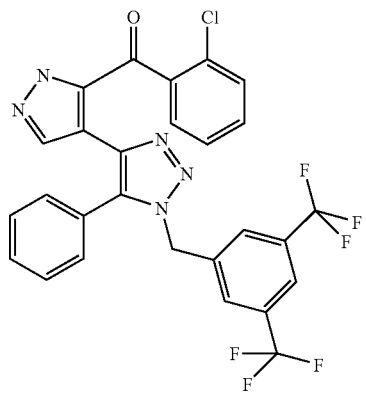

Combine 3-[1-(3,5-bis-trifluoromethyl-benzyl)-5-phenyl-1H-[1,2,3]triazol-4-yl]-1-(2-chloro-phenyl)-propynone (42 mg, 0.079 mmol), 1.0 mL of 50/50 mix of ether and THF, and (112.0 μL, of a 2.0 M solution of trimethylsilyl diazomethane in hexanes, 0.225 mmol) and stir at RT in a sealed tube. After 49 hours, concentrate to 1.0 mL and apply to a 2 mm chromatotron plate with $CH_2Cl_2$ and elute with a EtOAc/hexanes gradient to provide 29.0 mg of a clear colorless liquid. Exact Mass 575.1: mass spectrum (IS): m/z=575.9 (M+1), 573.9 (M−1); $^1$H NMR (300 MHz, CDCl$_3$) δ 8.53 (s, 0.33H), 7.69 (s, 1H), 7.67 (s, 0.66H), 7.35-6.99 (m, 12H), 5.44 (s, 2H).

Example 166

4-(5-Benzyl-1H-imidazol-4-yl)-1-(3,5-bis-trifluoromethyl-benzyl)-5-phenyl-1H-[1,2,3]triazole

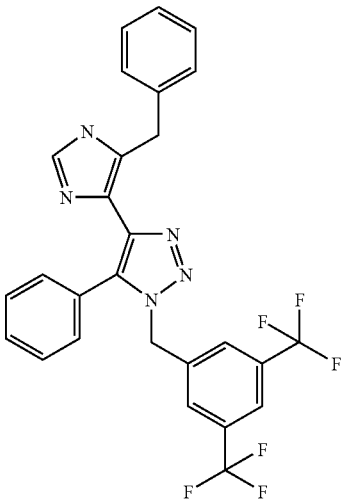

Combine 4-[4-benzyl-4-(toluene-4-sulfonyl)-4,5-dihydro-oxazol-5-yl]-1-(3,5-bis-trifluoromethyl-benzyl)-5-phenyl-1H-[1,2,3]triazole (0.084 mmol), 1.0 mL of xylene, and 7N solution of ammonia in methanol (48.0 µL, 0.337 mmol). Heat in a sealed pyrex tube to 136° C. After 18 hours, cool to RT, and concentrate the mixture to 1.0 mL and apply to a 2 mm chromatotron plate with $CH_2Cl_2$ and elute with a EtOAc/hexanes gradient to provide the title compound. Exact Mass 527.2: mass spectrum (IS): m/z=529.1 (M+1), 527.1 (M−1); $^1$H NMR (250 MHz, CDCl$_3$) δ7.84 (s, 1H), 7.67 (s, 1H), 7.65-7.05 (m, 13H), 5.60 (s, 2H), 4.28 (s, 2H).

Example 167

1-(3,5-bis-trifluoromethyl-benzyl)-4-[5-(2-chloro-benzyl)-1H-imidazol-4-yl]-5-phenyl-1H-[1,2,3]triazole

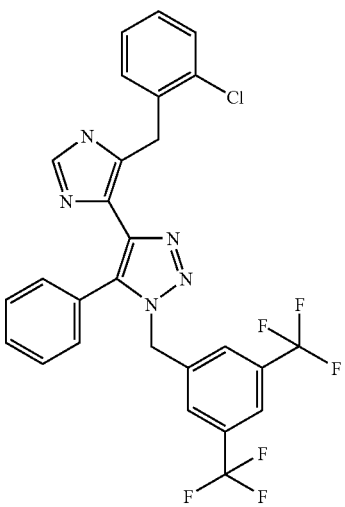

Combine 1-(3,5-bis-trifluoromethyl-benzyl)-4-[4-(2-chloro-benzyl)-4-(toluene-4-sulfonyl)-4,5-dihydro-oxazol-5-yl]-5-phenyl-1H-[1,2,3]triazole (0.100 mmol), 2.5 mL of xylene, and 2N solution of methylamine in methanol (0.2 mL, 0.40 mmol) and heat in a sealed pyrex tube to 135° C. After 19 hours, cool to RT. Concentrate the mixture to 1.0 mL and apply to a 2 mm chromatotron plate with $CH_2Cl_2$ and EtOAc and elute with a 100 mL of Hexanes, and 200 mL each of 20:80 EtOAc/Hexanes, 30:70 EtOAc/Hexanes, 50:50 Hexanes/EtOAc, 85:15 EtOAc/Hexanes to provide the title compound: Exact Mass 561.1: mass spectrum (IS): m/z=563.1 (M+1), 561.1 (M−1); $^1$H NMR (250 MHz, CDCl$_3$) δ7.74 (s, 1H), 7.62 (s, 1H), 7.48-7.32 (m, 6H), 7.30-7.00 (m, 6H), 5.52 (s, 2H), 4.20 (s, 2H).

Example 168

{5-[1-(3,5-bis-trifluoromethyl-benzyl)-5-phenyl-1H-[1,2,3]triazol-4-yl]-3-methyl-isoxazol-4-yl}-(2-chloro-phenyl)-methanone:

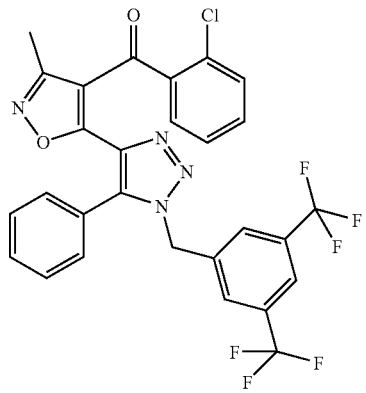

Combine 3-[1-(3,5-bis-trifluoromethyl-benzyl)-5-phenyl-1H-[1,2,3]triazol-4-yl]-1-(2-chloro-phenyl)-propynone (150 mg, 0.281 mmol), 12 mL of benzene, nitroethane (32 mg, 31 µL, 0.421 mmol), 1,4-diisocyanato-benzene (135 mg, 0.842 mmol) and then 6 drops of triethyl amine (~50 µL) and heat to benzene reflux. After 19 hours, cool to RT. Dilute the mixture with 0.5 mL of water, stir for 10 min. and add one scoop of MgSO$_4$. Pour the mix through a plug of Celite® (1 cm), concentrate to 3 mL and purify by chromatotron (EtOAc/hexanes) to provide the title compound: Exact Mass 590.1: mass spectrum (IS): m/z=591.0 (M+1), 589.0 (M−1); $^1$H NMR (250 MHz, CDCl$_3$) δ7.81 (s, 1H), 7.51 (m, 1H), 7.41-7.47 (m, 3H), 7.38 (bs, 2H), 7.22-7.17 (m, 2H), 7.15-7.09 (s, 3H), 5.43 (s, 2H), 2.42 (s, 3H).

General Example M

Dissolve the appropriate alkyne (1 eq) in toluene (0.1 M) and treat the solution with nitroalkoxy-tetrahydropyran (4 eq), 1,4-diisocyanato-benzene (4 eq), and triethylamine (4 eq). Heat the solution at 110° C. for 4 hours, then add water (20 mL) and filter through a pad of Celite®. Rinse filter cake with EtOAc then wash the filtrate with brine. Dry, filter, and concentrate the organic solution and use material directly in the next reaction. Dissolve the above material in MeOH (0.1M) and treat with p-TsOH.H$_2$O (2eq). Stir the solution at RT for 18 hours Concentrate the solution and re-dissolve the crude material in EtOAc. Wash the organic solution with saturated NaHCO$_3$, then dry, filter, and concentrate. Purify the crude material by flash chromatography to give the title compound.

By using a method similar to General Example M, the title compounds may be prepared and isolated.

| Ex. # | Product | Physical Data |
|---|---|---|
| 169 | {5-[1-(3,5-bis-trifluoromethyl-benzyl)-5-chloro-1H-[1,2,3]triazol-4-yl]-3-hydroxymethyl-isoxazol-4-yl}-(2-chloro-phenyl)-methanone | MS(IS) 564.8(M+1). $^1$H NMR(400MHz, CDCl$_3$) δ 7.93(s, 1H), 7.71(s, 2H), 7.39(m, 1H), 7.11(m, 2H), 7.01(m, 1H), 5.51(s, 2H), 4.90(d, 2H, J=7.3), 3.74(t, 1H, J=7.3). |
| 170 | [5-[1-(3,5-bis-trifluoromethyl-benzyl)-5-chloro-1H-[1,2,3]triazol-4-yl]-3-(2-hydroxy-ethyl)-isoxazol-4-yl]-(2-chloro-phenyl)-methanone | MS(IS) 578.8(M+1)$^+$. $^1$H NMR(400MHz, CDCl$_3$) δ 7.92(s, 1H), 7.70(s, 2H), 7.43(m, 1H), 7.26(m, 1H), 7.12(m, 2H), 5.52(s, 2H), 4.06(m, 2H), 3.19(s, 2H), 2.26(m, 1H). |

Example 171

{4-[1-(3,5-bis-trifluoromethyl-benzyl)-5-phenyl-1H-[1,2,3]triazol-4-yl]-3-methyl-isoxazol-5-yl}-(2-chloro-phenyl)-methanone

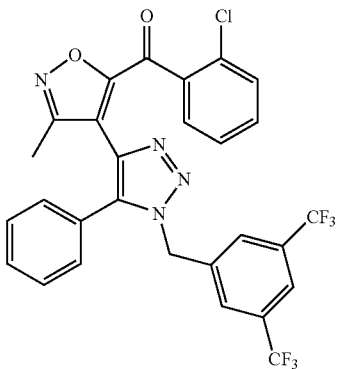

Combine 3-[1-(3,5-bis-trifluoromethyl-benzyl)-5-phenyl-1H-[1,2,3]triazol-4-yl]-1-(2-chloro-phenyl)-propynone (150 mg, 0.281 mmol), 12 mL of benzene, nitroethane (32 mg, 31 μL, 0.421 mmol), phenyl diisocyanate (135 mg, 0.842 mmol) and then 6 drops of triethyl amine (~50 μL) and heat to benzene reflux. After 19 h cool to RT., dilute the mixture with 0.5 mL of water, stir for 10 min. and add one scoop of MgSO$_4$. Pour the mix through a plug of Celite® 1 cm and concentrate. Purify by chromatotron (EtOAc/hexanes gradient) to give the title compound: Exact Mass 590.1: mass spectrum (IS): m/z=591.0 (M+1), 589.0 (M−1); $^1$H NMR (250 MHz, CDCl$_3$) δ7.82 (s, 1H), 7.50 (s, 1H), 7.49-7.20 (m, 8H), 7.06 (dd, 10.0, 3.0 Hz, 2H), 5.62 (s, 2H), 2.32 (s, 3H).

Example 172

{4-[1-(3,5-bis-trifluoromethyl-benzyl)-5-phenyl-1H-[1,2,3]triazol-4-yl]-2H-pyrazol-3-yl}-2-chloro-phenyl)-methanol

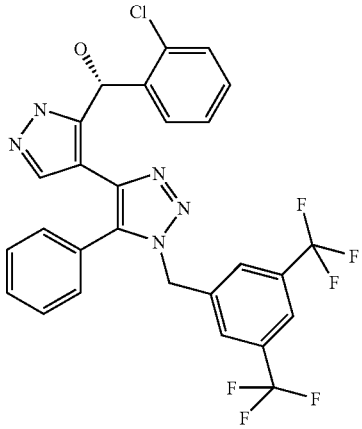

Dissolve {4-[1-(3,5-bis-trifluoromethyl-benzyl)-5-phenyl-1H-[1,2,3]triazol-4-yl]-2H-pyrazol-3-yl}-(2-chloro-phenyl)-methanone (80 mg, 0.140 mmol) in THF (4 mL) and MeOH (4 mL). Add NaBH$_4$ (13.2 mg, 0.35 mmol) and stir at RT for 2 hours. Add additional NaBH$_4$ (7.52 mg, 0.17 mmol) and stir for 2.5 hours. Quench in 10 mL of saturated aqueous NH$_4$Cl and 20 mL of CH$_2$Cl$_2$. Extract with CH$_2$Cl$_2$ and EtOAc. Combine organics and dry over MgSO$_4$ and filter through paper and concentrate. Purify by chromatotron (EtOAc/hexanes gradient) to provide the title compound. Exact Mass 577.1: mass spectrum (IS): m/z=578.0 (M+1), 576.0 (M−1); $^1$H NMR (250 MHz, CDCl$_3$) δ7.81-7.70 (m, 2H), 7.55-7.35 (m, 4H), 7.32-7.05 (m, 4H), 6.93 (s, 1H), 6.36 (s, 1H), 5.45 (abq, J=18.4, 15.23 Hz, 2H).

By using a method similar to Example 172, using the appropriate starting materials, the title compounds may be prepared and isolated.

| Ex. # | Product | Physical Data |
|---|---|---|
| 173 | [1'-(3,5-bis-trifluoromethyl-benzyl)-5'-phenyl-1H,1'H-[4,4']bi[[1,2,3]triazolyl]-5-yl]-(2-chloro-phenyl)-methanol | Exact Mass 578.1: mass spectrum(IS): m/z=579.0(M+1), 577.0(M−1); $^1$H NMR(250MHz, CDCl$_3$) δ 7.82-7.72 (m, 3H), 7.54-7.38(m, 5H), 7.35-7.15(m, 5H), 6.47(s, 1H), 5.55(s, 2H). |
| 174 | {5-[1-(3,5-bis-trifluoromethyl-benzyl)-5-phenyl-1H-[1,2,3]triazol-4-yl]-3-methyl-isoxazol-4-yl}-(2-chloro-phenyl)-methanol | Exact Mass 592.1: mass spectrum(IS): m/z=593.0(M+1), 591.0(M−1); $^1$H NMR(250MHz, CDCl$_3$) δ 7.75(s, 1H), 7.65-7.55(m, 2H), 7.52-7.35(m, 5H), 7.30-7.10(m, 5H), 6.27(s, 1H), 5.52(abq, J=8.1, 3.0Hz, 2H) |

Example 175

1-(3,5-bis-trifluoromethyl-benzyl)-5'-(2-chloro-benzyl)-5-phenyl-1H,1'H-[4,4']bi[1,2,3]triazole

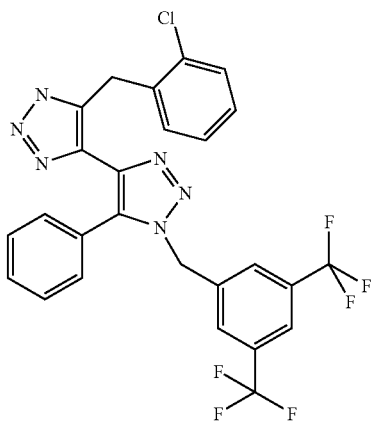

Dissolve [1'-(3,5-bis-trifluoromethyl-benzyl)-5'-phenyl-1H,1'H-[4,4']bi[[1,2,3]triazolyl]-5-yl]-(2-chloro-phenyl)-methanol (38 mg, 0.066 mmol) and 1.5 mL $CH_2Cl_2$. Carefully add triethylsilane (23 mg, 31.4 µL, 0.197 mmol). Cool to 0° C. and add trifluoroacetic acid (452 mg, 305 µL, 3.96 mmol) and stir. After 15 hours, pour into 10 mL of (saturated aqueous $NaHCO_3$) and 20 mL of $CH_2Cl_2$. Extract 3 times with $CH_2Cl_2$ and 1 time with EtOAc. Combine the organics, dry over $MgSO_4$ and filter and concentrate. Apply the mixture to a 2 mm chromatotron plate with $CH_2Cl_2$ and EtOAc and elute with a 100 mL of Hexanes, and then 200 mL each of of 10:90 EtOAc/Hexanes, 20:80 EtOAc/Hexanes, 30:70 EtOAc/Hexanes, 50:50 Hexanes/EtOAc to provide the title compound. Exact Mass 562.1: mass spectrum (IS): m/z=563.1 (M+1), 561.1 (M−1); $^1$H NMR (250 MHz, $CDCl_3$) δ7.72 (s, 1H), 7.42-7.28 (m, 5H), 7.24 (m, 1H), 7.16-6.97 (m, 6H), 5.52 (s, 2H), 4.37 (s, 2H).

By using a method similar to Example 175, using the appropriate starting materials, the title compounds may be prepared and isolated.

| Ex. # | Product | Physical Data |
|---|---|---|
| 176 | 1-(3,5-bis-trifluoromethyl-benzyl)-4-[5-(2-chloro-benzyl)-1H-pyrazol-4-yl]-5-phenyl-1H-[1,2,3]triazole | Exact Mass 561.1: mass spectrum(IS): m/z=562.1(M+1), 560.1(M−1); $^1$H NMR(250MHz, $CDCl_3$) δ7.80-7.68(m, 3H), 7.55-7.32(m, 4H), 7.30-6.90(m, 6H), 6.40(s, 0.5H), 5.46(s, 0.5H), 5.44(s, 2H), 4.38(s, 2H). |
| 177 | 1-(3,5-bis-trifluoromethyl-benzyl)-4-[4-(2-chloro-benzyl)-3-methyl-isoxazol-5-yl]-5-phenyl-1H-[1,2,3]triazole | Exact Mass 576.1: mass spectrum(IS): m/z=577.0(M+1), 575.1(M−1); $^1$H NMR(250MHz, $CDCl_3$) δ7.67(s, 1H), 7.48-7.25(m, 5H), 7.40(m, 1H), 7.12-7.05(m, 2H), 7.05-6.95(m, 2H), 6.90(m, 1H), 5.44(s, 2H), 4.14(s, 2H), 1.92(s, 3H). |

General Example N

Dissolve 5-chlorotriazole (1 eq) in amine (20-120 eq) and stir at 80-110° C. for 2-20 hours. Dilute the solution with a suitable solvent, such as EtOAc or DMSO, and wash with 1N HCl, water, and saturated $NaHCO_3$. Dry, filter, and concentrate the organic phase then purify the crude material by flash chromatography to give the title compound.

By using a method similar to General Example N, using the appropriate starting materials, the title compounds are prepared and isolated.

| Ex. # | Product | Physical Data |
|---|---|---|
| 178 | {5-[1-(3,5-bis-trifluoromethyl-benzyl)-5-morpholin-4-yl-1H-[1,2,3]triazol-4-yl]-3-hydroxymethyl-isoxazol-4-yl}-(2-chloro-phenyl)-methanone | MS(IS) 615.9(M+1), MS(ES−) 613.9(M−1). $^1$HNMR(400MHz, $CDCl_3$) δ 7.89(s, 1H), 7.67(s, 2H), 7.46(dd, 1H, J=2.0, 7.4), 7.18(dt, 1H, J=1.5, 7.4), 7.13(dt, 1H, J=2.0, 7.9), 6.95(dd, 1H, J=1.5, 7.9), 5.40(s, 2H), 4.89(d, 2H, J=7.4), 3.83(t, 1H, J=7.6), 3.70(m, 4H), 2.90(m, 4H). |
| 179 | {5-[1-(3,5-bis-trifluoromethyl-benzyl)-5-dimethylamino-1H-[1,2,3]triazol-4-yl]-3- | MS(IS) 574.1(M+H). $^1$H NMR(400MHz, $CDCl_3$) δ 7.91(s, 1H), 7.67(s, 2H), 7.48(dd, 1H J=7.4, 1.8), 7.12-7.22(m, 2H), 6.99(dd, 1H, J=7.8, 1.4), 5.39(s, |

| Ex. # | Product | Physical Data |
|---|---|---|
| | hydroxymethyl-isoxazol-4-yl}-(2-chloro-phenyl)-methanone | 2H), 4.91(d, 2H, J=7.1), 3.90(t, 1H, J=7.1), 2.71(s, 6H). |
| 180 | {5-[1-(3,5-bis-trifluoromethyl-benzyl)-5-(thiomorpholin-4-yl)-1H-[1,2,3]triazol-4-yl]-3-hydroxymethyl-isoxazol-4-yl}-(2-chloro-phenyl)-methanone | MS(IS) 632.1(M+H). $^1$H NMR(400MHz, CDCl$_3$) δ 7.91(s, 1H), 7.67(s, 2H)), 7.50(dd, 1H J=7.5, 1.9), 7.14-7.24(m, 2H), 6.99(dd, 1H, J=7.8, 1.4), 5.39(s, 2H), 4.92(s, 2H), 3.85(brs, 1H), 3.17(m, 4H), 2.68(m, 4H). |
| 181 | [5-[1-(3,5-bis-trifluoromethyl-benzyl)-5-morpholin-4-yl-1H-[1,2,3]triazol-4-yl]-3-(2-hydroxy-ethyl)-isoxazol-4-yl]-(2-chloro-phenyl)-methanone | MS(IS) 630.2(M+1), MS(ES−) 628.2(M−1). $^1$HNMR(400MHz, CDCl$_3$) δ 7.89(s, 1H), 7.67(s, 2H), 7.50(m, 1H), 7.15(m, 2H), 6.99(m, 1H), 5.41(s, 2H), 4.07(m, 2H), 3.72(m, 4H), 3.23(s, 2H), 2.91(m, 4H), 2.36(br s, 1H). |
| 182 | [5-[1-(3,5-bis-trifluoromethyl-benzyl)-5-dimethylamino-1H-[1,2,3]triazol-4-yl]-3-(2-hydroxy-ethyl)-isoxazol-4-yl]-(2-chloro-phenyl)-methanone | MS(IS) 588.1(M+H). $^1$H NMR(400MHz, CDCl$_3$) δ 7.89(s, 1H), 7.67(s, 2H), 7.51(dd, 1H J=7.8, 1.8), 7.10-7.20(m, 2H), 7.02(dd, 1H, J=7.8, 1.4), 5.39(s, 2H), 4.09(m, 2H) 3.25(t, 2H, J=5.6), 2.70(s, 6H), 2.36(brs, 1H). |

Example 183

{5-[1-(3,5-bis-trifluoromethyl-benzyl)-5-chloro-1H-[1,2,3]triazol-4-yl]-3-hydroxymethyl-isoxazol-4-yl}-(2-morpholin-4-yl-phenyl)-methanone

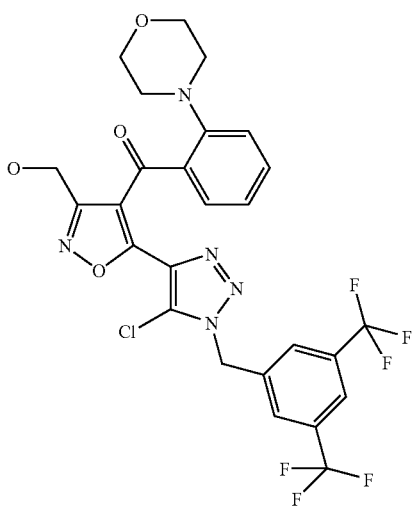

Dissolve {5-[1-(3,5-bis-trifluoromethyl-benzyl)-5-chloro-1H-[1,2,3]triazol-4-yl]-3-hydroxymethyl-isoxazol-4-yl}-(2-chloro-phenyl)-methanone (0.10 g, 018 mmol) in morpholine (1.0 mL) and stir at 80° C. for 20 hours. Dilute the solution with EtOAc (25 mL) and wash with 1N HCl (20 mL), water (20 mL), and saturated NaHCO$_3$ (20 mL) then dry, filter, and concentrate. Purify the crude material by flash chromatography to give the title compound: MS (IS) 615.9 (M+1), MS (ES−) 613.9 (M−1): $^1$HNMR (400 MHz, CDCl$_3$) δ 7.95 (s, 1H), 7.74 (s, 2H), 7.45 (dd, 1H, J=1.4, 7.5), 6.93 (dt, 1H, J=1.5, 7.4), 6.83 (dt, 1H, J=1.0, 7.4), 6.40 (m, 1H), 5.42 (s, 2H), 4.85 (d, 2H, J=7.3), 3.80 (t, 1H, J=7.3), 3.44 (m, 4H), 2.64 (m, 4H).

General Example O

Dissolve 1 eq of the appropriate amide in 1,2-dichloroethane (0.05-0.21M). Add PCl$_5$ (1 eq-4 eq) and stir at RT. After 30 min., add the desired hydrazide (3 equiv to 8 equiv) and stir at 70° C. overnight. Pour into aqueous NaHCO$_3$ and extract with CH$_2$Cl$_2$. Wash the organic layer with 1N HCl and then with brine. Dry with Na$_2$SO$_4$ and concentrate. Purify via radial chromatography using a gradient of 1:1 to 1:5 hexanes: EtOAc to give the title compound.

By using a method analogous to General Example O, using the appropriate starting materials, the title compounds may be prepared and isolated.

| Ex | Product | Physical Data |
|---|---|---|
| 184 | 1-(3,5-bis-trifluoromethyl-benzyl)-4-[4-(2-chloro-benzyl)-5-methyl-4H-[1,2,4]triazol-3-yl]-5-phenyl-1H-[1,2,3]triazole | MS(IS) 577.2(M+1) Rf=0.14(1:5 hexanes:EtOAc) |
| 185 | 1-(3,5-bis-trifluoromethyl-benzyl)-4-[5-methyl-4-(2-methyl-benzyl)-4H-[1,2,4]triazol-3-yl]-5-phenyl-1H-[1,2,3]triazole | MS(IS) 557.3(M+1) Rf=0.06(1:5 hexanes:EtOAc) |
| 186 | 1-(3,5-bis-trifluoromethyl-benzyl)-4-[5-methyl-4-(2-trifluoromethyl-benzyl)-4H-[1,2,4]triazol-3-yl]-5-phenyl-1H-[1,2,3]triazole | MS(IS) 611.3(M+1) Rf=0.19(1:5 hexanes:EtOAc) |
| 187 | 1-(3,5-bis-trifluoromethyl-benzyl)-4-[4-(2-bromo-benzyl)-5-methyl-4H-[1,2,4]triazol-3-yl]-5-phenyl-1H-[1,2,3]triazole | MS(IS) 621.2(M+1) Rf=0.14(1:5 hexanes:EtOAc) |
| 188 | 1-(3,5-bis-trifluoromethyl-benzyl)-4-[4-(2,3-dichloro-benzyl)-5-methyl-4H-[1,2,4]triazol-3-yl]-5-phenyl-1H-[1,2,3]triazole | MS(IS) 611.3(M+1) Rf=0.10(1:5 hexanes:EtOAc) |
| 189 | 1-(3,5-bis-trifluoromethyl-benzyl)-4-[4-(2-chloro-4-fluoro-benzyl)-5-methyl-4H-[1,2,4]triazol-3-yl]-5-phenyl-1H-[1,2,3]triazole | MS(IS) 595.5(M+1) Rf=0.11(1:5 hexanes:EtOAc) |
| 190 | 1-(3,5-bis-trifluoromethyl-benzyl)-4-(5-methyl-4-phenyl-4H-[1,2,4]triazol-3-yl)-5-phenyl-1H-[1,2,3]triazole | MS(IS) 529.3(M+1) Rf=0.13(1:5 hexanes:EtOAc) |
| 191 | 1-(3,5-bis-trifluoromethyl-benzyl)-4-[4-(2-chloro-4-methyl-phenyl)-5-methyl-4H-[1,2,4]triazol-3-yl]-5-phenyl-1H-[1,2,3]triazole | MS(IS) 577.1(M+1) Rf=0.19(1:5 hexanes:EtOAc) |

| Ex | Product | Physical Data |
|---|---|---|
| 192 | 1-(3,5-bis-trifluoromethyl-benzyl)-4-[4-(2,4-dichloro-phenyl)-5-methyl-4H-[1,2,4]triazol-3-yl]-5-phenyl-1H-[1,2,3]triazole | MS(IS) 597.0(M+1) Rf=0.16(1:5 hexanes:EtOAc) |
| 193 | 1-(3,5-bis-trifluoromethyl-benzyl)-4-[4-(2-chloro-benzyl)-4H-[1,2,4]triazol-3-yl]-5-phenyl-1H-[1,2,3]triazole | MS(IS) 563.0(M+1) Rf=0.16(1:5 hexanes:EtOAc) |
| 194 | 1-(3,5-bis-trifluoromethyl-benzyl)-4-[5-methyl-4-((R)-1-phenyl-ethyl)-4H-[1,2,4]triazol-3-yl]-5-phenyl-1H-[1,2,3]triazole | MS(IS) 557.1(M+1) Rf=0.13(1:5 hexanes:EtOAc) |
| 195 | 1-(3,5-bis-trifluoromethyl-benzyl)-4-[4-(2-chloro-4-fluoro-phenyl)-5-methyl-4H-[1,2,4]triazol-3-yl]-5-phenyl-1H-[1,2,3]triazole | MS(IS) 581.1(M+1) Rf=0.18(1:5 hexanes:EtOAc) |
| 196 | [5-[1-(3,5-bis-trifluoromethyl-benzyl)-5-phenyl-1H-[1,2,3]triazol-4-yl]-4-(2-chloro-benzyl)-4H-[1,2,4]triazol-3-yl]-acetic acid ethyl ester | MS(IS) 649.1(M+1) Rf=0.14(1:1 hexanes:EtOAc) |
| 197 | [5-[1-(3,5-bis-trifluoromethyl-benzyl)-5-dimethylamino-1H-[1,2,3]triazol-4-yl]-4-(2-chloro-4-fluoro-benzyl)-4H-[1,2,4]triazol-3-yl]acetic acid ethyl ester | MS(IS) 633.9(M+1) Rf=0.07(1:1 hexanes:EtOAc) |
| 198 | 1-(3,5-bis-trifluoromethyl-benzyl)-4-{4-[(R)-1-(2-chlorophenyl)-ethyl]-5-methyl-4H-[1,2,4]triazol-3-yl}-5-phenyl-1H-[1,2,3]triazole | Rf=0.17 in 1:5 hexanes/EtOAc MS(IS) 591.1(M+1) |

General Example P

Combine the amide of interest (1 eq), anhydrous toluene, and PCl$_5$ (5 eq) in a sealed tube and heat at 50-60° C. for 0.5-1.0 hour. Add the appropriate hydrazide (3-6 eq), TEA (0-6.0 eq) and heat at 55-80° C. overnight. Dilute with 20% i-PrOH/CHCl$_3$, wash with saturated NaHCO$_3$ solution, and brine. Dry the combined organic layers over MgSO$_4$, filter, and concentrate. Purify the residue by flash chromatography on silica gel to afford the title compounds.

By using a method similar to General Example P, using the appropriate starting materials, the title compounds are prepared and isolated.

| Ex. # | Product | Physical Data |
|---|---|---|
| 199 | 4-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-morpholine | MS(IS) 586(M+1). $^1$H NMR(CDCl$_3$): 2.41(s, 3H); 3.06(t, 4H, J=4.4Hz); 3.73(t, 4H, J=4.4Hz); 5.55(s, 2H); 5.69(s, 2H); 6.60(d, 1H, J=6.6Hz); 7.06(m, 1H); 7.18(m, 1H); 7.36(m, 1H); 7.80(s, 2H); 7.87(s, 1H) (No TEA used) |
| 200 | 4-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-pyridine | MS(IS) 578(M+1). $^1$H NMR(400MHz, CDCl$_3$): 2.35(s, 3H); 5.58(s, 2H); 5.66(s, 2H); 6.56(d, 1H, J=7.6Hz); 7.08(m, 1H); 7.21(m, 1H); 7.38(m, 1H); 7.49(s, 2H); 7.84(s, 1H); 8.74(m, 2H). (No TEA used) |
| 201 | 3-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-pyridine | MS(IS) 578(M+1). $^1$H NMR(400MHz, CDCl$_3$): 2.35(s, 3H); 5.60(s, 2H); 5.68(s, 2H); 6.53(d, 1H, J=7.8Hz); 7.07(t, 1H, J=1.5Hz); 7.22(t, 1H, J=1.5Hz); 7.41(m, 4H); 7.82(m, 2H); 8.44(s, 1H); 8.73(s, 1H). |
| 202 | {3-(3,5-bis-trifluoromethyl-benzyl)-5-[4-(2-chloro-benzyl)-5-methyl-4H-[1,2,4]triazol-3-yl]-3H-[1,2,3]triazol-4-yl}-dimethyl-amine | MS(IS) 544(M+1). TLC: R$_f$=0.31(5% MeOH/CHCl$_3$) |
| 203 | 1-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-4-methyl-piperazine | MS(IS) 599(M+1). TLC(5% MeOH/CHCl$_3$) R$_f$=0.07. |
| 204 | 4-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-thiomorpholine | MS(IS) 602(M+1) $^1$H NMR(400MHz, CDCl$_3$): 2.41(s, 3H); 2.65(t, 4H, J=4.9Hz); 3.28(t, 4H, J=4.9Hz); 5.51(s, 2H); 5.68(s, 2H); 6.59(d, 1H, J=7.8Hz); 7.07(m, 1H); 7.18(m, 1H); 7.36(d, 1H, J=7.8Hz); 7.78(s, 2H); 7.87(s, 1H). |

-continued

| Ex. # | Product | Physical Data |
|---|---|---|
| 205 | 1-(3,5-bis-trifluoromethyl-benzyl)-4-[5-methyl-4-((R)-1-(2-chloro-phenyl)-ethyl)-4H-[1,2,4]triazol-3-yl]-5-pyrid-4-yl-1H-[1,2,3]triazole | MS(IS) 592(M+1)<br>TLC: $R_f$=0.27(5% MeOH/CHCl$_3$) |
| 206 | 1-(3,5-bis-trifluoromethyl-benzyl)-4-[5-methyl-4-((R)-1-(2-chloro-phenyl)-ethyl)-4H-[1,2,4]triazol-3-yl]-5-morpholin-4-yl-1H-[1,2,3]triazole | MS(IS) 600(M+1)<br>TLC: $R_f$=0.27(3% MeOH/CHCl$_3$) |
| 207 | 1-(3,5-bis-trifluoromethyl-benzyl)-4-[5-methyl-4-((R)-1-(2-chloro-phenyl)-ethyl)-4H-[1,2,4]triazol-3-yl]-5-(4-methylpiperazin-1yl)-1H-[1,2,3]triazole | MS(IS) 613(M+1) TLC: $R_f$=0.08(3% MeOH/CHCl$_3$) |
| 208 | 4-{3-(3,5-bis-trifluoromethyl-benzyl)-5-[4-(2-chloro-4-fluoro-benzyl)-5-methyl-4H-[1,2,4]triazol-3-yl]-3H-[1,2,3]triazol-4-yl}-morpholine | MS(IS) 604(M+1) TLC: $R_f$=0.24(3% MeOH/CHCl$_3$) |
| 209 | 1-{3-(3,5-bis-trifluoromethyl-benzyl)-5-[4-(2-chloro-4-fluoro-benzyl)-5-methyl-4H-[1,2,4]triazol-3-yl]-3H-[1,2,3]triazol-4-yl}-4-methyl-piperazine | MS(IS) 617(M+1) TLC: $R_f$=0.09(3% MeOH/CHCl$_3$) |
| 210 | {3-(3,5-bis-trifluoromethyl-benzyl)-5-[4-(2-chloro-4-fluoro-benzyl)-5-methyl-4H-[1,2,4]triazol-3-yl]-3H-[1,2,3]triazol-4-yl}-dimethyl-amine | MS(IS) 562(M+1) TLC: $R_f$=0.33(3% MeOH/CHCl$_3$) |
| 211 | 1-(3,5-bis-trifluoromethyl-benzyl)-4-[5-methyl-4-((R)-1-(2-chloro-phenyl)-ethyl)-4H-[1,2,4]triazol-3-yl]-5-pyrid-3-yl-1H-[1,2,3]triazole | MS(IS) 592(M+1) TLC: $R_f$=0.27(5% MeOH/CHCl$_3$) |
| 212 | 4-{3-(3,5-bis-trifluoromethyl-benzyl)-5-[4-(2-chloro-4-fluoro-benzyl)-5-methyl-4H-[1,2,4]triazol-3-yl]-3H-[1,2,3]triazol-4-yl}-pyridine | MS(IS) 596(M+1) TLC: $R_f$=0.15(5% MeOH/CHCl$_3$) |
| 213 | 1-(3,5-bis-trifluoromethyl-benzyl)-4-[4-((R)-1-(2-chloro-phenyl)-ethyl)-4H-[1,2,4]triazol-3-yl]-5-morpholin-4-yl-1H-[1,2,3]triazole | MS(IS) 586(M+1) TLC: $R_f$=0.30(3% MeOH/CHCl$_3$) |
| 214 | 4-{3-(3,5-bis-trifluoromethyl-benzyl)-5-[4-(2-chloro-4-fluoro-benzyl)-5-chloromethyl-4H-[1,2,4]triazol-3-yl]-3H-[1,2,3]triazol-4-yl}-morpholine | MS(IS) 638(M+1) TLC: $R_f$=0.36(3% MeOH/CH$_2$Cl$_2$) |
| 215 | 4-[5-[4-(2-chloro-benzyl)-5-methyl-4H-[1,2,4]triazol-3-yl]-3-(3,5-dichloro-benzyl)-3H-[1,2,3]triazole-4-yl]-pyridine | MS(IS) 510.1(M+1) |
| 216 | 4-[5-[4-(2-chloro-benzyl)-5-methyl-4H-[1,2,4]triazol-3-yl]-3-(3,5-dichloro-benzyl)-3H-[1,2,3]triazole-4-yl]-morpholine | MS(IS) 518.1(M+1)<br>Rf=0.27(6.7% MeOH/CH$_2$Cl$_2$ |

General Example Q

Dissolve the appropriate thioamide in THF:i-PrOH (3:1 or 4:1). Add hydrazine (5 eq) and stir at room temperature until thioamide is consumed. Remove solvent and redissolve in EtOAc. Cool to 0° C., add TEA (5 eq) then slowly add the appropriate acylating agent (2.5 eq) such as AcBr, triflouroacetic anhydride, isobutyric anhydride. Add more acylating agent if necessary to drive reaction to completion. Pour into separatory funnel containing water. Extract with EtOAc. Wash organic layer with NaHCO$_3$ and brine. Remove solvent and dissolve the crude material in a toluene. Add a catalytic amount of TsOH (0.4 eq) and heat to 115° C. while monitoring the reaction by MS to see the conversion of the intermediate to product. Once complete, cool to RT, dilute with EtOAc, wash with saturated NaHCO$_3$. Dry the organic layer with anhydrous Na$_2$SO$_4$, filter, and concentrate. Purify via radial chromatography using a gradient of 1:1 to 1:5 hexanes: EtOAc to give the title compound.

By using a method similar to General Example Q, using the appropriate starting materials, the title compounds are prepared and isolated.

| Ex # | Product | Physical Data |
|---|---|---|
| 217 | 1-(3,5-bis-trifluoromethyl-benzyl)-4-[5-methyl-4-((S)-1-phenyl-ethyl)-4H-[1,2,4]triazol-3-yl]-5-phenyl-1H-[1,2,3]triazole | MS(IS) 557.2(M+Na)$^+$<br>Rf=0.11(1:5 hexanes:EtOAc) |

-continued

| Ex # | Product | Physical Data |
|---|---|---|
| 218 | 1-(3,5-bis-trifluoromethyl-benzyl)-4-(5-methyl-4-p-tolyl-4H-[1,2,4]triazol-3-yl)-5-phenyl-1H-[1,2,3]triazole | MS(IS) 543.1(M+1) Rf=0.08(1:5 hexanes:EtOAc) |
| 219 | 1-(3,5-bis-trifluoromethyl-benzyl)-4-[4-(2-chloro-benzyl)-5-trifluoromethyl-4H-[1,2,4]triazol-3-yl]-5-phenyl-1H-[1,2,3]triazole | MS(IS) 631.0(M+1) Rf=0.22(3:1 hexanes:EtOAc) |
| 220 | 1-(3,5-bis-trifluoromethyl-benzyl)-4-[4-(2-chloro-benzyl)-5-isopropyl-4H-[1,2,4]triazol-3-yl]-5-phenyl-1H-[1,2,3]triazole | MS(IS) 605.4(M+1) Rf=0.41(1:5 hexanes:EtOAc) |
| 221 | 1-(3,5-bis-trifluoromethyl-benzyl)-4-[4-(2-chloro-phenyl)-5-methyl-4H-[1,2,4]triazol-3-yl]-5-phenyl-1H-[1,2,3]triazole | MS(IS) 563.0(M+1) Rf=0.13(1:5 hexanes:EtOAc) |
| 222 | 1-(3,5-bis-trifluoromethyl-benzyl)-4-[4-(3,4-dichloro-phenyl)-5-methyl-4H-[1,2,4]triazol-3-yl]-5-phenyl-1H-[1,2,3]triazole | MS(IS) 597.0(M+1) Rf=0.16(1:5 hexanes:EtOAc) |

General Example R

Dissolve the appropriate silyl ether in THF and cool to 0° C. Add TBAF (1 eq, 1.0 M solution in THF). Stir overnight while slowly warming to RT. Pour into separatory funnel containing saturated NaHCO$_3$ and extract with Et$_2$O. Purify via silica gel chromatography using 1:5 hexanes:EtOAc to give the title compound.

By using a method similar to General Example R, using the appropriate starting materials, the title compounds may be prepared and isolated.

| Ex# | Product | Physical Data |
|---|---|---|
| 223 | [5-[1-(3,5-bis-trifluoromethyl-benzyl)-5-phenyl-1H-[1,2,3]triazol-4-yl]-4-(2-chloro-benzyl)-4H-[1,2,4]triazol-3-yl]methanol | MS(IS) 593.1(M+1) Rf=0.08(1:5 hexanes:EtOAc) |
| 224 | [5-[1-(3,5-bis-trifluoromethyl-benzyl)-5-dimethylamino-1H-[1,2,3]triazol-4-yl]-4-(2-chloro-benzyl)-4H-[1,2,4]triazol-3-yl]-methanol | MS(IS) 561.2(M+1) Rf=0.22(1:5 hexanes:EtOAc) |

Example 225

5-[1-(3,5-bis-trifluoromethyl-benzyl)-5-phenyl-1H-[1,2,3]triazol-4-yl]-4-(2-chloro-benzyl)-4H-[1,2,4]triazole-3-carbaldehyde

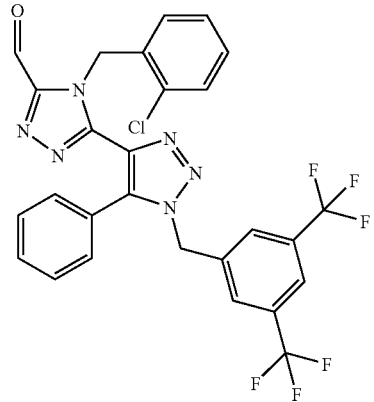

Dissolve [5-[1-(3,5-bis-trifluoromethyl-benzyl)-5-phenyl-1H-[1,2,3]triazol-4-yl]-4-(2-chloro-benzyl)-4H-[1,2,4]triazol-3-yl]methanol in DMSO. Add sulfur trioxide pyridine complex (4 eq) and add TEA (10 eq). Stir overnight at RT. Pour into water and extract with CH$_2$Cl$_2$. Purify via silica gel chromatography using a gradient of 4:1 to 1:1 hexanes:EtOAc to give the title compound. MS (IS) 589.0 (M−1). Rf=0.43 (1:1 hexanes:EtOAc)

General Example S

Cool a mixture of the appropriate aldehyde in 1,2-dicholorethane to 0° C. Add NaBH(OAc)$_3$ (3 eq) then add the desired amine (1.1 eq) and stir for 60 h while warming to RT. Quench by adding 1N NaOH. Extract with CH$_2$Cl$_2$ and pass through a drying column. Purify via silica gel chromatography to give the title compound.

By using a method similar to General Example S, using the appropriate starting materials, the title compounds are prepared and isolated.

| Ex# | Product | Physical Data |
|---|---|---|
| 226 | [5-[1-(3,5-bis-trifluoromethyl-benzyl)-5-phenyl-1H-[1,2,3]triazol-4-yl]-4-(2-chloro-benzyl)-4H-[1,2,4]triazol-3-ylmethyl]-dimethyl-amine | MS(IS) 620.1(M+1) Rf=0.08(1:5 hexanes:EtOAc) |
| 227 | 4-[5-[1-(3,5-bis-trifluoromethyl-benzyl)-5-phenyl-1H-[1,2,3]triazol-4-yl]-4-(2-chloro-benzyl)-4H-[1,2,4]triazol-3-ylmethyl]-morpholine | MS(IS) 662.1(M+1) Rf=0.08(1:5 hexanes:EtOAc) |

General Example T

Add the chloromethyl substituted (1,2,4) triazole (1 eq) and the appropriate amine (10-40 eq) to a sealed tube purged with N$_2$. Shake at RT for 2-24 h then concentrate. Dissolve residue in 20% i-PrOH/CHCl₃, wash with saturated NaHCO₃ solution, and brine. Dry the combined organic layers over MgSO₄ and concentrate. Purify the residue by flash chromatography to give the title compound.

By using a method similar to General Example T, using the appropriate starting materials, the following compounds can be prepared and isolated.

| Ex # | Product | Physical Data |
|------|---------|---------------|
| 228 | [5-[1-(3,5-bis-trifluoromethyl-benzyl)-5-morpholin-4-yl-1H-[1,2,3]triazol-4-yl]-4-(2-chloro-4-fluoro-benzyl)-4H-[1,2,4]triazol-3-ylmethyl]-dimethyl-amine | MS(IS) 647(M+1)<br>TLC: R$_f$=0.28(5% MeOH/CHCl₃) |
| 229 | 4-{3-(3,5-bis-trifluoromethyl-benzyl)-5-[4-(2-chloro-4-fluoro-benzyl)-5-pyrrolidin-1-ylmethyl-4H-[1,2,4]triazol-3-yl]-3H-[1,2,3]triazol-4-yl}-morpholine | MS(IS) 673(M+1)<br>TLC: R$_f$=0.56(5% MeOH/CHCl₃) |

Example 230

5-[1-(3,5-bis-trifluoromethyl-benzyl)-5-phenyl-1H-[1,2,3]triazolyl]4(2-chloro-benzyl)-4H-[1,2,4]triazole-3-carbaldehyde oxime

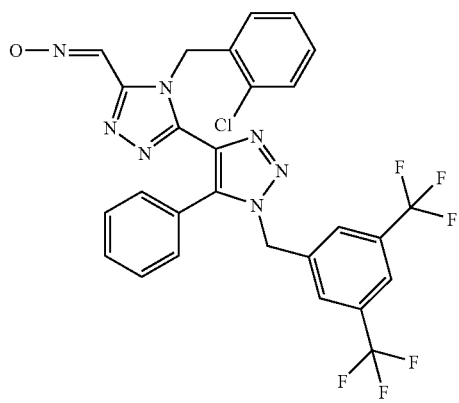

Add hydroxylamine hydrochloride (7 mg) to a 0° C. solution 5-[1-(3,5-bis-trifluoromethyl-benzyl)-5-phenyl-1H-[1,2,3]triazol-4-yl]-4-(2-chloro-benzyl)-4H-[1,2,4]triazole-3-carbaldehyde (50 mg) in 1,2-dichloroethane (1 mL). Stir 60 hours while allowing reaction to slowly warm to RT. Quench reaction by slowly adding 1 N NaOH (1 mL). Extract with CH₂Cl₂ (2×2 mL) and dry. Purification via silica gel chromatography using 3:1 to 1:1 hexanes:EtOAc gradient gives the desired product (18 mg, 35%). MS (IS) 606.1 (M+1); Rf=0.52 (1:1 hexanes:EtOAc).

Example 231

2-[5-[1-(3,5-bis-trifluoromethyl-benzyl)-5-dimethylamino-1H-[1,2,3]triazol-4-yl]-4-(2-chloro-benzyl)-4H-[1,2,4]triazol-3-yl]-ethanol

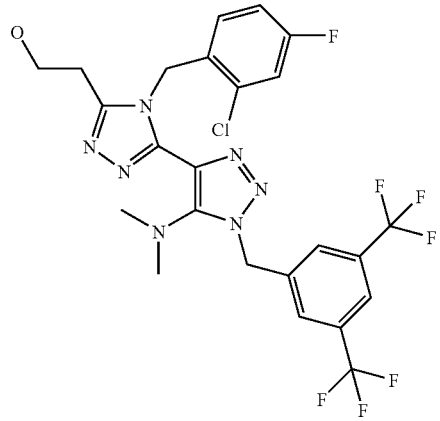

Dissolve [5-[1-(3,5-bis-trifluoromethyl-benzyl)-5-dimethylamino-1H-[1,2,3]triazol-4-yl]-4-(2-chloro-4-fluoro-benzyl)-4H-[1,2,4]triazol-3-yl]-acetic acid ethyl ester (338 mg) in THF (5 mL). Cool to 0° C., add 2M LiBH₄ (0.8 mL, 2M soln in THF) and stir overnight while slowly warming to RT. Pour reaction into aqueous NH₄Cl (15 mL) and extract with EtOAc (2×15 mL). Purify via radial chromatography using a gradient of 1:1 to 1:5 hexanes:EtOAc to give the title compound (137 mg, 44%). MS (IS) 592.0 (M+1); Rf=0.11 (1:5 hexanes:EtOAc).

Example 232

2-[5-[1-(3,5-bis-trifluoromethyl-benzyl)-5-phenyl-1H-[1,2,3]triazol-4-yl]-4-(2-chloro-benzyl)-4H-[1,2,4]triazol-3-yl]-ethanol

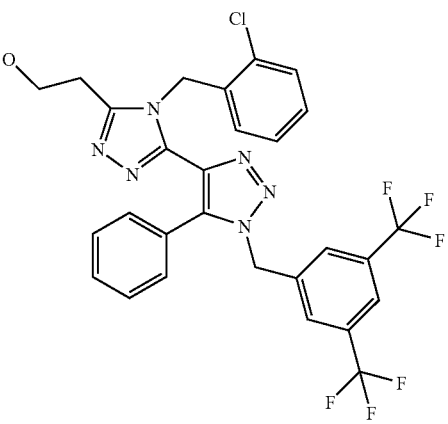

Dissolve [5-[1-(3,5-bis-trifluoromethyl-benzyl)-5-phenyl-1H-[1,2,3]triazol-4-yl]-4-(2-chloro-benzyl)-4H-[1,2,4]triazol-3-yl]-acetic acid ethyl ester (400 mg) in THF (10 mL). Add LAH (47 mg, soln in 10 mL of THF) at 0° C. and warm to RT overnight. Quench by slowly adding water (0.5 ml), 5N NaOH (0.5 ml) and then more water (3 ml). Filter reaction through Celite® to remove aluminum salts and then purify via radial chromatography using a gradient of 1:1 hexanes:EtOAc to 100% EtOAc to give the title compound (119 mg, 32%). MS (IS) 592.0 (M+1). Rf=0.11 (1:5 hexanes:EtOAc).

Example 233

4-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-thiomorpholine 1-oxide

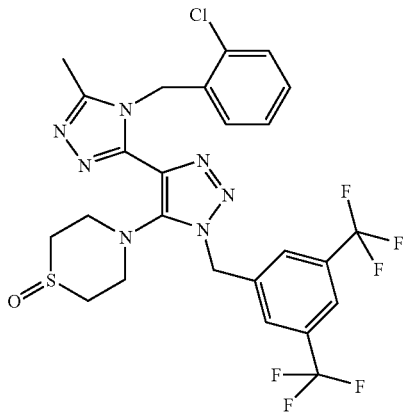

Add m-chloro-perbenzoic acid (29 mg, 0.13 mmol) to a solution of 4-{3-(3,5-bis-trifluoromethyl-benzyl)-5-[4-(2-chloro-benzyl)-5-methyl-4H-[1,2,4]triazol-3-yl]-3H-[1,2,3]triazol-4-yl}-thiomorpholine (69 mg, 0.11 mmol) in THF (1 mL) at −78° C. After 30 minutes, quench with 1N Na$_2$S$_2$O$_3$ at −78° C., warm to RT. Dilute with 20% i-PrOH/CHCl$_3$, wash with 1N HCl, saturated NaHCO$_3$ solution, and brine. Dry the combined organic layers over MgSO$_4$ and concentrate. Purify the residue by flash chromatography on silica gel eluting with 0-4% MeOH/CHCl$_3$ to afford the title compound: MS(IS) 618 (M+1). TLC: R$_f$=0.18 (5% MeOH/CHCl$_3$).

General Example U

Dissolve the appropriate amide (1 eq) in CH$_2$Cl$_2$ (0.01-0.02M). Add PCl$_5$ (3eq). Stir for 35 minutes at RT, then remove solvent and redissolve the resulting residue in DMF. CAUTION: It is important to make sure all the CH$_2$Cl$_2$ is removed at this point as it is dangerous to mix CH$_2$Cl$_2$ and NaN$_3$. Add this solution via syringe to a 0° C. solution of NaN$_3$ (6 eq) in DMF (total concentration=0.01M). After the addition is complete, warm the solution to RT and stir overnight. Quench the reaction with water and extract with ether (2×15 ml). Purify via chromatography (2:1 hexanes: EtOAc.) to give the title compound.

By using a method analogous to General Example U, using the appropriate starting materials, the title compounds are prepared and isolated.

| Ex | Product | Physical Data |
|---|---|---|
| 234 | 5-[1-(3,5-bis-trifluoromethyl-benzyl)-5-phenyl-1H-[1,2,3]triazol-4-yl]-1-phenyl-1H-tetrazole | MS(IS) 516.1(M+1) Rf=0.16(3:1 hexanes:EtOAc) |
| 235 | 1-Benzyl-5-[1-(3,5-bis-trifluoromethyl-benzyl)-5-phenyl-1H-[1,2,3]triazol-4-yl]-1H-tetrazole | MS(IS) 530.1(M+1) Rf=0.21(3:1 hexanes:EtOAc) |
| 236 | 5-[1-(3,5-bis-trifluoromethyl-benzyl)-5-phenyl-1H-[1,2,3]triazol-4-yl]-1-(2-chloro-benzyl)-1H-tetrazole | MS(IS) 564.2(M+1) $^1$H NMR(250MHz, CDCl$_3$) δ 7.75(s, 1H); 7.49-7.05(m, 12H); 6.02(s, 2H); 5.51(s, 2H). |

General Example V

Dissolve the appropriate amino-amide (1 eq) in warm CHCl$_3$. Add PCl$_5$ (3 eq) and heat overnight at 110° C. in a sealed tube. Cool to RT and wash with saturated aqueous NaHCO$_3$ and brine. Dry (Na$_2$SO$_4$), filter, and concentrate to dryness. Purify by reverse phase HPLC.

By using a method similar to General Example V, using the appropriate starting materials, the title compounds may be prepared and isolated.

| Ex # | Product | Physical Data |
|---|---|---|
| 237 | 4-{3-(3,5-bis-trifluoromethyl-benzyl)-5-[1-(2-chloro-benzyl)-4,5-dihydro-1H-imidazol-2-yl]-3H-[1,2,3]triazol-4-yl}-pyridine | MS(IS) 565.1(M+1) TLC R$_f$=0.14(10% MeOH/CHCl$_3$) |
| 238 | 4-{3-(3,5-bis-trifluoromethyl-benzyl)-5-[1-(2-chloro-benzyl)-4,5-dihydro-1H-imidazol-2-yl]-3H-[1,2,3]triazol-4-yl}-morpholine | MS(IS) 573.0(M+1) HPLC trace(100%) |
| 239 | 4-(3-(3,5-bis-trifluoromethyl-benzyl)-5-{1-[1-(2-chloro-phenyl)-ethyl]-4,5-dihydro-1H-imidazol-2-yl}-3H-[1,2,3]triazol-4-yl)-morpholine | MS(IS) 587.2(M+1) HPLC trace(87%) |
| 240 | 4-(3-(3,5-bis-trifluoromethyl-benzyl)-5-{1-[1-(2-chloro-phenyl)-ethyl]-4,5-dihydro-1H-imidazol-2-yl}-3H-[1,2,3]triazol-4-yl)-pyridine | MS(IS) 579.1(M+1) HPLC trace(97%) |

Example 241

1-(3,5-bis-trifluoromethyl-benzyl)-4-[1-(2-chloro-benzyl)-4,5-dihydro-1H-imidazol-2-yl]-5-phenyl-1H-[1,2,3]triazole

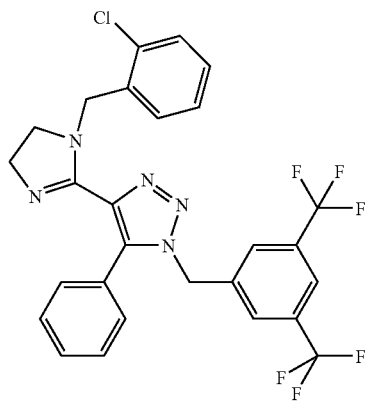

To a solution of 1-(3,5-bis-trifluoromethyl-benzyl)-4-(4,5-dihydro-1H-imidazol-2-yl)-5-phenyl-1H-[1,2,3]triazole (50 mg, 0.11 mmol) in DMF (1 mL) with $K_2CO_3$ (32 mg, 0.23 mmol) and a catalytic amount of NaI add 1-chloro-2-chloromethylbeneze (13 µL, 0.10 mmol, Aldrich). Heat reaction in a sealed tube at 50° C. for 18 hours. Cool to RT, add $H_2O$ (2 mL) and extract with xylenes (2 mL×3). Dry organic layer over $MgSO_4$ and concentrate. Purify by chromatography using a gradient of 50:1 to 20:1 $CHCl_3$/MeOH to afford title compound: MS (IS) 564.2 (M+1)

Example 242

1-(3,5-bis-trifluoromethyl-benzyl)-4-[1-(2-chloro-benzyl)-1H-imidazol-2-yl]-5-phenyl-1H-[1,2,3]triazole

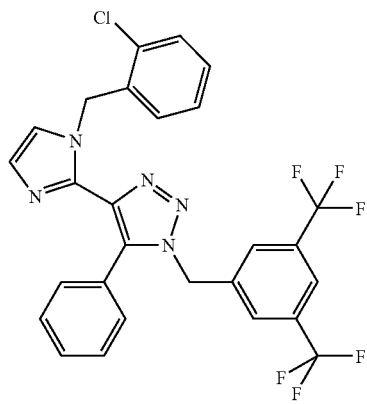

To a solution of 1-(3,5-bis-trifluoromethyl-benzyl)-4-[1-(2-chloro-benzyl)-4,5-dihydro-1H-imidazol-2-yl]-5-phenyl-1H-[1,2,3]triazole (300 mg, 0.53 mmol) in xylenes (2.66 mL) add 10% Pd/C (300 mg). Heat to 137° C. After 72 hours, cool reaction, filter, and concentrate. Purify by chromatography using a gradient of 50:1 to 10:1 $CHCl_3$/MeOH to afford the title compound: MS (IS) 562.0 (M+1).

Example 243

1-(3,5-bis-trifluoromethyl-benzyl)-4-[1-(2-chloro-5-fluoro-benzyl)-4,5-dihydro-1H-imidazol-2-yl]-5-phenyl-1H-[1,2,3]triazole

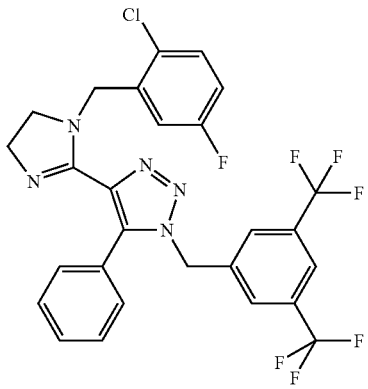

To a 0° C. solution of $Me_3Al$ (0.85 mL, 2M in toluene) in toluene (1.25 ml) at 0° C. under $N_2$ add N1-(2-chloro-4-fluoro-benzyl)-ethane-1,2-diamine (137 mg, 0.68 mmol) and stir for several minutes while warming to RT. Add 1-(3,5-bis-trifluoromethyl-benzyl)-5-phenyl-1H-[1,2,3]triazole-4-carboxylic acid methyl ester (150 mg, 0.34 mmol) dissolved in toluene (1.3 mL) to this solution. Heat reaction at reflux for 3.5 hours. Cool to RT and quench with MeOH (1 mL) and $H_2O$ (1 mL) then extract with $CH_2Cl_2$ (4 mL×2). Dry and concentrate. Purify by chromatography using a gradient of 50:1 to 20:1 $CHCl_3$/MeOH to afford title compound: Rf=0.11 (20:1 $CHCl_3$/MeOH). MS (IS) 582.1 (M+1).

By using a method similar to Example 243, using the appropriate ethylenediamine, the title compounds are prepared and isolated.

| Ex | Product | Data |
|---|---|---|
| 244 | 1-(3,5-bis-trifluoromethyl-benzyl)-4-[1-(2,3-dichloro-benzyl)-4,5-dihydro-1H-imidazol-2-yl]-5-phenyl-1H-[1,2,3]triazole | Rf=0.11 20:1 $CHCl_3$/MeOH MS(IS) 598.2(M+1) |
| 245 | 1-(3,5-bis-trifluoromethyl-benzyl)-5-phenyl-4-[1-(2-trifluoromethyl-benzyl)-4,5-dihydro-1H-imidazol-2-yl]-1H-[1,2,3]triazole | Rf=0.12 20:1 $CHCl_3$/MeOH MS(IS) 598.3(M+1) |
| 246 | 1-(3,5-bis-trifluoromethyl-benzyl)-4-[1-(2-methyl-benzyl)-4,5-dihydro-1H-imidazol-2-yl]-5-phenyl-1H-[1,2,3]triazole | 52% Yield Rf=0.12 20:1 $CHCl_3$/MeOH MS(IS) 544.3(M+1) |
| 247 | 1-(3,5-bis-trifluoromethyl-benzyl)-4-[1-(2-chloro-benzyl)-4,4-dimethyl-4,5-dihydro-1H-imidazol-2-yl]-5-phenyl-1H-[1,2,3]triazole | Rf=0.10 20:1 $CHCl_3$/MeOH MS(IS) 592.1(M+1) |

-continued

| Ex | Product | Data |
|---|---|---|
| 248 | 1-(3,5-bis-trifluoromethyl-benzyl)-5-phenyl-4-(1-p-tolyl-4,5-dihydro-1H-imidazol-2-yl)-1H-[1,2,3]triazole | Rf=0.07 20:1 CHCl₃/MeOH MS(IS) 530.1(M+1) |
| 249 | R-1-(3,5-bis-trifluoromethyl-benzyl)-5-phenyl-4-[1-(1-phenyl-ethyl)-4,5-dihydro-1H-imidazol-2-yl]-1H-[1,2,3]triazole | Rf=0.59 100% MeOH MS(IS) 544.4(M+1) |
| 250 | S-1-(3,5-bis-trifluoromethyl-benzyl)-5-phenyl-4-[1-(1-phenyl-ethyl)-4,5-dihydro-1H-imidazol-2-yl]-1H-[1,2,3]triazole | Rf=0.57 100% MeOH MS(IS) 544.4(M+1) |
| 251 | 1-(3,5-bis-trifluoromethyl-benzyl)-5-phenyl-4-(1-phenyl-4,5-dihydro-1H-imidazol-2-yl)-1H-[1,2,3]triazole | MS(IS) 516.2(M+1) |
| 252 | 2-[1-(3,5-bis-trifluoromethyl-benzyl)-5-phenyl-1H-[1,2,3]triazol-4-yl]-1-(2-chloro-benzyl)-1,4,5,6-tetrahydro-pyrimidine | MS(IS) 578.4(M+1). |

General Example W

Add the appropriate thioamide or thiourea (1-2 eq) to a solution of 1-[1-(3,5-bis-trifluoromethyl-benzyl)-5-pyridin-3-yl-1H-[1,2,3]triazol-4-yl]-2-bromo-3-(2-chloro-phenyl)-propane-1,3-dione (178 mg, 0.28 mmol) in anhydrous ethanol (2 mL) or acetone. Add 4 Å molecular sieves and stir the solution at RT for 4 hours. Filter the solution through a pad of Celite® and concentrate the filtrate in vacuo. Purify the crude material by flash chromatography on silica gel to give the title compound.

By using a method analogous to General Example W, the title compounds may be prepared and isolated.

Example 256

{4-[1-(3,5-bis-trifluoromethyl-benzyl)-5-pyridin-3-yl-1H-[1,2,3]triazol-4-yl]-thiazol-5-yl}-(2-chloro-phenyl)-methanone

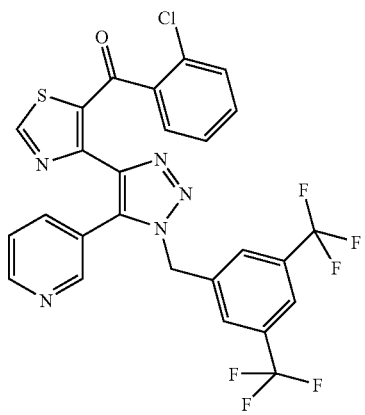

Add isoamylnitrite (29 μL, 0.21 mmol) to a solution of {2-amino-4-[1-(3,5-bis-trifluoromethyl-benzyl)-5-pyridin-3-yl-1H-[1,2,3]triazol-4-yl]-thiazol-5-yl}-(2-chloro-phenyl)-methanone (63 mg, 0.103 mmol) in THF (1.5 mL). Stir the solution at RT for 30 min. then warm to reflux for an additional 30 min. Cool solution to RT and dilute with EtOAc (30 mL). Wash the organic solution with saturated NaHCO₃ (15 mL) and brine (15 mL) then dry, filter, and concentrate. Purify the crude material by flash chromatography then triturate with ether (2×0.3 mL) and dry to give the title compound: MS (IS) 594.1 (M+1), MS (ES−) 592.0 (M−1); ¹HNMR (400 MHz, CDCl₃): δ 9.17 (s, 1H), 8.60 (d, 1H, J=5.0), 8.50 (s, 1H), 7.97 (s, 1H), 7.76 (s, 1H), 7.65 (s, 2H), 7.41 (m, 2H), 7.24 (m, 2H), 7.19 (m, 1H), 5.77 (s, 2H).

| Ex | Product | Physical Data |
|---|---|---|
| 253 | {4-[1-(3,5-bis-trifluoromethyl-benzyl)-5-pyridin-3-yl-1H-[1,2,3]triazol-4-yl]-2-methyl-thiazol-5-yl}-(2-chloro-phenyl)-methanone | MS(IS) 608.1(M+1). ¹HNMR(400MHz, CDCl₃): δ 8.66(dd, 1H, J=2.0, 4.8), 8.44(d, 1H, J=1.5), 7.80(s, 1H), 7.52(dt, 1H, J=2.0, 7.8), 7.44(s, 2H), 7.31(m, 2H), 7.18(m, 2H), 7.12(m, 1H), 5.48(s, 2H), 2.67(s, 3H). |
| 254 | {4-[1-(3,5-bis-trifluoromethyl-benzyl)-5-pyridin-3-yl-1H-[1,2,3]triazol-4-yl]-2-cyclopropyl-thiazol-5-yl}-(2-chloro-phenyl)-methanone | MS(IS) 634.0(M+1). ¹HNMR(400MHz, CDCl₃): δ 8.68(m, 1H), 8.45(s, 1H), 7.81(s, 1H), 7.50(m, 1H), 7.44(s, 2H), 7.34(m, 2H), 7.18(m, 2H), 7.09(m, 1H), 5.44(s, 2H), 2.21(m, 1H), 1.12(m, 2H), 0.98(m, 2H). |
| 255 | {2-Amino-4-[1-(3,5-bis-trifluoromethyl-benzyl)-5-pyridin-3-yl-1H-[1,2,3]triazol-4-yl]-thiazol-5-yl}-(2-chloro-phenyl)-methanone | MS(IS) 609.0(M+1), MS(ES−) 607.1(M−1). ¹HNMR(400MHz, DMSO-d6): δ 8.62(dd, 1H, J=1.2, 5.3), 8.50(d, 1H, J=2.4), 8.20(s, 2H), 8.08(s, 1H), 7.75(dt, 1H, J=2.0, 8.0), 7.61(s, 2H), 7.47(dd, 1H, J=5.0, 7.8), 7.17(m, 1H), 7.15(m, 1H), 7.10(m, 1H), 7.02(m, 1H), 5.74(s, 2H). |

Example 257

{4-Amino-2-[1-(3,5-bistrifluoromethylbenzyl)-5-phenyl-1H-[1,2,3]triazol-4-yl]-pyridin-3-yl}-(2-chlorophenyl)-methanone hemihydrate

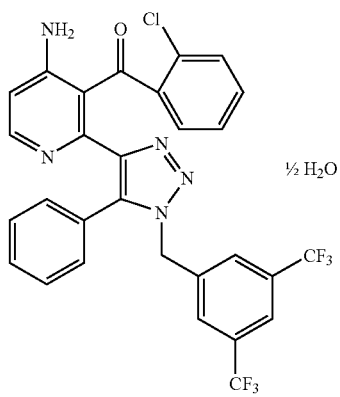

Dissolve {4-amino-2-[1-(3,5-bistrifluoromethylbenzyl)-5-phenyl-1H-[1,2,3]triazol-4-yl]-pyridin-3-yl}-(2-chlorophenyl)-methanone (582 g, 0.97 mol) in ethyl acetate (1880 mL), heptane (1990 mL) and water (90 mL) at 70° C. Cool to room temperature and stir for 18.5 hours. Add heptane (3980 mL) dropwise over 4 hours. Filter and dry in a vacuum oven at 40° C. for approximately 15 hours to give the title compound. $K_f$=1.52%.

Example 258

{3-[1-(3,5-bis-trifluoromethyl-benzyl)-5-pyridin-4-yl-1H-[1,2,3]triazol-4-yl]-pyridin-2-yl}-(2-chlorophenyl)-methanone

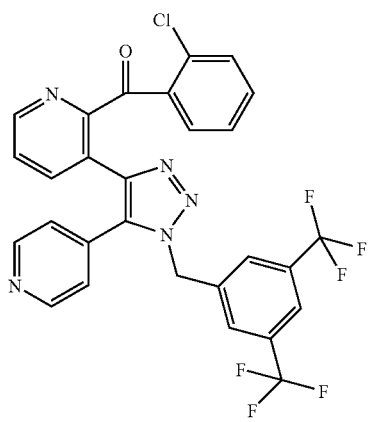

Add $Pd_2(dba)_3 \cdot CHCl_3$ (42 mg, 0.04 mmol) to a degassed solution of trifluoro-methanesulfonic acid 2-(2-chloro-benzoyl)-pyridin-3-yl ester (149 mg, 0.41 mmol) and 4-[3-(3,5-bis-trifluoromethyl-benzyl)-5-tributylstannanyl-3H-[1,2,3]triazol-4-yl]-pyridine (296 mg, 0.45 mmol) in toluene (2 mL). Seal the mixture under $N_2$ and heat at 120° C. for 2 hours. Add $Pd(PPh_3)_4$ (94 mg, 0.08 mmol), seal and heat at 120° C. for another 48 hours. Concentrate, dissolve in ACN, wash with hexanes (×3), dry over $MgSO_4$ and concentrate. Purify the residue by flash chromatography on silica gel eluting with 0-10% $ACN/Et_2O$ to afford the title compound (26 mg, 11%) as tan solid. MS(IS) 588 (M+1). TLC: $R_f$=0.33 (10% $ACN/Et_2O$).

The compounds of the present invention can be administered alone or in the form of a pharmaceutical composition, that is, combined with pharmaceutically acceptable carriers, or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

Thus, the present invention provides pharmaceutical compositions comprising a compound of the Formula I and a pharmaceutically acceptable diluent.

The compounds of Formula I can be administered by a variety of routes. In effecting treatment of a patient afflicted with disorders described herein, a compound of Formula I can be administered in any form or mode that makes the compound bioavailable in an effective amount, including oral and parenteral routes. For example, compounds of Formula I can be administered orally, by inhalation, subcutaneously, intramuscularly, intravenously, transdermally, intranasally, rectally, occularly, topically, sublingually, buccally, and the like. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose; disintegrating agents such as alginic acid, Primogel, corn starch and the like; lubricants such as magnesium stearate or Sterotex; glidants such as colloidal silicon dioxide; and sweetening agents, such as sucrose or saccharin, or a flavoring agent, such as peppermint, methyl salicylate or orange flavoring, may be added. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.001% of a compound of the invention, but may be varied to be between 0.001 and about 90% of the weight thereof. The amount of the compound of Formula I present in such compositions is such that a suitable dosage will be obtained. The solutions or suspensions may also include one or more of the following adjuvants: sterile diluents, such as water for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylene diaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so, the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of a compound of Formula I or its pharmaceutical salt from about 0.1 to about 10% w/v (weight per unit volume).

The compounds of Formula I are antagonists of NK-1 receptors. Furthermore, the compounds of Formula I selectively antagonize NK-1 receptors relative to other tachykinin receptors. The antagonist activity of NK-1 receptor antagonists may be determined by the methods below.

NK-1 Receptor Binding Assay

The IM-9 cell line is a well-characterized and readily available human cell line. See, e.g., Annals of the New York Academy of Science, 190: 221-234 (1972); Nature (London), 251:443-444 (1974); Proceedings of the National Academy of Sciences (USA). 71:84-88 (1974). These cells are routinely cultured in RPMI 1640 supplemented with 50 µg/ml gentamicin sulfate and 10% fetal calf serum.

The IM-9 cells are homogenized from cell pellets for crude membranes. The membranes are isolated by homogenizing tissue samples in 30 ml w/v with 50 mM Tris buffer (pH 7.4). After an initial spin at 900×g, the supernatant is transferred to a clean centrifuge tube and the membranes isolated by centrifugation at 38,000×g.

Approximately 25 µg of membranes are incubated with 0.2 nM [$^{125}$I]-substance P (NEN, Boston, Mass.) in a receptor binding assay. The assay buffer contains 50 mM Tris, 3 mM $MnCl_2$, 0.02% bovine serum albumin, 40 µg/ml bacitracin, 2 µg/ml chymostatin, 4 µg/ml leupeptin and 40 µg/ml thiorphan (pH 7.4). Binding studies are conducted in a final volume of 200 µl containing various concentrations of test compounds. Non-specific binding is determined by incubating some tubes in the presence of 1 µM substance P (Peninsula, Belmont, Calif.).

Binding is terminated 1 hour later by rapid filtration using a TOMTEC 96-well cell harvester (TOMTEC, Orange, Conn.) through GF/A filters that have been presoaked with 0.3% polyethyleneimine (Sigma, St Louis) for 1 hour. The filters are washed with 5 ml of ice-cold 50 mM Tris buffer (pH 7.4) and placed in a drying oven at 60° C. The dried filters are treated with MeltiLex A melt-on scintillator sheets (Wallac, Gaithersburg, Md.), and the radioactivity retained on the filters counted using the Wallac 1205 Betaplate scintillation counter. The results are analyzed using a Log-Logit plot from a Microsoft Excel™ workbook and converted to Ki values with the Cheng-Prusoff equation. Protein concentrations are measured using Coomassie® protein assay reagent (Pierce, Rockford, Ill.), with BSA for standards (Bradford, 1976).

Binding studies are carried out to evaluate the ability of compounds of the present invention to inhibit NK-1 receptor activation. Such studies provide in vitro data regarding the efficacy of the compounds of the present invention. Compounds described herein as EXAMPLES have been demonstrated to have binding affinities ($K_i$ values) of ≦100 nM.

The results of NK-1 receptor binding studies demonstrate the ability of compounds of the present invention to act as antagonists of NK-1 receptors. It is recognized that the compounds of the present invention would be expected to inhibit the effects of NK-1 receptor activation. Thus, the compounds of the present invention are expected to be useful in the treatment of various disorders associated with excess tachykinins, as described to be treated herein, and other disorders that can be treated by such antagonists, as are appreciated by those skilled in the art.

In one embodiment, the present invention provides methods of treating disorders selected from the group consisting of anxiety, depression, psychosis, schizophrenia and other psychotic disorders, neurodegenerative disorders (including senile dementia of the Alzheimer's type, Alzheimer's disease, AIDS-associated dementia, and Down's syndrome), demyelinating diseases (including multiple sclerosis and amyotrophic lateral sclerosis), neuropathological disorders (including peripheral neuropathy, diabetic and chemotherapy-induced neuropathy, and post-herpetic and other neuralgias), acute and chronic obstructive airway diseases (including adult respiratory distress syndrome, bronchopneumonia, bronchospasm, chronic bronchitis, drivercough, and asthma), inflammatory diseases (including inflammatory bowel disease, psoriasis, fibrositis, osteoarthritis, and rheumatoid arthritis), disorders of the musculo-skeletal system (such as osteoporosis), allergies (including eczema and rhinitis), hypersensitivity disorders (such as poison ivy), ophthalmic diseases (such as conjunctivitis, vernal conjunctivitis, and the like), cutaneous diseases (including contact dermatitis), atopic dermatitis, urticaria, other eczematoid dermatites, addiction disorders (including alcoholism), stress-related somatic disorders, reflex sympathetic dystrophy (such as shoulder/hand syndrome), dysthymic disorders, adverse immunological reactions (such as rejection of transplanted tissues), disorders related to immune enhancement or suppression (such as systemic lupus erythematosis), gastrointestinal disorders, diseases associated with the neuronal control of viscera (such as ulcerative colitis, Crohn's disease and irritable bowel syndrome); disorders of bladder function (such as bladder detrusor hyper-reflexia and incontinence), atherosclerosis, fibrosis and collagen diseases (such as scleroderma and eosinophilic fascioliasis), irritative symptoms of benign prostatic hypertrophy, disorders associated with blood pressure (such as hypertension), disorders of blood flow caused by vasodilation or vasospastic diseases (such as angina, migraine, and Reynaud's disease), emesis (including chemotherapy-induced nausea and acute or delayed emesis), and pain or nociception (including that attributable to or associated with any of the foregoing conditions), comprising: administering to a patient in need thereof an effective amount of a compound of Formula I or a pharmaceutical composition thereof. That is, the present invention provides methods of treating disorders associated with an excess of tachykinins, comprising: administering to a patient in need thereof an effective amount of a compound of Formula I or a pharmaceutical composition thereof.

The present invention contemplates the various disorders described to be treated herein and others that can be treated by such antagonists, as appreciated by those skilled in the art.

The disorders associated with an excess of tachykinins are treated by administering an effective amount of a compound or pharmaceutical composition of Formula I. An effective amount can be readily determined by the attending diagnostician, as one skilled in the art, by the use of conventional techniques and by observing results obtained under analogous circumstances. In determining an effective amount, the dose of a compound of Formula I, a number of factors are considered by the attending diagnostician, including, but not limited to: the compound of Formula I to be administered; the species of mammal—its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.001 milligram per kilogram of body weight per day (mg/kg/day) to about 100 mg/kg/day. Preferred amounts may be readily determined by one skilled in the art.

Of the disorders associated with an excess of tachykinins that are treated according to the present invention, the treatment of depression and anxiety are particularly preferred.

Thus, in a preferred embodiment, the present invention provides a method for treating a depressive disorder, including major depressive disorder, comprising: administering to a patient in need thereof an effective amount of a compound of Formula I or a pharmaceutical composition thereof.

According to the fourth edition of the Diagnostic and Statistical Manual of Mental Disorders (DSM-IV™) (1994, American Psychiatric Association, Washington, D.C.), major depressive disorders are characterized by one or more major depressive episodes. Thus, the skilled artisan will recognize that the present invention is useful for the treatment of a single episode and recurrent episodes of major depressive disorder.

In another preferred embodiment, the present invention provides a method for treating anxiety, including generalized anxiety disorder, panic disorder, and obsessive-compulsive disorder, comprising: administering to a patient in need thereof an effective amount of a compound of Formula I or a pharmaceutical composition thereof.

At present, the fourth edition of the Diagnostic and Statistical Manual of Mental Disorders (DSM-IV™) (1994, American Psychiatric Association, Washington, D.C.), provides a diagnostic tool for anxiety and related disorders. These disorders include: panic disorder with or without agoraphobia, agoraphobia without history of panic disorder, specific phobia, social phobia or social anxiety disorder, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein, the term "anxiety" includes treatment of those anxiety disorders and related disorder as described in the DSM-IV. The skilled artisan will recognize that there are alternative nomenclatures, nosologies, and classification systems for neurological and psychiatric disorders, particularly anxiety, and that these systems evolve with medical scientific progress. Thus, the term "anxiety" is intended to include like disorders that are described in other diagnostic sources.

Several preclinical laboratory animal models have been described for a number of the disorders associated with an excess of tachykinins. One such in vivo assay, described below, may be used to determine whether NK-1 receptor antagonists are CNS-penetrant.

Gerbil Foot-Tapping

The gerbil foot-tapping assay is well recognized in the art. For example, see Rupniak et al., *Eur. J. Pharmacol.* (1997) 326: 201-209.

Male Gerbils (Mongolian), weighing between 20-40 gm (Harlan Labs, Indianapolis, Ind.) are used for the experiments. Animals are allowed to acclimate prior to any testing.

An NK-1 receptor agonist, such as GR73632 (δ-Aminovaleryl [$Pro^9$, N-Me-$Leu^{10}$]-Substance P(7-11)) (Peninsula Labs), is dissolved in acidified saline (1 ml acetic acid in 1 liter of 0.09% saline) to make a 1 mg/ml solution (corrected for peptide content). The stock solution is further diluted to 10 µg/ml in saline (0.9% normal saline), aliquoted and kept frozen until use. The stock solution is further diluted to 3 pmol/5 µl in saline for i.c.v. injections.

Test compounds are formulated in appropriate vehicle to a concentration of 1 ml/100 gm body weight. Compounds are dosed by oral gavage (p.o.) or subcutaneously (s.c.) or intraperitoneally (i.p.) at pre-determined times prior to intracerebroventricular (i.c.v.) challenge of agonist. For i.c.v. administration, test compound is co-injected with agonist.

Free hand i.c.v. injection is performed by direct vertical insertion of a cuffed 27-gauge needle with a Hamilton 50 µl syringe, to a depth of 4.5 mm below bregma. Light anesthesia with isoflurane may be needed prior to the injection, but is not used routinely.

Following i.c.v. injection of agonist, animals are placed in a plexiglas observation box, and hind foot tapping events are counted for 5 minutes. Data collection is computerized.

Data are analyzed by ANOVA followed by Dunnett's test using JMP statistical program (IBM platform). Data are expressed as number of events/5 minutes.

What is claimed is:

1. A compound of Formula I:

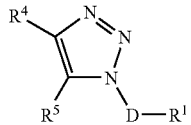
(I)

wherein:

D is a $C_1$-$C_3$ alkane-diyl;

$R^1$ is phenyl,
which is optionally substituted with one to three substitutents independently selected from the group consisting of halo, $C_1$-$C_4$ alkyl, $C_1$-$C_4$ alkoxy, cyano, difluoromethyl, trifluoromethyl, and trifluoromethoxy;

$R^4$ is a radical selected from the group consisting of:

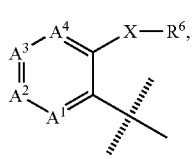
(IA)

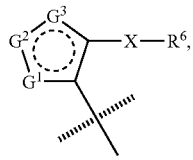
(IB)

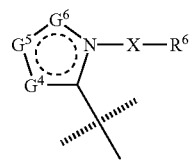
(IC)

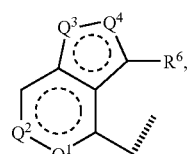
(ID)

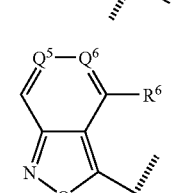
(IE)

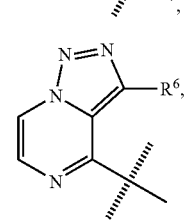
(IF)

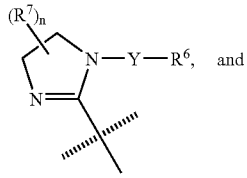
(IG)

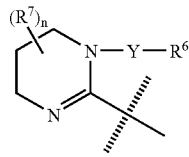
(IH)

wherein
-$A^1$-$A^2$-$A^3$-$A^4$-, together with the atoms to which they are attached, form an aromatic carbocyclic or heterocyclic ring in which each of $A^1$, $A^2$, $A^3$, and $A^4$ is independently —$CR^8$— or nitrogen, wherein at least one of $A^1$, $A^2$, $A^3$, and $A^4$ must be —$CR^8$—;

-$G^1$-$G^2$-$G^3$-, together with the atoms to which they are attached, form an aromatic heterocyclic ring in which each of $G^1$, $G^2$, and $G^3$ is independently —$CR^8$—, nitrogen, oxygen, or sulfur, wherein only one of $G^1$, $G^2$, and $G^3$ can be oxygen or sulfur;

-$G^4$-$G^5$-$G^6$-, together with the atoms to which they are attached, form an aromatic heterocyclic ring in which each of $G^4$, $G^5$, and $G^6$ is independently —$CR^8$—, or nitrogen;

each $R^8$ is independently selected from the group consisting of hydrogen, halo, $C_1$-$C_4$ alkyl, substituted $C_1$-$C_4$ alkyl, $C_3$-$C_6$ cycloalkyl, —$NR^{12}R^{13}$, trifluoromethyl, and trifluoromethoxy;

$R^{12}$ and $R^{13}$ are each independently hydrogen, $C_1$-$C_4$ alkyl, or —C(O)—$CH_3$, or $R^{12}$ and $R^{13}$, together with the nitrogen to which they are attached, form a 4-7 membered ring;

$Q^1$, $Q^2$, $Q^5$, and $Q^6$ are each independently —CH—, or nitrogen;

$Q^3$ and $Q^4$ are each independently oxygen or nitrogen, wherein at least one of $Q^3$ and $Q^4$ must be nitrogen;

$R^6$ is $C_1$-$C_4$ alkyl, $C_3$-$C_6$ cycloalkyl, phenyl, or pyridyl,
which phenyl or pyridyl is optionally substituted with one to three substituents independently selected from the group consisting of halo, cyano, $C_1$-$C_4$ alkyl, $C_1$-$C_4$ alkoxy, trifluoromethyl, trifluoromethoxy, morpholino, and —$NR^{14}R^{15}$;

$R^{14}$ and $R^{15}$ are each independently hydrogen or $C_1$-$C_4$ alkyl, or $R^{14}$ and $R^{15}$, together with the nitrogen to which they are attached, form a 4-7 membered ring;

X is a bond, $C_1$-$C_3$ alkane-diyl, —CH(OH)—, —C(O)—, —O—, —S(O)$_p$—, or —C=N—$OR^9$—;

p is 0, 1, or 2;

$R^9$ is hydrogen, $C_1$-$C_4$ alkyl, or benzyl;

Y is a bond, $C_1$-$C_3$ alkane-diyl, or —C(O)—;

n is 0, 1, or 2;

each $R^7$ is independently $C_1$-$C_4$ alkyl;

$R^5$ is halo, trifluoromethyl, $C_1$-$C_4$ alkyl, $C_3$-$C_6$ cycloalkyl, furyl, thienyl, pyrrolyl, imidazolyl, —$NR^{16}R^{17}$, pyridyloxy, phenyl, phenoxy, phenylthio, anilino,
which phenyl, phenoxy, phenylthio, or anilino group may be optionally substituted on the phenyl ring with one or two substituents independently selected from the group consisting of halo, $C_1$-$C_4$ alkyl, $C_1$-$C_4$ alkoxy, and —S(O)$_q$($C_1$-$C_4$ alkyl), or a radical selected from the group consisting of:

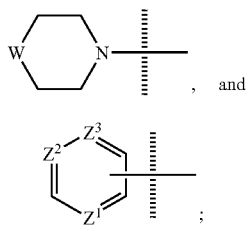

(IJ)

, and

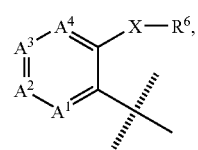

(IK)

;

wherein

W is a bond, —CH$_2$—, —O—, —NR$^{11}$—, or —S(O)$_q$—;

q is 0, 1, or 2;

R$^{11}$ is selected from the group consisting of hydrogen, $C_1$-$C_4$ alkyl, acetyl, phenyl, benzyl, and —S(O)$_2$CH$_3$;

Z$^1$, Z$^2$, and Z$^3$ are each independently —CH— or nitrogen;

R$^{16}$ and R$^{17}$ are each independently $C_1$-$C_4$ alkyl;

or a pharmaceutically acceptable salt thereof.

2. The compound of claim 1 wherein

D is methylene;

R$^1$ is phenyl, which is optionally substituted with one or two substitutents independently selected from the group consisting of halo, $C_1$-$C_4$ alkyl, trifluoromethyl, and trifluoromethoxy;

R$^4$ is a radical selected from the group consisting of:

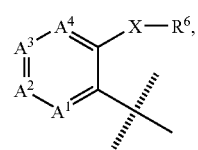

(IA)

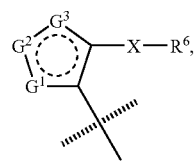

(IB)

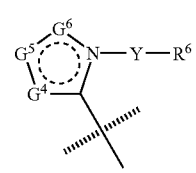

(IC)

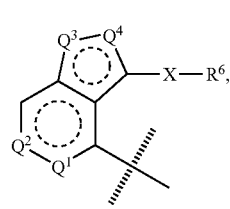

(ID)

-continued

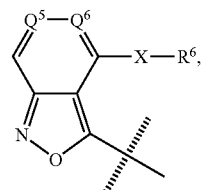

(IE)

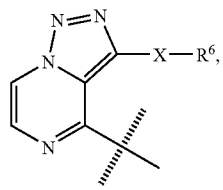

(IF)

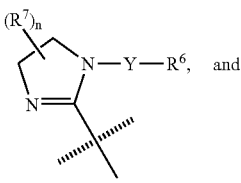

(IG)

, and

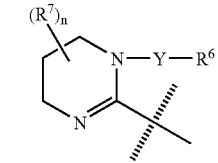

(IH)

wherein

-A$^1$-A$^2$-A$^3$-A$^4$- is selected from the group consisting of —N—CR$^8$—CR$^8$—CR$^8$—, —CR$^8$—CR$^8$—CR$^8$—CR$^8$—, —CR$^8$—N—CR$^8$—CR$^8$—, —N—N—CR$^8$—CR$^8$—, —CR$^8$—N—CR$^8$—N—, —N—CR$^8$—CR$^8$—N—, and —CR$^8$—CR$^8$—CR$^8$—N—, -G$^1$-G$^2$-G$^3$- is selected from the group consisting of —N—O—CR$^8$—, —O—N—CR$^8$—, —CR$^8$—N—O—, —N—N—NH—, —NH—N—N—, —CR$^8$—N—NH—, —N—CR$^8$—NH—, and —N—CR$^8$—S—;

-G$^4$-G$^5$-G$^6$- is selected from the group consisting of —N—N—CR$^8$—, —N—CR$^8$—CR$^8$—, and —N—N—N—;

each R$^8$ is independently selected from the group consisting of hydrogen, $C_1$-$C_4$ alkyl, substituted $C_1$-$C_4$ alkyl, $C_3$-$C_6$ cycloalkyl, —NR$^{12}$R$^{13}$, and trifluoromethyl;

R$^{12}$ is hydrogen;

R$^{13}$ is hydrogen or —C(O)—CH$_3$;

Q$^1$ is nitrogen;

Q$^2$ is —CH— or nitrogen;

Q$^3$ is nitrogen or oxygen;

Q$^4$ is nitrogen or oxygen;

Q$^5$ is —CH— or nitrogen;

Q$^6$ is nitrogen;

R$^6$ is phenyl, which phenyl is optionally substituted with one or two substituents independently selected from the group consisting of halo, cyano, $C_1$-$C_4$ alkyl, $C_1$-$C_4$ alkoxy, trifluoromethyl, and morpholino;

X is a bond, $C_1$-$C_3$ alkane-diyl, —CH(OH)—, —C(O)—, or —C=N—OR$^9$—;
$R^9$ is hydrogen;
Y is a bond or $C_1$-$C_3$ alkane-diyl;
n is 0 or 2;
each $R^7$ is independently $C_1$-$C_4$ alkyl;
$R^5$ is halo, $C_1$-$C_4$ alkyl, $C_3$-$C_6$ cycloalkyl, phenyl, —NR$^{16}$R$^{17}$, or a radical selected from the group consisting of:

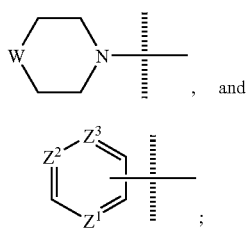

wherein
W is —O—, —NR$^{11}$—, or —S(O)$_q$—;
q is 0, 1, or 2;
$R^{11}$ is $C_1$-$C_4$ alkyl;
$Z^1$, $Z^2$, and $Z^3$ are each independently —CH— or nitrogen;
$R^{16}$ is $C_1$-$C_4$ alkyl;
$R^{17}$ is $C_1$C$_4$ alkyl;
or a pharmaceutically acceptable salt thereof.

3. The compound of claim 2 wherein $R^1$ is phenyl substituted with two substituents independently selected from the group consisting of halo and trifluoromethyl.

4. The compound of claim 3 wherein $R^1$ is 3,5-bis-trifluoromethyl-phenyl.

5. The compound of claim 1 wherein $R^6$ is phenyl, which phenyl is optionally substituted with one or two substituents independently selected from the group consisting of halo, cyano, $C_1$-$C_4$ alkyl, $C_1$-$C_4$ alkoxy, trifluoromethyl, and morpholino.

6. The compound of claim 5 wherein $R^6$ is 2-chloro-phenyl.

7. The compound of claim 2 wherein X is —C(O)—.

8. The compound of claim 2 wherein $R^5$ is phenyl or a radical of Formula (IK).

9. The compound of claim 8 wherein $R^5$ is phenyl.

10. The compound of claim 8 wherein $R^5$ is a radical of Formula (IK) in which $Z^2$ is nitrogen.

11. The compound of claim 10 wherein $R^5$ is pyridin-4-yl.

12. The compound of claim 2 wherein $R^4$ is a radical of Formula (IA), (IB), or (IC).

13. The compound of claim 12 wherein $R^4$ is a radical of Formula (IA).

14. The compound of claim 13 wherein -A$^1$-A$^2$-A$^3$-A$^4$- is —N—CR$^8$—CR$^8$—CR$^8$—, —CR$^8$—CR$^8$—CR$^8$—N—, or —N—N—CR$^8$—CR$^8$—.

15. The compound of claim 14 wherein -A$^1$-A$^2$-A$^3$-A$^4$- is —N—CH—CH—CR$^8$—.

16. The compound of claim 1 wherein the compound is selected from the group consisting of:
{2-[1-(3,5-bis-trifluoromethyl-benzyl)-5-pyridin-4-yl-1H-[1,2,3]triazol-4-yl]-pyridin-3-yl}-(2-chloro-phenyl)-methanone,
{4-Amino-2-[1-(3,5-bistrifluoromethylbenzyl)-5-phenyl-1H-[1,2,3]triazol-4-yl]-pyridin-3-yl}-(2-chloro-phenyl)-methanone,
{5-Amino-3-[1-(3,5-bis-trifluoromethyl-benzyl)-5-phenyl-1H-[1,2,3]triazol-4-yl]-pyridazin-4-yl}-(2-chloro-phenyl)-methanone,
{4Amino-2-[1-(3,5-bis-trifluoromethyl-benzyl)-5-pyridin-4-yl-1H-[1,2,3]triazol-4-yl]-pyridin-3-yl}-(2-chloro-phenyl)-methanone,
{5-Amino-3-[1-(3,5-bis-trifluoromethyl-benzyl)-5-pyridin-4-yl-1H-[1,2,3]triazol-4-yl]-pyridazin-4-yl}-(2-chloro-phenyl)-methanone,
{2-[1-(3,5-bis-trifluoromethyl-benzyl)-5-pyridin-3-yl-1H-[1,2,3]triazol-4-yl]-pyridin-3-yl}-(2-chloro-phenyl)-methanone,
{2-[1-(3,5-bis-trifluoromethyl-benzyl)-5-pyridin-4-yl-1H-[1,2,3]triazol-4-yl]-pyridin-3-yl}-phenyl-methanone,
{5-Amino-3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone,
{4-Amino-2-[1-(3,5-bis-trifluoromethyl-benzyl)-5-morpholin-4-yl-1H-[1,2,3]triazol-4-yl]-pyridin-3-yl}-(2-chloro-phenyl)-methanone,
{2-[1-(3,5-bis-trifluoromethyl-benzyl)-5-pyrazin-2-yl-1H-[1,2,3]triazol-4-yl]-pyridin-3-yl}-(2-chloro-phenyl)-methanone,
{3-[1-(3,5-bis-trifluoromethyl-benzyl)-5-pyridin-3-yl-1H-[1,2,3]triazol-4-yl]-pyridazin-4-yl}-(2-chloro-phenyl)-methanone,
{3-[1-(3,5-bis-trifluoromethyl-benzyl)-5-pyrimidin-5-yl-1H-[1,2,3]triazol-4-yl]-pyridazin-4-yl}-(2-chloro-phenyl)-methanone,
{2-[1-(3,5-bis-trifluoromethyl-benzyl)-5-pyridin-4-yl-1H-[1,2,3]triazol-4-yl]-pyridin-3-yl}-(2-trifluoromethyl-phenyl)-methanone,
{2-[1-(3,5-bis-trifluoromethyl-benzyl)-5-pyridin-4-yl-1H-[1,2,3]triazol-4-yl]-pyridin-3-yl}-(2-fluoro-phenyl)-methanone,
{3-[1-(3,5-bis-trifluoromethyl-benzyl)-5-pyridin-4-yl-1H-[1,2,3]triazol-4-yl]-pyridin-2-yl}-(2-chloro-phenyl)-methanone,
[3-[1-(3,5-bis-trifluoromethyl-benzyl)-5-pyridin-4-yl-1H-[1,2,3]triazol-4-yl]-5-(1-hydroxy-1-methyl-ethyl)-isoxazol-4-yl]-(2-chloro-phenyl)-methanone,
[3-[1-(3,5-bis-trifluoromethyl-benzyl)-5-pyridin-3-yl-1H-[1,2,3]triazol-4-yl]-5-(1-hydroxy-1-methyl-ethyl)-isoxazol-4-yl]-(2-chloro-phenyl)-methanone, and
{2-[1-(3,5-bis-trifluoromethyl-benzyl)-5-pyridin-4-yl-1H-[1,2,3]triazol-4-yl]-pyridin-3-yl}-(2-chloro-phenyl)-methanol.

17. A compound that is {4-Amino-2-[1-(3,5-bistrifluoromethylbenzyl)-5-phenyl-1H-[1,2,3]triazol-4-yl]-pyridin-3-yl}-(2-chlorophenyl)-methanone hemihydrate.

18. A compound that is {5-[1-(3,5-bis-trifluoromethyl-benzyl)-5-pyridin-4-yl-1H-[1,2,3]triazol-4-yl]-isoxazol-3-yl}-methanol.

19. A compound selected from the group consisting of:
[1-(3,5-bis-trifluoromethyl-benzyl)-5-phenyl-1H-[1,2,3,]triazol-4-yl]-[5-(2-chloro-phenyl)-3-(tetrahydro-pyran-2-yloxymethyl)-isoxazol-4-yl]-methanone, [1-(3,5-bis-trifluoromethyl-benzyl)-5-phenyl-1H-[1,2,3]triazol-4-yl]-[5-(2-chloro-phenyl)-3-(2,2-dimethoxy-ethyl)-isoxazol-4-yl]-methanone, [1-(3,5-bis-trifluoromethyl-benzyl)-5-phenyl-1H-[1,2,3]triazol-4-yl]-[5-(2-chloro-phenyl)-3-[1,3]dioxolan-2-ylmethyl-isoxazol-4-yl]-methanone, [1-(3,5-bis-trifluoromethyl-benzyl)-5-pyrazin-2-yl-1H-[1,2,3]triazol-4-yl]-[5-(2-chloro-phenyl)-3-(tetrahydro-pyran-2-yloxymethyl)-isoxazol-4-yl]-methanone, {2[[1-(3,5-bis-trifluoromethyl-benzyl)-5-pyridin-4-yl-1H-[1,2,3]triazole- 4-carbonyl]-(2-chloro-benzyl)-amino]-ethyl}-carbamic acid tert-butyl ester, {2-[[1-(3,5-bis-trifluoromethyl-benzyl)-5-chloro-1H-[1,2,3]triazole-4-carbonyl]-(2-chloro-benzyl)-amino]-ethyl}-carbamic acid tert-butyl ester, (2-{[1-(3,5-bis-trifluoromethyl-benzyl)-5-chloro-1H-[1,2,3]triazole-4-carbonyl[-]1-(2-chloro-phenyl)-ethyl]-amino}-ethyl)-carbamic acid tert-butyl ester, (2-{[1-(3,5-bis-trifluoromethyl-benzyl)-5-pyridin-4-yl-1H-[1,2,3]triazole-4-carbonyl]-[1-(2-chloro-phenyl)-ethyl]-amino}-ethyl)-carbamic acid tert-butyl ester, {2-[[1-(3,5-bis-trifluoromethyl-benzyl)-5-morpholin-4-yl-1H-[1,2,3]triazole-4-carbonyl]-(2-chloro-benzyl)-amino]-ethyl}-carbamic acid tert-butyl ester, (2-{[1-(3,5-bis-trifluoromethyl-benzyl)-5-morpholin-4-yl-1H-[1,2,3]triazole-4-carbonyl]-[1-(2-chloro-phenyl)-ethyl]-amino}-ethyl)-carbamic acid tert-butyl ester, 1-(3,5-bis-trifluoromethyl-benzyl)-5-pyridin-4-yl-1H-[1,2,3]triazole-4-carboxylic acid (2-amino-ethyl)-(2-chloro-benzyl)-amide dihydrochloride, 1-(3,5-bis-trifluoromethyl-benzyl)-5-morpholin-4-yl-1H-[1,2,3]triazole-4-carboxylic acid (2-amino-ethyl)-(2-chloro-benzyl)-amide hydrochloride, 1-(3,5-bis-trifluoromethyl-benzyl)-5-morpholin-4-yl-1H-[1,2,3]triazole-4-carboxylic acid (2-amino-ethyl)-[1-(2-chloro-phenyl)-ethyl]-amide dihydrochloride, and 1-(3,5-bis-trifluoromethyl-benzyl)-5-pyridin-4-yl-1H-[1,2,3]triazole-4-carboxylic acid (2-amino-ethyl)-[1-(2-chloro-phenyl)-ethyl]-amide dihydrochloride.

20. A pharmaceutical composition comprising a compound of claim 1, or a pharmaceutically acceptable salt thereof, in combination with a pharmaceutically acceptable carrier, excipient, or diluent.

21. A method for treating a condition associated with an excess of tachykinins, wherein the condition associated with an excess of tachykinins is depression and anxiety, comprising: administering to a patient in need thereof an effective amount of a compound of Formula I:

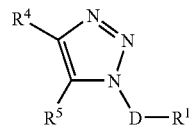
(I)

wherein:
D is a $C_1$-$C_3$ alkane-diyl;
R'is phenyl,
which is optionally substituted with one to three substitutents independently selected from the group consisting of halo, $C_1$-$C_4$ alkyl, $C_1$-$C_4$ alkoxy, cyano, difluoromethyl, trifluoromethyl, and trifluoromethoxy;
$R^4$ is a radical selected from the group consisting of:

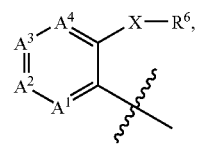
(IA)

-continued

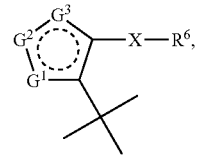
(IB)

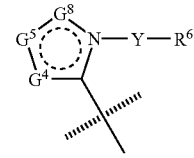
(IC)

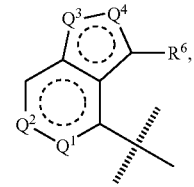
(ID)

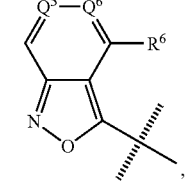
(IE)

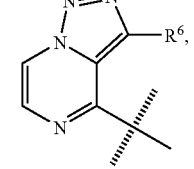
(IF)

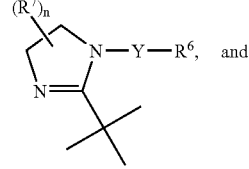
(IG)

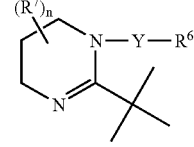
(IH)

wherein
-$A^1$-$A^2$-$A^3$-$A^4$-, together with the atoms to which they are attached, form an aromatic carbocyclic or heterocyclic ring in which each of $A^1$, $A^2$, $A^3$, and $A^4$ is independently —$CR^8$— or nitrogen, wherein at least one of $A^1$, $A^2$, $A^3$, and $A^4$ must be —$CR^8$—;
-$G^1$-$G^2$-$G^3$-, together with the atoms to which they are attached, form an aromatic heterocyclic ring in which each of $G^1$, $G^2$, and $G^3$ is independently —$CR^8$—, nitrogen, oxygen, or sulfur, wherein only one of $G^1$, $G^2$, and $G^3$ can be oxygen or sulfur;

-$G^4$-$G^5$-$G^6$-, together with the atoms to which they are attached, form an aromatic heterocyclic ring in which each of $G^4$, $G^5$, and $G^6$ is independently —$CR^8$—, or nitrogen;

each $R^8$ is independently selected from the group consisting of hydrogen, halo, $C_1$-$C_4$ alkyl, substituted $C_1$-$C_4$ alkyl, $C_3$-$C_6$ cycloalkyl, —$NR^{12}R^{13}$, trifluoromethyl, and trifluoromethoxy;

$R^{12}$ and $R^{13}$ are each independently hydrogen, $C_1$-$C_4$ alkyl, or —C(O)—$CH_3$, or $R^{12}$ and $R^{13}$, together with the nitrogen to which they are attached, form a 4-7 membered ring;

$Q^1$, $Q^2$, $Q^5$, and $Q^6$ are each independently —CH—, or nitrogen;

$Q^3$ and $Q^4$ are each independently oxygen or nitrogen, wherein at least one of $Q^3$ and $Q^4$ must be nitrogen;

$R^6$ is $C_1$-$C_4$ alkyl, $C_3$-$C_6$ cycloalkyl, phenyl, or pyridyl, which phenyl or pyridyl is optionally substituted with one to three substituents independently selected from the group consisting of halo, cyano, $C_1$-$C_4$ alkyl, $C_1$-$C_4$ alkoxy, trifluoromethyl, trifluoromethoxy, morpholino, and —$NR^{14}R^{15}$;

$R^{14}$ and $R^{15}$ are each independently hydrogen or $C_1$-$C_4$ alkyl, or $R^{14}$ and $R^{15}$, together with the nitrogen to which they are attached, form a 4-7 membered ring;

X is a bond, $C_1$-$C_3$ alkane-diyl, —CH(OH)—, —C(O)—, —O—, —S(O)$_p$—, or —C=N—$OR^9$—;

p is 0, 1, or 2;

$R^9$ is hydrogen, $C_1$-$C_4$ alkyl, or benzyl;

Y is a bond, $C_1$-$C_3$ alkane-diyl, or —C(O)—;

n is 0, 1, or 2;

each $R^7$ is independently $C_1$-$C_4$ alkyl;

$R^5$ is hydrogen, halo, trifluoromethyl, $C_1$-$C_4$ alkyl, $C_3$-$C_6$ cycloalkyl, furyl, thienyl, pyrrolyl, imidazolyl, —$NR^{16}R^{17}$, pyridyloxy, phenyl, phenoxy, phenylthio, anilino, which phenyl, phenoxy, phenylthio, or anilino group may be optionally substituted on the phenyl ring with one or two substituents independently selected from the group consisting of halo, $C_1$-$C_4$ alkyl, $C_1$-$C_4$ alkoxy, and —S(O)$_q$($C_1$-$C_4$ alkyl), or a radical selected from the group consisting of:

(IJ)

, and (IK)

wherein

W is a bond, —$CH_2$—, —O—, —$NR^{11}$—, or —S(O)$_q$—;

q is 0, 1, or 2;

$R^{11}$ is selected from the group consisting of hydrogen, $C_1$-$C_4$ alkyl, acetyl, phenyl, benzyl, and —S(O)$_2CH_3$;

$Z^1$, $Z^2$, and $Z^3$ are each independently —CH— or nitrogen;

$R^{16}$ and $R^{17}$ are each independently hydrogen or $C_1$-$C_4$ alkyl;

or a pharmaceutically acceptable salt thereof.

22. The compound of claim 16 wherein the compound is {2-[1-(3,5-bis-trifluoromethyl-benzyl)-5-pyridin-4-yl-1H-[1,2,3]triazol-4-yl]-pyridin-3-yl}-(2-chloro-phenyl)-methanone.

23. The compound of claim 16 wherein the compound is {4-Amino-2-[1-(3,5-bistrifluoromethylbenzyl)-5-phenyl-1H-[1,2,3]triazol -4-yl]-pyridin-3-yl}-(2-chloro-phenyl)-methanone.

24. The compound of claim 16 wherein the compound is {5-Amino-3-[1-(3,5-bis-trifluoromethyl-benzyl)-5-phenyl-1H-[1,2,3]triazol-4-yl]-pyridazin-4-yl}-(2-chloro-phenyl)-methanone.

25. The compound of claim 16 wherein the compound is {2-[1-(3,5-bis-trifluoromethyl-benzyl)-5-pyridin-3-yl-1H-[1,2,3]triazol-4-yl]-pyridin-3-yl}-(2-chloro-phenyl)-methanone.

26. The method of claim 21 wherein the depression condition associated with an excess of tachykinins is major depressive disorder.

27. The method of claim 21 wherein the condition associated with an excess of tachykinins is anxiety.

28. The method of claim 27 wherein the anxiety is generalized anxiety disorder.

29. The compound of claim 4 wherein $R^5$ is phenyl or a radical of Formula (IK).

30. The compound of claim 29 wherein $R^4$ is a radical of Formula (IA).

31. The compound of claim 30 wherein X is —C(O)—.

32. The compound of claim 16 wherein the compound is {2-[1-(3,5-bis-trifluoromethyl-benzyl)-5-pyridin-4-yl-1H-[1,2,3]triazol-4-yl]-pyridin-3-yl}-(2-chloro-phenyl)-methanol.

33. The method of claim 26 comprising administering to a patient in need thereof an effective amount of a compound selected from the group consisting of:

{2-[1-(3,5-bis-trifluoromethyl-benzyl)-5-pyridin-4-yl-1H-[1,2,3]triazol-4-yl]-pyridin-3-yl}-(2-chloro-phenyl)-methanone;

{4-Amino-2-[1-(3,5-bistrifluoromethylbenzyl)-5-phenyl-1H-[1,2,3]triazol-4-yl]-pyridin-3-yl}-(2-chloro-phenyl)-methanone;

{5-Amino-3-[1-(3,5-bis-trifluoromethyl-benzyl)-5-phenyl-1H-[1,2,3]triazol-4-yl]-pyridazin-4-yl}-(2-chloro-phenyl)-methanone;

{2-[1-(3,5-bis-trifluoromethyl-benzyl)-5-pyridin-3-yl-1H-[1,2,3]triazol-4-yl]-pyridin-3-yl}-(2-chloro-phenyl)-methanone; and {2-[1-(3,5-bis-trifluoromethyl-benzyl)-5-pyridin-4-yl-1H-[1,2,3]triazol-4-yl]-pyridin-3-yl}-(2-chloro-phenyl)-methanol.

34. The method of claim 28 comprising administering to a patient in need thereof an effective amount of a compound selected from the group consisting of:

{2-[3,5-bis-trifluoromethyl-benzyl)-5-pyridin-4-yl-1H-[1,2,3]triazol-4-yl]-pyridin-3-yl}-(2-chloro-phenyl)-methanone;

{4-Amino-2-[1-(3,5-bistrifluoromethylbenzyl)-5-phenyl-1H-[1,2,3]triazol-4-yl]-pyridin-3-yl}-(2-chloro-phenyl)-methanone;

{5-Amino-3-[1-(3,5-bis-trifluoromethyl-benzyl)-5-phenyl-1H-[1,2,3]triazol-4-yl]-pyridazin-4-yl}-(2-chloro-phenyl)-methanone;

{2-[1-(3,5-bis-trifluoromethyl-benzyl)-5-pyridin-3-yl-1H-[1,2,3]triazol-4-yl]-pyridin-3-yl}-(2-chloro-phenyl)-methanone; and {2-[1-(3,5-bis-trifluoromethyl-benzyl)-5-pyridin-4-yl-1H-[1,2,3]triazol-4-yl]-pyridin-3-yl}-(2-chloro-phenyl)-methanol.

* * * * *